(12) United States Patent
Hoffmann et al.

(10) Patent No.: US 10,231,453 B2
(45) Date of Patent: Mar. 19, 2019

(54) 5-SUBSTITUTED IMIDAZOLE DERIVATIVES

(71) Applicant: BAYER CROPSCIENCE AKTIENGESELLSCHAFT, Monheim Am Rhein (DE)

(72) Inventors: Sebastian Hoffmann, Neuss (DE); Hendrik Helmke, Liederbach (DE); Peter Dahmen, Neuss (DE); Ulrike Wachendorff-Neumann, Neuweid (DE); David Bernier, Lyons (FR); Ricarda Miller, Lyons (FR); Pierre-Yves Coqueron, Lyons (FR); Pierre Genix, Lyons (FR); Sven Wittrock, Berlin (DE); Jean-Pierre Vors, Sainte Foy les Lyon (FR); Philippe Kennel, Biot (FR); Stephane Brunet, St Andre de Corcy (FR); Sebastien Naud, Lyons (FR); Ruth Meissner, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/563,414

(22) PCT Filed: Mar. 29, 2016

(86) PCT No.: PCT/EP2016/056764
§ 371 (c)(1),
(2) Date: Sep. 29, 2017

(87) PCT Pub. No.: WO2016/156290
PCT Pub. Date: Oct. 6, 2016

(65) Prior Publication Data
US 2018/0084780 A1 Mar. 29, 2018

(30) Foreign Application Priority Data
Apr. 2, 2015 (EP) .................... 15162437

(51) Int. Cl.
| | |
|---|---|
| *A01N 43/50* | (2006.01) |
| *C07D 233/58* | (2006.01) |
| *C07D 233/60* | (2006.01) |
| *C07D 233/68* | (2006.01) |
| *C07D 233/74* | (2006.01) |
| *C07D 233/84* | (2006.01) |
| *C07D 233/92* | (2006.01) |
| *C07D 233/61* | (2006.01) |
| *C07D 401/06* | (2006.01) |

(52) U.S. Cl.
CPC .......... *A01N 43/50* (2013.01); *C07D 233/58* (2013.01); *C07D 233/60* (2013.01); *C07D 233/61* (2013.01); *C07D 233/68* (2013.01); *C07D 233/74* (2013.01); *C07D 233/84* (2013.01); *C07D 233/92* (2013.01); *C07D 401/06* (2013.01)

(58) Field of Classification Search
None
See application file for complete search history.

(56) References Cited

U.S. PATENT DOCUMENTS

| | | |
|---|---|---|
| 4,085,209 A | 4/1978 | Miller et al. |
| 9,095,136 B2 | 8/2015 | Helmke et al. |

FOREIGN PATENT DOCUMENTS

| | | |
|---|---|---|
| EP | 0679634 A2 | 11/1995 |
| EP | 2746259 A1 | 6/2014 |
| GB | 1155529 A | 6/1969 |
| WO | 2013076228 A1 | 5/2013 |
| WO | 2014118170 A1 | 8/2014 |

OTHER PUBLICATIONS

Database Registry Chemical Abstracts Service, Columbus, Ohio, Accession No. RN 1557580-56-9, Entered STN: Feb. 27, 2014.*
Kikuchi, Masamichi. Synthesis and Plant Growth Regulatory Activity of 1,5-Disubstituted Imidazoles. J. Fac. Agr. 34(4), 397-404, 1990.*
Todoroki, et al., "Abscinazole-F1, a conformationally restricted analogue of the plant growth retardant uniconazole and an inhibitor of ABA 8'-hydroxylase CYP707A with no growth-retardant effect," Bioorganic & Medicinal Chemistry (2009) vol. 17: 6620-6630.
Database Registry [Online] Chemical Abstracts Service, Columbus, Ohio, US; Feb. 23, 2014 (Feb. 23, 2014), 11 1H-Imidazole-5-carboxylic acid, 1-(2-oxoethyl)-, methylester11 , XP002740395, Database accession No. 1552535-35-9.
Database Registry [Online] Chemical Abstracts Service, Columbus, Ohio, US; Feb. 17, 2014 (Feb. 17, 2014), 11 1H-Imidazole-5-carboxylic acid, 1-(2-oxopropyl)-, methyl ester11 , XP002740396, Database accession No. 1547109-85-2.
Database Registry [Online] Chemical Abstracts Service, Columbus, Ohio, US; Dec. 19, 2013 (Dec. 19, 2013), 11 1H-Imidazole-5-carboxylic acid, 1-(2-oxoethyl)-11 , XP002740397, Database accession No. 1499007-61-2.
PCT International Search Report for PCT/EP2016/056764, dated May 30, 2016.

\* cited by examiner

*Primary Examiner* — Samantha L Shterengarts
(74) *Attorney, Agent, or Firm* — McBee Moore Woodward & Vanik IP, LLC

(57) ABSTRACT

The present invention relates to novel 5-substituted imidazolylmethyl derivatives, to processes for preparing these compounds, to compositions comprising these compounds, and to the use thereof as biologically active compounds, especially for control of harmful microorganisms in crop protection and in the protection of materials and as plant growth regulators.

18 Claims, No Drawings

5-SUBSTITUTED IMIDAZOLE DERIVATIVES

CROSS-REFERENCE TO RELATED APPLICATIONS

This application is a National Stage entry of International Application No. PCT/EP2016/056764, filed Mar. 29, 2016, which claims priority to European Patent Application No. 15162437.6, filed Apr. 2, 2015.

BACKGROUND

Field

The present invention relates to novel 5-substituted imidazolylmethyl derivatives, to processes for preparing these compounds, to compositions comprising these compounds, and to the use thereof as biologically active compounds, especially for control of harmful microorganisms in crop protection and in the protection of materials and as plant growth regulators.

Description of Related Art

It is already known that particular 2-iodo-substituted imidazole derivatives can be used in crop protection as fungicides (cf. WO-A 2013/076228). Moreover, U.S. Pat. No. 4,085,209 discloses the preparation and safening effect of certain imidazole metal salt complexes, wherein the imidazole ring may be unsubstituted or substituted by up to 3 methyl groups or halogen atoms. WO-A 2014/076228 discloses microbiocides and their use in compositions and methods for the control and/or prevention of microbial infection, particularly fungal infection, in plants. The microbiocides may be based on a tetrazole, triazole, oxazole, thiazole, or imidazole structure.

Since the ecological and economic demands made on modern active ingredients, for example fungicides, are increasing constantly, for example with respect to activity spectrum, toxicity, selectivity, application rate, formation of residues and favourable manufacture, and there can also be problems, for example, with resistances, there is a constant need to develop novel fungicidal compounds and compositions which have advantages over the known compounds and compositions at least in some areas.

SUMMARY

Accordingly, the present invention provides novel imidazole derivatives of the formula (I)

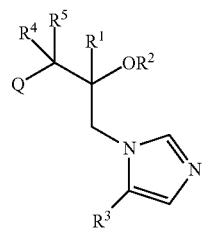

(I)

wherein $R^1$ represents hydrogen, in each case optionally branched $C_1$-$C_8$-alkyl, $C_1$-$C_8$-haloalkyl, $C_2$-$C_7$-alkenyl, $C_2$-$C_7$-haloalkenyl, $C_2$-$C_8$-alkynyl, $C_2$-$C_8$-haloalkynyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted bicycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_8$-cycloalkylalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-halocycloalkyl-$C_1$-$C_4$-alkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-halocycloalkyl-$C_1$-$C_4$-haloalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl-$C_1$-$C_4$-haloalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl-$C_3$-$C_7$-cycloalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkenyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted tri($C_1$-$C_8$-alkyl)silyl-$C_1$-$C_4$-alkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted tri($C_1$-$C_8$-alkyl)silyl-$C_3$-$C_7$-cycloalkyl;

$R^2$ represents H, $C_1$-$C_8$-alkyl, —Si($R^{6a}$)($R^{6b}$)($R^{6c}$), —P(O)(OH)$_2$, —CH$_2$—O—P(O)(OH)$_2$, —C(O)—$C_1$-$C_8$-alkyl, —C(O)—$C_3$-$C_7$-cycloalkyl, —C(O)NH—$C_1$-$C_8$-alkyl; —C(O)N-di-$C_1$-$C_8$-alkyl; —C(O)O—$C_1$-$C_8$-alkyl; wherein the —C(O)—$C_1$-$C_8$-alkyl, —C(O)—$C_3$-$C_7$-cycloalkyl, —C(O)NH—$C_1$-$C_8$-alkyl; —C(O)N-di-$C_1$-$C_8$-alkyl or —C(O)O—$C_1$-$C_8$-alkyl may be non-substituted or substituted by one or more group(s) selected from halogen or $C_1$-$C_8$-alkoxy;

wherein $R^{6a}$, $R^{6b}$, $R^{6c}$ represent independent from each other a phenyl or $C_1$-$C_8$-alkyl;

$R^3$ represents halogen; hydroxyl; cyano; isocyano; nitro; amino; sulfanyl; pentafluoro-$\lambda^6$-sulfanyl; carboxaldehyde, hydroxycarbonyl, $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; tri($C_1$-$C_8$-alkyl)silyl; tri($C_1$-$C_8$-alkyl)silyl-$C_1$-$C_8$-alkyl; $C_3$-$C_7$-cycloalkyl; $C_3$-$C_7$-halogencycloalkyl; $C_3$-$C_7$-cycloalkenyl; $C_3$-$C_7$-halogencycloalkenyl; $C_4$-$C_{10}$-cycloalkylalkyl; $C_4$-$C_{10}$-halocycloalkylalkyl; $C_6$-$C_{12}$-cycloalkylcycloalkyl; $C_1$-$C_8$-alkyl-$C_3$-$C_7$-cycloalkyl; $C_1$-$C_8$-alkoxy-$C_3$-$C_7$-cycloalkyl; tri($C_1$-$C_8$-alkyl)silyl-$C_3$-$C_7$-cycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_1$-$C_8$-alkylamino; $C_1$-$C_8$-halogenalkylamino; $C_1$-$C_8$-cyanoalkoxy; $C_4$-$C_8$-cycloalkylalkoxy; $C_3$-$C_6$-cycloalkoxy; $C_1$-$C_8$-alkylsulfanyl; $C_1$-$C_8$-halogenoalkylsulfanyl; $C_1$-$C_8$-alkylcarbonyl; $C_1$-$C_8$-halogenoalkylcarbonyl; arylcarbonyl; $C_3$-$C_8$-cycloalkylcarbonyl; $C_3$-$C_8$-halogenocycloalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$- halogenoalkoxycarbonyl; C₃-C₈-cycloalkoxycarbonyl; C₂-C₈-alkoxyalkylcarbonyl; C₂-C₈-halogenoalkoxyalkylcarbonyl; C₃-C₁₀-cycloalkoxyalkylcarbonyl; C₁-C₈-alkylaminocarbonyl; di-C₁-C₈-alkylaminocarbonyl; C₃-C₈-cycloalkylaminocarbonyl; C₁-C₈-alkylcarbonyloxy; C₁-C₈-halogenoalkylcarbonyloxy; C₃-C₈-cycloalkylcarbonyloxy; C₁-C₈-alkylcarbonylamino; C₁-C₈-halogenoalkylcarbonylamino; C₁-C₈-alkylaminocarbonyloxy; di-C₁-C₈-alkylaminocarbonyloxy; C₁-C₈-alkyloxycarbonyloxy; C₁-C₈-alkylsulfinyl; C₁-C₈-halogenoalkylsulfinyl; C₁-C₈-alkylsulfonyl; C₁-C₈-halogenoalkylsulfonyl; C₁-C₈-alkylsulfonyloxy; C₁-C₈-halogenoalkylsulfonyloxy; C₁-C₈-alkylaminosulfamoyl; di-C₁-C₈-alkylaminosulfamoyl; (C₁-C₈-alkoxyimino)-C₁-C₈-alkyl; (C₃-C₇-cycloalkoxyimino)-C₁-C₈-alkyl; hydroxyimino-C₁-C₈-alkyl; (C₁-C₈-alkoxyimino)-C₃-C₇-cycloalkyl; hydroxyimino-C₃-C₇-cycloalkyl; (C₁-C₈-alkylimino)-oxy; (C₁-C₈-alkylimino)-oxy-C₁-C₈-alkyl; (C₃-C₇-cycloalkylimino)-oxy-C₁-C₈-alkyl; (C₁-C₆-alkylimino)-oxy-C₃-C₇-cycloalkyl; (C₁-C₈-alkenyloxyimino)-C₁-C₈-alkyl; (C₁-C₈-alkynyloxyimino)-C₁-C₈-alkyl; (benzyloxyimino)-C₁-C₈-alkyl; C₁-C₈-alkoxyalkyl; C₁-C₈-alkylthioalkyl; C₁-C₈-alkoxyalkoxyalkyl; C₁-C₈-halogenoalkoxyalkyl; benzyl; phenyl; 5-membered heteroalyl; 6-membered heteroaryl; benzyloxy; phenyloxy; benzylsulfanyl; benzylamino; phenylsulfanyl; or phenylamino; wherein the benzyl, phenyl, 5-membered heteroalyl, 6-membered heteroaryl, benzyloxy or phenyloxy may be optionally substituted by one or more group(s) selected from halogen; hydroxyl; cyano; amino; sulfanyl; pentafluoro-λ⁶-sulfanyl; carboxaldehyde, hydroxycarbonyl, C₁-C₈-alkyl; C₁-C₈-haloalkyl; C₁-C₈-cyanoalkyl; C₁-C₈-alkyloxy; C₁-C₈-halogenalkyloxy; tri(C₁-C₈-alkyl)silyl; tri(C₁-C₈-alkyl)silyl-C₁-C₈-alkyl; C₃-C₇-cycloalkyl; C₃-C₇-halogencycloalkyl; C₃-C₇-cycloalkenyl; C₃-C₇-halogencycloalkenyl; C₄-C₁₀-cycloalkylalkyl; C₄-C₁₀-halocycloalkylalkyl; C₆-C₁₂-cycloalkylcycloalkyl; C₁-C₈-alkyl-C₃-C₇-cycloalkyl; C₁-C₈-alkoxy-C₃-C₇-cycloalkyl; tri(C₁-C₈-alkyl)silyl-C₃-C₇-cycloalkyl; C₂-C₈-alkenyl; C₂-C₈-alkynyl; C₂-C₈-alkenyloxy; C₂-C₈-halogenalkenyloxy; C₃-C₈-alkynyloxy; C₃-C₈-halogenoalkynyloxy; C₁-C₈-alkylamino; C₁-C₈-halogenoalkylamino; C₁-C₈-cyanoalkoxy; C₄-C₅-cycloalkylalkoxy; C₃-C₆-cycloalkoxy; C₁-C₈-alkylsulfanyl; C₁-C₈-halogenoalkylsulfanyl; C₁-C₈-alkylcarbonyl; C₁-C₈-halogenoalkylcarbonyl; arylcarbonyl; C₃-C₈-cycloalkylcarbonyl; C₃-C₈-halogenocycloalkylcarbonyl; C₁-C₈-alkylcarbamoyl; di-C₁-C₈-alkylcarbamoyl; N—C₁-C₈-alkyloxycarbamoyl; C₁-C₈-alkoxycarbamoyl; N—C₁-C₈-alkyl-C₁-C₈-alkoxycarbamoyl; C₁-C₈-alkoxycarbonyl; C₁-C₈-halogenoalkoxycarbonyl; C₃-C₈-cycloalkoxycarbonyl; C₂-C₈-alkoxyalkylcarbonyl; C₂-C₈-halogenoalkoxyalkylcarbonyl; C₃-C₁₀-cycloalkoxyalkylcarbonyl; C₁-C₈-alkylaminocarbonyl; di-C₁-C₈-alkylaminocarbonyl; C₃-C₈-cycloalkylaminocarbonyl; C₁-C₈-alkylcarbonyloxy; C₁-C₈-halogenoalkylcarbonyloxy; C₃-C₈-cycloalkylcarbonyloxy; C₁-C₈-alkylcarbonylamino; C₁-C₈-halogenoalkylcarbonylamino; C₁-C₈-alkylaminocarbonyloxy; di-C₁-C₈-alkylaminocarbonyloxy; C₁-C₈-alkyloxycarbonyloxy; C₁-C₈-alkylsulfinyl; C₁-C₈-halogenoalkylsulfinyl; C₁-C₈-alkylsulfonyl; C₁-C₈-halogenoalkylsulfonyl; C₁-C₈-alkylsulfonyloxy; C₁-C₈-halogenoalkylsulfonyloxy; C₁-C₈-alkylaminosulfamoyl; di-C₁-C₈-alkylaminosulfamoyl; (C₁-C₈-alkoxyimino)-C₁-C₈-alkyl; (C₃-C₇-cycloalkoxyimino)-C₁-C₈-alkyl; hydroxyimino-C₁-C₈-alkyl; (C₁-C₈-alkoxyimino)-C₃-C₇-cycloalkyl; hydroxyimino-C₃-C₇-cycloalkyl; (C₁-C₈-alkylimino)-oxy; (C₁-C₈-alkylimino)-oxy-C₁-C₈-alkyl; (C₃-C₇-cycloalkylimino)-oxy-C₁-C₈-alkyl; (C₁-C₆-alkylimino)-oxy-C₃-C₇-cycloalkyl; (C₁-C₈-alkenyloxyimino)-C₁-C₈-alkyl; (C₁-C₈-alkynyloxyimino)-C₁-C₈-alkyl; (benzyloxyimino)-C₁-C₈-alkyl; C₁-C₈-alkoxyalkyl; C₁-C₈-alkylthioalkyl; C₁-C₈-alkoxyalkoxyalkyl; C₁-C₈-halogenoalkoxyalkyl; benzyl; phenyl; 5-membered heteroalyl; 6-membered heteroaryl; benzyloxy; phenyloxy; benzylsulfanyl; benzylamino; phenylsulfanyl; or phenylamino;

$R^4$ represents hydrogen, fluorine, $C_1$-$C_8$-alkyl, $C_1$-$C_8$-haloalkyl or $C_1$-$C_8$-alkyloxy;

$R^5$ represents hydrogen, fluorine, $C_1$-$C_8$-alkyl, $C_1$-$C_8$-haloalkyl or $C_1$-$C_8$-alkyloxy;

$R^4$ and $R^5$ may form together with the carbon atom to which they are attached an optionally halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl ring;

Q represents a 6-membered aromatic cycle of formula (Q-I)

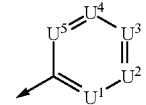

(Q-I)

wherein $U^1$ represents $CX^1$ or N;

wherein $X^1$ represents hydrogen, halogen, nitro, cyano, hydroxy, sulfanyl, carboxaldehyde, substituted or non-substituted carbaldehyde O—($C_1$-$C_8$-alkyl)oxime, pentafluoro-λ⁶-sulfenyl, substituted or non-substituted $C_1$-$C_8$-alkyl, substituted or non-substituted $C_3$-$C_8$-cycloalkyl, substituted or non-substituted $C_3$-$C_7$-halogencycloalkyl having 1 to 5 halogen atoms; substituted or non-substituted $C_3$-$C_7$-cycloalkenyl; substituted or non-substituted $C_1$-$C_8$-halogenoalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted $C_3$-$C_6$-cycloalkoxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, $C_1$-$C_8$-alkylaminocarbonyl; di-$C_1$-$C_8$-alkylaminocarbonyl, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted ($C_1$-$C_8$-alkoxyimino)-$C_1$-$C_8$-alkyl; substituted or non-substituted ($C_3$-$C_7$-cycloalkoxyimino)-$C_1$-$C_8$-alkyl; substituted or non-substituted hydroxyimino-$C_1$-$C_8$-alkyl, substituted or non-substituted phenyloxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

$U^2$ represents $CX^2$ or N;

wherein $X^2$ represents hydrogen, halogen, nitro, cyano, hydroxy, sulfanyl, carboxaldehyde, substituted or non-substituted carbaldehyde O—($C_1$-$C_8$-alkyl)oxime, pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_3$-$C_7$-halogencycloalkyl having 1 to 5 halogen atoms; substituted or non-substituted $C_3$-$C_7$-cycloalkenyl; substituted or non-substituted $C_1$-$C_8$-halogenoalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted $C_3$-$C_6$-cycloalkoxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, $C_1$-$C_8$-alkylaminocarbonyl; di-$C_1$-$C_8$-alkylaminocarbonyl, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted ($C_1$-$C_8$-alkoxyimino)-$C_1$-$C_8$-alkyl; substituted or non-substituted ($C_3$-$C_7$-cycloalkoxyimino)-$C_1$-$C_8$-alkyl; substituted or non-substituted hydroxyimino-$C_1$-$C_8$-alkyl, substituted or non-substituted phenyloxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

$U^3$ represents $CX^3$ or N;

wherein $X^3$ represents hydrogen, halogen, nitro, cyano, hydroxy, sulfanyl, carboxaldehyde, substituted or non-substituted carbaldehyde O—($C_1$-$C_8$-alkyl)oxime, pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_3$-$C_7$-halogencycloalkyl having 1 to 5 halogen atoms; substituted or non-substituted $C_3$-$C_7$-cycloalkenyl; substituted or non-substituted $C_1$-$C_8$-halogenoalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted $C_3$-$C_6$-cycloalkoxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, $C_1$-$C_8$-alkylaminocarbonyl; di-$C_1$-$C_8$-alkylaminocarbonyl, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted ($C_1$-$C_8$-alkoxyimino)-$C_1$-$C_8$-alkyl; substituted or non-substituted ($C_3$-$C_7$-cycloalkoxyimino)-$C_1$-$C_8$-alkyl; substituted or non-substituted hydroxyimino-$C_1$-$C_8$-alkyl, substituted or non-substituted phenyloxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

$U^4$ represents $CX^4$ or N;

wherein $X^4$ represents hydrogen, halogen, nitro, cyano, hydroxy, sulfanyl, carboxaldehyde, substituted or non-substituted carbaldehyde O—($C_1$-$C_8$-alkyl)oxime, pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_3$-$C_7$-halogencycloalkyl having 1 to 5 halogen atoms; substituted or non-substituted $C_3$-$C_7$-cycloalkenyl; substituted or non-substituted $C_1$-$C_8$-halogenoalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted $C_3$-$C_6$-cycloalkoxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, $C_1$-$C_8$-alkylaminocarbonyl; di-$C_1$-$C_8$-alkylaminocarbonyl, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted ($C_1$-$C_8$-alkoxyimino)-$C_1$-$C_8$-alkyl; substituted or non-substituted ($C_3$-$C_7$-cycloalkoxyimino)-$C_1$-$C_8$-alkyl; substituted or non-substituted hydroxyimino-$C_1$-$C_8$-alkyl, substituted or non-substituted phenyloxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

$U^5$ represents $CX^5$ or N;

wherein $X^5$ represents hydrogen, halogen, nitro, cyano, hydroxy, sulfanyl, carboxaldehyde, substituted or non-substituted carbaldehyde O—($C_1$-$C_8$-alkyl)oxime, pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_3$-$C_7$-halogencycloalkyl having 1 to 5 halogen atoms; substituted or non-substituted $C_3$-$C_7$-cycloalkenyl; substituted or non-substituted $C_1$-$C_8$-halogenoalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_6$-alkynyloxy, substituted or non-substituted $C_3$-$C_6$-cycloalkoxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, $C_1$-$C_8$-alkylaminocarbonyl; di-$C_1$-$C_8$-alkylaminocarbonyl, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted ($C_1$-$C_8$-alkoxyimino)-$C_1$-$C_8$-alkyl; substituted or non-substituted ($C_3$-$C_7$-cycloalkoxyimino)-$C_1$-$C_8$-alkyl; substituted or non-substituted hydroxyimino-$C_1$-$C_8$-alkyl, substituted or non-substituted phenyloxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

and wherein at most two of $U^1$, $U^2$, $U^3$, $U^4$ or $U^5$ can represent N;

or $U^1$ and $U^2$ or $U^2$ and $U^3$ or $U^3$ and $U^4$ may form together an additional saturated or unsaturated 4 to 6-membered halogen- or $C_1$-$C_8$-alkyl-substituted or non-substituted ring;

and its salts or N-oxides.

DETAILED DESCRIPTION OF A PREFERRED EMBODIMENT

The salts or N-oxides of the imidazole derivatives of formula (I) also have fungicidal properties.

The formula (I) provides a general definition of the imidazole derivatives according to the invention. Preferred radical definitions for the formulae shown above and below are given below. These definitions apply to the end products of the formulae (I), (I-1), (I-1-Q-I-1), (I-1-Q-I-2) and (I-1-Q-I-3) and likewise to all intermediates.

$R^1$ preferably represents in each case optionally branched $C_1$-$C_8$-alkyl, $C_1$-$C_8$-haloalkyl, $C_2$-$C_7$-alkenyl, $C_2$-$C_7$-haloalkenyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl.

$R^1$ more preferably represents in each case optionally branched $C_1$-$C_4$-alkyl, $C_1$-$C_4$-haloalkyl, $C_2$-$C_8$-alkenyl, $C_2$-$C_8$-haloalkenyl, optionally halogen-, cyano-, $C_1$-$C_4$-alkyl-, $C_1$-$C_4$-haloalkyl-, $C_1$-$C_4$-haloalkoxy-, $C_1$-$C_4$-alkoxy-, $C_1$-$C_4$-alkylthio- or $C_1$-$C_4$-haloalkylthio-substituted $C_3$-$C_6$-cycloalkyl.

$R^1$ more preferably represents tert-butyl, isopropyl, 1-halocyclopropyl, 1-($C_1$-$C_4$-alkyl)cyclopropyl, 1-($C_1$-$C_4$-alkoxy)cyclopropyl or 1-($C_1$-$C_4$-alkylthio)cyclopropyl.

$R^1$ most preferably represents tert-butyl, isopropyl, 1-chlorocyclopropyl, 1-fluorocyclopropyl or 1-methylcyclopropyl.

$R^2$ preferably represents H, $C_1$-$C_8$-alkyl, halogen- or $C_1$-$C_8$-alkoxy-substituted or non-substituted —C(O)—$C_1$-$C_8$-alkyl.

$R^2$ more preferably represents H, $C_1$-$C_4$-alkyl, non-substituted —C(O)—$C_1$-$C_4$-alkyl.

$R^2$ most preferably represents H.

$R^3$ preferably represents halogen; hydroxyl; cyano; isocyano; nitro; carboxaldehyde, hydroxycarbonyl, $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_1$-$C_8$-alkylsulfanyl; $C_1$-$C_8$-halogenoalkylsulfanyl; $C_1$-$C_8$-alkylcarbonyl; $C_1$-$C_8$-halogenoalkylcarbonyl; arylcarbonyl; aryl-$C_1$-$C_6$-alkylcarbonyl; $C_3$-$C_8$-cycloalkylcarbonyl; $C_3$-$C_8$-halogenocycloalkylcarbonyl; aminothiocarbonyl; $C_1$-$C_8$-alkoxycarbonyl; $C_1$-$C_8$-halogenoalkoxycarbonyl; $C_3$-$C_8$-cycloalkoxycarbonyl; $C_1$-$C_8$-alkylcarbonyloxy; $C_1$-$C_8$-halogenoalkylcarbonyloxy; $C_3$-$C_8$-cycloalkylcarbonyloxy; benzyl; phenyl; 5-membered heteroaryl; 6-membered heteroaryl; benzyloxy; or phenyloxy; wherein the benzyl, phenyl, 5-membered heteroalyl, 6-membered heteroaryl, benzyloxy or phenyloxy may be optionally substituted by one or more group(s) selected from halogen; hydroxyl; cyano; isocyano; amino; sulfanyl; pentafluoro-$\lambda^6$-sulfanyl; $C_1$-$C_8$-alkyl; $C_1$-$C_8$-haloalkyl; $C_1$-$C_8$-alkyloxy; $C_1$-$C_8$-halogenalkyloxy; tri($C_1$-$C_8$-alkyl)silyl; $C_3$-$C_7$-cycloalkyl; $C_2$-$C_8$-alkenyl; $C_2$-$C_8$-alkynyl.

$R^3$ more preferably represents halogen; cyano; carboxaldehyde, hydroxycarbonyl, $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_1$-$C_8$-alkylsulfanyl; $C_1$-$C_8$-halogenoalkylsulfanyl; $C_1$-$C_8$-alkylcarbonyl; $C_1$-$C_8$-halogenoalkylcarbonyl; $C_1$-$C_8$-alkoxycarbonyl; $C_1$-$C_8$-halogenoalkoxycarbonyl; benzyl; phenyl; 5-membered heteroaryl; 6-membered heteroaryl; benzyloxy; or phenyloxy; wherein the benzyl, phenyl, 5-membered heteroalyl, 6-membered heteroaryl, benzyloxy or phenyloxy may be optionally substituted by one or more group(s) selected from halogen; hydroxyl; cyano; amino; sulfanyl; pentafluoro-$\lambda^6$-sulfanyl; $C_1$-$C_8$-alkyl; $C_1$-$C_8$-haloalkyl; $C_1$-$C_8$-alkyloxy; $C_1$-$C_8$-halogenalkyloxy; tri($C_1$-$C_8$-alkyl)silyl; $C_3$-$C_7$-cycloalkyl; $C_2$-$C_8$-alkenyl; $C_2$-$C_8$-alkynyl.

$R^3$ most preferably represents halogen; cyano; carboxaldehyde, hydroxycarbonyl, $C_1$-$C_4$-alkyl; $C_1$-$C_4$-haloalkyl; $C_1$-$C_4$-cyanoalkyl; $C_1$-$C_4$-alkyloxy; $C_1$-$C_4$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_1$-$C_4$-alkylsulfanyl; $C_1$-$C_4$-halogenoalkylsulfanyl; $C_1$-$C_4$-alkylcarbonyl; $C_1$-$C_4$-halogenoalkylcarbonyl; $C_1$-$C_4$-alkoxycarbonyl; $C_1$-$C_4$-halogenoalkoxycarbonyl; benzyl; phenyl; furyl; pyrrolyl; thienyl; pyridyl; benzyloxy; or phenyloxy; wherein the benzyl, phenyl, 5-membered heteroalyl, 6-membered heteroaryl, benzyloxy or phenyloxy may be optionally substituted by one or more group(s) selected from halogen; $C_1$-$C_8$-alkyl; $C_1$-$C_8$-haloalkyl; $C_1$-$C_8$-alkyloxy; $C_1$-$C_8$-halogenalkyloxy.

In preferred embodiments of the present invention $R^3$ represents fluorine; chlorine; bromine; iodine; cyano; hydroxycarbonyl, carboxaldehyde, $C_1$-$C_4$-alkyl; $C_1$-$C_4$-haloalkyl; $C_1$-$C_4$-cyanoalkyl; $C_1$-$C_4$-alkyloxy; $C_3$-$C_7$-cycloalkyl; $C_2$-$C_8$-alkynyl; $C_1$-$C_4$-alkylsulfanyl; $C_1$-$C_4$-alkylcarbonyl; $C_1$-$C_4$-alkoxycarbonyl; phenyl; or thienyl; wherein the phenyl, or thienyl may be optionally substituted by one or more group(s) selected from halogen; $C_1$-$C_8$-alkyl; $C_1$-$C_8$-haloalkyl; $C_1$-$C_8$-alkyloxy; $C_1$-$C_8$-halogenalkyloxy.

In further preferred embodiments of the present invention $R^3$ represents fluorine; chlorine; bromine; iodine; cyano;

hydroxycarbonyl, carboxaldehyde, methyl; trifluoromethyl; cyanomethyl; methoxy; methylsulfanyl; cyclopropyl; ethinyl; methylcarbonyl (acetyl); carboxyl; methoxycarbonyl; ethoxycarbonyl; phenyl; or 2-thienyl.

In even further preferred embodiments of the present invention $R^3$ represents fluorine; chlorine; bromine; iodine; or cyano.

In further preferred embodiments of the present invention $R^3$ represents chlorine or cyano.

$R^4$ preferably represents hydrogen, fluorine, $C_1$-$C_4$-alkyl.

$R^4$ more preferably represents hydrogen, fluorine, $C_1$-$C_3$-alkyl.

$R^4$ even more preferably represents hydrogen, fluorine, methyl $R^5$ preferably represents hydrogen, fluorine, $C_1$-$C_4$-alkyl.

$R^5$ more preferably represents hydrogen, fluorine, $C_1$-$C_3$-alkyl.

$R^5$ even more preferably represents hydrogen, fluorine, methyl $R^4$ and $R^5$ may preferably form together with the carbon atom to which they are attached an optionally halogen-, $C_1$-$C_4$-alkyl-substituted $C_3$-$C_6$-cycloalkyl ring.

$R^4$ and $R^5$ may more preferably form together with the carbon atom to which they are attached a $C_3$-$C_6$-cycloalkyl ring.

$R^4$ and $R^5$ may even more preferably form together with the carbon atom to which they are attached a cyclopropyl ring.

In preferred embodiments $X^1$, $X^2$, $X^3$, $X^4$ or $X^5$ in the definitions for $U^1$, $U^2$, $U^3$, $U^4$ or $U^5$ represent hydrogen or halogen.

Q preferably represents a substituted 6-membered aromatic heterocycle containing one or two nitrogen atoms or a substituted 6-membered aromatic carbocycle. Substituted means that the cycle of the given formula comprises at least one of $X^1$, $X^2$, $X^3$, $X^4$ or $X^5$ not being hydrogen.

Q also preferably represents a, preferably substituted, 6-membered aromatic cycle of formula (Q-I-1) to (Q-I-10)

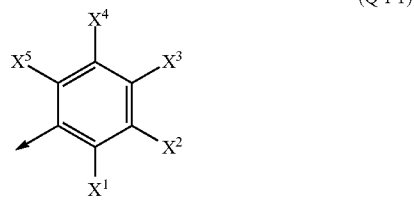
(Q-I-1)

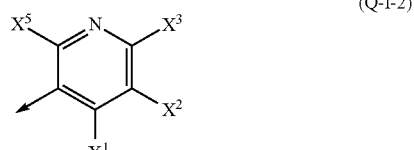
(Q-I-2)

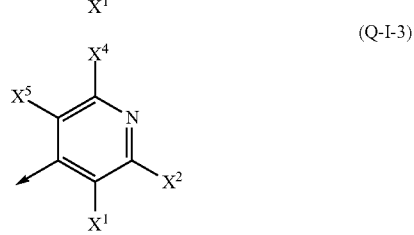
(Q-I-3)

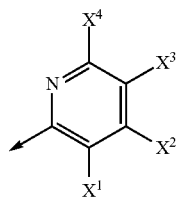
(Q-I-4)

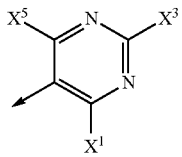
(Q-I-5)

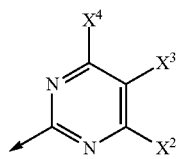
(Q-I-6)

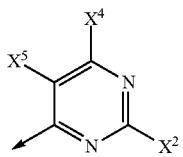
(Q-I-7)

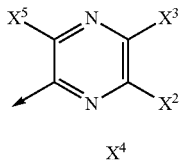
(Q-I-8)

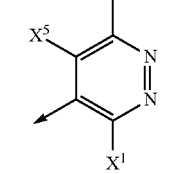
(Q-I-9)

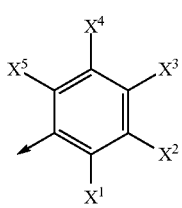
(Q-I-10)

wherein $X^1$, $X^2$, $X^3$, $X^4$ or $X^5$ have the same definition as given for formula (I) above. $X^1$, $X^2$, $X^3$, $X^4$ or $X^5$ preferably represent hydrogen or halogen.

Q more preferably represents a, preferably substituted, phenyl, 3-pyridyl or 4-pyridyl of formula (Q-I-1) to (Q-I-3)

(Q-I-1)

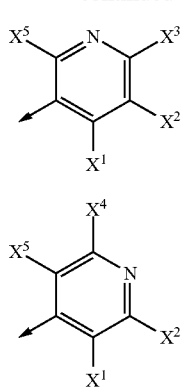

(Q-I-2)

(Q-I-3)

wherein $X^1$, $X^2$, $X^3$, $X^4$ or $X^5$ have the same definition as given for formula (I) above. $X^1$, $X^2$, $X^3$, $X^4$ or $X^5$ preferably represent hydrogen or halogen.

Q most preferably represents a, preferably substituted, phenyl or 3-pyridyl of formula (Q-I-1) or (Q-I-2)

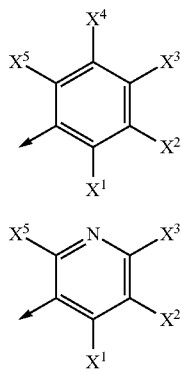

(Q-I-1)

(Q-I-2)

wherein $X^1$, $X^2$, $X^3$, $X^4$ or $X^5$ have the same definition as given for formula (I) above. $X^1$, $X^2$, $X^3$, $X^4$ or $X^5$ preferably represent hydrogen or halogen.

In preferred embodiments of the present invention Q represents a, preferably substituted, phenyl or 3-pyridyl of formula (Q-I-1a) or (Q-I-2a)

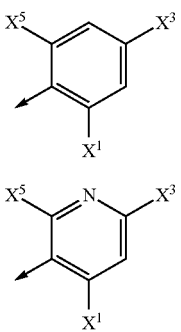

(Q-I-1a)

(Q-I-2a)

wherein $X^1$, $X^3$ or $X^5$ have the same definition as given for formula (I) above.

$X^1$, $X^2$, $X^3$, $X^4$ or $X^5$ preferably represent hydrogen or halogen.

More preferably $X^2$ and $X^4$ represent hydrogen and $X^1$, $X^3$ or $X^5$ represents hydrogen or halogen.

Most preferably $X^1$, $X^2$ and $X^4$ represent hydrogen and $X^3$ or $X^5$ represents hydrogen or halogen.

Preferred embodiments according to the present invention are compounds of formula (I), wherein $R^3$ represents halogen or cyano; and Q, $R^1$, $R^2$, $R^4$ and $R^5$ have the same definition as given for formula (I).

In such preferred embodiments according to the present invention $R^3$ preferably represents fluorine; chlorine; bromine; iodine or cyano and Q, $R^1$, $R^2$, $R^4$ and $R^5$ have the same definition as given for formula (I).

Other preferred embodiments according to the present invention are compounds of formula (I), wherein $R^3$ represents $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; $C_3$-$C_7$-cycloalkyl; $C_3$-$C_7$-halogencycloalkyl; $C_3$-$C_7$-cycloalkenyl; $C_3$-$C_7$-halogencycloalkenyl; $C_4$-$C_{10}$-cycloalkylalkyl; $C_4$-$C_{10}$-halocycloalkylalkyl; $C_6$-$C_{12}$-cycloalkylcycloalkyl; $C_1$-$C_8$-alkyl-$C_3$-$C_7$-cycloalkyl; $C_1$-$C_8$-alkoxy-$C_3$-$C_7$-cycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_4$-$C_8$-cycloalkylalkoxy; $C_3$-$C_6$-cycloalkoxy; benzyl; phenyl; 5-membered heteroaryl; 6-membered heteroaryl; benzyloxy or phenyloxy; wherein the benzyl, phenyl, 5-membered heteroaryl, 6-membered heteroaryl, benzyloxy or phenyloxy may be optionally substituted by one or more group(s) selected from halogen; hydroxyl; cyano; amino; sulfanyl; pentafluoro-$\lambda^6$-sulfanyl; $C_1$-$C_8$-alkyl; $C_1$-$C_8$-haloalkyl; $C_1$-$C_8$-alkyloxy; $C_1$-$C_8$-halogenalkyloxy; tri($C_1$-$C_8$-alkyl)silyl; $C_3$-$C_7$-cycloalkyl; $C_2$-$C_8$-alkenyl; $C_2$-$C_8$-alkynyl; and Q, $R^1$, $R^2$, $R^4$ and $R^5$ have the same definition as given for formula (I).

In such preferred embodiments according to the present invention $R^3$ preferably represents $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_1$-$C_8$-alkylsulfanyl; $C_1$-$C_8$-halogenoalkylsulfanyl; benzyl; phenyl; 5-membered heteroalyl; 6-membered heteroaryl; benzyloxy or phenyloxy wherein the benzyl, phenyl, 5-membered heteroaryl, 6-membered heteroaryl, benzyloxy or phenyloxy may be optionally substituted by one or more group(s) selected from halogen; hydroxyl; cyano; amino; sulfanyl; pentafluoro-$\lambda^6$-sulfanyl; $C_1$-$C_8$-alkyl; $C_1$-$C_8$-haloalkyl; $C_1$-$C_8$-alkyloxy; $C_1$-$C_8$-halogenalkyloxy; tri($C_1$-$C_8$-alkyl)silyl; $C_3$-$C_7$-cycloalkyl; $C_2$-$C_8$-alkenyl; $C_2$-$C_8$-alkynyl;

and Q, $R^1$, $R^2$, $R^4$ and $R^5$ have the same definition as given for formula (I).

In such preferred embodiments according to the present invention $R^3$ most preferably represents $C_1$-$C_4$-alkyl; $C_1$-$C_4$-haloalkyl; $C_1$-$C_4$-cyanoalkyl; $C_1$-$C_4$-alkyloxy; $C_1$-$C_4$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_1$-$C_4$-alkylsulfanyl; $C_1$-$C_4$-halogenoalkylsulfanyl; benzyl; phenyl; furyl; pyrrolyl; thienyl; pyridyl; benzyloxy or phenyloxy; wherein the benzyl, phenyl, 5-membered heteroalyl, 6-membered heteroaryl, benzyloxy or phenyloxy may be optionally substituted by one or more group(s) selected from halogen; $C_1$-$C_8$-alkyl; $C_1$-$C_8$-haloalkyl; $C_1$-$C_8$-alkyloxy; $C_1$-$C_8$-halogenalkyloxy;

and Q, $R^1$, $R^2$, $R^4$ and $R^5$ have the same definition as given for formula (I)

In such preferred embodiments according to the present invention $R^3$ even more preferably represents $C_1$-$C_4$-alkyl; $C_1$-$C_4$-haloalkyl; $C_1$-$C_4$-cyanoalkyl; $C_1$-$C_4$-alkyloxy; $C_3$-$C_7$-cycloalkyl; $C_2$-$C_8$-alkynyl; $C_1$-$C_4$-alkylsulfanyl; phenyl; or thienyl; wherein the phenyl, or thienyl may be optionally substituted by one or more group(s) selected from halogen; $C_1$-$C_8$-alkyl; $C_1$-$C_8$-haloalkyl; $C_1$-$C_8$-alkyloxy; $C_1$-$C_8$-halogenalkyloxy;

and Q, $R^1$, $R^2$, $R^4$ and $R^5$ have the same definition as given for formula (I)

In such preferred embodiments according to the present invention
$R^3$ even more preferably represents methyl; trifluoromethyl; cyanomethyl; methoxy; methylsulfanyl; cyclopropyl; ethinyl; phenyl; or 2-thienyl;
and Q, $R^1$, $R^2$, $R^4$ and $R^5$ have the same definition as given for formula (I).

Other preferred embodiments according to the present invention are compounds of formula (I), wherein
$R^3$ represents carboxaldehyde, hydroxycarbonyl, $C_1$-$C_8$-alkylcarbonyl; $C_1$-$C_8$-halogenoalkylcarbonyl; arylcarbonyl; $C_3$-$C_8$-cycloalkylcarbonyl; $C_3$-$C_8$-halogenocycloalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl; $C_3$-$C_8$-cycloalkoxycarbonyl; $C_2$-$C_8$-alkoxyalkylcarbonyl; $C_2$-$C_8$-halogenoalkoxyalkylcarbonyl; $C_3$-$C_{10}$-cycloalkoxyalkylcarbonyl; $C_1$-$C_8$-alkylaminocarbonyl; di-$C_1$-$C_8$-alkylaminocarbonyl; $C_3$-$C_8$-cycloalkylaminocarbonyl; $C_1$-$C_8$-alkylcarbonyloxy; $C_1$-$C_8$-halogenoalkylcarbonyloxy; $C_3$-$C_8$-cycloalkylcarbonyloxy; $C_1$-$C_8$-alkylcarbonylamino; $C_1$-$C_8$-halogenoalkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfinyl; $C_1$-$C_8$-halogenoalkylsulfinyl; $C_1$-$C_8$-alkylsulfonyl; $C_1$-$C_8$-halogenoalkylsulfonyl; $C_1$-$C_8$-alkylsulfonyloxy; $C_1$-$C_8$-halogenoalkylsulfonyloxy; $C_1$-$C_8$-alkylaminosulfamoyl or di-$C_1$-$C_8$-alkylaminosulfamoyl; and
Q, $R^1$, $R^2$, $R^4$ and $R^5$ have the same definition as given for formula (I).

In such preferred embodiments according to the present invention
$R^3$ preferably represents carboxaldehyde, hydroxycarbonyl, $C_1$-$C_8$-alkylcarbonyl; $C_1$-$C_8$-halogenoalkylcarbonyl; arylcarbonyl; $C_3$-$C_8$-cycloalkylcarbonyl; $C_3$-$C_8$-halogenocycloalkylcarbonyl; $C_1$-$C_8$-alkoxycarbonyl; $C_1$-$C_8$-halogenoalkoxycarbonyl; $C_3$-$C_8$-cycloalkoxycarbonyl; $C_1$-$C_8$-alkylcarbonyloxy; $C_1$-$C_8$-halogenoalkylcarbonyloxy; or $C_3$-$C_8$-cycloalkylcarbonyloxy; and
Q, $R^1$, $R^2$, $R^4$ and $R^5$ have the same definition as given for formula (I).

In such preferred embodiments according to the present invention
$R^3$ more preferably represents carboxaldehyde, hydroxycarbonyl, $C_1$-$C_8$-alkylcarbonyl; $C_1$-$C_8$-halogenoalkylcarbonyl; $C_1$-$C_8$-alkoxycarbonyl; or $C_1$-$C_8$-halogenoalkoxycarbonyl; and
Q, $R^1$, $R^2$, $R^4$ and $R^5$ have the same definition as given for formula (I).

In such preferred embodiments according to the present invention
$R^3$ most preferably represents carboxaldehyde, hydroxycarbonyl, $C_1$-$C_4$-alkylcarbonyl; $C_1$-$C_4$-halogenoalkylcarbonyl; $C_1$-$C_4$-alkoxycarbonyl; or $C_1$-$C_4$-halogenoalkoxycarbonyl; and
Q, $R^1$, $R^2$, $R^4$ and $R^5$ have the same definition as given for formula (I).

In such preferred embodiments according to the present invention
$R^3$ even more preferably represents carboxaldehyde, hydroxycarbonyl, $C_1$-$C_4$-alkylcarbonyl; or $C_1$-$C_4$-alkoxycarbonyl; and
Q, $R^1$, $R^2$, $R^4$ and $R^5$ have the same definition as given for formula (I).

In such preferred embodiments according to the present invention
$R^3$ even more preferably represents carboxaldehyde, hydroxycarbonyl, methylcarbonyl (acetyl); carboxyl; methoxycarbonyl; or ethoxycarbonyl; and
Q, $R^1$, $R^2$, $R^4$ and $R^5$ have the same definition as given for formula (I).

A preferred embodiment of the present invention relates to compounds of the formula (I-1)

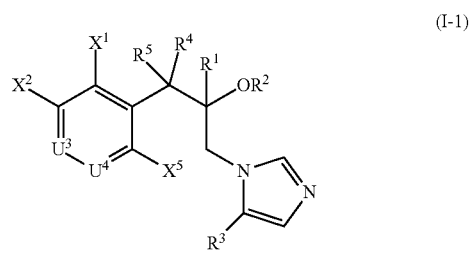

(I-1)

wherein $R^1$, $R^2$, $R^3$, $R^4$, $R^5$, $U^3$, $U^4$, $X^1$, $X^2$ and $X^5$ have the same definition as given for formula (I).

In a further preferred embodiment of the present invention relates to compounds of the formula (I-1-Q-I-1)

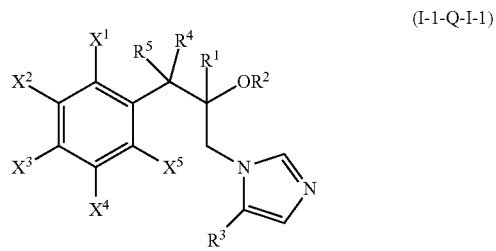

(I-1-Q-I-1)

wherein $R^1$, $R^2$, $R^3$, $R^4$, $R^5$, $X^1$, $X^2$, $X^3$, $X^4$ and $X^5$ have the same definition as given for formula (I).

In a further preferred embodiment of the present invention relates to compounds of the formula (I-1-Q-I-2)

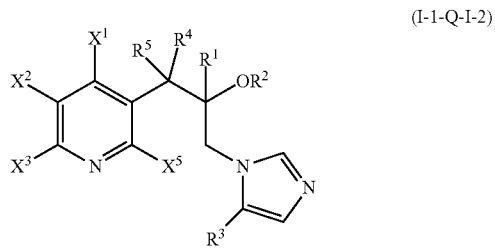

(I-1-Q-I-2)

wherein $R^1$, $R^2$, $R^3$, $R^4$, $R^5$, $X^1$, $X^2$, $X^3$ and $X^5$ have the same definition as given for formula (I).

In a further preferred embodiment of the present invention relates to compounds of the formula (I-1-Q-I-3)

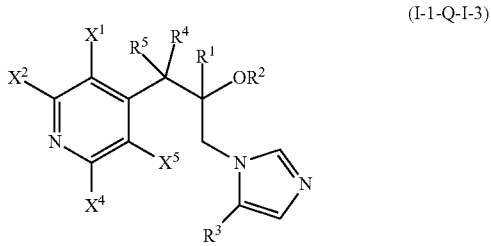

(I-1-Q-I-3)

wherein $R^1$, $R^2$, $R^3$, $R^4$, $R^5$, $X^1$, $X^2$, $X^4$ and $X^5$ have the same definition as given for formula (I).

The radical definitions and explanations given above in general terms or stated within preferred ranges can, however, also be combined with one another as desired, i.e. including between the particular ranges and preferred ranges. They apply both to the end products and correspondingly to precursors and intermediates. In addition, individual definitions may not apply.

Preference is given to those compounds of the formula (I) in which each of the radicals have the abovementioned preferred definitions.

Particular preference is given to those compounds of the formula (I) in which each of the radicals have the abovementioned more preferred definitions.

Very particular preference is given to those compounds of the formula (I) in which each of the radicals have the above mentioned most preferred definitions.

In the definitions of the symbols given in the above formulae, collective terms were used which are generally representative of the following substituents:

The definition $C_1$-$C_8$-alkyl comprises the largest range defined here for an alkyl radical. Specifically, this definition comprises the meanings methyl, ethyl, n-, isopropyl, n-, iso-, sec-, tert-butyl, and also in each case all isomeric pentyls, hexyls, heptyls and octyls, such as methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl and 2-propylpentyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl and 1-methyl-2-cyclopropylethyl. A preferred range is $C_1$-$C_4$-alkyl, such as methyl, ethyl, n-, isopropyl, n-, iso-, sec-, tert-butyl. The definition $C_1$-$C_3$-alkyl comprises methyl, ethyl, n-, isopropyl.

The definition halogen comprises fluorine, chlorine, bromine and iodine.

Halogen-substituted alkyl—referred to as $C_1$-$C_8$-haloalkyl—represents, for example, $C_1$-$C_8$-alkyl as defined above substituted by one or more halogen substituents which can be the same or different. Preferably $C_1$-$C_8$-haloalkyl represents chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1-fluoro-1-methylethyl, 2-fluoro-1,1-dimethylethyl, 2-fluoro-1-fluoromethyl-1-methylethyl, 2-fluoro-1,1-di(fluoromethyl)-ethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

Mono- or multiple fluorinated $C_1$-$C_4$-alkyl represents, for example, $C_1$-$C_4$-alkyl as defined above substituted by one or more fluorine substituent(s). Preferably mono- or multiple fluorinated $C_1$-$C_4$-alkyl represents fluoromethyl, difluoromethyl, trifluoromethyl, 1-fluoroethyl, 2-fluoroethyl, 2,2-difluoroethyl, 2,2,2-trifluoroethyl, pentafluoroethyl, 1-fluoro-1-methylethyl, 2-fluoro-1,1-dimethylethyl, 2-fluoro-1-fluoromethyl-1-methylethyl, 2-fluoro-1,1-di(fluoromethyl)-ethyl, 1-methyl-3-trifluoromethylbutyl, 3-methyl-1-trifluoromethylbutyl.

The definition $C_2$-$C_8$-alkenyl comprises the largest range defined here for an alkenyl radical. Specifically, this definition comprises the meanings ethenyl, n-, isopropenyl, n-, iso-, sec-, tert-butenyl, and also in each case all isomeric pentenyls, hexenyls, heptenyls, octenyls, 1-methyl-1-propenyl, 1-ethyl-1-butenyl, 2,4-dimethyl-1-pentenyl, 2,4-dimethyl-2-pentenyl. Halogen-substituted alkenyl—referred to as $C_2$-$C_8$-haloalkenyl—represents, for example, $C_2$-$C_8$-alkenyl as defined above substituted by one or more halogen substituents which can be the same or different. A preferred range is $C_2$-$C_4$-alkenyl, such as ethenyl, n-, isopropenyl, n-, iso-, sec- or tert-butenyl.

The definition $C_2$-$C_8$-alkynyl comprises the largest range defined here for an alkynyl radical. Specifically, this definition comprises the meanings ethynyl, n-, isopropynyl, n-, iso-, sec-, tert-butynyl, and also in each case all isomeric pentynyls, hexynyls, heptynyls, octynyls. Halogen-substituted alkynyl—referred to as $C_2$-$C_8$-haloalkynyl—represents, for example, $C_2$-$C_8$-alkynyl as defined above substituted by one or more halogen substituents which can be the same or different. A preferred range is $C_2$-$C_4$-alkynyl, such as ethynyl, n-, isopropynyl, n-, iso-, sec- or tert-butynyl.

The definition $C_3$-$C_7$-cycloalkyl comprises monocyclic saturated hydrocarbyl groups having 3 to 7 carbon ring members, such as cyclopropyl, cyclobutyl, cyclopentyl, cyclohexyl and cycloheptyl.

The definition halogen-substituted cycloalkyl and halocycloalkyl comprises monocyclic saturated hydrocarbyl groups having 3 to 7 carbon ring members, such as 1-fluorocyclopropyl and 1-chlorocyclopropyl.

The definition bicycloalkyl comprises spirocyclic alkyl wherein two substituents at the same carbon atom of a $C_3$-$C_7$-cycloalkyl can form together with the carbon atom to which they are attached a $C_3$-$C_7$-cycloalkyl, this definition comprises for example the meaning spiro[2.2]pentyl. The definition bicycloalkyl also comprises bicyclic alkyls wherein two substituents at different adjacent or non-adjacent carbon atoms of a $C_3$-$C_7$-cycloalkyl can form together with the carbon atoms to which they are attached a $C_3$-$C_7$-cycloalkyl, this definition comprises for example the meaning bicyclo[2.2.1]heptane-2-yl, bicyclo[2.2.1]heptane-7-yl, bicyclo[4.1.0]heptane-2-yl, bicyclo[4.1.0]heptane-3-yl, bicyclo[4.1.0]heptane-7-yl The definition bicycloalkyl also comprises bicyclic alkyls wherein two substituents at different adjacent or non-adjacent carbon atoms of a $C_3$-$C_7$-cycloalkyl can form an alkylene bridge between the carbon atoms to which they are attached, this definition comprises for example the meaning bicyclo[2.2.1]hept-2-ene-2-yl, bicyclo[2.2.1]hept-2-ene-5-yl, bicyclo[2.2.1]hept-2-ene-7-yl.

The definition aryl comprises aromatic, mono-, bi- or tricyclic ring, for example phenyl, naphthyl, anthracenyl (anthryl), phenanthracenyl (phenanthryl).

The definition hetaryl or heteroaryl comprises unsaturated, benzoannulated or not benzoannulated heterocyclic 5- to 10-membered ring containing up to 4 heteroatoms selected from N, O and S. Preferably The definition hetaryl or heteroaryl comprises unsubstituted or substituted, unsaturated heterocyclic 5- to 7-membered ring containing up to 4 heteroatoms selected from N, O and S: for example 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 1-pyrazolyl, 1H-imidazol-2-yl, 1H-imidazol-4-yl, 1H-imidazol-5-yl, 1H-imidazol-1-yl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-3-yl, 1H-1,2,4-triazol-5-yl, 1H-1,2,4-triazol-1-yl, 4H-1,2,4-triazol-3-yl, 4H-1,2,4-triazol-4-yl, 1H-tetrazol-1-yl, 1H-tetrazol-5-yl, 2H-tetrazol-2-yl, 2H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,3-oxadiazol-4-yl, 1,2,3-oxadiazol-5-yl, 1,2,3-thiadiazol-4-yl, 1,2,3-thiadiazol-5-yl, 1,2,5-oxadiazol-3-yl, 1,2,5-thiadiazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl.

The definition 5-membered heteroaryl comprises an unsaturated heterocyclic 5-membered ring containing up to 4 heteroatoms selected from N, O and S: for example 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 1-pyrazolyl, 1H-imidazol-2-yl, 1H-imidazol-4-yl, 1H-imidazol-5-yl, 1H-imidazol-1-yl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-3-yl, 1H-1,2,4-triazol-5-yl, 1H-1,2,4-triazol-1-yl, 4H-1,2,4-triazol-3-yl, 4H-1,2,4-triazol-4-yl, 1H-tetrazol-1-yl, 1H-tetrazol-5-yl, 2H-tetrazol-2-yl, 2H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,3-oxadiazol-4-yl, 1,2,3-oxadiazol-5-yl, 1,2,3-thiadiazol-4-yl, 1,2,3-thiadiazol-5-yl, 1,2,5-oxadiazol-3-yl, 1,2,5-thiadiazol-3-yl.

The definition 6-membered heteroaryl comprises an unsaturated heterocyclic 6-membered ring containing up to 4 heteroatoms selected from N, O and S: for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl.

The definition heterocycloalkyl comprises saturated or partially unsaturated mono-, bi- or tricyclic ring systems consisting of C-atoms and containing up to 4 heteroatoms selected from N, O and S: for example aziridinyl, pyrrolidinyl, dihydropyridyl, piperidinyl, piperazinyl, morpholinyl, thiomorpholinyl, tetrahydrofuranyl, tetrahydrothiofuranyl, tetrahydropyranyl, pyranyl, isoxazolidinyl, isoxazolinyl, pyrazolinyl, dihydropyrrolyl, tetrahydropyridinyl, dioxolanyl, dioxanyl, oxathiolanyl, oxathianyl, dithhiolanyl, dithianyl. The term partially unsaturated refers to ring systems that are neither saturated, i.e. comprising no double bound, nor fully unsaturated, i.e. comprising the maximum possible number of double bonds. In other words, partially unsaturated ring systems comprise at least one double bond, but not the maximum possible number of double bonds.

Optionally substituted radicals may be mono- or polysubstituted, where in the case of polysubstitution, the substituents may be identical or different.

Unless indicated otherwise, a group or a substituent which is substituted according to the invention preferably can be substituted by one or more group(s) selected from the list consisting of halogen; SH; nitro; hydroxyl; cyano; amino; sulfanyl; pentafluoro-$\lambda^6$-sulfanyl; formyl; formyloxy; formylamino; carbamoyl; N-hydroxycarbamoyl; carbamate; (hydroxyimino)-$C_1$-$C_6$-alkyl; $C_1$-$C_8$-alkyl; $C_1$-$C_8$-halogenalkyl; $C_1$-$C_8$-alkyloxy; $C_1$-$C_8$-halogenalkyloxy; $C_1$-$C_8$-alkylthio; $C_1$-$C_8$-halogenalkylthio; tri($C_1$-$C_8$-alkyl)silyl; tri($C_1$-$C_8$-alkyl)silyl-$C_1$-$C_8$-alkyl; $C_3$-$C_7$-cycloalkyl; $C_3$-$C_7$-halocycloalkyl; $C_3$-$C_7$-cycloalkenyl; $C_3$-$C_7$-halocycloalkenyl; $C_4$-$C_{10}$-cycloalkylalkyl; $C_4$-$C_{10}$-halocycloalkylalkyl; $C_6$-$C_{12}$-cycloalkylcycloalkyl; tri($C_1$-$C_8$-alkyl)silyl-$C_3$-$C_7$-cycloalkyl; $C_1$-$C_8$-halogenoalkyl; $C_3$-$C_7$-halogenocycloalkyl; $C_2$-$C_8$-alkenyl; $C_2$-$C_8$-alkynyl; $C_2$-$C_8$-alkenyloxy; $C_2$-$C_8$-halogenalkenyloxy; $C_2$-$C_8$-alkynyloxy; $C_1$-$C_8$-alkylamino; di-$C_1$-$C_8$-alkylamino; $C_1$-$C_8$-halogenalkylamino; di-$C_1$-$C_8$-halogenalkylamino; $C_1$-$C_8$-alkylaminoalkyl; di-$C_1$-$C_8$-alkylaminoalkyl; $C_1$-$C_8$-alkoxy; $C_1$-$C_8$-halogenoalkoxy; $C_1$-$C_8$-cyanoalkoxy; $C_4$-$C_5$-cycloalkylalkoxy; $C_3$-$C_6$-cycloalkoxy; $C_2$-$C_8$-alkoxyalkoxy; $C_1$-$C_8$-alkylcarbonylalkoxy; $C_1$-$C_8$-alkylsulfanyl; $C_1$-$C_8$-halogenoalkylsulfanyl; $C_2$-$C_8$-alkenyloxy; $C_2$-$C_8$-halogenoalkenyloxy; $C_3$-$C_8$-alkynyloxy; $C_3$-$C_8$-halogenoalkynyloxy; $C_1$-$C_8$-alkylcarbonyl; $C_1$-$C_8$-halogenoalkylcarbonyl; $C_3$-$C_8$-cycloalkylcarbonyl; $C_3$-$C_8$-halogenocycloalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl; $C_3$-$C_8$-cycloalkoxycarbonyl; $C_2$-$C_8$-alkoxyalkylcarbonyl; $C_2$-$C_8$-halogenoalkoxyalkylcarbonyl; $C_3$-$C_{10}$-cycloalkoxyalkylcarbonyl; $C_1$-$C_8$-alkylaminocarbonyl; di-$C_1$-$C_8$-alkylaminocarbonyl; $C_3$-$C_8$-cycloalkylaminocarbonyl; $C_1$-$C_8$-alkylcarbonyloxy; $C_1$-$C_8$-halogenoalkylcarbonyloxy; $C_3$-$C_8$-cycloalkylcarbonyloxy; $C_1$-$C_8$-alkylcarbonylamino; $C_1$-$C_8$-halogenoalkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfinyl; $C_1$-$C_8$-halogenoalkylsulfinyl; $C_1$-$C_8$-alkylsulfonyl; $C_1$-$C_8$-halogenoalkylsulfonyl; $C_1$-$C_8$-alkylsulfonyloxy; $C_1$-$C_8$-halogenoalkylsulfonyloxy; $C_1$-$C_8$-alkylaminosulfamoyl; di-$C_1$-$C_8$-alkylaminosulfamoyl; ($C_1$-$C_8$-alkoxyimino)-$C_1$-$C_8$-alkyl; ($C_3$-$C_7$-cycloalkoxyimino)-$C_1$-$C_8$-alkyl; hydroxyimino-$C_1$-$C_8$-alkyl; ($C_1$-$C_8$-alkoxyimino)-$C_3$-$C_7$-cycloalkyl; hydroxyimino-$C_3$-$C_7$-cycloalkyl; ($C_1$-$C_8$-alkylimino)-oxy; ($C_1$-$C_8$-alkylimino)-oxy-$C_1$-$C_8$-alkyl; ($C_3$-$C_7$-cycloalkylimino)-oxy-$C_1$-$C_8$-alkyl; ($C_1$-$C_6$-alkylimino)-oxy-$C_3$-$C_7$-cycloalkyl; ($C_1$-$C_8$-alkenyloxyimino)-$C_1$-$C_8$-alkyl; ($C_1$-$C_8$-alkynyloxyimino)-$C_1$-$C_8$-alkyl; 2-oxopyrrolidin-1-yl; (benzyloxyimino)-$C_1$-$C_8$-alkyl; $C_1$-$C_8$-alkoxyalkyl; $C_1$-$C_8$-alkylthioalkyl; $C_1$-$C_8$-alkoxyalkoxyalkyl; $C_1$-$C_8$-halogenoalkoxyalkyl; benzyl; phenyl; 5-membered heteroalyl; 6-membered heteroaryl; benzyloxy; phenyloxy; benzylsulfanyl; benzylamino; phenoxy; phenylsulfanyl; or phenylamino; wherein the benzyl, phenyl, 5-membered heteroalyl, 6-membered heteroaryl, benzyloxy or phenyloxy may be optionally substituted by one or more group(s) selected from the aforementioned list.

Depending on the nature of the substituents, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers, and also the threo and erythro, and the optical isomers, any mixtures of these isomers, and the possible tautomeric forms.

Depending on the nature of the substituents, the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

Depending on the nature of the substituents, the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Depending on the nature of the substituents, the compounds of the present invention can also exist in one or more geometric isomer forms depending on the relative position (syn/anti or cis/trans) of the substituents of ring B. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

The compounds of formula (I) wherein Q is substituted by a hydroxy, a sulfanyl or an amino substituent may be found in its tautomeric form resulting from the shift of the proton of said hydroxy, sulfanyl or amino group. All tautomeric forms of such compounds of the present invention) wherein Q is substituted by a hydroxy, a sulfanyl or an amino substituent are also part of the present invention.

Illustration of the Processes and Intermediates

The present invention furthermore related to processes for preparing compounds of formula (I). The present invention furthermore relates to intermediates such as compounds of formula (XVII) and the preparation thereof.

The compounds (I) can be obtained by various routes in analogy to prior art processes known (see e.g. EP-A 461 502, DE-A 40 27 608, DE-A 32 35 935 and references therein) and by synthesis routes shown schematically below and in the experimental part of this application. Unless indicated otherwise, the radicals Q, $R^1$, $R^2$, $R^3$, $R^4$ and $R^5$ have the meanings given above for the compounds of formula (I). These definitions apply not only to the end products of the formula (I) but likewise to all intermediates.

Process A (Scheme 1):
Scheme 1: Process A-Preparation of Ketones (V).

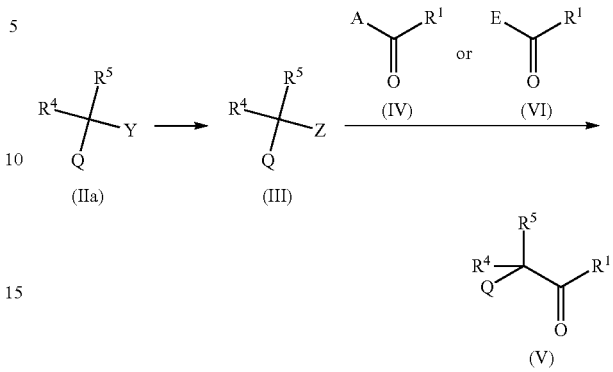

Y = ──H or ──OH
Z = halogen, ──$OSO_2$──$C_1$-$C_8$-alkyl, ──$OSO_2$-aryl,
── OP(O)(O──$C_1$-$C_8$-alkyl)$_2$ or ──OP(O)(O-aryl)$_2$,
preferably ── Cl or ── Br
A = halogen, preferably ── Cl
E = ──O──$C_1$-$C_8$-alkyl, preferably ──O-methyl, ──O-ethyl;
── O-aryl; ── S──$C_1$-$C_8$-alkyl, ── S-aryl; ── $NHR^a$; ── $NR^aR^b$;
$R^a$: is aryl, $C_1$-$C_8$-alkyl, or $C_3$-$C_7$-cycloalkyl, $R^b$: is $C_1$-$C_8$-alkyl or $C_1$-$C_8$-alkyloxy,
preferably ── $NMe_2$, ── NMeOMe;
or heterocyclic leaving groups, such as imidazole, triazole and hydroxybenzotriazole.

Compounds (IIa) and/or (III) are either commercially available or producible by processes described in the literature (see, for example, "Comprehensive Heterocyclic Chemistry III", Pergamon Press, 2008; vol. 7, pages 101-169; 217-308 & vol. 7, pages 1-331 and references cited therein; "Comprehensive Heterocyclic Chemistry II", Pergamon Press, 1996; vol. 5, pages 37-243 & vol. 6, pages 1-278 and references cited therein; "Comprehensive Heterocyclic Chemistry I", Pergamon Press, 1984; vol. 2, pages 395-510 & vol. 3, pages 1-197 and references cited therein; "Comprehensive Heterocyclic Chemistry III", Pergamon Press, 2008; vol. 3, pages 45-388 & vol. 4, pages 1-364 and references cited therein; "Comprehensive Heterocyclic Chemistry II", Pergamon Press, 1996; vol. 2, pages 39-257 & vol. 3, pages 1-220 and references cited therein; "Comprehensive Heterocyclic Chemistry I", Pergamon Press, 1984; vol. 4, pages 155-376 & vol. 5, pages 167-498 and references cited therein).

The compounds (IIa) (Scheme 1) can be converted by means of methods described in the literature to the corresponding compounds (Ill) and subsequently to compounds (V). In a first process, for example, compounds (IIa) are halogenated.

In case Y stands for hydrogen, the compounds (IIa) can be halogenated e.g. with Bromo- or Chlorosuccinimide (see e.g. WO-A 2011/012622, WO-A 2008/003622, WO-A 2005/111003; Synthesis, 18, 2008, 2996 and references cited therein), preferably in the presence of a radical initiator such as Azobisisobutyronitrile or dibenzoyl peroxide and in the presence of an organic solvent, e.g. a chlorinated organic solvent such as tetrachloromethane. Alternatively, compounds (IIa) undergo side-chain halogenation in the presence of bromine or chlorine (see e.g. EP 557967) to obtain compounds (III). Optionally, a radical initiator such as Azobisisobutyronitrile or dibenzoyl peroxide can be used. Alternatively, compounds (IIa) are reacted with a base, e.g. methyl lithium, and subsequently with a halogen source such as Magnesiumbromide to obtain compounds (II) (see e.g. WO-A 2012/087784)

Compounds (IIa) where Y stands for ──OH are reacted with halogenating agents, such as $PBr_3$, $PCl_3$ or thionyl chloride, to obtain compounds (III) (see e.g. WO-A 2009/

153554, Bioorganic & Medicinal Chemistry Letters, 22, 2012, 901-906, WO-A 2010/132999 and references cited therein). Alternatively, compounds (IIa) can be reacted with sulfonyl halides, such as e.g. Mesylchloride or Tosylchloride, or with phosphonic acid halides, such as e.g. diphenylphosphoryl chloride, to obtain the respective sulfonates and phosphates (see e.g. J. Org. Chem. 1992, 57, 5425-5431 and references cited therein)

The compounds (III) can subsequently be reacted with compounds (IV) or (VI) wherein A and E represent a replaceable group such as halide, —OR, NHR$^a$ or NR$^a$R$^b$, preferably chloro, —O-methyl, —O-ethyl, —NMe$_2$ or —NMeOMe. To obtain compounds (V), compounds (III) are reacted in a first step with e.g. Zink, Magnesium or isopropylmagnesium chloride, followed by a carbonyl compound (IV) or (VI) preferably under anhydrous conditions and optionally in the presence of a metal catalyst, such as palladium- or nickel-based catalysts. The metal catalyst can be used such as (Ph$_3$P)$_2$PdCl$_2$ (e.g. WO-A 2012/087784, EP-A 461 502), PEPPSI-IPr (Chem. Eur. J. 2006, 12, 4743-4748) or prepared in-situ by the mixing of a metals salt (e.g. Pd(OAc)$_2$) and a ligand (such as e.g. PPh$_3$, 2-dicyclohexylphosphino-2',6'-dimethoxybiphenyl (S-Phos)). The Insertion of the metal can be enhanced by the addition of ionic salts, such as LiBr, LiCl, LiI, CuI, Zn(OPiv)$_2$, MgCl$_2$, CuCN (see e.g. Dissertation Albrecht Metzer 2010 (University Munich); Angew. Chem. Int. Ed. 2011, 50, 9205-9209), or by activation of the metal using halogenated alkanes (1,2-dibromoethane) or halogenated alkylsilanes (TMSCl). Alternatively this sequence may be carried out in a one-pot fashion (see e.g. Beller et al., Chem. Asian J., 2011, 7(1) 40-44).

The reaction is preferably performed at temperatures between room temperature and refluxing temperature of the solvent.

As the solvent, all common solvents inert under the reaction conditions, such as for example ethers (such as e.g. tetrahydrofurane, diethyl ether) can be used and the reaction can be effected in mixtures of two or more of these solvents.

Process B (Scheme 2):
Scheme 2: Process B-Preparation of Ketones (V).

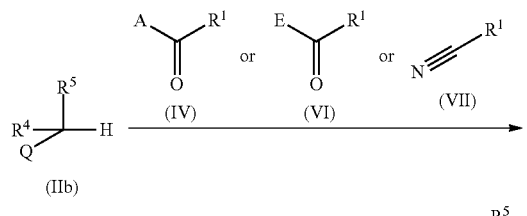

A = halogen, preferably Cl
E = —O—C$_1$-C$_8$-alkyl, preferably —O-methyl, —O-ethyl;
—O-aryl; —S—C$_1$-C$_8$-alkyl; —S-aryl; —NHR$^a$; —NR$^a$R$^b$;
R$^a$: is aryl, C$_1$-C$_8$-alkyl or C$_3$-C$_7$-cycloalkyl, R$^b$: is C$_1$-C$_8$-alkyl or C$_1$-C$_8$-alkyloxy, preferably —NMe$_2$, —NMeOMe;
or heterocyclic leaving groups, such as imidazole, triazole and hydroxybenzotriazole.

Compounds (IIb) are either commercially available or producible by processes described in the literature (see, for example, "Comprehensive Heterocyclic Chemistry III", Pergamon Press, 2008; vol. 7, pages 101-169; 217-308 & vol. 7, pages 1-331 and references cited therein; "Comprehensive Heterocyclic Chemistry II", Pergamon Press, 1996; vol. 5, pages 37-243 & vol. 6, pages 1-278 and references cited therein; "Comprehensive Heterocyclic Chemistry I", Perga-mon Press, 1984; vol. 2, pages 395-510 & vol. 3, pages 1-197 and references cited therein; "Comprehensive Heterocyclic Chemistry III", Pergamon Press, 2008; vol. 3, pages 45-388 & vol. 4, pages 1-364 and references cited therein; "Comprehensive Heterocyclic Chemistry II", Pergamon Press, 1996; vol. 2, pages 39-257 & vol. 3, pages 1-220 and references cited therein; "Comprehensive Heterocyclic Chemistry I", Pergamon Press, 1984; vol. 4, pages 155-376 & vol. 5, pages 167-498 and references cited therein).

There are numerous literature methods for the preparation of ketones (see e.g. WO-A 2012/055942, WO-A 2012/100342, WO-A 2012/087784, WO-A 2012/087833, US-A 2012/0010190, Dalton Transaction, 2011, 2366-2374, Journal of the American Chemical Society, 1955, 3858-3860, Journal of the American Chemical Society, 1937, 1494-1497, WO-A 2012/085815, WO-A 2011/042389, WO-A 2003/026663, Heterocycles, 1998, 2103-2109, Bioorganic & Medicinal Chemistry Letters, 2010, 2634-2640).

In general, it is possible to prepare compounds of the formula (V) from corresponding compounds (IIb) and (IV) and/or from corresponding compounds (IIb) and (VI) with suitable groups A and E (see Scheme 2, process B). Compounds (IIb) are optionally reacted sequentially with a base, e.g. n-butyllithium, lithium-diisopropylamide, lithium bis (trimethylsilyl)amide, sodium bis(trimethylsilyl)amide, potassium bis(trimethylsilyl)amide sodium amide, potassium amide, potassium tert-butoxide, methyl lithium, TMP$_2$Zn.2MgCl$_2$.2LiCl (see e.g. Dissertation Albrecht Metzer 2010, University Munich), followed by compounds (IV) or (VI), preferably under anhydrous conditions. Optionally, the reaction of compounds (IIb) and compounds (IV) or (VI) is carried out in the presence of a base in a one-pot fashion. The possible groups for A and E are, for example, halide, —OR, NHR$^a$ or NR$^a$R$^b$, preferably chloro, —O-methyl, —O-ethyl, —NMe$_2$ or —NMeOMe, etc., which can act as appropriate leaving groups to form the desired ketones (V) under suitable reaction conditions (Scheme 2).

In an alternative route compounds (IIb) are reacted with compounds (VII) in the presence of a base, e.g. phenyl lithium or methyl lithium, to obtain compounds (V) (see e.g. Journal of the American Chemical Society, 2011, 11194-11204; Journal of Medicinal Chemistry 1963, 205-207 and references cited therein).

Process C (Scheme 3):
Scheme 3: Process C-Preparation of Ketones (V).

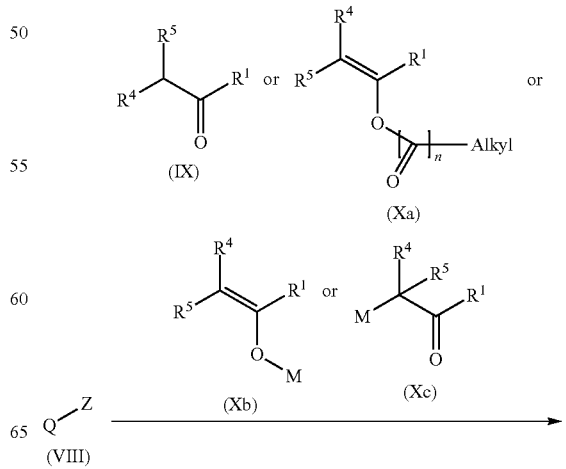

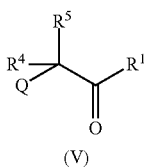

(V)

Z = halogen, preferably Cl or Br
n = 0 or 1
M = Li, MgZ$^M$, ZnZ$^M$, Si(C$_1$-C$_8$-alkyl)$_3$, Sn(C$_1$-C$_8$-alkyl)$_3$
Z$^M$ = halogen, hydroxyl preferably Cl or Br One means of preparin compounds of the formula (V) from corresponding compounds (VIII) with the compounds (IX) or (X) is shown in Scheme 3 (Process C). Compounds (X) include compounds (Xa), (Xb) and (Xc)

Compounds (VIII) are either commercially available or producible by processes described in the literature (see, for example, "Comprehensive Heterocyclic Chemistry III", Pergamon Press, 2008; vol. 7, pages 101-169; 217-308 & vol. 7, pages 1-331 and references cited therein; "Comprehensive Heterocyclic Chemistry II", Pergamon Press, 1996; vol. 5, pages 37-243 & vol. 6, pages 1-278 and references cited therein; "Comprehensive Heterocyclic Chemistry I", Pergamon Press, 1984; vol. 2, pages 395-510 & vol. 3, pages 1-197 and references cited therein; "Comprehensive Heterocyclic Chemistry III", Pergamon Press, 2008; vol. 3, pages 45-388 & vol. 4, pages 1-364 and references cited therein; "Comprehensive Heterocyclic Chemistry II", Pergamon Press, 1996; vol. 2, pages 39-257 & vol. 3, pages 1-220 and references cited therein; "Comprehensive Heterocyclic Chemistry I", Pergamon Press, 1984; vol. 4, pages 155-376 & vol. 5, pages 167-498 and references cited therein).

Compounds (IX) and (X) are either commercially available or producible by processes described in the literature (see, for example, WO-A 2010/029066; Chemische Berichte, 1986, 2995-3026 and references cited therein).

A compound having the general formula (V) can be synthesized analogously to methods described in the literature (see, for example Organic letters, 2009, 1773-1775; European Journal of Organic Chemistry, 2011, 1570-1574), by a coupling reaction of a compound with the corresponding general formula (VIII) with a substrate of the general formula (IX) or (X) where Z is halogen, preferably chlorine or bromine.

Compounds (VIII) are reacted with compounds of the general structure (IX) or (X) to obtain compounds (V) analogously to methods described in the literature (e.g. Organic letters, 2009, 1773-1775, European Journal of Organic Chemistry, 2011, 1570-1574, Chemical & Pharmaceutical Bulletin, 1970, 1457-1464, Chemical & Pharmaceutical Bulletin, 1980, 337-342, WO-A 2005/044785). Those reactions can be optionally carried out in the presence of a catalyst and a base.

As catalysts for the reaction various metal based catalysts can be used which are either used directly or being in situ prepared from a metal precursor (e.g. Pd$_2$dba$_3$, Pd(OAc)$_2$) and a ligand (e.g. phosphine based ligands like Xanthphos, 2-(dicyclohexylphosphino)-2'-methylbiphenyl, 2-Diphenylphosphino-2'-(N,N-dimethylamino)biphenyl, tri-t-butylphosphine, Tri-o-tolylphosphine) (see e.g. WO-A 2008/147544, WO-A 2005/027837).

As bases various organic and inorganic bases can be used such as potassium phosphate, base, e.g. sodium amide, sodium hydride or sodium tert-butoxide. Alternatively, silicon containing bases can be used (e.g. NaHMDS, KHMDS, LiHMDS).

Process D (Scheme 4):
Scheme 4: Process D-Preparation of Epoxides (XII).

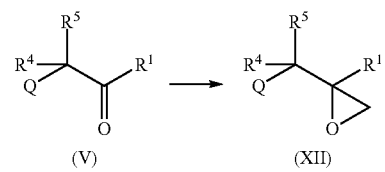

The compounds (V) (Scheme 4) can be converted by means of methods described in the literature to the corresponding compounds (XII) (see e.g. EP-A 461 502, DE-A 33 15 681, EP-A 291 797, Bioorganic & Medicinal Chemistry Letters (1996), 6(16), 2031-2036). Intermediates (V) are preferably reacted with trimethylsulfoxonium- or trimethylsulfonium-salts, preferably trimethylsulfoxonium halides, trimethylsulfonium halides, trimethylsulfoxonium methylsulfates or trimethylsulfonium methylsulfates, preferably in the presence of a base such as sodium hydride.

Process E (Scheme 5):
Scheme 5: Process E - Preparation of Epoxides (XII).

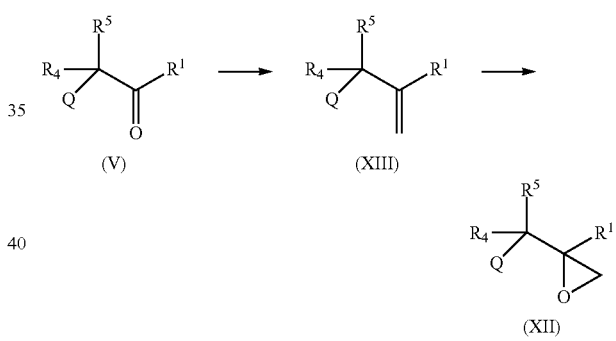

Alternatively, compounds (V) can be first converted to the corresponding olefins (XII), followed by an epoxidation to obtain epoxides (XII) (see e.g. EP-A 291 797).

Process F (Scheme 6):
Scheme 6: Process F-Preparation of Epoxides (XII).

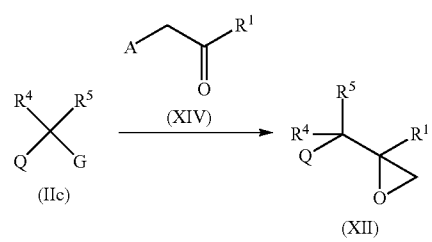

G = halogen or hydrogen
A = halogen, O—SO$_2$—C$_1$-C$_8$-alkyl or O—SO$_2$-aryl, preferably Cl or Br Alternatively, a compound having the general formula (XII) can be synthesized analogously to methods described in the literature by a coupling reaction of a compound having the corresponding general formula (IIc) with a substrate of the general formula (XIV) (see e.g. DE-A 40 27 608, WO-A 93/02086, WO-A 93/12121, Journal of Organic Chemistry, 2001, 2149-2153 and references cited therein).

Compounds (IIc) are either commercially available or producible by processes described in the literature (see, for example, "Comprehensive Heterocyclic Chemistry III", Pergamon Press, 2008; vol. 7, pages 101-169; 217-308 & vol. 7, pages 1-331 and references cited therein; "Comprehensive Heterocyclic Chemistry II", Pergamon Press, 1996; vol. 5, pages 37-243 & vol. 6, pages 1-278 and references cited therein; "Comprehensive Heterocyclic Chemistry I", Pergamon Press, 1984; vol. 2, pages 395-510 & vol. 3, pages 1-197 and references cited therein; "Comprehensive Heterocyclic Chemistry III", Pergamon Press, 2008; vol. 3, pages 45-388 & vol. 4, pages 1-364 and references cited therein; "Comprehensive Heterocyclic Chemistry II", Pergamon Press, 1996; vol. 2, pages 39-257 & vol. 3, pages 1-220 and references cited therein; "Comprehensive Heterocyclic Chemistry I", Pergamon Press, 1984; vol. 4, pages 155-376 & vol. 5, pages 167-498 and references cited therein).

If G stands for halogen, preferably chloride or bromide, compounds (IIc) are first transformed into Grignard reagents by the reaction with magnesium or with halogen/metal exchange reagents such as isopropylmagnesium halides and subsequently reacted with ketones (XIV) preferably under anhydrous conditions to obtain compounds of the general formula (XII) (see e.g. DE4027608). Alternatively, if G stands for halogen, the halides (IIc) can be converted to the corresponding zinc reagents and subsequently reacted with ketones (XIV) (e.g. ChemComm, 2008, 5824-5826; Journal of Organic Chemistry, 2004, 908-914 and references cited therein).

In an alternative route compounds (IIc) (G=hydrogen) are reacted with compounds (XIV) preferably in the presence of a base. Compounds (IIc) (G=hydrogen) are optionally reacted with a base upfront, e.g. n-butyllithium, lithium-diisopropylamide, lithium bis(trimethylsilyl)amide, sodium bis(trimethylsilyl)amide, potassium bis(trimethylsilyl) amide sodium amide, potassium amide, potassium tert-butoxide, methyl lithium, $TMP_2Zn-2MgCl_2\cdot2LiCl$ (see e.g. Dissertation Albrecht Metzer 2010, University Munich), followed by compounds of the general structure (XIV) preferably under anhydrous conditions. The possible groups for A are, for example, halides which can act as appropriate leaving groups to form the desired compounds (XII) under suitable reaction conditions.

Process G (Scheme 7):
Scheme 7: Process G-Preparation of Alcohol (XV).

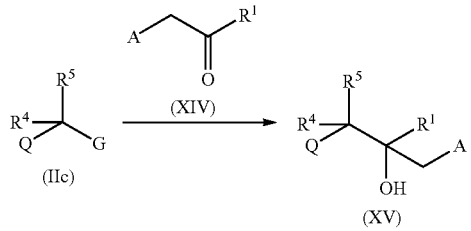

A = halogen, O—$SO_2$—$C_1$-$C_8$-alkyl or O—$SO_2$-aryl, preferably Cl or Br

A compound having the general formula (XV) can be synthesized analogously to methods described in the literature by a coupling reaction of a compound having the corresponding general formula (IIc) with a substrate of the general formula (XIV) (see e.g. DE-A 40 27 608, WO-A 93/02086, WO-A 93/12121, Journal of Organic Chemistry, 2001, 2149-2153).

If G stands for halogen, preferably chloride or bromide, compounds (IIc) are first transformed into Grignard reagents by the reaction with magnesium or with halogen/metal exchange reagents, such as isopropylmagnesium halides, and subsequently reacted with ketones (XIV) preferably under anhydrous conditions to obtain compounds of the general formula (XV) (see e.g. DE-A 4027608). Alternatively, if G stands for halogen, the halides (IIc) can be converted to the corresponding zinc reagents and subsequently reacted with ketones (XIV) (e.g. ChemComm, 2008, 5824-5826; Journal of Organic Chemistry, 2004, 908-914 and references cited therein).

In an alternative route compounds (IIc) (G=hydrogen) are reacted with compounds (XIV) preferably in the presence of a base. Compounds (IIc) (G=hydrogen) are optionally reacted with a base upfront, e.g. n-butyllithium, lithium-diisopropylamide, lithium bis(trimethylsilyl)amide, methyl lithium, followed by compounds of the general structure (XIV) preferably under anhydrous conditions. The possible groups for A are, for example, halides which can act as appropriate leaving groups to form the desired compounds (XV) under suitable reaction conditions.

Process H (Scheme 8):
Scheme 8: Process H-Preparation of compounds (Ia).

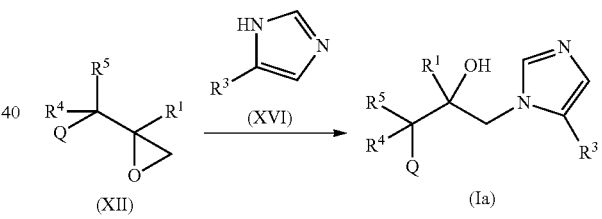

The compounds (XII) obtained according to Process D, E or F can be converted by means of methods described in the literature to the corresponding compounds (Ia) (see e.g. DE-A 40 27 608, EP-A 461 502, DE-A 33 15 681, EP-A 291 797, WO9529901, EP0291797,). The starting materials (XII) can be reacted with an imidazole of formula (XVI) which are commercially available or can be obtained by means of methods described in the literature, optionally in the presence of a base, such as potassium carbonate and/or potassium tert-butoxide, optionally in the presence of a Lewis acid, such as magnesium dichloride or $BF_3/Et_2O$. Alternatively, organomagnesium bases such as MeMgCl, TMPMgCl or analogues may also be employed (see Org. Lett., 2016, 18 (1), pp 16-19 DOI: 10.1021/acs.orglett.5b02994).

As the solvent, all common solvents inert under the reaction conditions, such as for example nitriles (such as e.g. acetonitrile, propionitrile) can be used and the reaction can be effected in mixtures of two or more of these solvents.

Process I (Scheme 9):
Scheme 9: Process I-Preparation of compounds (Ia).

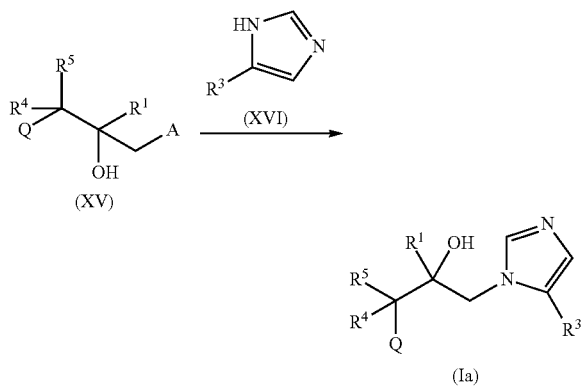

A = halogen, O—SO$_2$—C$_1$-C$_8$-alkyl or O—SO$_2$-aryl, preferably Cl or Br

The compounds (XV) obtained according to Process G can be converted by means of methods described in the literature to the corresponding compounds (Ia) (see e.g. DE-A 40 27 608). The starting materials (XV) can be reacted with an imidazole of formula (XVI) which are commercially available or can be obtained by means of methods described in the literature, optionally in the presence of a base, such as potassium carbonate and/or potassium tert-butoxide, optionally in the presence of a Lewis acid, such as magnesium dichloride or BF$_3$/Et$_2$O. Alternatively, organomagnesium bases such as MeMgCl, TMPMgCl or analogues may also be employed (see Org. Lett., 2016, 18 (1), pp 16-19 DOI: 10.1021/acs.orglett.5b02994).

As the solvent, all common solvents inert under the reaction conditions, such as for example nitriles (such as e.g. acetonitrile, propionitrile) can be used and the reaction can be effected in mixtures of two or more of these solvents.

Process J (Scheme 10):
Scheme 10: Process J-Preparation of ketones (XVII).

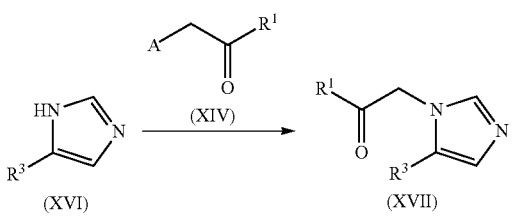

A = halogen, O—SO$_2$—C$_1$-C$_8$-alkyl or O—SO$_2$-aryl, preferably Cl or Br

The imidazoles of formula (XVI) which are commercially available or can be obtained by means of methods described in the literature can be alkylated by compounds of formula (XIV) by means of methods described in the literature to the corresponding ketones (XVII) (see e.g Chemical Biology & Drug Design (2010), 75(1), 68-90, Acta Chemica Scandinavica (1990), 44(1), 1050-1057). The reaction is optionally in the presence of a base, such as potassium carbonate, triethylamine, and/or potassium tert-butoxide, optionally in the presence of a Lewis acid, such as magnesium dichloride or BF$_3$/Et$_2$O, optionally in the presence of a metal oxide, such as zinc oxide or barium oxide. Alternatively, organo-magnesium bases such as MeMgCl, TMPMgCl or analogues may also be employed (see Org. Lett., 2016, 18 (1), pp 16-19 DOI: 10.1021/acs.orglett.5b02994).

As the solvent, all common solvents inert under the reaction conditions, such as for example nitriles (such as e.g. acetonitrile, propionitrile) can be used and the reaction can be effected in mixtures of two or more of these solvents.

Process K (Scheme 11):
Scheme 11: Process K - Preparation of ketones (XVII).

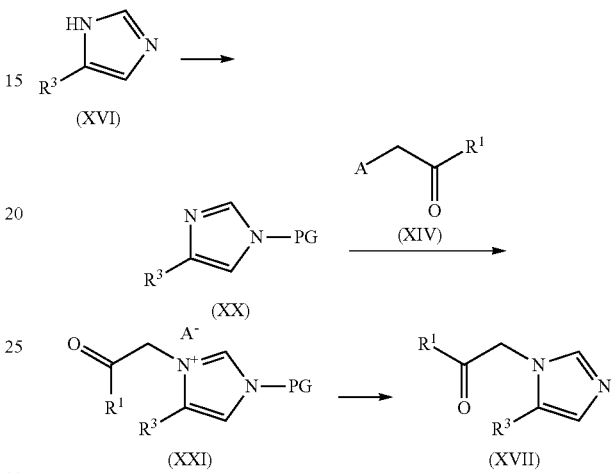

A = halogen, O-SO$_2$-C$_1$-C$_8$-alkyl or O-SO$_2$-aryl, preferable Cl or Br
PG = formyl; C$_1$-C$_8$-alkyl; C$_1$-C$_8$-halogenalkyl; tri(C$_1$-C$_8$-alkyl)silyl; tri(C$_1$-C$_8$-alkyl)silyl-C$_1$-C$_8$-alkyl; C$_2$-C$_8$-alkenyl; C$_2$-C$_8$-alkynyl, C$_1$-C$_8$-alkylsulfonyl; C$_1$-C$_8$-alkylcarbonyl; C$_1$-C$_8$-halogenoalkylcarbonyl; C$_3$-C$_8$-cycloalkylcarbonyl; C$_1$-C$_8$-alkylcarbamoyl; di-C$_1$-C$_8$-alkylcarbamoyl; N-C$_1$-C$_8$-alkyloxycarbamoyl; C$_1$-C$_8$-alkoxycarbamoyl; N-C$_1$-C$_8$-alkyl-C$_1$-C$_8$-alkoxycarbamoyl; C$_1$-C$_8$-alkoxycarbonyl; C$_1$-C$_8$-halogenoalkoxycarbonyl; C$_3$-C$_8$-cycloalkoxycarbonyl; C$_2$-C$_8$-alkoxyalkylcarbonyl; C$_2$-C$_8$-halogenoalkoxyalkylcarbonyl; C$_3$-C$_{10}$-cycloalkoxycarbonyl; C$_1$-C$_8$-alkylaminocarbonyl; di-C$_1$-C$_8$-alkylaminocarbonyl; C$_3$-C$_8$-cycloalkylaminocarbonyl; C$_1$-C$_8$-alkoxyalkyl; C$_1$-C$_8$-alkylthioalkyl; C$_1$-C$_8$-alkoxyalkoxyalkyl; C$_1$-C$_8$-halogenoalkoxyalkyl; aryl; arylalkyl; arylalkenyl; arylalkynyl; arylsulfonyl; phenoxyalkyl; heterocycloalkyl; heterocycloalkyl-C$_1$-C$_8$-alkyl,; 5-membered heteroaryl; 6-membered heteroaryl; wherein aryl; arylalkyl; arylalkenyl; arylalkynyl; arylsulfonyl; phenoxyalkyl; heterocycloalkyl; heterocycloalkyl-C$_1$-C$_8$-alkyl,; 5-membered heteroaryl; 6-membered heteroaryl may be optionally substituted by halogen, C$_1$-C$_8$-alkyl, C$_1$-C$_8$-alkoxy, nitro.

The imidazoles of formula (XVI) which are commercially available or can be obtained by means of methods described in the literature can be converted into imidazoles of formula (XX) by means of methods described in the literature (see e.g "Protective groups in organic synthesis", Wiley Interscience, 1999; 3$^{rd}$ edition, T. Greene & P. Wuts, p. 615-632 and references cited therein, Journal of organic chemistry (2013), 78, 12220-12223). The reaction is optionally in the presence of a base, such as potassium carbonate, triethylamine, and/or potassium tert-butoxide, optionally in the presence of a Lewis acid, such as magnesium dichloride or BF$_3$/Et$_2$O, optionally in the presence of a metal oxide, such as zinc oxide or barium oxide.

The imidazoles of formula (XX) can consequently be converted into imidazolium salts of formula (XXI) by means of methods described in the literature (see e.g "Protective groups in organic synthesis", Wiley Interscience, 1999; 3$^{rd}$ edition, T. Greene & P. Wuts, p. 615-632 and references cited therein, Journal of organic chemistry (2013), 78, 12220-12223). The reaction is optionally in the presence of a base, such as potassium carbonate, triethylamine, and/or potassium tert-butoxide, optionally in the presence of a Lewis acid, such as magnesium dichloride or BF$_3$/Et$_2$O, optionally in the presence of a metal oxide, such as zinc oxide or barium oxide.

Finally, imidazolium salts of formula (XXI) can be converted into ketones of formula (XVII) by means of methods described in the literature (see e.g "Protective groups in organic synthesis", Wiley Interscience, 1999; 3$^{rd}$ edition, T. Greene & P. Wuts, p. 615-632 and references cited therein, Journal of organic chemistry (2013), 78, 12220-12223).

As the solvent, all common solvents inert under the reaction conditions, such as for example nitriles (such as e.g. acetonitrile, propionitrile) or alcohols (such as e.g. methanol, ethanol), can be used and the reaction can be effected in mixtures of two or more of these solvents.

Process L (Scheme 12):

Scheme 12: Process L - Preparation of ketones (XVIIb).

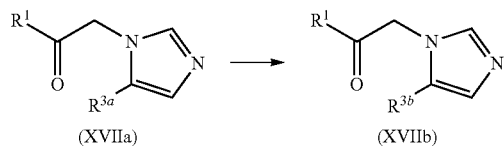

(XVIIa)    (XVIIb)

$R^{3a}$ = halogen, O-SO$_2$-C$_1$-C$_8$-alkyl or O-SO$_2$-aryl, preferably Br or I
$R^{3b}$ = cyano; amino; hydroxycarbonyl, C$_1$-C$_8$-alkyl; C$_1$-C$_8$-haloalkyl; C$_1$-C$_8$-cyanoalkyl; C$_1$-C$_8$-alkyloxy; C$_1$-C$_8$-halogenalkyloxy; tri(C$_1$-C$_8$-alkyl)silyl-C$_1$-C$_8$-alkyl; C$_3$-C$_7$-cycloalkyl; C$_3$-C$_7$-halogenocycloalkyl; C$_3$-C$_7$-cycloalkenyl; C$_3$-C$_7$-halogencycloalkenyl; C$_4$-C$_{10}$-cycloalkylalkyl; C$_4$-C$_{10}$-halocycloalkylalkyl; C$_6$-C$_{12}$-cycloalkylcycloalkyl; C$_1$-C$_8$-alkyl-C$_3$-C$_7$-cycloalkyl; C$_1$-C$_8$-alkoxy-C$_3$-C$_7$-cycloalkyl; tri(C$_1$-C$_8$-alkyl)silyl-C$_3$-C$_7$-cycloalkyl; C$_2$-C$_8$-alkenyl; C$_2$-C$_8$-alkynyl; C$_2$-C$_8$-alkenyloxy; C$_2$-C$_8$-halogenalkenyloxy; C$_3$-C$_8$-alkynyloxy; C$_3$-C$_8$-halogenoalkynyloxy; C$_1$-C$_8$-alkylamino; C$_1$-C$_8$-halogenalkylamino; C$_1$-C$_8$-cyanoalkoxy; C$_4$-C$_8$-cycloalkylalkoxy; C$_3$-C$_6$-cycloalkoxy; C$_1$-C$_8$-alkylcarbonyl; C$_1$-C$_8$-halogenoalkylcarbonyl; arylcarbonyl; C$_3$-C$_8$-cycloalkylcarbonyl; C$_3$-C$_8$-halogenocycloalkylcarbonyl; C$_1$-C$_8$-alkylcarbamoyl; di-C$_1$-C$_8$-alkylcarbamoyl; N-C$_1$-C$_8$-alkyloxycarbamoyl; C$_1$-C$_8$-alkoxycarbamoyl; N-C$_1$-C$_8$-alkyl-C$_1$-C$_8$-alkoxycarbamoyl; C$_1$-C$_8$-alkoxycarbonyl; C$_1$-C$_8$-halogenoalkoxycarbonyl; C$_3$-C$_8$-cycloalkoxycarbonyl; C$_2$-C$_8$-alkoxyalkylcarbonyl; C$_2$-C$_8$-halogenoalkoxyalkylcarbonyl; C$_3$-C$_{10}$-cycloalkoxyalkylcarbonyl; C$_1$-C$_8$-alkylaminocarbonyl; di-C$_1$-C$_8$-alkylaminocarbonyl; C$_3$-C$_8$-cycloalkylaminocarbonyl; (C$_1$-C$_8$-alkoxyimino)-C$_1$-C$_8$-alkyl; (C$_3$-C$_7$-cycloalkoxyimino)-C$_1$-C$_8$-alkyl; benzyl; phenyl; 5-membered heteroaryl; 6-membered heteroaryl; benzyloxy; phenyloxy; benzylsulfanyl; benzylamino; phenylsulfanyl; or phenylamino; wherein the benzyl, phenyl, 5-membered heteroaryl, 6-membered heteroaryl, benzyloxy or phenyloxy may be optionally substituted by one or more group(s) selected from halogen; hydroxyl; cyano; amino; sulfanyl; pentafluoro-$\lambda^6$-sulfanyl; carboxaldehyde, hydroxycarbonyl, C$_1$-C$_8$-alkyl; C$_1$-C$_8$-haloalkyl; C$_1$-C$_8$-cyanoalkyl; C$_1$-C$_8$-alkyloxy; C$_1$-C$_8$-halogenalkyloxy;

tri(C$_1$-C$_8$-alkyl)silyl; tri(C$_1$-C$_8$-alkyl)silyl-C$_1$-C$_8$-alkyl; C$_3$-C$_7$-cycloalkyl; C$_3$-C$_7$-halogenocycloalkyl; C$_3$-C$_7$-cycloalkenyl; C$_3$-C$_7$-halogencycloalkenyl; C$_4$-C$_{10}$-cycloalkylalkyl; C$_4$-C$_{10}$-halocycloalkylalkyl; C$_6$-C$_{12}$-cycloalkylcycloalkyl; C$_1$-C$_8$-alkyl-C$_3$-C$_7$-cycloalkyl; C$_1$-C$_8$-alkoxy-C$_3$-C$_7$-cycloalkyl; tri(C$_1$-C$_8$-alkyl)silyl-C$_3$-C$_7$-cycloalkyl; C$_2$-C$_8$-alkenyl; C$_2$-C$_8$-alkynyl; C$_2$-C$_8$-alkenyloxy; C$_2$-C$_8$-halogenalkenyloxy; C$_3$-C$_8$-alkynyloxy; C$_3$-C$_8$-halogenoalkynyloxy; C$_1$-C$_8$-alkylamino; C$_1$-C$_8$-halogenalkylamino; C$_1$-C$_8$-cyanoalkoxy; C$_4$-C$_8$-cycloalkylalkoxy; C$_3$-C$_6$-cycloalkoxy; C$_1$-C$_8$-alkylsulfanyl; C$_1$-C$_8$-halogenoalkylsulfanyl; C$_1$-C$_8$-alkylcarbonyl; C$_1$-C$_8$-halogenoalkylcarbonyl; arylcarbonyl; C$_3$-C$_8$-cycloalkylcarbonyl; C$_3$-C$_8$-halogenocycloalkylcarbonyl; C$_1$-C$_8$-alkylcarbamoyl; di-C$_1$-C$_8$-alkylcarbamoyl; N-C$_1$-C$_8$-alkyloxycarbamoyl; C$_1$-C$_8$-alkoxycarbamoyl; N-C$_1$-C$_8$-alkyl-C$_1$-C$_8$-alkoxycarbamoyl; C$_1$-C$_8$-alkoxycarbonyl; C$_1$-C$_8$-halogenoalkoxycarbonyl; C$_3$-C$_8$-cycloalkoxycarbonyl; C$_2$-C$_8$-alkoxyalkylcarbonyl; C$_2$-C$_8$-halogenoalkoxyalkylcarbonyl; C$_3$-C$_{10}$-cycloalkoxyalkylcarbonyl; C$_1$-C$_8$-alkylaminocarbonyl; di-C$_1$-C$_8$-alkylaminocarbonyl; C$_3$-C$_8$-cycloalkylaminocarbonyl; C$_1$-C$_8$-alkylcarbonyloxy; C$_1$-C$_8$-halogenalkylcarbonyloxy; C$_3$-C$_8$-cycloalkylcarbonyloxy; C$_1$-C$_8$-alkylcarbonylamino; C$_1$-C$_8$-halogenoalkylcarbonylamino; C$_1$-C$_8$-alkylaminocarbonyloxy; di-C$_1$-C$_8$-alkylaminocarbonyloxy; C$_1$-C$_8$-alkyloxycarbonyloxy; C$_1$-C$_8$-alkylsulfinyl; C$_1$-C$_8$-halogenoalkylsulfinyl; C$_1$-C$_8$-alkylsulfonlyl; C$_1$-C$_8$-halogenoalkylsulfonyl; C$_1$-C$_8$-alkylsulfonyloxy; C$_1$-C$_8$-halogenoalkylsulfonyloxy; C$_1$-C$_8$-alkylaminosulfamoyl; di-C$_1$-C$_8$-alkylaminosulfamoyl; (C$_1$-C$_8$-alkoxyimino)-C$_1$-C$_8$-alkyl; (C$_3$-C$_7$-cycloalkoxyimino)-C$_1$-C$_8$-alkyl; hydroxyimino-C$_1$-C$_8$-alkyl; (C$_1$-C$_8$-alkoxyimino)-C$_3$-C$_7$-cycloalkyl; hydroxyimino-C$_3$-C$_7$-cycloalkyl; (C$_1$-C$_8$-alkylimino)-oxy; (C$_1$-C$_8$-alkylimino)-oxy-C$_1$-C$_8$-alkyl; (C$_3$-C$_7$-cycloalkylimino)-oxy-C$_1$-C$_8$-alkyl; (C$_1$-C$_8$-alkylimino)-oxy-C$_3$-C$_7$-cycloalkyl; (C$_1$-C$_8$-alkenyloxyimino)-C$_1$-C$_8$-alkyl; (C$_1$-C$_8$-alkynyloxyimino)-C$_1$-C$_8$-alkyl; (benzyloxyimino)-C$_1$-C$_8$-alkyl; C$_1$-C$_8$-alkoxyalkyl; C$_1$-C$_8$-alkylthioalkyl; C$_1$-C$_8$-alkoxyalkoxyalkyl; C$_1$-C$_8$-halogenoalkoxyalkyl; benzyl; phenyl; 5-membered heteroaryl; 6-membered heteroaryl; benzyloxy; phenyloxy; benzylsunfanyl; benzylamino; phenylsuflanyl; or phenylamino.

The ketones of formula (XVIIa) obtained according to Processes J or K can be converted by means of methods described in the literature to the corresponding compounds (XVIIb) (see e.g "Palladium in heterocyclic chemistry", Pergamon Press, 2000; 1$^{st}$ edition, J. Li & G. Gribble) via a coupling reaction, optionally in the presence of a catalyst, preferably a transition metal catalyst, such as copper salts, palladium salts or complexes for example palladium (II) chloride, palladium (II) acetate, tetrakis-(triphenylphosphine) palladium(0), bis-(triphenylphosphine) palladium dichloride (II), tris(dibenzylideneacetone) dipalladium(0), bis(dibenzylideneacetone) palladium(0), or 1,1'-bis(diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl) phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis (diphenylphosphino)ferrocene, tris-(2,4-tert-butylphenyl)-phosphite, (R)-(−)-1-[(S)-2-(diphenylphosphino)ferrocenyl] ethyldi-tert-butylphosphine, (S)-(+)-1-[(R)-2-(diphenylphosphino)ferrocenyl] ethyldicyclohexylphosphine, (R)-(−)-1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine.

Such coupling reactions are optionally performed in the presence of a base such as an inorganic or an organic base; preferably an alkaline earth metal or alkali metal hydride, hydroxide, amide, alcoholate, acetate, carbonate or hydrogen carbonate, such as sodium hydride, sodium amide, lithium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amine, such as trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), For example, a compound of formula (XVIIa) is reacted with a cyanide reagent such as a metallic cyanide for example sodium cyanide, potassium cyanide, zinc cyanide; a metalloïdic cyanide, an organo-metallic cyanide for example di-C$_1$-C$_6$-alkylaluminum cyanide notably di-ethylaluminum cyanide; an organo-metalloïdic cyanide for example tri-C$_1$-C$_6$-alkylsilylcyanide notably tri-methylsilylcyanide in order to yield a compound of formula (XVIIb) wherein $R^{3b}$ represents a cyano.

Process M (Scheme 13):

Scheme 13: Process M-Preparation of compounds (Ia).

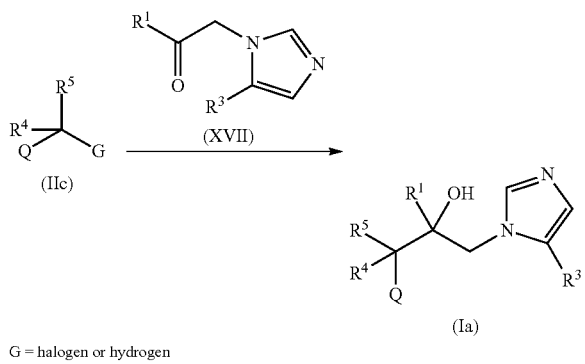

G = halogen or hydrogen

In a process according to Scheme 13, the ketones of formula (XVII) obtained according to Processes J to L are reacted with derivatives (IIc), wherein G stands for halogen or hydrogen. If G stands for halogen, compounds (IIc) are first transformed into Grignard reagents by the reaction with magnesium or with transmetallation reagents such as iso-propylmagenesium halides and subsequently reacted with ketone (XVII), preferably under anhydrous conditions to obtain compounds (Ia).

In case G stands for hydrogen, compounds (IIc) can be reacted with an organolithium reagent such as methyllithium or n-butyllithium preferably under anhydrous conditions to obtain a lithiated species. Optionally, a base such as lithiumdiisopropylamide or lithium bis(trimethylsilyl)amide, can be used. The obtained intermediates are subsequently reacted with ketones (XVII), preferably under anhydrous conditions to obtain compounds of the general formula (Ia).

Process N (Scheme 14):

Scheme 14: Process N - Preparation of compounds (Ic).

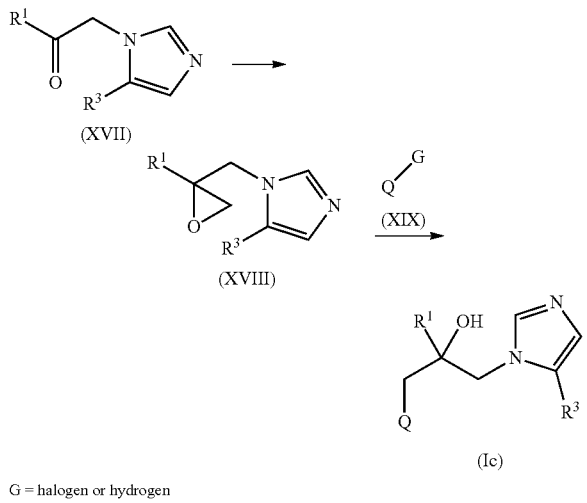

G = halogen or hydrogen

The compounds (XVII) (Scheme 14) can be converted by means of methods described in the literature to the corresponding compounds (XVIII) (see e.g. DE-A 31 11 238, DE-A 33 07 217). Compounds of the general formula (XVII) are preferably reacted with trimethylsulfoxonium halides, trimethylsulfonium halides, trimethylsulfoxonium methylsulfates or trimethylsulfonium methylsulfates, preferably in the presence of a base, such as sodium hydroxide, to obtain compounds (XVIII).

Compounds (XIX) are either commercially available or producible by processes described in the literature (see, for example, "Comprehensive Heterocyclic Chemistry III", Pergamon Press, 2008; vol. 7, pages 101-169; 217-308 & vol. 7, pages 1-331 and references cited therein; "Comprehensive Heterocyclic Chemistry II", Pergamon Press, 1996; vol. 5, pages 37-243 & vol. 6, pages 1-278 and references cited therein; "Comprehensive Heterocyclic Chemistry I", Pergamon Press, 1984; vol. 2, pages 395-510 & vol. 3, pages 1-197 and references cited therein; "Comprehensive Heterocyclic Chemistry III", Pergamon Press, 2008; vol. 3, pages 45-388 & vol. 4, pages 1-364 and references cited therein; "Comprehensive Heterocyclic Chemistry II", Pergamon Press, 1996; vol. 2, pages 39-257 & vol. 3, pages 1-220 and references cited therein; "Comprehensive Heterocyclic Chemistry I", Pergamon Press, 1984; vol. 4, pages 155-376 & vol. 5, pages 167-498 and references cited therein).

Subsequently, compounds (Ic) can be obtained by the reaction of (XVIII) with (XIX). If G stands for halogen, preferably chloride or bromide, compounds (XIX) are first transformed into Grignard reagents by the reaction with magnesium or with transmetallation reagents such as iso-propylmagnesium halides and subsequently reacted with epoxides (XVIII) preferably under anhydrous conditions.

In an alternative route compounds (XIX) (G=hydrogen or halogen) are reacted with compounds (XVIII) preferably in the presence of a base. Compounds (XIX) (G=hydrogen or halogen) are optionally reacted with a base upfront, e.g. n-butyllithium, lithium-di-isopropylamide, lithium bis(trimethylsilyl)amide, methyl lithium, followed by compounds of the general structure (XVIII) preferably under anhydrous conditions to form the desired compounds (Ic).

Process O (Scheme 15):

Scheme 15: Process O - Preparation of compounds (Ib).

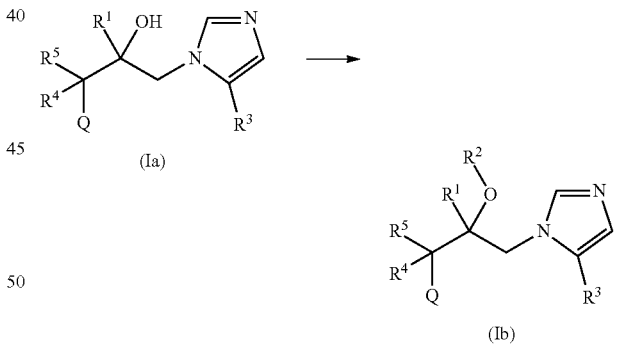

The compounds (Ia) obtained according to Processes H, I, M or N can be converted by means of methods described in the literature to the corresponding compounds (Ib) (see e.g. DE-A 3202604, JP-A 02101067, EP-A 225 739, CN-A 101824002, FR-A 2802772; WO-A 2012/175119, Bioorganic & Medicinal Chemistry Letters, 7207-7213, 2012; Journal of the American Chemical Society, 19358-19361, 2012, Journal of Organic Chemistry, 9458-9472, 2012; Organic Letters, 554-557, 2013; Journal of the American Chemical Society, 15556, 2012). Compounds of the general structure (Ia) are preferably reacted with alkylhalides, dialkylsulfates, anhydrides, acid chlorides, phosphorylchloride, alkylisocyanate, carbamoyl chlorides, carbono chloridates or imidocarbonates preferably in the presence of a base to obtain compounds (Ib).

Process P (Scheme 16)

Scheme 16: Process P - Preparation of compounds (Ie).

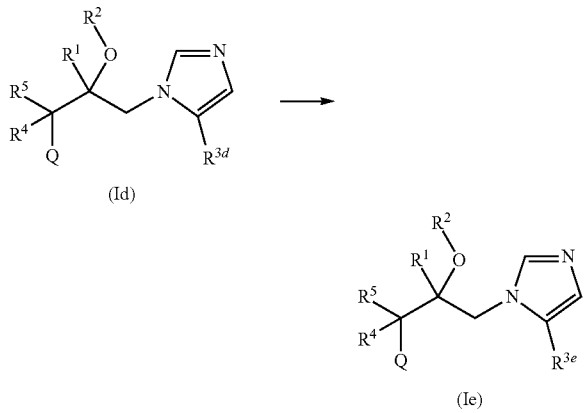

$R^{3d}$ = halogen, O-SO$_2$-C$_1$-C$_8$-alkyl or O-SO$_2$-aryl, preferably Br or I $R^{3e}$ = cyano; amino; hydroxycarbonyl, C$_1$-C$_8$-alkyl; C$_1$-C$_8$-haloalkyl; C$_1$-C$_8$-cyanoalkyl; C$_1$-C$_8$-alkyloxy; C$_1$-C$_8$-halogenalkyloxy; tri(C$_1$-C$_8$-alkyl)silyl-C$_1$-C$_8$-alkyl; C$_3$-C$_7$-cycloalkyl; C$_3$-C$_7$-halogenocycloalkyl; C$_3$-C$_7$-cycloalkenyl; C$_3$-C$_7$-halogencycloalkenyl; C$_4$-C$_{10}$-cycloalkylalkyl; C$_4$-C$_{10}$-halocycloalkylalkyl; C$_6$-C$_{12}$-cycloalkylcycloalkyl; C$_1$-C$_8$-alkyl-C$_3$-C$_7$-cycloalkyl; C$_1$-C$_8$-alkoxy-C$_3$-C$_7$-cycloalkyl; tri(C$_1$-C$_8$-alkyl)silyl-C$_3$-C$_7$-cycloalkyl; C$_2$-C$_8$-alkenyl; C$_2$-C$_8$-alkynyl; C$_2$-C$_8$-alkenyloxy; C$_2$-C$_8$-halogenalkenyloxy; C$_3$-C$_8$-alkynyloxy; C$_3$-C$_8$-halogenoalkynyloxy; C$_1$-C$_8$-alkylamino; C$_1$-C$_8$-halogenalkylamino; C$_1$-C$_8$-cyanoalkoxy; C$_4$-C$_8$-cycloalkylalkoxy; C$_3$-C$_6$-cycloalkoxy; C$_1$-C$_8$-alkylcarbonyl; C$_1$-C$_8$-halogenoalkylcarbonyl; arylcarbonyl; C$_3$-C$_8$-cycloalkylcarbonyl; C$_3$-C$_8$-halogenocylcoalkylcarbonyl; C$_1$-C$_8$-alkylcarbamoyl; di-C$_1$-C$_8$-alkylcarbamoyl; N-C$_1$-C$_8$-alkyloxycarbamoyl; C$_1$-C$_8$-alkoxycarbamoyl; N-C$_1$-C$_8$-alkyl-C$_1$-C$_8$-alkoxycarbamoyl; C$_1$-C$_8$-alkoxycarbonyl; C$_1$-C$_8$-halogenoalkoxycarbonyl; C$_3$-C$_8$-cycloalkoxycarbonyl; C$_2$-C$_8$-alkoxyalkylcarbonyl; C$_2$-C$_8$-halogenoalkoxyalkycarbonyl; C$_3$-C$_{10}$-cycloalkoxyalkylcarbonyl; C$_1$-C$_8$-alkylaminocarbonyl; di-C$_1$-C$_8$-alkylaminocarbonyl; C$_3$-C$_8$-cycloalkylaminocarbonyl; (C$_1$-C$_8$-alkoxyimino)-C$_1$-C$_8$-alkyl; (C$_3$-C$_7$-cycloalkoxyimino)-C$_1$-C$_8$-alkyl; benzyl; phenyl; 5-membered heteroaryl; 6-membered heteroaryl; benzyloxy; phenyloxy; benzylsulfanyl; benzylamino; phenylsulfanyl; or phenylamino; wherein the benzyl, phenyl, 5-membered heteroaryl, 6-membered heteroaryl, benzyloxy or phenyloxy may be optionally substituted by one or more group(s) selected from halogen; hydroxyl; cyano; amino; sulfanyl; pentafluoro-λ$^6$- sulfanyl; carboxaldehyde, hydroxycarbonyl, C$_1$-C$_8$-alkyl; C$_1$-C$_8$-haloalkyl; C$_1$-C$_8$-cyanoalkyl; C$_1$-C$_8$-alkyloxy; C$_1$-C$_8$-halogenalkyloxy; tri(C$_1$-C$_8$-alkyl)silyl; tri(C$_1$-C$_8$-alkyl)silyl-C$_1$-C$_8$-alkyl; C$_3$-C$_7$-cycloalkyl; C$_3$-C$_7$-halogencycloalkyl; C$_3$-C$_7$-cycloalkenyl; C$_3$-C$_7$-halogencycloalkenyl; C$_4$-C$_{10}$-cycloalkylalkyl; C$_4$-C$_{10}$-halocycloalkylalkyl; C$_6$-C$_{12}$-cycloalkylcycloalkyl; C$_1$-C$_8$-alkoxy-C$_3$-C$_7$-cycloalkyl; C$_1$-C$_8$-alkoxy-C$_3$-C$_7$-cycloalkyl; tri(C$_1$-C$_8$-alkyl)silyl-C$_3$-C$_7$-cycloalkyl; C$_2$-C$_8$-alkenyl; C$_2$-C$_8$-alkynyl; C$_2$-C$_8$-alkenyloxy; C$_2$-C$_8$-halogenalkenyloxy; C$_3$-C$_8$-alkynolxy; C$_3$-C$_8$-halogenoalkynyloxy; C$_1$-C$_8$-alkylamino; C$_1$-C$_8$-halogenalkylamino; C$_1$-C$_8$-cyanoalkoxy; C$_4$-C$_8$-cycloalkylalkoxy; C$_3$-C$_6$-cycloalkoxy; C$_1$-C$_8$-alkylsulfanyl; C$_1$-C$_8$-halogenoalkylsulfanyl; C$_1$-C$_8$-alkylcarbonyl; C$_1$-C$_8$-halogenoalkylcarbonyl; arylcarbonyl; C$_3$-C$_8$-cycloalkylcarbonyl; C$_3$-C$_8$-halogenocycloalkylcarbonyl; C$_1$-C$_8$-alkylcarbamoyl; di-C$_1$-C$_8$-alkylcarbamoyl; N-C$_1$-C$_8$-alkyloxycarbamoyl; C$_1$-C$_8$-alkoxycarbamoyl; N-C$_1$-C$_8$-alkyl-C$_1$-C$_8$- alkoxycarbamoyl; C$_1$-C$_8$-alkoxycarbonyl; C$_1$-C$_8$-halogenoalkoxycarbonyl; C$_3$-C$_8$-cycloalkoxycarbonyl; C$_2$-C$_8$-alkoxyalkylcarbonyl; C$_2$-C$_8$-halogenoalkoxyalkylcarbonyl; C$_3$-C$_{10}$-cycloalkoxyalkylcarbonyl; C$_1$-C$_8$-alkylaminocarbonyl; di-C$_1$-C$_8$-alkylaminocarbonyl; C$_3$-C$_8$-cycloalkylaminocarbonyl; C$_1$-C$_8$-alkylcarbonyloxy; C$_1$-C$_8$-halogenoalkylcarbonyloxy; C$_3$-C$_8$-cycloalkylcarbonyloxy; C$_1$-C$_8$-alkylcarbonylamino; C$_1$-C$_8$-halogenoalkylcarbonylamino; C$_1$-C$_8$-alkylaminocarbonyloxy; di-C$_1$-C$_8$-alkylaminocarbonyloxy; C$_1$-C$_8$-alkyloxycarbonyloxy; C$_1$-C$_8$-alkylsulfinyl; C$_1$-C$_8$-halogenoalkylsulfinyl; C$_1$-C$_8$-alkylsulfonyl; C$_1$-C$_8$-halogenoalkylsulfonyl; C$_1$-C$_8$-alkylsulfonyloxy; C$_1$-C$_8$-halogenoalkysulfonyloxy; C$_1$-C$_8$-alkylaminosulfamoyl; di-C$_1$-C$_8$-alkylaminosulfamoyl; (C$_1$-C$_8$-alkoxyimino)-C$_1$-C$_8$-alkyl; (C$_3$-C$_7$-cycloalkoxyimino)-C$_1$-C$_8$-alkyl; hydroxyimino-C$_1$-C$_8$-alkyl; (C$_1$-C$_8$-alkoxyimino)-C$_3$-C$_7$-cycloalkyl; hydroxyimino-C$_3$-C$_7$-cycloalkyl; (C$_1$-C$_8$-alkylimino)-oxy; (C$_1$-C$_8$-alkylimino)-oxy-C$_1$-C$_8$-alkyl; (C$_3$-C$_7$-cycloalkylimino)-oxy-C$_1$-C$_8$-alkyl; (C$_1$-C$_6$-alkylimino)-oxy-C$_3$-C$_7$-cycloalkyl; (C$_1$-C$_8$-alkenyloxyimino)-C$_1$-C$_8$-alkyl; (C$_1$-C$_8$-alkynyloxyimino)-C$_1$-C$_8$-alkyl; (benzyloxyimino)-C$_1$-C$_8$-alkyl; C$_1$-C$_8$-alkoxyalkyl; C$_1$-C$_8$-alkythioalkyl; C$_1$-C$_8$-alkoxyalkoxyalkyl; C$_1$-C$_8$-halogenoalkoxyalkxyl; benzyl; phenyl; 5-membered heteroaryl; 6-membered heteroaryl; benzyloxy; phenyloxy; benzylsulfanyl; benzylamino; phenylsulfanyl; or phenylamino.

The compounds (Ia) obtained according to Processes H, I, M, N or P wherein $R^3$ represents halogen, O—SO$_2$—C$_1$-C$_8$-alkyl or O—SO$_2$-aryl, preferably Br or I are in Scheme 16 and process P referred to as compounds (Id). Such compounds (Id) can be converted by means of methods described in the literature to the corresponding compounds (Ie) (see e.g "Palladium in heterocyclic chemistry", Pergamon Press, 2000; 1$^{st}$ edition, J. Li & G. Gribble) via a coupling reaction, optionally in the presence of a catalyst, preferably a transition metal catalyst, such as copper salts, palladium salts or complexes for example palladium (II) chloride, palladium (II) acetate, tetrakis-(triphenylphosphine) palladium(0), bis-(triphenylphosphine) palladium dichloride (II), tris(dibenzylideneacetone) dipalladium(0), bis(dibenzylideneacetone) palladium(0), or 1,1'-bis(diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl) phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino)ferrocenyl]ethyldicyclohexylphosphine, (R)-(−)-1-[(S)-2-(diphenylphosphino)ferrocenyl]ethyldicyclohexylphosphine, (S)-(+)-1-[(R)-2-(diphenylphosphino)ferrocenyl]ethyldi-t-butylphosphine.

Such coupling reactions are optionally performed in the presence of a base such as an inorganic or an organic base; preferably an alkaline earth metal or alkali metal hydride, hydroxide, amide, alcoholate, acetate, carbonate or hydrogen carbonate, such as sodium hydride, sodium amide, lithium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amine, such as trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), For example, a compound of formula (Id) is reacted with a cyanide reagent such as a metallic cyanide for example sodium cyanide, potassium cyanide, zinc cyanide; a metalloïdic cyanide, an organo-metallic cyanide for example di-C$_1$-C$_6$-alkylaluminum cyanide notably di-ethylaluminum cyanide; an organo-metalloïdic cyanide for example tri-C$_1$-C$_6$-alkylsilylylcyanide notably tri-methylsilylcyanide in order to yield a compound of formula (Ie) wherein $R^{3e}$ represents a cyano.

The preferred compounds of the formulae (I-I), (I-1-Q-I-1), (I-1-Q-I-2) and (I-1-Q-I-3) can also be obtained according to the processes A to P according to the invention. Unless indicated otherwise, the radicals $R^1$, $R^2$, $R^3$, $R^4$, $R^5$ and Q have the meanings given above for the compounds of formulae (I-I), (I-1-Q-I-1), (I-1-Q-I-2) and (I-1-Q-I-3).

These definitions apply not only to the end products of the formulae (I-I), (I-1-Q-I-1), (I-1-Q-I-2) and (I-1-Q-I-3) but likewise to all intermediates.

General

The processes A to P according to the invention for preparing compounds of the formula (I) are optionally performed using one or more reaction auxiliaries.

Useful reaction auxiliaries are, as appropriate, inorganic or organic bases or acid acceptors. These preferably include alkali metal or alkaline earth metal acetates, amides, carbonates, hydrogencarbonates, hydrides, hydroxides or alkoxides, for example sodium acetate, potassium acetate or calcium acetate, lithium amide, sodium amide, potassium amide or calcium amide, sodium carbonate, potassium carbonate or calcium carbonate, sodium hydrogencarbonate, potassium hydrogencarbonate or calcium hydrogencarbonate, lithium hydride, sodium hydride, potassium hydride or calcium hydride, lithium hydroxide, sodium hydroxide, potassium hydroxide or calcium hydroxide, n-butyllithium, sec-butyllithium, tert-butyllithium, lithium diisopropylamide, lithium bis(trimethylsilyl)amide, sodium methoxide, ethoxide, n- or i-propoxide, n-, i-, s- or t-butoxide or potassium methoxide, ethoxide, n- or i-propoxide, n-, i-, s- or t-butoxide; and also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]-octane (DABCO), 1,5-diazabicyclo[4.3.0]-non-5-ene (DBN) or 1,8-diazabicyclo[5.4.0]-undec-7-ene (DBU).

Useful reaction auxiliaries are, as appropriate, inorganic or organic acids. These preferably include inorganic acids, for example hydrogen fluoride, hydrogen chloride, hydrogen bromide and hydrogen iodide, sulphuric acid, phosphoric acid and nitric acid, and acidic salts such as $NaHSO_4$ and $KHSO_4$, or organic acids, for example formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), aiylsulphonic acids or aiyldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), aiylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

The processes A to P according to the invention are optionally performed using one or more diluents. Useful diluents are virtually all inert organic solvents. Unless otherwise indicated for the above described processes A to P, these preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether, dibutyl ether and methyl tert-butyl ether, glycol dimethyl ether and diglycol dimethyl ether, tetrahydrofuran and dioxane, ketones such as acetone, methyl ethyl ketone, methyl isopropyl ketone and methyl isobutyl ketone, esters, such as methyl acetate and ethyl acetate, nitriles, for example acetonitrile and propionitrile, amides, for example dimethylformamide, dimethylacetamide and N-methylpyrrolidone, and also dimethyl sulphoxide, tetramethylenesulphone and hexamethylphosphoramide and DMPU.

In the processes according to the invention, the reaction temperatures can be varied within a relatively wide range. In general, the temperatures employed are between −78° C. and 250° C., preferably temperatures between −78° C. and 150° C.

The reaction time varies as a function of the scale of the reaction and of the reaction temperature, but is generally between a few minutes and 48 hours.

The processes according to the invention are generally performed under standard pressure. However, it is also possible to work under elevated or reduced pressure.

For performance of the processes according to the invention, the starting materials required in each case are generally used in approximately equimolar amounts. However, it is also possible to use one of the components used in each case in a relatively large excess.

After a reaction has ended, the compounds are optionally separated from the reaction mixture by one of the customary separation techniques. If necessary, the compounds are purified by recrystallization or chromatography.

If appropriate, in the processes A to P according to the invention also salts and/or N-oxides of the starting compounds can be used.

The invention further relates to novel intermediates of the compounds of formula (I), which form part of the invention.

Novel intermediates according to the present invention are novel compounds of formula (XVII)

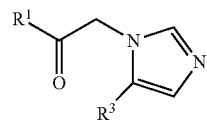

(XVII)

wherein $R^1$ represents hydrogen, in each case optionally branched $C_1$-$C_8$-alkyl, $C_1$-$C_8$-haloalkyl, $C_2$-$C_7$-alkenyl, $C_2$-$C_7$-haloalkenyl, $C_2$-$C_8$-alkynyl, $C_2$-$C_8$-haloalkynyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted bicycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_8$-cycloalkylalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-halocycloalkyl-$C_1$-$C_4$-alkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-halocycloalkyl-$C_1$-$C_4$-haloalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl-$C_1$-$C_4$-haloalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl-$C_3$-$C_7$-cycloalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkenyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted tri($C_1$-$C_8$-alkyl)silyl-$C_1$-$C_4$-alkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted tri($C_1$-$C_8$-alkyl)silyl-$C_3$-$C_7$-cycloalkyl;

and $R^3$ represents halogen; hydroxyl; cyano; isocyano; nitro; amino; sulfanyl; pentafluoro-$\lambda^6$-sulfanyl; carboxaldehyde, $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; tri($C_1$-$C_8$-alkyl)silyl; tri($C_1$-$C_8$-alkyl)silyl-$C_1$-$C_8$-alkyl; $C_3$-$C_7$-cycloalkyl; $C_3$-$C_7$-halogencycloalkyl; $C_3$-$C_7$-cycloalkenyl; $C_3$-$C_7$-halogencycloalkenyl; $C_4$-$C_{10}$-cycloalkylalkyl; $C_4$-$C_{10}$-halocycloalkylalkyl; $C_6$-$C_{12}$-cycloalkylcycloalkyl; $C_1$-$C_8$-alkyl-$C_3$-$C_7$-cycloalkyl; $C_1$-$C_8$-alkoxy-$C_3$-$C_7$-cycloalkyl; tri($C_1$-$C_8$-alkyl)silyl-$C_3$-$C_7$-cycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_1$-$C_8$-alkylamino; $C_1$-$C_8$-halogenalkylamino; $C_1$-$C_8$-cyanoalkoxy; $C_4$-$C_8$-cycloalkylalkoxy; $C_3$-$C_6$-cycloalkoxy; $C_1$-$C_8$-alkylsulfanyl; $C_1$-$C_8$-halogenoalkylsulfanyl; $C_1$-$C_8$-alkylcarbonyl; $C_1$-$C_8$-halogenoalkylcarbonyl; alylcarbonyl; aryl-$C_1$-$C_6$-alkylcarbonyl; $C_3$-$C_8$-cycloalkylcarbonyl; $C_3$-$C_8$-halogenocycloalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; aminothiocarbonyl; $C_2$-$C_8$-alkoxycarbonyl; $C_1$-$C_8$-halogenoalkoxycarbonyl; $C_3$-$C_8$-cycloalkoxycarbonyl; $C_2$-$C_8$-alkoxyalkylcarbonyl; $C_2$-$C_8$-halogenoalkoxyalkylcarbonyl; $C_3$-$C_{10}$-cycloalkoxyalkylcarbonyl; $C_1$-$C_8$-alkylaminocarbonyl; di-$C_1$-$C_8$-alkylaminocarbonyl; $C_3$-$C_8$-cycloalkylaminocarbonyl; $C_1$-$C_8$-alkylcarbonyloxy; $C_1$-$C_8$-halogenoalkylcarbonyloxy; $C_3$-$C_8$-cycloalkylcarbonyloxy; $C_1$-$C_8$-alkylcarbonylamino; $C_1$-$C_8$-halogenoalkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfinyl; $C_1$-$C_8$-halogenoalkylsulfinyl; $C_1$-$C_8$-alkylsulfonyl; $C_1$-$C_8$-halogenoalkylsulfonyl; $C_1$-$C_8$-alkylsulfonyloxy; $C_1$-$C_8$-halogenoalkylsulfonyloxy; $C_1$-$C_8$-alkylaminosulfamoyl; di-$C_1$-$C_8$-alkylaminosulfamoyl; ($C_1$-$C_8$-alkoxyimino)-$C_1$-$C_8$-alkyl; ($C_3$-$C_7$-cycloalkoxyimino)-$C_1$-$C_8$-alkyl; hydroxyimino-$C_1$-$C_8$-alkyl; ($C_1$-$C_8$-alkoxyimino)-$C_3$-$C_7$-cycloalkyl; hydroxyimino-$C_3$-$C_7$-cycloalkyl; ($C_1$-$C_8$-alkylimino)-oxy; ($C_1$-$C_8$-alkylimino)-oxy-$C_1$-$C_8$-alkyl; ($C_3$-$C_7$-cycloalkylimino)-oxy-$C_1$-$C_8$-alkyl; ($C_1$-$C_6$-alkylimino)-oxy-$C_3$-$C_7$-cycloalkyl; ($C_1$-$C_8$-alkenyloxyimino)-$C_1$-$C_8$-alkyl; ($C_1$-$C_8$-alkynyloxyimino)-$C_1$-$C_8$-alkyl; (benzyloxyimino)-$C_1$-$C_8$-alkyl; $C_1$-$C_8$-alkoxyalkyl; $C_1$-$C_8$-alkylthioalkyl; $C_1$-$C_8$-alkoxyalkoxyalkyl; $C_1$-$C_8$-halogenoalkoxyalkyl; benzyl; phenyl; 5-membered heteroalyl; 6-membered heteroaryl; benzyloxy; phenyloxy; benzylsulfanyl; benzylamino; phenylsulfanyl; or phenylamino; wherein the benzyl, phenyl, 5-membered heteroalyl, 6-membered heteroaryl, benzyloxy or phenyloxy may be optionally substituted by one or more group(s) selected from halogen; hydroxyl; cyano; isocyano; amino; sulfanyl; pentafluoro-$\lambda^6$-sulfanyl; carboxaldehyde, hydroxycarbonyl, $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; tri($C_1$-$C_8$-alkyl)silyl; tri($C_1$-$C_8$-alkyl)silyl-$C_1$-$C_8$-alkyl; $C_3$-$C_7$-cycloalkyl; $C_3$-$C_7$-halogencycloalkyl; $C_3$-$C_7$-cycloalkenyl; $C_3$-$C_7$-halogencycloalkenyl; $C_4$-$C_{10}$-cycloalkylalkyl; $C_4$-$C_{10}$-halocycloalkylalkyl; $C_6$-$C_{12}$-cycloalkylcycloalkyl; $C_1$-$C_8$-alkyl-$C_3$-$C_7$-cycloalkyl; $C_1$-$C_8$-alkoxy-$C_3$-$C_7$-cycloalkyl; tri($C_1$-$C_8$-alkyl)silyl-$C_3$-$C_7$-cycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_1$-$C_8$-alkylamino; $C_1$-$C_8$-halogenalkylamino; $C_1$-$C_8$-cyanoalkoxy; $C_4$-$C_8$-cycloalkylalkoxy; $C_3$-$C_6$-cycloalkoxy; $C_1$-$C_8$-alkylsulfanyl; $C_1$-$C_8$-halogenoalkylsulfanyl; $C_1$-$C_8$-alkylcarbonyl; $C_1$-$C_8$-halogenoalkylcarbonyl; arylcarbonyl; aryl-$C_1$-$C_6$-alkylcarbonyl; $C_3$-$C_8$-cycloalkylcarbonyl; $C_3$-$C_8$-halogenocycloalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; aminothiocarbonyl; $C_1$-$C_8$-alkoxycarbonyl; $C_1$-$C_8$-halogenoalkoxycarbonyl; $C_3$-$C_8$-cycloalkoxycarbonyl; $C_2$-$C_8$-alkoxyalkylcarbonyl; $C_2$-$C_8$-halogenoalkoxyalkylcarbonyl; $C_3$-$C_{10}$-cycloalkoxyalkylcarbonyl; $C_1$-$C_8$-alkylaminocarbonyl; di-$C_1$-$C_8$-alkylaminocarbonyl; $C_3$-$C_8$-cycloalkylaminocarbonyl; $C_1$-$C_8$-alkylcarbonyloxy; $C_1$-$C_8$-halogenoalkylcarbonyloxy; $C_3$-$C_8$-cycloalkylcarbonyloxy; $C_1$-$C_8$-alkylcarbonylamino; $C_1$-$C_8$-halogenoalkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfinyl; $C_1$-$C_8$-halogenoalkylsulfinyl; $C_1$-$C_8$-alkylsulfonyl; $C_1$-$C_8$-halogenoalkylsulfonyl; $C_1$-$C_8$-alkylsulfonyloxy; $C_1$-$C_8$-halogenoalkylsulfonyloxy; $C_1$-$C_8$-alkylaminosulfamoyl; di-$C_1$-$C_8$-alkylaminosulfamoyl; ($C_1$-$C_8$-alkoxyimino)-$C_1$-$C_8$-alkyl; ($C_3$-$C_7$-cycloalkoxyimino)-$C_1$-$C_8$-alkyl; hydroxyimino-$C_1$-$C_8$-alkyl; ($C_1$-$C_8$-alkoxyimino)-$C_3$-$C_7$-cycloalkyl; hydroxyimino-$C_3$-$C_7$-cycloalkyl; ($C_1$-$C_8$-alkylimino)-oxy; ($C_1$-$C_8$-alkylimino)-oxy-$C_1$-$C_8$-alkyl; ($C_3$-$C_7$-cycloalkylimino)-oxy-$C_1$-$C_8$-alkyl; ($C_1$-$C_6$-alkylimino)-oxy-$C_3$-$C_7$-cycloalkyl; ($C_1$-$C_8$-alkenyloxyimino)-$C_1$-$C_8$-alkyl; ($C_1$-$C_8$-alkynyloxyimino)-$C_1$-$C_8$-alkyl; (benzyloxyimino)-$C_1$-$C_8$-alkyl; $C_1$-$C_8$-alkoxyalkyl; $C_1$-$C_8$-alkylthioalkyl; $C_1$-$C_8$-alkoxyalkoxyalkyl; $C_1$-$C_8$-halogenoalkoxyalkyl; benzyl; phenyl; 5-membered heteroalyl; 6-membered heteroaryl; benzyloxy; phenyloxy; benzylsulfanyl; benzylamino; phenylsulfanyl; or phenylamino;

and its salts or N-oxides.

For the compounds of formula (XVII) the following preferred definitions apply:

$R^1$ preferably represents in each case optionally branched $C_1$-$C_8$-alkyl, $C_1$-$C_8$-haloalkyl, $C_2$-$C_7$-alkenyl, $C_2$-$C_7$-haloalkenyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl;

$R^1$ more preferably represents in each case optionally branched $C_1$-$C_4$-alkyl, $C_1$-$C_4$-haloalkyl, $C_2$-$C_8$-alkenyl, $C_2$-$C_8$-haloalkenyl, optionally halogen-, cyano-, $C_1$-$C_4$- alkyl-, $C_1$-$C_4$-haloalkyl-, $C_1$-$C_4$-haloalkoxy-, $C_1$-$C_4$-alkoxy-, $C_1$-$C_4$-alkylthio- or $C_1$-$C_4$-haloalkylthio-substituted $C_3$-$C_6$-cycloalkyl.

$R^1$ most preferably represents tert-butyl, isopropyl, 1-halocyclopropyl, 1-($C_1$-$C_4$-alkyl)cyclopropyl, 1-($C_1$-$C_4$-alkoxy) cyclopropyl or 1-($C_1$-$C_4$-alkylthio)cyclopropyl.

In preferred embodiments of the present invention $R^1$ represents tert-butyl, isopropyl, 1-chlorocyclopropyl, 1-fluorocyclopropyl or 1-methylcyclopropyl.

$R^3$ preferably represents halogen; hydroxyl; cyano; isocyano; nitro; carboxaldehyde, $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_1$-$C_8$-alkylsulfanyl; $C_1$-$C_8$-halogenoalkylsulfanyl; $C_1$-$C_8$-alkylcarbonyl; $C_1$-$C_8$-halogenoalkylcarbonyl; arylcarbonyl; aryl-$C_1$-$C_6$-alkylcarbonyl; $C_3$-$C_8$-cycloalkylcarbonyl; $C_3$-$C_8$-halogenocycloalkylcarbonyl; aminothiocarbonyl; $C_2$-$C_8$-alkoxycarbonyl; $C_1$-$C_8$-halogenoalkoxycarbonyl; $C_3$-$C_8$-cycloalkoxycarbonyl; $C_1$-$C_8$-alkylcarbonyloxy; $C_1$-$C_8$-halogenoalkylcarbonyloxy; $C_3$-$C_8$-cycloalkylcarbonyloxy; benzyl; phenyl; 5-membered heteroaryl; 6-membered heteroaryl; benzyloxy; or phenyloxy; wherein the benzyl, phenyl, 5-membered heteroalyl, 6-membered heteroaryl, benzyloxy or phenyloxy may be optionally substituted by one or more group(s) selected from halogen; hydroxyl; cyano; amino; sulfanyl; pentafluoro-$\lambda^6$-sulfanyl; $C_1$-$C_8$-alkyl; $C_1$-$C_8$-haloalkyl; $C_1$-$C_8$-alkyloxy; $C_1$-$C_8$-halogenalkyloxy; tri($C_1$-$C_8$-alkyl)silyl; $C_3$-$C_7$-cycloalkyl; $C_2$-$C_8$-alkenyl; $C_2$-$C_8$-alkynyl.

$R^3$ more preferably represents halogen; cyano; carboxaldehyde, $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_1$-$C_8$-alkylsulfanyl; $C_1$-$C_8$-halogenoalkylsulfanyl; $C_1$-$C_8$-alkylcarbonyl; $C_1$-$C_8$-halogenoalkylcarbonyl; $C_2$-$C_8$-alkoxycarbonyl; $C_1$-$C_8$-halogenoalkoxycarbonyl; benzyl; phenyl; 5-membered heteroalyl; 6-membered heteroaryl; benzyloxy; or phenyloxy; wherein the benzyl, phenyl, 5-membered heteroalyl, 6-membered heteroaryl, benzyloxy or phenyloxy may be optionally substituted by one or more group(s) selected from halogen; hydroxyl; cyano; amino; sulfanyl; pentafluoro-$\lambda^6$-sulfanyl; $C_1$-$C_8$-alkyl; $C_1$-$C_8$-haloalkyl; $C_1$-$C_8$-alkyloxy; $C_1$-$C_8$-halogenalkyloxy; tri($C_1$-$C_8$-alkyl)silyl; $C_3$-$C_7$-cycloalkyl; $C_2$-$C_8$-alkenyl; $C_2$-$C_8$-alkynyl.

$R^3$ most preferably represents halogen; cyano; carboxaldehyde, $C_1$-$C_4$-alkyl; $C_1$-$C_4$-haloalkyl; $C_1$-$C_4$-cyanoalkyl; $C_1$-$C_4$-alkyloxy; $C_1$-$C_4$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_1$-$C_4$-alkylsulfanyl; $C_1$-$C_4$-halogenoalkylsulfanyl; $C_1$-$C_4$-alkylcarbonyl; $C_1$-$C_4$-halogenoalkylcarbonyl; $C_2$-$C_4$-alkoxycarbonyl; $C_1$-$C_4$-halogenoalkoxycarbonyl; benzyl; phenyl; furyl; pyrrolyl; thienyl; pyridyl; benzyloxy; or phenyloxy; wherein the benzyl, phenyl, 5-membered heteroalyl, 6-membered heteroaryl, benzyloxy or phenyloxy may be optionally substituted by one or more group(s) selected from halogen; $C_1$-$C_8$-alkyl; $C_1$-$C_8$-haloalkyl; $C_1$-$C_8$-alkyloxy; $C_1$-$C_8$-halogenalkyloxy.

In preferred embodiments of the present invention $R^3$ represents fluorine; chlorine; bromine; iodine; cyano; carboxaldehyde, $C_1$-$C_4$-alkyl; $C_1$-$C_4$-haloalkyl; $C_1$-$C_4$-cyanoalkyl; $C_1$-$C_4$-alkyloxy; $C_3$-$C_7$-cycloalkyl; $C_2$-$C_8$-alkynyl; $C_1$-$C_4$-alkylsulfanyl; $C_1$-$C_4$-alkylcarbonyl; $C_2$-$C_4$-alkoxycarbonyl; phenyl; or thienyl; wherein the phenyl, or thienyl may be optionally substituted by one or more group(s) selected from halogen; $C_1$-$C_8$-alkyl; $C_1$-$C_8$-haloalkyl; $C_1$-$C_8$-alkyloxy; $C_1$-$C_8$-halogenalkyloxy.

In further preferred embodiments of the present invention $R^3$ represents fluorine; chlorine; bromine; iodine; cyano; carboxaldehyde, methyl; trifluoromethyl; cyanomethyl; methoxy; methylsulfanyl; cyclopropyl; ethinyl; methylcarbonyl (acetyl); carboxyl; ethoxycarbonyl; phenyl; or 2-thienyl.

Preferred embodiments according to the present invention are compounds of formula (XVII), wherein
$R^3$ represents halogen or cyano; and
$R^1$ has the same definition as given for formula (XVII).

In such preferred embodiments according to the present invention $R^3$ preferably represents fluorine; chlorine; bromine; iodine or cyano $R^1$ has the same definition as given for formula (XVII).

Other preferred embodiments according to the present invention are compounds of formula (XVII), wherein
$R^3$ represents $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; $C_3$-$C_7$-cycloalkyl; $C_3$-$C_7$-halogencycloalkyl; $C_3$-$C_7$-cycloalkenyl; $C_3$-$C_7$-halogencycloalkenyl; $C_4$-$C_{10}$-cycloalkylalkyl; $C_4$-$C_{10}$-halocycloalkylalkyl; $C_6$-$C_{12}$-cycloalkylcycloalkyl; $C_1$-$C_8$-alkyl-$C_3$-$C_7$-cycloalkyl; $C_1$-$C_8$-alkoxy-$C_3$-$C_7$-cycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_4$-$C_8$-cycloalkylalkoxy; $C_3$-$C_6$-cycloalkoxy; benzyl; phenyl; 5-membered heteroaryl; 6-membered heteroaryl; benzyloxy or phenyloxy; wherein the benzyl, phenyl, 5-membered heteroaryl, 6-membered heteroaryl, benzyloxy or phenyloxy may be optionally substituted by one or more group(s) selected from halogen; hydroxyl; cyano; amino; sulfanyl; pentafluoro-$\lambda^6$-sulfanyl; $C_1$-$C_8$-alkyl; $C_1$-$C_8$-haloalkyl; $C_1$-$C_8$-alkyloxy; $C_1$-$C_8$-halogenalkyloxy; tri($C_1$-$C_8$-alkyl)silyl; $C_3$-$C_7$-cycloalkyl; $C_2$-$C_8$-alkenyl; $C_2$-$C_8$-alkynyl; and
$R^1$ has the same definition as given for formula (XVII).

In such preferred embodiments according to the present invention
$R^3$ preferably represents $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_1$-$C_8$-alkylsulfanyl; $C_1$-$C_8$-halogenoalkylsulfanyl; benzyl; phenyl; 5-membered heteroalyl; 6-membered heteroaryl; benzyloxy or phenyloxy wherein the benzyl, phenyl, 5-membered heteroaryl, 6-membered heteroaryl, benzyloxy or phenyloxy may be optionally substituted by one or more group(s) selected from halogen; hydroxyl; cyano; amino; sulfanyl; pentafluoro-$\lambda^6$-sulfanyl; $C_1$-$C_8$-alkyl; $C_1$-$C_8$-haloalkyl; $C_1$-$C_8$-alkyloxy; $C_1$-$C_8$-halogenalkyloxy; tri($C_1$-$C_8$-alkyl)silyl; $C_3$-$C_7$-cycloalkyl; $C_2$-$C_8$-alkenyl; $C_2$-$C_8$-alkynyl;
and $R^1$ has the same definition as given for formula (XVII).

In such preferred embodiments according to the present invention
$R^3$ most preferably represents $C_1$-$C_4$-alkyl; $C_1$-$C_4$-haloalkyl; $C_1$-$C_4$-cyanoalkyl; $C_1$-$C_4$-alkyloxy; $C_1$-$C_4$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_1$-$C_4$-alkylsulfanyl; $C_1$-$C_4$-halogenoalkylsulfanyl; benzyl; phenyl; furyl; pyrrolyl; thienyl; pyridyl; benzyloxy or phenyloxy; wherein the benzyl, phenyl, 5-membered heteroalyl, 6-membered heteroaryl, benzyloxy or phenyloxy may be optionally substituted by one or more group(s) selected from halogen; $C_1$-$C_8$-alkyl; $C_1$-$C_8$-haloalkyl; $C_1$-$C_8$-alkyloxy; $C_1$-$C_8$-halogenalkyloxy;
and $R^1$ has the same definition as given for formula (XVII).

In such preferred embodiments according to the present invention
$R^3$ even more preferably represents $C_1$-$C_4$-alkyl; $C_1$-$C_4$-haloalkyl; $C_1$-$C_4$-cyanoalkyl; $C_1$-$C_4$-alkyloxy; $C_3$-$C_7$-cycloalkyl; $C_2$-$C_8$-alkynyl; $C_1$-$C_4$-alkylsulfanyl; phenyl; or thienyl; wherein the phenyl, or thienyl may be optionally substituted by one or more group(s) selected from halogen; $C_1$-$C_8$-alkyl; $C_1$-$C_8$-haloalkyl; $C_1$-$C_8$-alkyloxy; $C_1$-$C_8$-halogenalkyloxy;
and $R^1$ has the same definition as given for formula (XVII).

In such preferred embodiments according to the present invention
$R^3$ even more preferably represents methyl; trifluoromethyl; cyanomethyl; methoxy; methylsulfanyl; cyclopropyl; ethinyl; phenyl; or 2-thienyl;
and $R^1$ has the same definition as given for formula (XVII).

Other preferred embodiments according to the present invention are compounds of formula (XVII), wherein
$R^3$ represents carboxaldehyde, $C_1$-$C_8$-alkylcarbonyl; $C_1$-$C_8$-halogenoalkylcarbonyl; arylcarbonyl; $C_3$-$C_8$-cycloalkylcarbonyl; $C_3$-$C_8$-halogenocycloalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_2$-$C_8$-alkoxycarbonyl; $C_1$-$C_8$-halogenoalkoxycarbonyl; $C_3$-$C_8$-cycloalkoxycarbonyl; $C_2$-$C_8$-alkoxyalkylcarbonyl; $C_2$-$C_8$-halogenoalkoxyalkylcarbonyl; $C_3$-$C_{10}$-cycloalkoxyalkylcarbonyl; $C_1$-$C_8$-alkylaminocarbonyl; di-$C_1$-$C_8$-alkylaminocarbonyl; $C_3$-$C_8$-cycloalkylaminocarbonyl; $C_1$-$C_8$-alkylcarbonyloxy; $C_1$-$C_8$-halogenoalkylcarbonyloxy; $C_3$-$C_8$-cycloalkylcarbonyloxy; $C_1$-$C_8$-alkylcarbonylamino; $C_1$-$C_8$-halogenoalkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfinyl; $C_1$-$C_8$-halogenoalkylsulfinyl; $C_1$-$C_8$-alkylsulfonyl; $C_1$-$C_8$-halogenoalkylsulfonyl; $C_1$-$C_8$-alkylsulfonyloxy; $C_1$-$C_8$-halogenoalkylsulfonyloxy; $C_1$-$C_8$-alkylaminosulfamoyl or di-$C_1$-$C_8$-alkylaminosulfamoyl; and
and $R^1$ has the same definition as given for formula (XVII).

In such preferred embodiments according to the present invention
$R^3$ preferably represents carboxaldehyde, $C_2$-$C_8$-alkylcarbonyl; $C_1$-$C_8$-halogenoalkylcarbonyl; arylcarbonyl; $C_3$-$C_8$-cycloalkylcarbonyl; $C_3$-$C_8$-halogenocycloalkylcarbonyl; $C_2$-$C_8$-alkoxycarbonyl; $C_1$-$C_8$-halogenoalkoxycarbonyl; $C_3$-$C_8$-cycloalkoxycarbonyl; $C_1$-$C_8$-alkylcarbonyloxy; $C_1$-$C_8$-halogenoalkylcarbonyloxy; or $C_3$-$C_8$-cycloalkylcarbonyloxy; and
and $R^1$ has the same definition as given for formula (XVII).

In such preferred embodiments according to the present invention
$R^3$ more preferably represents carboxaldehyde, $C_1$-$C_8$-alkylcarbonyl; $C_1$-$C_8$-halogenoalkylcarbonyl; $C_2$-$C_5$-alkoxycarbonyl; or $C_1$-$C_8$-halogenoalkoxycarbonyl; and
and $R^1$ has the same definition as given for formula (XVII).

In such preferred embodiments according to the present invention
$R^3$ most preferably represents carboxaldehyde, $C_1$-$C_4$-alkylcarbonyl; $C_1$-$C_4$-halogenoalkylcarbonyl; $C_2$-$C_4$-alkoxycarbonyl; or $C_1$-$C_4$-halogenoalkoxycarbonyl; and
and $R^1$ has the same definition as given for formula (XVII).

In such preferred embodiments according to the present invention
$R^3$ even more preferably represents carboxaldehyde, $C_1$-$C_4$-alkylcarbonyl; or $C_2$-$C_4$-alkoxycarbonyl; and and $R^1$ has the same definition as given for formula (XVII).

In such preferred embodiments according to the present invention
$R^3$ even more preferably represents carboxaldehyde, methylcarbonyl (acetyl); carboxyl; or ethoxycarbonyl; and
and $R^1$ has the same definition as given for formula (XVII).

The compounds of the formula (I) according to the invention can be converted into physiologically acceptable salts, e.g. as acid addition salts or metal salt complexes.

Depending on the nature of the substituents defined above, the compounds of the formula (I) have acidic or basic properties and can form salts, if appropriate also inner salts, or adducts with inorganic or organic acids or with bases or with metal ions. If the compounds of the formula (I) carry amino, alkylamino or other groups which induce basic properties, these compounds can be reacted with acids to give salts, or they are directly obtained as salts in the synthesis. If the compounds of the formula (I) carries hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having ($C_1$-$C_4$)-alkyl groups, mono-, di- and trialkanolamines of ($C_1$-$C_4$)-alkanols, choline and also chlorocholine.

The salts obtainable in this manner also have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as $NaHSO_4$ and $KHSO_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, maleic acid, fumaric acid, tartaric acid, sorbic acid oxalic acid, alkylsulphonic acids (sulphonic acids having straight-chain or branched alkyl radicals of 1 to 20 carbon atoms), arylsulphonic acids or aryldisulphonic acids (aromatic radicals, such as phenyl and naphthyl, which carry one or two sulphonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulphonic acid, 1,5-naphthalenedisulphonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminium, tin and lead, and also of the first to eighth transition group, in particular chromium, manganese, iron, cobalt, nickel, copper, zinc and others. Particular preference is given to the metal ions of the elements of the fourth period. Here, the metals can be present in various valencies that they can assume.

The acid addition salts of the compounds of the formula (I) can be obtained in a simple manner by customary methods for forming salts, for example by dissolving a compound of the formula (I) in a suitable inert solvent and adding the acid, for example hydrochloric acid, and be isolated in a known manner, for example by filtration, and, if required, be purified by washing with an inert organic solvent.

Suitable anions of the salts are those which are preferably derived from the following acids: hydrohalic acids, such as, for example, hydrochloric acid and hydrobromic acid, furthermore phosphoric acid, nitric acid and sulphuric acid.

The metal salt complexes of compounds of the formula (I) can be obtained in a simple manner by customary processes, for example by dissolving the metal salt in alcohol, for example ethanol, and adding the solution to the compound of the formula (I). Metal salt complexes can be isolated in a known manner, for example by filtration, and, if required, be purified by recrystallization.

Salts of the intermediates can also be prepared according to the processes mentioned above for the salts of compounds of formula (I).

N-oxides of compounds of the formula (I) or intermediates thereof can be obtained in a simple manner by customary processes, for example by N-oxidation with hydrogen peroxide ($H_2O_2$), peracids, for example peroxy sulfuric acid or peroxy carboxylic acids, such as meta-chloroperoxybenzoic acid or peroxymonosulfuric acid (Caro's acid).

Methods and Uses

The invention also relates to a method for controlling unwanted microorganisms, characterized in that the compounds of the formula (I) are applied to the microorganisms and/or in their habitat.

The invention further relates to seed which has been treated with at least one compound of the formula (I).

The invention finally provides a method for protecting seed against unwanted microorganisms by using seed treated with at least one compound of the formula (I).

The compounds of the formula (I) have potent microbicidal activity and can be used for control of unwanted microorganisms, such as fungi and bacteria, in crop protection and in the protection of materials.

The compounds of the formula (I) have very good fungicidal properties and can be used in crop protection, for example for control of Plasmodiophoromycetes, Oomycetes, Chytridiomycetes, Zygomycetes, Ascomycetes, Basidiomycetes and Deuteromycetes.

Bactericides can be used in crop protection, for example, for control of Pseudomonadaceae, Rhizobiaceae, Enterobacteriaceae, Corynebacteriaceae and Streptomycetaceae.

The compounds of the formula (I) can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

Plants

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Plants which can be treated in accordance with the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *hMusaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

Pathogens

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita*, *Puccinia graminis* oder *Puccinia striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidial form: *Drechslera*, syn: *Helminthosporium*) or *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola*, *Mycosphaerella arachidicola* or *Mycosphaerella fijiensis*; *Phaeosphaeria* species, for example *Phaeosphaeria nodorum*; *Pyrenophora* species, for example *Pyrenophora teres* or *Pyrenophora tritici repentis*; *Ramularia* species, for example *Ramularia collo-cygni* or *Ramularia areola*; *Rhynchosporium* species, for example *Rhynchosporium secalis*; *Septoria* species, for example *Septoria apii* or *Septoria lycopersici*; *Stagonospora* species, for example *Stagonospora nodorum*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Plasmodiophora* species, for example *Plasmodiophora brassicae*; *Rhizoctonia* species, for example *Rhizoctonia solani*; *Sarocladium* species, for example *Sarocladium oryzae*; *Sclerotium* species, for example *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmomm*; *Gibberella* species, for example *Gibberella zeae*; *Monographella* species, for example *Monographella nivalis*; *Stagnospora* species, for example *Stagnospora nodorum*;

diseases caused by smut fungi, for example *Sphacelotheca* species, for example *Sphacelotheca reiliana*; *Tilletia* species, for example *Tilletia caries* or *Tilletia controversa*; *Urocystis* species, for example *Urocystis occulta*; *Ustilago* species, for example *Ustilago nuda*;

fruit rot caused, for example, by *Aspergillus* species, for example *Aspergillus flavus*; *Botrytis* species, for example *Botrytis cinerea*; *Penicillium* species, for example *Penicillium expansum* or *Penicillium purpurogenum*; *Rhizopus* species, for example *Rhizopus stolonifer*; *Sclerotinia* species, for example *Sclerotinia sclerotiorum*; *Verticilium* species, for example *Verticilium alboatrum*;

seed- and soil-borne rot and wilt diseases, and also diseases of seedlings, caused, for example, by *Alternaria* species, for example *Alternaria brassicicola*; *Aphanomyces* species, for example *Aphanomyces euteiches*; *Ascochyta* species, for example *Ascochyta lentis*; *Aspergillus* species, for example *Aspergillus flavus*; *Cladosporium* species, for example *Cladosporium herbarum*; *Cochliobolus* species, for example *Cochliobolus sativus* (conidial form: *Drechslera*, *Bipolaris* Syn: *Helminthosporium*); *Colletotrichum* species, for example *Colletotrichum coccodes*; *Fusarium* species, for example *Fusarium culmorum*; *Gibberella* species, for example *Gibberella zeae*; *Macrophomina* species, for example *Macrophomina phaseolina*; *Microdochium* species, for example *Microdochium nivale*; *Monographella* species, for example *Monographella nivalis*; *Penicillium* species, for example *Penicillium expansum*; *Phoma* species, for example *Phoma lingam*; *Phomopsis* species, for example *Phomopsis sojae*; *Phytophthora* species, for example *Phytophthora cactorum*; *Pyrenophora* species, for example *Pyrenophora graminea*; *Pyricularia* species, for example *Pyricularia oryzae*; *Pythium* species, for example *Pythium ultimum*; *Rhizoctonia* species, for example *Rhizoctonia solani*; *Rhizopus* species, for example *Rhizopus oryzae*; *Sclerotium* species, for example *Sclerotium rolfsii*; *Septoria* species, for example *Septoria nodorum*; *Typhula* species, for example *Typhula incarnata*; *Verticillium* species, for example *Verticillium dahliae*;

cancers, galls and witches' broom caused, for example, by *Nectria* species, for example *Nectria galligena*;

wilt diseases caused, for example, by *Monilinia* species, for example *Monilinia laxa*;

deformations of leaves, flowers and fruits caused, for example, by *Exobasidium* species, for example *Exobasidium vexans*; *Taphrina* species, for example *Taphrina deformans*;

degenerative diseases in woody plants, caused, for example, by *Esca* species, for example *Phaeomoniella chlamydospora*, *Phaeoacremonium aleophilum* or *Fomitiporia mediterranea*; *Ganoderma* species, for example *Ganoderma boninense*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Preference is given to controlling the following diseases of soya beans:

Fungal diseases on leaves, stems, pods and seeds caused, for example, by *Alternaria* leaf spot (*Alternaria* spec. *atrans tenuissima*), Anthracnose (*Colletotrichum gloeosporioides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*, *Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum*, *Fusarium orthoceras*, *Fusarium semitectum*, *Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum*, *Pythium irregulare*, *Pythium debaryanum*, *Pythium myriotylum*, *Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Plant Growth Regulation

In some cases, the compounds of the formula (I) can, at particular concentrations or application rates, also be used as growth regulators or agents to improve plant properties, or as microbicides, for example as fungicides, antimycotics, bactericides, viricides (including compositions against viroids) or as compositions against MLO (*Mycoplasma*-like organisms) and RLO (*Rickettsia*-like organisms).

The compounds of the formula (I) intervene in physiological processes of plants and can therefore also be used as plant growth regulators. Plant growth regulators may exert various effects on plants. The effect of the substances depends essentially on the time of application in relation to the developmental stage of the plant, and also on the amounts of active ingredient applied to the plants or their environment and on the type of application. In each case, growth regulators should have a particular desired effect on the crop plants.

Growth regulating effects, comprise earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased or improved yield is referring to total biomass per hectare, yield per hectare, kernel/fruit weight, seed size and/or hectoliter weight as well as to improved product quality, comprising:
improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;
further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;
further comprising increased desired ingredients such as e.g. protein content, fatty acids, oil content, oil quality, amino-acid composition, sugar content, acid content (pH), sugar/acid ratio (Brix), polyphenols, starch content, nutritional quality, gluten content/index, energy content, taste, etc.;
and further comprising decreased undesired ingredients such as e.g. less mycotoxines, less aflatoxines, geosmin level, phenolic aromas, lacchase, polyphenol oxidases and peroxidases, nitrate content etc.

Plant growth-regulating compounds can be used, for example, to slow down the vegetative growth of the plants. Such growth depression is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, vegetative growth depression allows denser planting, and it is thus possible to achieve higher yields based on the soil surface. Another advantage of the smaller plants obtained in this way is that the crop is easier to cultivate and harvest.

Reduction of the vegetative plant growth may also lead to increased or improved yields because the nutrients and assimilates are of more benefit to flower and fruit formation than to the vegetative parts of the plants.

Alternatively, growth regulators can also be used to promote vegetative growth. This is of great benefit when harvesting the vegetative plant parts. However, promoting vegetative growth may also promote generative growth in that more assimilates are formed, resulting in more or larger fruits.

Furthermore, beneficial effects on growth or yield can be achieved through improved nutrient use efficiency, especially nitrogen (N)-use efficiency, phosphours (P)-use efficiency, water use efficiency, improved transpiration, respiration and/or $CO_2$ assimilation rate, better nodulation, improved Ca-metabolism etc.

Likewise, growth regulators can be used to alter the composition of the plants, which in turn may result in an improvement in quality of the harvested products. Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Furthermore, growth regulators can modulate plant senescence, which may result in prolonged green leaf area duration, a longer grain filling phase, improved yield quality, etc.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"). In addition it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to synchronize maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

Resistance Induction/Plant Health and Other Effects

The compounds of the formula (I) also exhibit a potent strengthening effect in plants. Accordingly, they can be used for mobilizing the defences of the plant against attack by undesirable microorganisms.

Plant-strengthening (resistance-inducing) substances in the present context are substances capable of stimulating the defence system of plants in such a way that the treated plants, when subsequently inoculated with undesirable microorganisms, develop a high degree of resistance to these microorganisms.

Further, in context with the present invention plant physiology effects comprise the following:

Abiotic stress tolerance, comprising tolerance to high or low temperatures, drought tolerance and recovery after drought stress, water use efficiency (correlating to reduced water consumption), flood tolerance, ozone stress and UV tolerance, tolerance towards chemicals like heavy metals, salts, pesticides etc.

Biotic stress tolerance, comprising increased fungal resistance and increased resistance against nematodes, viruses and bacteria. In context with the present invention, biotic stress tolerance preferably comprises increased fungal resistance and increased resistance against nematodes.

Increased plant vigor, comprising plant health/plant quality and seed vigor, reduced stand failure, improved appearance, increased recovery after periods of stress, improved pigmentation (e.g. chlorophyll content, stay-green effects, etc.) and improved photosynthetic efficiency.

Mycotoxins

In addition, the compounds of the formula (I) can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The compounds of the formula (I) can also be used in the protection of materials, for protection of industrial materials against attack and destruction by phytopathogenic fungi.

In addition, the compounds of the formula (I) can be used as antifouling compositions, alone or in combinations with other active ingredients.

Industrial materials in the present context are understood to mean inanimate materials which have been prepared for use in industry. For example, industrial materials which are to be protected by inventive compositions from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compounds of the formula (I) may prevent adverse effects, such as rotting, decay, discoloration, decoloration or formation of mould.

In the case of treatment of wood the compounds of the formula (I) may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting a composition according to the invention; this includes for example direct application, spraying, dipping, injection or any other suitable means.

In addition, the compounds of the formula (I) can be used to protect objects which come into contact with saltwater or brackish water, especially hulls, screens, nets, buildings, moorings and signalling systems, from fouling.

The compounds of the formula (I) can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)dying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive compositions may prevent adverse effects, such as rotting, decay, discoloration, decoloration or formation of mould.

Microorganisms capable of degrading or altering the industrial materials include, for example, bacteria, fungi, yeasts, algae and slime organisms. The compounds of the formula (I) preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae*.

Formulations

The present invention further relates to a composition for controlling unwanted microorganisms, comprising at least one of the compounds of the formula (I). These are preferably fungicidal compositions which comprise agriculturally suitable auxiliaries, solvents, carriers, surfactants or extenders.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid carriers include: for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or aiylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural products impregnated with active ingredient, synthetic substances impregnated with active ingredient, fertilizers and also microencapsulations in polymeric substances.

The active ingredients can be applied as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspoemulsion concentrates, natural products impregnated with active ingredient, synthetic substances impregnated with active ingredient, fertilizers and also microencapsulations in polymeric substances. Application is accomplished in a customary manner, for example by watering, spraying, atomizing, broadcasting, dusting, foaming, spreading-on and the like. It is also possible to deploy the active ingredients by the ultra-low volume method or to inject the active ingredient preparation/the active ingredient itself into the soil. It is also possible to treat the seed of the plants.

The formulations mentioned can be prepared in a manner known per se, for example by mixing the active ingredients with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

The present invention includes not only formulations which are already ready for use and can be deployed with a suitable apparatus to the plant or the seed, but also commercial concentrates which have to be diluted with water prior to use.

The compounds of the formula (I) may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The auxiliaries used may be those substances which are suitable for imparting particular properties to the composition itself or and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Compositions comprising compounds of the formula (I) may additionally comprise further components, for example surfactants. Suitable surfactants are emulsifiers and/or foam formers, dispersants or wetting agents having ionic or non-ionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, other additional components may also be present, for example protective colloids, binders, adhesives, thickeners, thixotropic substances, penetrants, stabilizers, sequestering agents, complex formers. In general, the active ingredients can be combined with any solid or liquid additive commonly used for formulation purposes.

The formulations contain generally between 0.05 and 99% by weight, 0.01 and 98% by weight, preferably between 0.1 and 95% by weight, more preferably between 0.5 and 90% of active ingredient, most preferably between 10 and 70 percent by weight.

The formulations described above can be used for controlling unwanted microorganisms, in which the compositions comprising compounds of the formula (I) are applied to the microorganisms and/or in their habitat.

Mixtures

Compounds of the formula (I) can be used as such or in formulations thereof and can be mixed with known fungicides, bactericides, acaricides, nematicides or insecticides, in order thus to broaden, for example, the activity spectrum or to prevent development of resistance.

Useful mixing partners include, for example, known fungicides, insecticides, acaricides, nematicides or else bactericides (see also Pesticide Manual, 14th ed.).

A mixture with other known active ingredients, such as herbicides, or with fertilizers and growth regulators, safeners and/or semiochemicals, is also possible.

Seed Treatment

The invention furthermore includes a method for treating seed.

A further aspect of the present invention relates in particular to seeds (dormant, primed, pregerminated or even with emerged roots and leaves) treated with at least one of the compounds of the formula (I). The inventive seeds are used in methods for protection of seeds and emerged plants from the seeds from phytopathogenic harmful fungi. In these methods, seed treated with at least one inventive active ingredient is used.

The compounds of the formula (I) are also suitable for the treatment of seeds and young seedlings. A large part of the damage to crop plants caused by harmful organisms is triggered by the infection of the seeds before sowing or after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

It is also desirable to optimize the amount of the active ingredient used so as to provide the best possible protection for the seeds, the germinating plants and emerged seedlings from attack by phytopathogenic fungi, but without damaging the plants themselves by the active ingredient used. In particular, methods for the treatment of seed should also take into consideration the intrinsic phenotypes of transgenic plants in order to achieve optimum protection of the seed and the germinating plant with a minimum of crop protection compositions being employed.

The present invention therefore also relates to a method for protecting seeds, germinating plants and emerged seedlings against attack by animal pests and/or phytopathogenic harmful microorganisms by treating the seeds with an inventive composition. The invention also relates to the use of the compositions according to the invention for treating seeds for protecting the seeds, the germinating plants and emerged seedlings against animal pests and/or phytopathogenic microorganisms. The invention further relates to seeds which has been treated with an inventive composition for protection from animal pests and/or phytopathogenic microorganisms.

One of the advantages of the present invention is that the treatment of the seeds with these compositions not only protects the seed itself, but also the resulting plants after emergence, from animal pests and/or phytopathogenic harmful microorganisms. In this way, the immediate treatment of the crop at the time of sowing or shortly thereafter protect plants as well as seed treatment in prior to sowing. It is likewise considered to be advantageous that the inventive active ingredients or compositions can be used especially also for transgenic seed, in which case the plant which grows from this seed is capable of expressing a protein which acts against pests, herbicidal damage or abiotic stress. The treatment of such seeds with the inventive active ingredients or compositions, for example an insecticidal protein, can result in control of certain pests. Surprisingly, a further synergistic effect can be observed in this case, which additionally increases the effectiveness for protection against attack by pests, microorganisms, weeds or abiotic stress.

The compounds of the formula (I) are suitable for protection of seed of any plant variety which is used in agriculture, in the greenhouse, in forests or in horticulture. More particularly, the seed is that of cereals (such as wheat, barley, lye, millet and oats), oilseed rape, maize, cotton, soybeen, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

As also described below, the treatment of transgenic seed with the inventive active ingredients or compositions is of particular significance. This refers to the seed of plants containing at least one heterologous gene which allows the expression of a polypeptide or protein, e.g. having insecticidal properties. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originates from *Bacillus* sp., in which case the gene product is effective against the European corn borer and/or the Western corn rootworm. Particularly preferably, the heterologous genes originate from *Bacillus thuringiensis*.

In the context of the present invention, the inventive composition is applied to seeds either alone or in a suitable formulation. Preferably, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pre-germinated seeds, or seeds sown on nursery trays, tapes or paper.

When treating the seeds, it generally has to be ensured that the amount of the inventive composition applied to the seed and/or the amount of further additives is selected such that the germination of the seed is not impaired, or that the resulting plant is not damaged. This must be ensured particularly in the case of active ingredients which can exhibit phytotoxic effects at certain application rates.

The compounds of the formula (I) can be applied directly, i.e. without containing any other components and without having been diluted. In general, it is preferable to apply the compositions to the seed in the form of a suitable formulation. Suitable formulations and methods for seed treatment are known to those skilled in the art. The compounds of the formula (I) can be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV formulations.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the dilute preparations thereof, can also be used for seeds of transgenic plants. In this case, additional synergistic effects may also occur in interaction with the substances formed by expression.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The application rate of the formulations usable in accordance with the invention can be varied within a relatively wide range. It is guided by the particular content of the active ingredients in the formulations and by the seeds. The application rates of each single active ingredient is generally between 0.001 and 15 g per kilogram of seed, preferably between 0.01 and 5 g per kilogram of seed.

Antimycotic Effects

In addition, the compounds of the formula (I) also have very good antimycotic effects. They have a very broad antimycotic activity spectrum, especially against dermatophytes and yeasts, moulds and diphasic fungi (for example against *Candida* species, such as *Candida albicans*, *Candida glabrata*), and *Epidermophyton floccosum*, *Aspergillus* species, such as *Aspergillus niger* and *Aspergillus fumigatus*, *Trichophyton* species, such as *Trichophyton mentagrophytes*, *Microsporon* species such as *Microsporon canis* and *audouinii*. The enumeration of these fungi by no means constitutes a restriction of the mycotic spectrum covered, and is merely of illustrative character.

The compounds can be used also to control important fungal pathogens in fish and crustacea farming, e.g. saprolegnia diclina in trouts, saprolegnia *parasitica* in crayfish.

The compounds of the formula (I) can therefore be used both in medical and in non-medical applications.

The compounds of the formula (I) can be used as such, in the form of their formulations or the use forms prepared therefrom, such as ready-to-use solutions, suspensions, wettable powders, pastes, soluble powders, dusts and granules. Application is accomplished in a customary manner, for example by watering, spraying, atomizing, broadcasting, dusting, foaming, spreading-on and the like. It is also possible to deploy the active ingredients by the ultra-low volume method or to inject the active ingredient preparation/the active ingredient itself into the soil. It is also possible to treat the seed of the plants.

GMO

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as Tobacco plants, with altered post-translational protein modification patterns.

Application Rates

When using the compounds of the formula (I) as fungicides, the application rates can be varied within a relatively wide range, depending on the kind of application. The application rate of the inventive active ingredients is
- in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used);
- in the case of seed treatment: from 0.1 to 200 g per 100 kg of seed, preferably from 1 to 150 g per 100 kg of seed, more preferably from 2.5 to 25 g per 100 kg of seed, even more preferably from 2.5 to 12.5 g per 100 kg of seed;
- in the case of soil treatment: from 0.1 to 10 000 g/ha, preferably from 1 to 5000 g/ha.

These application rates are merely by way of example and are not limiting for the purposes of the invention.

The invention is illustrated by the examples below. However, the invention is not limited to the examples.

EXAMPLES

Preparation Examples

Preparation of Compounds of the Formula (I-27) According to Process H

Preparation of 2-(1-chlorocyclopropyl)-1-(4-chloro-2-fluorophenyl)-3-(5-chloro-1H-imidazol-1-yl)propan-2-ol (I-27)

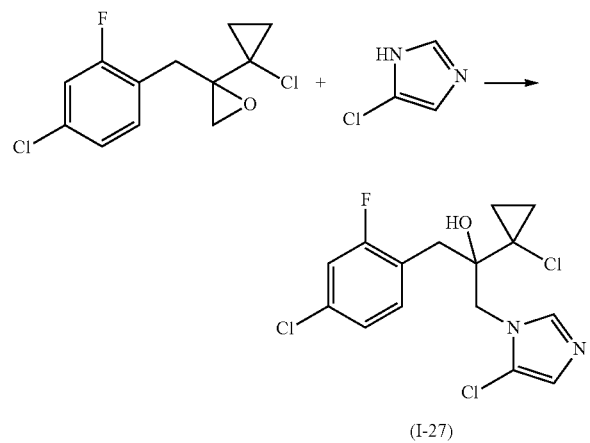

(I-27)

A solution of 4-chloro-1H-imidazole (1.10 g, 4 eq, 10.7 mmol) and 2-(1-chlorocyclopropyl)-2-(4-chloro-2-fluorobenzyl)oxirane (700 mg, 1 eq, 2.68 mmol) in 5 mL acetonitrile was heated up to 150° C. by microwave irradiation for 90 min. Thereafter the reaction mixture was diluted with dichloromethane, the organic layer washed with sat. aq. NaHCO$_3$ and dried (MgSO$_4$), then concentrated to dryness in vacuo. The residue was purified by chromatography over silica gel, eluted with a mixture of n-heptane/ethyl acetate (100:0 to 50:50). After evaporation of the solvent 251 mg (24%) of 2-(1-chlorocyclopropyl)-1-(4-chloro-2-fluorophenyl)-3-(5-chloro-1H-imidazol-1-yl)propan-2-ol (I-27) were obtained as colourless solid.

MS (ESI): 363.0 ([M+H]$^+$)

Preparation of Compounds of the Formula (I-27) According to Process M

Preparation of 2-(1-chlorocyclopropyl)-1-(4-chloro-2-fluorophenyl)-3-(5-chloro-1H-imidazol-1-yl)propan-2-ol (I-27)

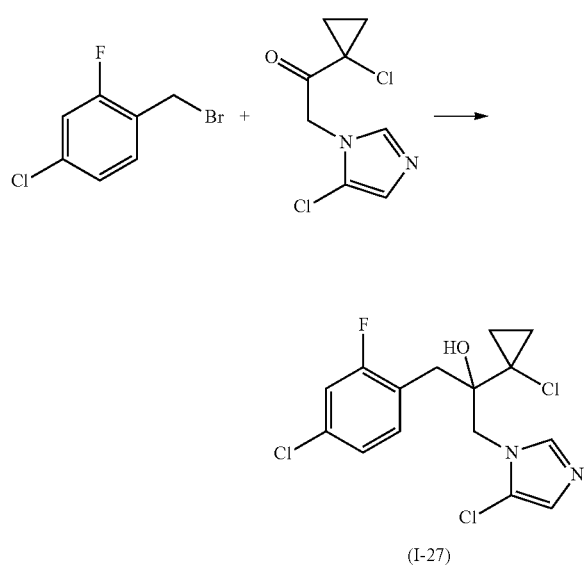

(I-27)

At 0-5° C. (ice/NaCl bath) a solution of 4-chloro-2-fluorobenzyl bromide (5.97 g, 26.7 mmol, 1.3 eq) in Et$_2$O (5 mL) was added dropwise to a suspension of magnesium turnings (1.50 g, 61.6 mmol, 3.0 equiv; activated by stirring 1 h at rt under Argon in the presence of a catalytic amount of iodine) in Et$_2$O (15 mL). The mixture was stirred 45 min at 5° C. Titration of the resulting solution using N-phenylsalicylhydrazone as an indicator (Love & Jones, J. Org. Chem. 1999, 64, 3755) gave the concentration as 1.2 M.

To this solution at 5° C. was added a solution of 1-(1-chlorocyclopropyl)-2-(5-chloro-1H-imidazol-1-yl)ethanone (5.00 g, 20.5 mmol, 1.0 eq) in Et$_2$O (30 mL) dropwise over 5 min. The reaction mixture was further stirred while allowed to warm up to room temperature over 1 h. To the resulting solution, cooled down to 5° C., was added sat. aq. NH$_4$Cl. The resulting mixture was diluted with water, then extracted with ethyl acetate (3×20 mL). The combined organic layers were washed with sat. aq. NaHCO$_3$, dried (MgSO$_4$), then concentrated to dryness in vacuo. The oily residue was purified by chromatography over silica gel, eluted with a mixture of n-heptane/ethyl acetate (100:0 to 60:40). After evaporation of the solvent, followed by trituration in n-heptane:Et$_2$O (50:50), a colourless solid precipitated which was filtered off and washed with n-heptane to afford 2.27 g (30%) of 2-(1-chlorocyclopropyl)-1-(4-chloro-2-fluorophenyl)-3-(5-chloro-1H-imidazol-1-yl)propan-2-ol (I-27) as a colourless solid.

MS (ESI): 363.0 ([M+H]$^+$)

Preparation of Compounds of the Formula (I-06) According to Process H

Preparation of 1-[2-(1-chlorocyclopropyl)-3-(2-chlorophenyl)-2-hydroxypropyl]-1H-imidazole-5-carbonitrile (I-06)

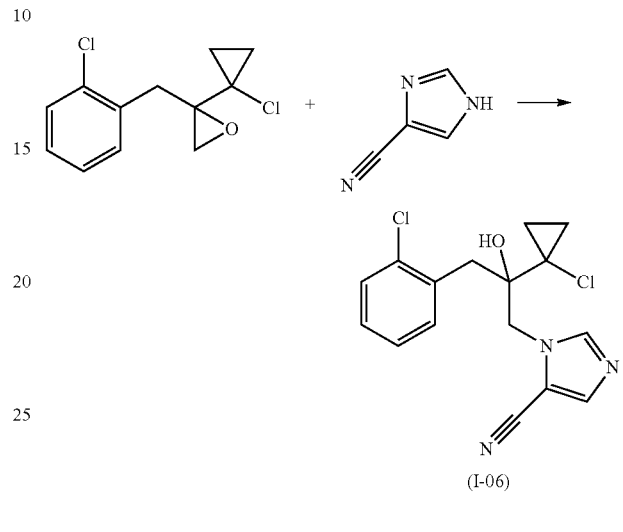

(I-06)

A solution of 4-cyano-1H-imidazole (500 mg, 1.0 eq, 5.37 mmol) and 2-(2-chlorobenzyl)-2-(1-chlorocyclopropyl)oxirane (1.96 g, 1.5 eq, 8.05 mmol) in a mixture of acetonitrile (3 mL) and DMF (1 mL) was heated up to 160° C. by microwave irradiation for 90 min. Thereafter the reaction mixture was diluted with dichloromethane, the organic layer washed with sat. aq. NaHCO$_3$ and dried (MgSO$_4$), then concentrated to dryness in vacuo. Purification of the residue by flash chromatography [over silica gel, eluted with a mixture of n-heptane/ethyl acetate (100:0 to 50:50)] followed by preparative HPLC afforded, after evaporation of the solvents, afforded 112 mg (6%) 1-[2-(1-chlorocyclopropyl)-3-(2-chlorophenyl)-2-hydroxypropyl]-1H-imidazole-5-carbonitrile (I-06) as a colourless oil.

MS (ESI): 336.1 ([M+H]$^+$)

Preparation of Compounds of the Formula (I-34) According to Process M

Preparation of 1-[2-(1-chlorocyclopropyl)-3-(2-fluorophenyl)-2-hydroxypropyl]-1H-imidazole-5-carbonitrile (I-34)

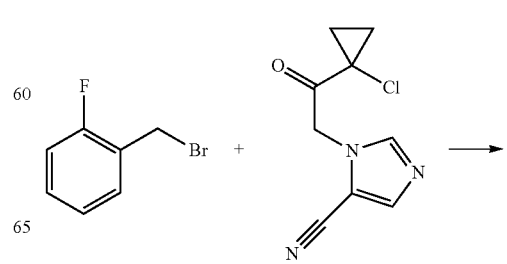

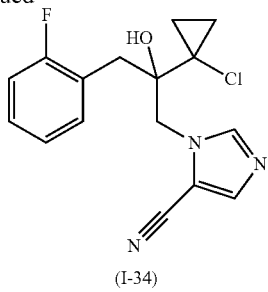

(I-34)

At 0-5° C. (ice/NaCl bath) a solution of 2-fluorobenzyl bromide (1.30 g, 6.86 mmol, 1.2 eq) in Et$_2$O (5 mL) was added dropwise to a suspension of magnesium turnings (417 mg, 17.1 mmol, 3.0 equiv; activated by stirring at rt under Argon in the presence of a catalytic amount of iodine) in Et$_2$O (15 mL). The mixture was stirred 45 min at 5° C.

To this solution at 0-5° C. was added a solution of 1-[2-(1-chlorocyclopropyl)-2-oxoethyl]-1H-imidazole-5-carbonitrile (2.00 g, 60% purity, 5.72 mmol, 1.0 eq) in Et$_2$O (30 mL) dropwise over 5 min. The reaction mixture was further stirred while allowed to warm up to room temperature over 1 h. To the resulting solution, cooled down to 5° C., was added sat. aq. NH$_4$Cl. The resulting mixture was diluted with water, then extracted with ethyl acetate (3×20 mL). The combined organic layers were washed with sat. aq. NaHCO$_3$, dried (MgSO$_4$), then concentrated to dryness in vacuo. The oily residue was purified by chromatography over silica gel, eluted with a mixture of n-heptane/ethyl acetate (100:0 to 60:40). After evaporation of the solvent, 218 mg (12%) of 1-[2-(1-chlorocyclopropyl)-3-(2-fluorophenyl)-2-hydroxypropyl]-1H-imidazole-5-carbonitrile (I-34) were obtained as a yellow oil.

MS (ESI): 320.1 ([M+H]$^+$)

Preparation of Intermediates of the Formula (XII-1) According to Process D

Preparation of 2-(1-chlorocyclopropyl)-2-(4-chloro-2-fluorobenzyl)oxirane (XII-1)

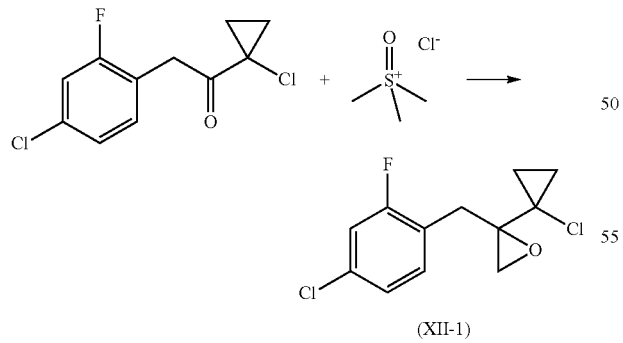

(XII-1)

To a solution of trimethylsulfoxonium chloride (2.50 g, 1.2 eq, 19.4 mmol) in THF (80 mL) at 0° C. and under Argon atmosphere was added sodium hydride (60% in mineral oil, 777 mg, 1.2 eq, 19.4 mmol). The resulting suspension was stirred at 0° C. for 30 min, then a solution of 1-(1-chlorocyclopropyl)-2-(4-chloro-2-fluorophenyl)ethanone (4.00 g, 1.0 eq, 16.1 mmol) in THF (10 mL) was added. The mixture was stirred for 2 h at 0° C., then for 20 h at room temperature. After careful addition of water, the obtained solution extracted with ethyl acetate. The organic phase was dried (MgSO$_4$), then concentrated to dryness in vacuo. Purification by column chromatography over silica gel (eluent n-heptane/ethyl acetate 95:5) afforded, after evaporation of the solvent, 3.69 g (81%) of 2-(1-chlorocyclopropyl)-2-(4-chloro-2-fluorobenzyl)oxirane (XII-1) as a colourless oil.

MS (EI): 260.0 ([M]$^+$)

Preparation of Intermediates of the Formula (XVII) According to Process K

Preparation of 1-(1-chlorocyclopropyl)-2-(5-chloro-1H-imidazol-1-yl)ethanone (XVII-1)

Step 1: Preparation of 1-allyl-4-chloro-1H-imidazole

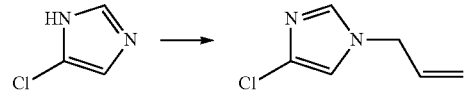

To a solution of 4-chloro-1H-imidazole (180 g, 1.76 mol, 1.00 eq) in dry dichloromethane (3.0 L) at 0° C. was added aq. NaOH (1 M, 2.11 L, 2.11 mmol, 1.20 eq) followed by tetra-n-butylammonium bromide (56.6 g, 0.176 mol, 0.10 eq). To this biphasic solution was added dropwise allyl bromide (167 mL, 1.93 mol, 1.10 eq) and the resulting mixture was stirred at room temperature for 20 h. Thereafter the reaction mixture was diluted with water (1 L), extracted with dichloromethane (2×1 L), the combined organic layers were dried (MgSO$_4$) and concentrated in vacuo, to provide 290 g of a mixture of regioisomers (80% purity, 93% yield), which were separated by distillation at reduced pressure (0.1 mbar).

MS (EI): 142.1 ([M]$^+$)

Step 2: Preparation of 1-allyl-4-chloro-3-[2-(1-chlorocyclopropyl)-2-oxoethyl]-1H-imidazol-3-ium iodide

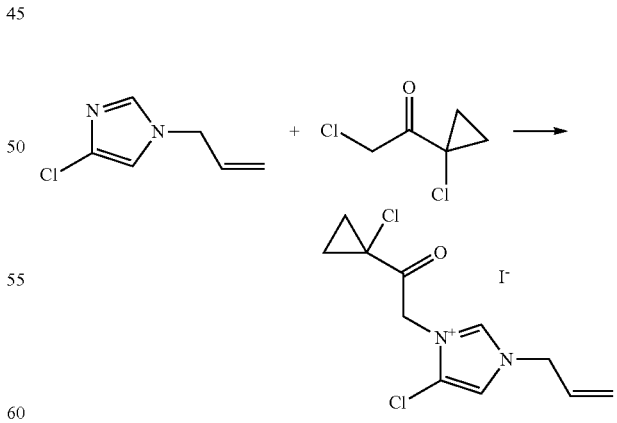

A solution of 1-allyl-4-chloro-1H-imidazole (15.0 g, 105 mmol, 1 eq), 2-chloro-1-(1-chlorocyclopropyl)ethanone (19.3 g, 126 mmol, 1.20 eq) and potassium iodide (21.1 g, 127 mmol, 1.21 eq) in dry methanol (100 mL) was stirred at room temperature for 1 h, then at 70° C. for 21 h. Thereafter, the reaction mixture was concentrated in vacuo, and diluted with cold ethyl acetate, whereupon a solid precipitated. The precipitate was filtered off to afford 34.6 g (830%) of 1-allyl-4-chloro-3-[2-(1-chlorocyclopropyl)-2-oxoethyl]-1H-imidazol-3-ium iodide as an off-white solid.

MS (ESI): 259.1 ([M-I]$^+$)

Step 3: Preparation of 1-(1-chlorocyclopropyl)-2-(5-chloro-1H-imidazol-1-yl)ethanone (XVII-1)

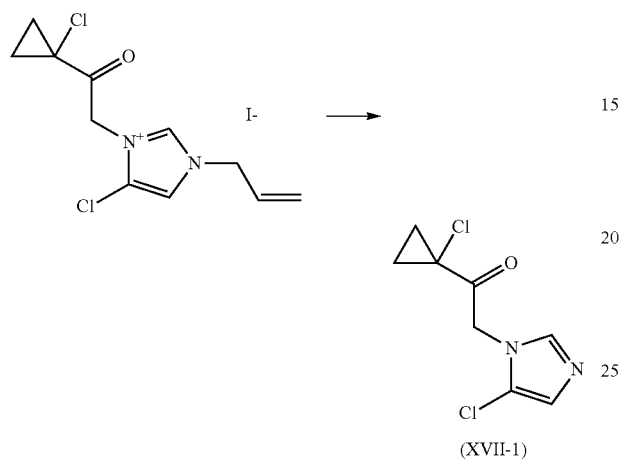

(XVII-1)

To a solution of 1-allyl-4-chloro-3-[2-(1-chlorocyclopropyl]-2-oxoethyl]-1H-imidazol-3-ium iodide (28.54 g, 75.6 mmol, 1 eq) and morpholine (10.1 g, 115 mmol, 1.52 eq) in dry dichloromethane (150 mL), previously degassed by bubbling a flow of Argon through it for 10 min, was added tetrakis(triphenylphosphine)palladium(0) (1.12 g, 0.96 mmol, 0.013 eq). The resulting mixture was stirred at room temperature for 2 h 30, then diluted with water and extracted with ethyl acetate (3×50 mL). The combined organic layers were washed with sat. aq. NH$_4$Cl, dried and concentrated to dryness in vacuo. Purification by column chromatography over silica gel (eluent DCM/MeOH 100:0 to 60:40) afforded, after evaporation of the solvent, 12.5 g (58%) of 1-(1-chlorocyclopropyl)-2-(5-chloro-1H-imidazol-1-yl)ethanone (XVII-1) as an orange-coloured oil.

MS (ESI): 219.1 ([M+H]$^+$)

Preparation of 1-(1-chlorocyclopropyl)-2-(5-chloro-1H-imidazol-1-yl)ethanone (XVII-2)

Step 1: Preparation of 1-allyl-1H-imidazole-4-carbonitrile

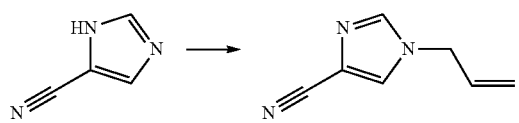

To a solution of 1-H-imidazole-5-carbonitrile (100 g, 1.02 mol, 1.00 eq) in dry dichloromethane (3.0 L) at 0° C. was added aq. NaOH (1 M, 1.23 L, 1.23 mmol, 1.20 eq) followed by tetra-n-butylammonium bromide (32.9 g, 0.102 mol, 0.10 eq). To this biphasic solution was added dropwise allyl bromide (92.7 mL, 1.07 mol, 1.05 eq) and the resulting mixture was stirred at room temperature for 20 h. Thereafter the reaction mixture was diluted with water (1 L), extracted with dichloromethane (2×1 L), the combined organic layers were dried (MgSO$_4$) and concentrated in vacuo, to provide 163 g of a 75:25 mixture of regioisomers (80% purity, 96% yield), which were separated by distillation at reduced pressure (0.1-0.2 mbar).

MS (EI): 133.1 ([M]$^+$)

Step 2: Preparation of 1-allyl-3-[2-(1-chlorocyclopropyl)-2-oxoethyl]-4-cyano-1H-imidazol-3-ium iodide

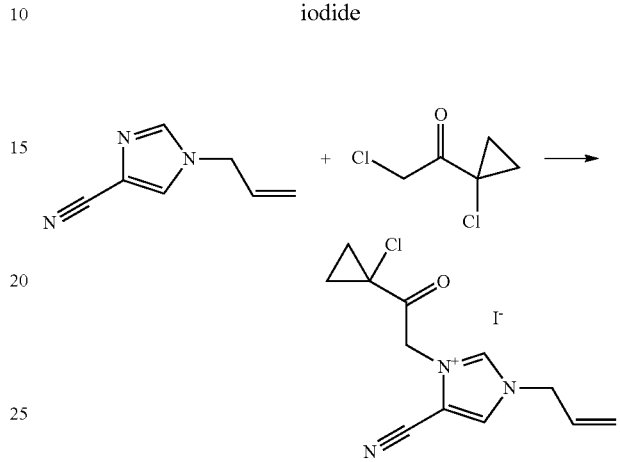

A solution of 1-allyl-4-chloro-1H-imidazole (50.0 g, 375 mmol, 1 eq), 2-chloro-1-(1-chlorocyclopropyl)ethanone (68.9 g, 450 mmol, 1.20 eq) and potassium iodide (31.2 g, 187 mmol, 0.50 eq) in dry methanol (150 mL) was stirred at 70° C. for 46 h. Thereafter, the reaction mixture was concentrated in vacuo, and diluted with toluene. The resulting solution was extracted with water, the aqueous phase washed with diisopropyl ether, then concentrated to dryness in vacuo. The residue was dissolved in acetonitrile, the insoluble were filtered off and the filtrate concentrated to dryness in vacuo to afford 98.6 g (46%) of 1-allyl-3-[2-(1-chlorocyclopropyl)-2-oxoethyl]-4-cyano-1H-imidazol-3-ium iodide (purity 66%) as a brown oil.

MS (ESI): 250.9 ([M-I]$^+$)

Step 3: Preparation of 1-[2-(1-chlorocyclopropyl)-2-oxoethyl]-1H-imidazole-5-carbonitrile (XVII-2)

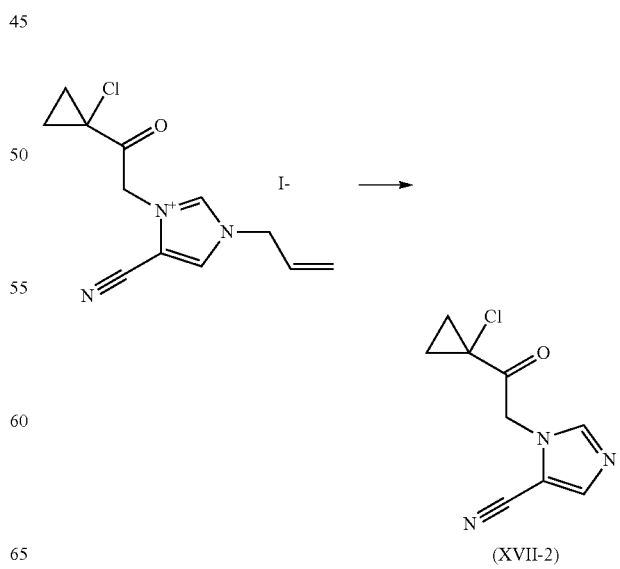

(XVII-2)

To a solution of 1-allyl-3-[2-(1-chlorocyclopropyl)-2-oxoethyl]-4-cyano-1H-imidazol-3-ium iodide (13.49 g, 67% purity, 23.9 mmol, 1 eq) and morpholine (2.51 g, 28.7 mmol, 1.2 eq) in dry dichloromethane (150 mL), previously degassed by bubbling a flow of Argon through it for 10 min, was added tetrakis(triphenylphosphine)palladium(0) (553 mg, 0.47 mmol, 0.020 eq). The resulting mixture was stirred at room temperature for 24 h, then diluted with water and extracted with dichloromethane. The combined organic layers were dried (MgSO$_4$) and concentrated to dryness in vacuo. Purification by 2 column chromatographies over silica gel (first one: eluent DCM/MeOH 100:0 to 60:40; second one: eluent DCM/MeCN 100:0 to 95:5) afforded, after evaporation of the solvents, 5.12 g (55% purity, 56% yield) of 1-[2-(1-chlorocyclopropyl)-2-oxoethyl]-1H-imidazole-5-carbonitrile (XVII-2) as an orange-coloured oil.

MS (ESI): 210.0 ([M+H]$^+$)

Preparation of Compounds of the Formula (XVII-2) According to Process L

Preparation of 3-[2-(1-chlorocyclopropyl)-2-oxoethyl]imidazole-4-carbonitrile (XVII-2)

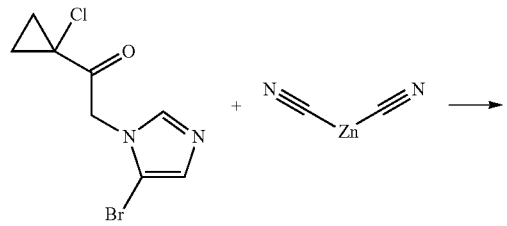

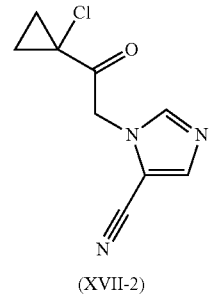

(XVII-2)

In a 500 mL teflon microwave reactor was placed 2-(5-bromoimidazol-1-yl)-1-(1-chlorocyclopropyl)ethanone (15.5 g, 1 eq, 58.8 mmol, 90% pure), Zn(CN)$_2$ (7.60 g, 1.1 eq, 64.7 mmol), and Pd(PPh$_3$)$_4$ (13.6 g, 0.2 eq, 11.7 mmol) in DMF (230 mL). The reactor was placed in the microwave and heated at 160° C. for 10 min. The mixture was then concentrated, and taken up in a mixture of water and ethyl acetate. To remove the palladium salts, the mixture was passed over a silica plug which was washed with ethyl acetate. To the filtrate was added water, the phases were separated, and the aqueous phase was extracted three times with ethyl acetate. The combined organic extracts were then washed with an aqueous solution of LiCl, dried, and concentrated. The crude product was purified by chromatography over silica (gradient 100% DCM to 100% of a mixture DCM/MeOH=9/1 as eluent). After evaporation of the solvent 14.2 g (61% yield, 53% pure) of the target compound (XVII-2) (contaminated with Ph$_3$P) was obtained as a brown oil which was used without further purification.

MS (ESI): 210.0 ([M+H]$^+$)

The following Table 1 illustrates in a non-limiting manner examples of compounds according to formula (I).

TABLE 1

(I)

| Ex N° | Q | R$^1$ | R$^2$ | R$^3$ | R$^4$ | R$^5$ | LogP |
|---|---|---|---|---|---|---|---|
| I-01 | 2-chlorophenyl | 1-chlorocyclopropyl | H | methoxycarbonyl | H | H | 2.82[a] |
| I-02 | 2-chlorophenyl | 1-chlorocyclopropyl | H | chloro | H | H | 2.32[a], 2.00[c] |
| I-03 | 2-chlorophenyl | 1-chlorocyclopropyl | H | methyl | H | H | 1.72[a] |
| I-04 | 2-chlorophenyl | 1-chlorocyclopropyl | H | bromo | H | H | 2.27[a] |
| I-05 | 2-chlorophenyl | 1-chlorocyclopropyl | H | chloro | fluoro | H | 2.17[a] |
| I-06 | 2-chlorophenyl | 1-chlorocyclopropyl | H | cyano | H | H | 2.92[a] |
| I-07 | 2-chloropyridin-3-yl | 1-chlorocyclopropyl | H | chloro | H | H | 1.57[a] |
| I-08 | 2-chloro-4-fluorophenyl | 1-chlorocyclopropyl | H | chloro | H | H | 2.47[a] |
| I-09 | 2-chlorophenyl | 1-chlorocyclopropyl | H | phenyl | H | H | 2.30[a] |
| I-10 | 2-chloropyridin-3-yl | 1-chlorocyclopropyl | H | methyl | H | H | 1.22[a] |
| I-11 | 2,4-dichloropyridin-3-yl | 1-chlorocyclopropyl | H | chloro | H | H | 2.02[a] |
| I-12 | 2-chlorophenyl | 1-chlorocyclopropyl | H | formyl | H | H | 2.80[a] |
| I-13 | 2-chlorophenyl | 1-chlorocyclopropyl | H | methyl | fluoro | H | 1.75[a] |
| I-14 | 2-chlorophenyl | 1-chlorocyclopropyl | H | iodo | H | H | 2.14[a] |
| I-15 | 2-chlorophenyl | 1-chlorocyclopropyl | H | trifluoromethyl | H | H | 3.63[a] |
| I-16 | 2-chlorophenyl | 1-chlorocyclopropyl | H | fluoro | H | H | 1.94[a] |
| I-17 | 2,5-dichloropyridin-4-yl | 1-chlorocyclopropyl | H | chloro | H | H | 2.18[a] |
| I-18 | 5-chloro-2-fluoropyridin-4-yl | 1-chlorocyclopropyl | H | chloro | H | H | 2.01[a] |
| I-19 | 2-chlorophenyl | 1-chlorocyclopropyl | H | acetyl | H | H | 2.90[a] |
| I-20 | 2-chlorophenyl | 1-chlorocyclopropyl | H | 2-thienyl | H | H | 2.21[a] |

TABLE 1-continued (I)

| Ex N° | Q | R¹ | R² | R³ | R⁴ | R⁵ | LogP |
|---|---|---|---|---|---|---|---|
| I-21 | 2-chlorophenyl | 1-chlorocyclopropyl | H | cyanomethyl | H | H | 1.66[a] |
| I-22 | 2-chlorophenyl | 1-chlorocyclopropyl | H | methylthio | H | H | 2.08[a] |
| I-23 | 2-chlorophenyl | 1-chlorocyclopropyl | H | bromo | fluoro | H | 2.32[a] |
| I-24 | 2-chlorophenyl | 1-chlorocyclopropyl | H | cyano | fluoro | H | 2.82[a] |
| I-25 | 2-chloropyridin-3-yl | 1-chlorocyclopropyl | H | bromo | H | H | 1.56[a] |
| I-26 | 2-chloropyridin-3-yl | 1-chlorocyclopropyl | H | cyano | H | H | 2.01[a] |
| I-27(*) | 4-chloro-2-fluorophenyl | 1-chlorocyclopropyl | H | chloro | H | H | 2.48[a] |
| I-28 | 2-fluorophenyl | 1-chlorocyclopropyl | H | chloro | fluoro | H | 2.01[a] |
| I-29(*) | 4-chloro-2-fluorophenyl | 1-chlorocyclopropyl | H | cyano | H | H | 3.02[a] |
| I-30 | 4-chloro-2-fluorophenyl | 1-chlorocyclopropyl | H | bromo | H | H | 2.55[a] |
| I-31 | 2-fluorophenyl | 1-chlorocyclopropyl | H | cyano | fluoro | H | 2.51[a] |
| I-32 | 2-fluorophenyl | 1-chlorocyclopropyl | H | chloro | H | H | 2.07[a] |
| I-33 | 2-fluorophenyl | 1-chlorocyclopropyl | H | bromo | H | H | 2.10[a] |
| I-34(*) | 2-fluorophenyl | 1-chlorocyclopropyl | H | cyano | H | H | 2.64[a] |
| I-35 | 2-fluorophenyl | 1-chlorocyclopropyl | H | methoxy | H | H | 1.67[a] |
| I-36 | 2-fluorophenyl | 1-chlorocyclopropyl | H | ethynyl | H | H | 1.89[a] |
| I-37 | 2-fluorophenyl | 1-chlorocyclopropyl | H | cyclopropyl | H | H | 1.86[a] |
| I-38 | 2-chlorophenyl | 1-chlorocyclopropyl | H | ethynyl | H | H | 2.09[a] |
| I-39 | phenyl | 1-chlorocyclopropyl | H | chloro | H | H | 2.04[a] |
| I-40 | 2-bromophenyl | 1-chlorocyclopropyl | H | cyano | H | H | 3.06[a] |
| I-41 | 4-bromo-2-chlorophenyl | 1-chlorocyclopropyl | H | cyano | H | H | 3.52[a] |
| I-42 | 4-bromo-2-fluorophenyl | 1-chlorocyclopropyl | H | cyano | H | H | 3.24[a] |
| I-43 | 4-bromo-2-chlorophenyl | 1-chlorocyclopropyl | H | chloro | H | H | 3.02[a] |
| I-44 | 4-bromo-2-fluorophenyl | 1-chlorocyclopropyl | H | chloro | H | H | 2.64[a] |
| I-45 | 3-bromophenyl | 1-chlorocyclopropyl | H | cyano | H | H | 3.04[a] |
| I-46 | 3-bromopyridin-4-yl | 1-chlorocyclopropyl | H | cyano | H | H | 1.94[a] |
| I-47 | 2,5-dibromopyridin-4-yl | 1-chlorocyclopropyl | H | cyano | H | H | 2.73[a] |
| I-48 | 2,3-dibromopyridin-4-yl | 1-chlorocyclopropyl | H | cyano | H | H | 2.60[a] |
| I-49 | 2,3-dichlorophenyl | 1-chlorocyclopropyl | H | cyano | H | H | 3.25[a] |
| I-50 | 2,3-dichloropyridin-4-yl | 1-chlorocyclopropyl | H | cyano | H | H | 2.47[a] |
| I-51 | 2,4-dimethylphenyl | 1-chlorocyclopropyl | H | cyano | H | H | 3.27[a] |
| I-52 | 2,4-dichlorophenyl | 1-chlorocyclopropyl | H | cyano | H | H | 3.42[a] |
| I-53 | 2-chloro-4-(4-chlorophenoxy)phenyl | 1-chlorocyclopropyl | H | cyano | H | H | 4.54[a] |
| I-54 | 2-methylphenyl | 1-chlorocyclopropyl | H | cyano | H | H | 2.96[a] |
| I-55 | 2-methoxyphenyl | 1-chlorocyclopropyl | H | cyano | H | H | 2.93[a] |
| I-56 | 2,5-dichloropyridin-4-yl | 1-chlorocyclopropyl | H | cyano | H | H | 2.62[a] |
| I-57 | 3-chloropyridin-4-yl | 1-chlorocyclopropyl | H | cyano | H | H | 1.88[a] |
| I-58 | 3,5-dichlorophenyl | 1-chlorocyclopropyl | H | cyano | H | H | 3.55[a] |
| I-59 | 3-methylphenyl | 1-chlorocyclopropyl | H | cyano | H | H | 3.17[a] |
| I-60 | 2-chloro-6-methylpyridin-4-yl | 1-chlorocyclopropyl | H | cyano | H | H |  |
| I-61 | 2,6-dichlorophenyl | 1-chlorocyclopropyl | H | cyano | H | H | 2.66[a] |
| I-62 | 2-chloropyridin-4-yl | 1-chlorocyclopropyl | H | cyano | H | H | 2.04[a] |
| I-63 | biphenyl-4-yl | 1-chlorocyclopropyl | H | cyano | H | H | 3.68[a] |
| I-64 | 4-chlorophenyl | 1-chlorocyclopropyl | H | cyano | H | H | 3.10[a] |
| I-65 | phenyl | 1-chlorocyclopropyl | H | cyano | H | H | 2.64[a] |
| I-66 | 2,3-dichlorophenyl | 1-chlorocyclopropyl | H | chloro | H | H | 2.69[a] |
| I-67 | 2,3-dichloropyridin-4-yl | 1-chlorocyclopropyl | H | chloro | H | H | 2.08[a] |
| I-68 | 2,4-dimethylphenyl | 1-chlorocyclopropyl | H | chloro | H | H | 2.69[a] |
| I-69 | 2,4-dichlorophenyl | 1-chlorocyclopropyl | H | chloro | H | H | 2.96[a] |
| I-70 | 2-chloro-4-(4-chlorophenoxy)phenyl | 1-chlorocyclopropyl | H | chloro | H | H | 4.06[a] |
| I-71 | 2-methylphenyl | 1-chlorocyclopropyl | H | chloro | H | H | 2.33[a] |
| I-72 | 3-chloropyridin-4-yl | 1-chlorocyclopropyl | H | chloro | H | H | 1.52[a] |
| I-73 | 3-methylphenyl | 1-chlorocyclopropyl | H | chloro | H | H | 2.30[a] |
| I-74 | 2,6-dichloropyridin-4-yl | 1-chlorocyclopropyl | H | chloro | H | H | 2.23[a] |
| I-75 | 2-chloropyridin-4-yl | 1-chlorocyclopropyl | H | chloro | H | H | 1.62[a] |
| I-76 | 4-methylphenyl | 1-chlorocyclopropyl | H | chloro | H | H | 2.30[a] |
| I-77 | 4-chlorophenyl | 1-chlorocyclopropyl | H | chloro | H | H | 2.45[a] |
| I-78 | 2-chlorophenyl | 1-chlorocyclopropyl | H | amino | H | H | 1.50[a] |
| I-79 | 2-chlorophenyl | 1-methylcyclopropyl | H | cyano | H | H | 2.87[a] |
| I-80 | 2-chlorophenyl | cyclopropyl | H | cyano | H | H | 2.57[a] |
| I-81 | 2-chlorophenyl | cyclobutyl | H | cyano | H | H | 2.96[a] |
| I-82 | 2-chlorophenyl | isopropyl | H | cyano | H | H | 2.67[a] |
| I-83 | 2-chlorophenyl | 2,2-dimethylpropyl | H | cyano | H | H | 3.55[a] |

TABLE 1-continued (I)

| Ex N° | Q | R¹ | R² | R³ | R⁴ | R⁵ | LogP |
|---|---|---|---|---|---|---|---|
| I-84 | 2-chlorophenyl | cyclopropylmethyl | H | cyano | H | H | 2.84[a] |
| I-85 | 2,3-dichlorophenyl | cyclobutyl | H | cyano | H | H | 3.31[a] |
| I-86 | 4-chlorophenyl | 2,2-dimethylpropyl | H | cyano | H | H | 3.37[a] |
| I-87 | 2-[1-(trifluoromethyl)-cyclopropyl]phenyl | 1-chlorocyclopropyl | H | cyano | H | H | 3.33[a] |
| I-88 | 2-(trifluoromethyl)phenyl | 1-chlorocyclopropyl | H | cyano | H | H | 3.15[a] |
| I-89 | 2-(trifluoromethyl)phenyl | 1-chlorocyclopropyl | H | chloro | H | H | 2.62[a] |
| I-90 | 2-chloro-4-(trifluoromethyl)-phenyl | 1-chlorocyclopropyl | H | cyano | H | H | 3.42[a] |
| I-91 | 2-chloro-4-(trifluoromethyl)-phenyl | 1-chlorocyclopropyl | H | chloro | H | H | 3.04[a] |
| I-92 | 3-(trifluoromethyl)pyridin-4-yl | 1-chlorocyclopropyl | H | cyano | H | H | 2.18[a] |
| I-93 | 2,3,4-trifluorophenyl | 1-fluorocyclopropyl | H | cyano | H | H | 2.52[a] |
| I-94 | 3-chloro-2-fluorophenyl | 1-fluorocyclopropyl | H | cyano | H | H | 2.68[a] |
| I-95 | 2,3-difluorophenyl | 1-fluorocyclopropyl | H | cyano | H | H | 2.37[a] |
| I-96 | 4-chloro-2-fluorophenyl | 1-fluorocyclopropyl | H | cyano | H | H | 2.78[a] |
| I-97 | 2,4-difluorophenyl | 1-fluorocyclopropyl | H | cyano | H | H | 2.39[a] |
| I-98 | 2-chlorophenyl | 1-fluorocyclopropyl | H | cyano | H | H | 2.53[a] |
| I-99 | 2-fluorophenyl | 1-fluorocyclopropyl | H | cyano | H | H | 2.01[a] |
| I-100 | 4-fluorophenyl | 1-fluorocyclopropyl | H | cyano | H | H | 2.35[a] |
| I-101 | 3-chloro-2,4-difluorophenyl | 1-chlorocyclopropyl | H | cyano | H | H | 3.17[a] |
| I-102 | 2,3,4-trifluorophenyl | 1-methylcyclopropyl | H | cyano | H | H | 2.82[a] |
| I-103 | 2,3,4-trifluorophenyl | 1-chlorocyclopropyl | H | cyano | H | H | 2.92[a] |
| I-104 | 2,3,4-trifluorophenyl | cyclobutyl | H | cyano | H | H | 2.78[a] |
| I-105 | 2,3,4-trifluorophenyl | isopropyl | H | cyano | H | H | 2.78[a] |
| I-106 | 2,3,4-trifluorophenyl | cyclopropylmethyl | H | cyano | H | H | 2.73[a] |
| I-107 | 2-fluoro-4-methylphenyl | 1-chlorocyclopropyl | H | cyano | H | H | 2.97[a] |
| I-108 | 2-fluoro-4-methylphenyl | 1-chlorocyclopropyl | H | chloro | H | H | 2.34[a] |
| I-109 | 3,4-difluorophenyl | 1-chlorocyclopropyl | H | cyano | H | H | 2.78[a] |
| I-110 | 3,4-difluorophenyl | 1-chlorocyclopropyl | H | chloro | H | H | 2.23[a] |
| I-111(*) | 4-chloro-2-fluorophenyl | 1-chlorocyclopropyl | H | cyano | H | H | 3.05[a] |
| I-112(*) | 4-chloro-2-fluorophenyl | 1-chlorocyclopropyl | H | cyano | H | H | 3.05[a] |
| I-113(*) | 4-chloro-2-fluorophenyl | 1-chlorocyclopropyl | H | chloro | H | H | 2.54[a] |
| I-114(*) | 4-chloro-2-fluorophenyl | 1-chlorocyclopropyl | H | chloro | H | H | |
| I-115 | 4-chloro-2-fluorophenyl | cyclopropyl | H | cyano | H | H | 2.66[a] |
| I-116 | 4-chloro-2-fluorophenyl | cyclopropyl | H | carbamoyl | H | H | 1.49[a] |
| I-117 | 4-chloro-2-fluorophenyl | cyclobutyl | H | cyano | H | H | 3.31[a] |
| I-118 | 4-chloro-2-fluorophenyl | isopropyl | H | cyano | H | H | 2.91[a] |
| I-119 | 4-chloro-2-fluorophenyl | 2,2-dimethylpropyl | H | cyano | H | H | 3.71[a] |
| I-120 | 4-chloro-2-fluorophenyl | cyclopropylmethyl | H | cyano | H | H | 2.95[a] |
| I-121 | 4-chloro-2-fluorophenyl | cyclopropyl | methyl | cyano | H | H | 3.31[a] |
| I-122 | 4-chloro-2-fluorophenyl | 1-chlorocyclopropyl | ethyl | chloro | H | H | 3.10[a] |
| I-123 | 4-chloro-2-fluorophenyl | 1-chlorocyclopropyl | allyl | chloro | H | H | 3.31[a] |
| I-124 | 2,4-difluorophenyl | 1-methylcyclopropyl | H | cyano | H | H | 2.65[a] |
| I-125 | 2,4-difluorophenyl | 1-chlorocyclopropyl | H | cyano | H | H | 2.78[a] |
| I-126 | 2,4-difluorophenyl | 1-chlorocyclopropyl | H | chloro | H | H | 2.20[a] |
| I-127 | 2,4-difluorophenyl | cyclobutyl | H | cyano | H | H | 2.80[a] |
| I-128 | 2,4-difluorophenyl | isopropyl | H | cyano | H | H | 2.52[a] |
| I-129 | 2,4-difluorophenyl | 2,2-dimethylpropyl | H | cyano | H | H | 3.33[a] |
| I-130 | 2,4-difluorophenyl | cyclopropylmethyl | H | cyano | H | H | 2.69[a] |
| I-131 | 2-fluorophenyl | 1-methylcyclopropyl | H | cyano | H | H | 2.68[a] |
| I-132(*) | 2-fluorophenyl | 1-chlorocyclopropyl | H | cyano | H | H | 2.59[a] |
| I-133(*) | 2-fluorophenyl | 1-chlorocyclopropyl | H | cyano | H | H | 2.59[a] |
| I-134 | 2-fluorophenyl | 1-chlorocyclopropyl | H | (2-fluorophenyl)acetyl | H | H | 3.60[a] |
| I-135 | 2-fluorophenyl | 1-chlorocyclopropyl | H | ethoxycarbonyl | H | H | 2.73[a] |
| I-136 | 2-fluorophenyl | cyclopropyl | H | cyano | H | H | 2.28[a] |
| I-137 | 2-fluorophenyl | cyclobutyl | H | cyano | H | H | 2.46[a] |
| I-138 | 2-fluorophenyl | tert-butyl | H | cyano | H | H | 2.73[a] |
| I-139 | 2-fluorophenyl | isopropyl | H | cyano | H | H | 2.40[a] |
| I-140 | 2-fluorophenyl | 2,2-dimethylpropyl | H | cyano | H | H | 3.23[a] |
| I-141 | 2-fluorophenyl | cyclopropylmethyl | H | cyano | H | H | 2.45[a] |
| I-142 | 2-fluoro-3-methylphenyl | 1-chlorocyclopropyl | H | cyano | H | H | 2.99[a] |
| I-143 | 2-fluoro-3-methylphenyl | 1-chlorocyclopropyl | H | chloro | H | H | 2.35[a] |
| I-144 | 2,3-difluorophenyl | 1-methylcyclopropyl | H | cyano | H | H | 2.75[a] |

TABLE 1-continued (I)

| Ex N° | Q | R¹ | R² | R³ | R⁴ | R⁵ | LogP |
|---|---|---|---|---|---|---|---|
| I-145 | 3-chloro-2-fluorophenyl | 1-chlorocyclopropyl | H | cyano | H | H | 3.02[a] |
| I-146 | 2,3-difluorophenyl | 1-chlorocyclopropyl | H | cyano | H | H | 2.75[a] |
| I-147 | 2,3-difluorophenyl | 1-chlorocyclopropyl | H | chloro | H | H | 2.17[a] |
| I-148 | 2,3-difluorophenyl | cyclobutyl | H | cyano | H | H | 2.57[a] |
| I-149 | 2,3-difluorophenyl | isopropyl | H | cyano | H | H | 2.47[a] |
| I-150 | 2,3-difluorophenyl | 2,2-dimethylpropyl | H | cyano | H | H | 3.27[a] |
| I-151 | 2,3-difluorophenyl | cyclopropylmethyl | H | cyano | H | H | 2.66[a] |
| I-152 | 2-chloro-3-fluoropyridin-4-yl | 1-chlorocyclopropyl | H | cyano | H | H | 2.25[a] |
| I-153 | 4-fluoro-2-methylphenyl | 1-chlorocyclopropyl | H | cyano | H | H | 2.96[a] |
| I-154 | 2-chloro-4-fluorophenyl | 1-chlorocyclopropyl | H | cyano | H | H | 3.00[a] |
| I-155 | 4-fluoro-2-methylphenyl | 1-chlorocyclopropyl | H | chloro | H | H | 2.46[a] |
| I-156 | 3,5-difluorophenyl | 1-chlorocyclopropyl | H | cyano | H | H | 2.86[a] |
| I-157 | 4-fluorophenyl | 1-chlorocyclopropyl | H | cyano | H | H | 2.75[a] |
| I-158 | 4-fluorophenyl | 1-chlorocyclopropyl | H | chloro | H | H | 2.13[a] |
| I-159 | 4-fluorophenyl | 1-chlorocyclobutyl | H | cyano | H | H | 2.98[a] |
| I-160 | 4-fluorophenyl | cyclobutyl | H | cyano | H | H | 2.56[a] |
| I-161 | 4-fluorophenyl | cyclopentyl | H | cyano | H | H | 2.82[a] |
| I-162 | 4-fluorophenyl | isopropyl | H | cyano | H | H | 2.44[a] |
| I-163 | 3-fluoropyridin-4-yl | 1-chlorocyclopropyl | H | cyano | H | H | 1.62[a] |
| I-164 | 3-fluoropyridin-4-yl | 1-chlorocyclopropyl | H | chloro | H | H | 1.46[a] |
| I-165 | 5-chloro-2-fluoropyridin-4-yl | 1-chlorocyclopropyl | H | cyano | H | H | 2.38[a] |
| I-166 | 2-iodophenyl | 1-chlorocyclopropyl | H | cyano | H | H | 3.13[a] |
| I-167 | 2-iodophenyl | 1-chlorocyclopropyl | H | chloro | H | H | 2.58[a] |
| I-168 | 3-chloropyridazin-4-yl | 1-chlorocyclopropyl | H | cyano | H | H | 1.59[a] |
| I-169 | phenyl | 1-chlorocyclopropyl | H | phenylacetyl | H | H | 3.56[a] |

Optical rotation
Concentration c is expressed in g/100 mL
(*)Ex I-113 and I-114 are the 2 enantiomers of Ex I-27
Ex I-113: Optical rotation: −4 (c = 1.00, MeOH, 20° C.)
Ex I-114: Optical rotation: +4 (c = 1.00, MeOH, 20° C.)
(*)Ex I-111 and I-112 are the 2 enantiomers of Ex I-29
Ex I-111: Optical rotation: −12 (c = 1.00, MeOH, 25° C.)
Ex I-112: Optical rotation: +12 (c = 1.00, MeOH, 25° C.)
(*)Ex I-132 and I-133 are the 2 enantiomers of Ex I-34
Ex I-132: Optical rotation: −16.2 (c = 0.99, MeOH, 20° C.)
Ex I-133: Optical rotation: +14.2 (c = 1.13, MeOH, 20° C.)
Measurement of LogP values was performed according to EEC directive 79/831 Annex V.A8 by HPLC (High Performance Liquid Chomatography) on reversed phase columns with the following methods:
[a]LogP value is determined by measurement of LC-UV, in an acidic range, with 0.1% formic acid in water and acetonitrile as eluent (linear gradient from 10% acetonitrile to 95% acetonitrile).
[b]LogP value is determined by measurement of LC-UV, in a neutral range, with 0.001 molar ammonium acetate solution in water and acetonitrile as eluent (linear gradient from 10% acetonitrile to 95% acetonitrile).
[c]LogP value is determined by measurement of LC-UV, in an acidic range, with 0.1% phosphoric acid and acetonitrile as eluent (linear gradient from 10% acetonitrile to 95% acetonitrile).
If more than one LogP value is available within the same method, all the values are given and separated by "+".
Calibration was done with straight-chain alkan2-ones (with 3 to 16 carbon atoms) with known LogP values (measurement of LogP values using retention times with linear interpolation beween successive alkanones).
Lambda-max-values were determined using UV-spectra from 200 nm to 400 nm and the peak values of the chromatographic signals.

The following Table 2 illustrates in a non-limiting manner examples of compounds according to formula (XVII).

TABLE 2

(XVII)

| Ex N° | R¹ | R³ | LogP |
|---|---|---|---|
| XVII-1 | 1-chlorocyclopropyl | chloro | 0.75[a] |
| XVII-2 | 1-chlorocyclopropyl | cyano | 1.35[a] |
| XVII-3 | cyclopropyl | cyano | 0.74[a] |
| XVII-4 | 1-fluorocyclopropyl | cyano | 1.05[a] |
| XVII-5 | 1-chlorocyclopropyl | fluoro | 0.32[a] |
| XVII-6 | 1-chlorocyclopropyl | methoxycarbonyl | 1.20[a] |
| XVII-7 | tert-butyl | cyano | 1.47[a] |
| XVII-8 | 2-chloropropan-2-yl | cyano | 1.65[a] |

TABLE 2-continued

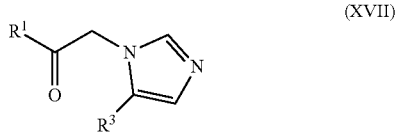
(XVII)

| Ex N° | R¹ | R³ | LogP |
|---|---|---|---|
| XVII-9 | 1-cyanocyclopropyl | cyano | 0.90[a] |
| XVII-10 | 1-chlorocyclopropyl | iodo | 0.70[a] |
| XVII-11 | 2-fluoropropan-2-yl | cyano | 1.31[a] |
| XVII-12 | cyclopropylmethyl | cyano | 1.27[a] |
| XVII-13 | 2,2-dimethylpropyl | cyano | 1.88[a] |
| XVII-14 | isopropyl | cyano | 1.14[a] |
| XVII-15 | cyclopentyl | cyano | 1.57[a] |
| XVII-16 | 1-fluorocyclopentyl | cyano | 1.81[a] |
| XVII-17 | cyclobutyl | cyano | 1.26[a] |
| XVII-18 | 1-chlorocyclobutyl | cyano | 1.86[a] |
| XVII-19 | butyl | cyano | 1.60[a] |

Measurement of Log P values was performed as outlined above.

NMR-Peak Lists

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:
$\delta_1$ (intensity$_1$); $\delta_2$ (intensity$_2$); . . . ; $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity>90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

Example I-01

$^1$H-NMR (499.9 MHz, CDCl$_3$): δ=7.934 (2.9); 7.744 (2.8); 7.511 (1.1); 7.508 (1.2); 7.496 (1.2); 7.493 (1.3); 7.411 (1.1); 7.408 (1.1); 7.395 (1.5); 7.392 (1.4); 7.293 (0.5); 7.290 (0.6); 7.278 (1.4); 7.275 (1.3); 7.263 (1.2); 7.260 (1.1); 7.255 (1.1); 7.251 (1.2); 7.240 (1.2); 7.236 (1.2); 7.225 (0.5); 7.221 (0.4); 4.780 (1.7); 4.750 (2.2); 4.541 (2.2); 4.511 (1.8); 4.118 (4.3); 3.765 (16.0); 3.663 (2.0); 3.635 (2.2); 3.162 (1.9); 3.135 (1.8); 2.002 (1.6); 0.858 (0.4); 0.846 (0.6); 0.843 (0.6); 0.836 (0.6); 0.831 (0.8); 0.825 (0.8); 0.821 (0.7); 0.810 (0.7); 0.788 (0.5); 0.776 (0.5); 0.773 (0.7); 0.766 (0.8); 0.762 (0.5); 0.755 (0.7); 0.752 (0.9); 0.741 (0.6); 0.675 (0.7); 0.664 (0.8); 0.661 (0.7); 0.654 (0.6); 0.649 (0.8); 0.643 (0.7); 0.640 (0.5); 0.628 (0.5); 0.509 (0.6); 0.498 (0.7); 0.495 (0.7); 0.488 (0.7); 0.484 (0.7); 0.477 (0.6); 0.474 (0.7); 0.462 (0.5); 0.000 (2.8)

Example I-02

$^1$H-NMR (499.9 MHz, CDCl$_3$): δ=7.710 (12.0); 7.529 (0.4); 7.519 (5.2); 7.514 (5.4); 7.504 (4.7); 7.500 (6.2); 7.394 (5.2); 7.391 (4.1); 7.380 (6.1); 7.376 (6.7); 7.365 (0.8); 7.357 (0.5); 7.291 (0.3); 7.284 (1.5); 7.280 (2.3); 7.269 (6.7); 7.263 (11.5); 7.261 (8.8); 7.255 (12.3); 7.251 (6.4); 7.246 (6.7); 7.242 (5.7); 7.231 (2.3); 7.227 (1.8); 7.206 (0.5); 6.942 (12.3); 4.441 (9.2); 4.411 (12.5); 4.388 (0.3); 4.249 (12.1); 4.219 (9.2); 3.384 (5.3); 3.355 (13.7); 3.321 (14.9); 3.292 (6.1); 2.432 (5.3); 2.037 (1.1); 1.847 (0.9); 1.269 (0.4); 1.255 (0.7); 1.241 (0.3); 0.818 (0.6); 0.811 (1.3); 0.797 (3.1); 0.791 (6.5); 0.781 (12.8); 0.779 (13.4); 0.774 (16.0); 0.767 (5.5); 0.764 (6.8); 0.757 (5.5); 0.754 (5.7); 0.748 (2.2); 0.743 (1.8); 0.731 (1.0); 0.720 (1.5); 0.711 (0.9); 0.696 (2.6); 0.689 (5.0); 0.682 (3.8); 0.679 (4.7); 0.673 (2.4); 0.665 (3.5); 0.660 (2.5); 0.644 (0.7); 0.636 (0.3); 0.000 (5.1); −0.007 (0.3)

Example I-03

$^1$H-NMR (499.9 MHz, CDCl$_3$): δ=7.628 (1.1); 7.468 (1.7); 7.463 (1.7); 7.450 (1.9); 7.320 (1.9); 7.316 (1.6); 7.306 (2.0); 7.302 (2.3); 7.198 (0.9); 7.190 (5.6); 7.182 (3.2); 7.175 (4.1); 7.167 (2.6); 7.162 (2.0); 7.151 (0.6); 6.692 (1.4); 4.350 (2.3); 4.320 (2.6); 3.978 (2.5); 3.949 (2.2); 3.394 (0.3); 3.365 (0.3); 3.314 (0.7); 3.285 (6.2); 3.280 (6.4); 3.251 (0.6); 2.145 (0.4); 2.108 (16.0); 1.214 (0.9); 1.185 (7.0); 1.162 (0.8); 1.140 (0.4); 0.823 (0.6); 0.809 (1.1); 0.795 (0.7); 0.784 (0.4); 0.777 (0.4); 0.768 (0.4); 0.689 (5.2); 0.680 (2.0); 0.670 (1.1); 0.656 (0.4); 0.646 (1.0); 0.635 (2.0); 0.626 (4.6); 0.611 (1.1); 0.017 (0.4); 0.000 (17.0); −0.071 (3.6)

Example I-04

$^1$H-NMR (499.9 MHz, CDCl$_3$): δ=7.817 (6.8); 7.516 (5.8); 7.512 (5.8); 7.502 (5.9); 7.498 (6.6); 7.408 (0.5); 7.397 (6.9); 7.393 (5.9); 7.383 (7.9); 7.379 (8.8); 7.367 (0.7); 7.361 (0.4); 7.346 (0.4); 7.284 (2.5); 7.273 (7.1);

7.270 (7.5); 7.264 (8.6); 7.259 (16.9); 7.249 (7.4); 7.245 (6.2); 7.234 (2.3); 7.231 (1.7); 7.219 (0.5); 7.211 (0.6); 7.161 (0.4); 7.025 (12.3); 4.451 (8.8); 4.422 (12.8); 4.305 (12.6); 4.275 (8.9); 3.726 (0.4); 3.388 (8.3); 3.360 (15.4); 3.300 (16.0); 3.272 (8.7); 2.256 (3.1); 2.039 (1.5); 1.676 (0.6); 1.333 (0.4); 1.307 (0.5); 1.300 (0.4); 1.284 (0.6); 1.271 (1.0); 1.256 (2.8); 1.242 (0.7); 1.230 (1.3); 0.961 (0.4); 0.894 (0.3); 0.880 (0.6); 0.867 (0.4); 0.836 (1.0); 0.828 (2.0); 0.815 (3.2); 0.806 (6.3); 0.801 (6.0); 0.793 (10.5); 0.784 (15.4); 0.774 (7.1); 0.772 (6.9); 0.763 (4.7); 0.751 (1.7); 0.741 (0.5); 0.715 (0.7); 0.692 (2.3); 0.681 (4.3); 0.671 (6.4); 0.657 (3.5); 0.650 (2.1); 0.633 (0.4); 0.554 (0.4); 0.070 (2.8); 0.006 (1.2); 0.000 (34.5); −0.007 (1.8)

Example I-05

$^1$H-NMR (499.9 MHz, $d_6$-DMSO): δ=7.934 (3.4); 7.920 (3.6); 7.845 (10.1); 7.844 (9.5); 7.518 (3.1); 7.502 (5.2); 7.463 (2.0); 7.460 (1.3); 7.448 (3.7); 7.435 (1.6); 7.433 (2.2); 7.429 (1.4); 7.418 (2.8); 7.416 (2.8); 7.403 (3.8); 7.388 (1.5); 6.966 (9.9); 6.955 (9.1); 6.396 (6.3); 6.306 (6.4); 6.290 (11.7); 4.734 (4.8); 4.704 (6.0); 4.474 (3.7); 4.471 (3.9); 4.444 (3.2); 4.441 (3.0); 3.286 (20.7); 2.507 (2.3); 2.503 (4.9); 2.500 (6.7); 2.496 (4.9); 2.493 (2.5); 1.986 (0.4); 0.494 (0.7); 0.483 (1.6); 0.471 (7.7); 0.461 (16.0); 0.450 (2.3); 0.440 (0.7); 0.428 (0.5); 0.319 (0.5); 0.292 (3.2); 0.273 (1.8); 0.267 (1.6); 0.261 (1.2); 0.000 (3.7)

Example I-06

$^1$H-NMR (499.9 MHz, $d_6$-DMSO): δ=7.916 (15.7); 7.786 (15.0); 7.659 (4.8); 7.655 (5.2); 7.644 (4.5); 7.641 (5.6); 7.630 (0.4); 7.465 (5.0); 7.462 (4.1); 7.451 (6.2); 7.447 (6.4); 7.434 (0.4); 7.340 (1.4); 7.337 (2.0); 7.326 (5.6); 7.322 (5.8); 7.315 (6.2); 7.312 (8.5); 7.310 (8.4); 7.308 (5.7); 7.300 (5.5); 7.296 (5.0); 7.286 (1.8); 7.282 (1.3); 5.404 (16.0); 4.652 (7.3); 4.623 (7.9); 3.919 (8.8); 3.890 (8.4); 3.578 (7.8); 3.549 (8.7); 3.299 (11.7); 3.102 (8.1); 3.074 (7.3); 2.506 (2.2); 2.503 (3.0); 2.499 (2.2); 2.496 (1.1); 1.036 (1.8); 1.023 (2.9); 1.021 (2.9); 1.014 (2.8); 1.009 (2.8); 1.002 (3.2); 1.000 (3.2); 0.987 (2.3); 0.763 (1.8); 0.748 (2.8); 0.742 (2.9); 0.736 (2.6); 0.729 (3.2); 0.727 (3.4); 0.715 (2.4); 0.576 (2.2); 0.565 (3.2); 0.562 (2.9); 0.555 (2.5); 0.550 (3.2); 0.543 (2.8); 0.540 (2.3); 0.529 (2.0); 0.487 (2.4); 0.476 (2.6); 0.473 (3.0); 0.466 (3.1); 0.462 (2.6); 0.455 (2.5); 0.451 (2.7); 0.440 (1.7); 0.000 (1.9)

Example I-07

$^1$H-NMR (499.9 MHz, $d_6$-DMSO): δ=12.333 (1.1); 8.324 (0.5); 8.320 (0.6); 8.315 (0.6); 8.311 (0.6); 7.962 (0.5); 7.958 (0.6); 7.947 (0.6); 7.943 (0.6); 7.598 (13.0); 7.597 (13.1); 7.547 (1.2); 7.545 (1.3); 7.412 (0.6); 7.403 (0.6); 7.397 (0.6); 7.387 (0.6); 7.176 (16.0); 7.174 (15.9); 7.164 (1.8); 7.161 (1.5); 4.505 (0.8); 4.476 (0.9); 3.955 (0.8); 3.926 (0.8); 3.324 (0.8); 3.296 (1.1); 3.185 (1.0); 3.157 (0.7); 2.508 (1.7); 2.504 (2.4); 2.501 (1.8); 0.664 (0.3); 0.550 (0.4); 0.539 (0.4); 0.535 (0.4); 0.529 (0.5); 0.523 (0.5); 0.517 (0.4); 0.000 (1.2)

Example I-08

$^1$H-NMR (300.2 MHz, CDCl$_3$): δ=7.759 (9.6); 7.576 (3.6); 7.556 (3.8); 7.548 (4.2); 7.527 (3.9); 7.300 (20.4); 7.204 (3.8); 7.195 (4.2); 7.176 (3.8); 7.167 (4.1); 7.081 (2.5); 7.072 (2.3); 7.054 (3.6); 7.045 (3.2); 7.026 (2.6); 7.012 (10.2); 7.009 (9.9); 4.471 (5.4); 4.422 (10.1); 4.314 (9.6); 4.265 (5.2); 3.412 (4.0); 3.364 (8.3); 3.283 (9.2); 3.234 (4.4); 2.194 (14.0); 2.083 (1.0); 1.653 (16.0); 1.321 (0.5); 1.291 (3.1); 1.273 (0.6); 0.919 (0.3); 0.894 (0.6); 0.884 (1.0); 0.862 (2.1); 0.852 (2.7); 0.844 (3.1); 0.833 (6.9); 0.825 (8.4); 0.817 (9.3); 0.809 (2.9); 0.800 (4.0); 0.789 (3.6); 0.785 (3.5); 0.775 (1.3); 0.768 (1.0); 0.760 (1.1); 0.744 (0.7); 0.723 (1.1); 0.716 (1.3); 0.707 (4.4); 0.690 (3.4); 0.680 (1.4); 0.665 (1.8); 0.658 (1.2); 0.048 (0.6); 0.037 (14.4); 0.027 (0.6)

Example I-09

$^1$H-NMR (499.9 MHz, CDCl$_3$): δ=7.813 (12.6); 7.343 (6.3); 7.327 (9.5); 7.314 (9.9); 7.301 (21.2); 7.278 (9.4); 7.265 (18.3); 7.208 (3.1); 7.194 (6.1); 7.179 (4.2); 7.155 (5.3); 7.140 (6.6); 7.126 (2.9); 7.066 (12.8); 4.571 (6.5); 4.541 (8.3); 4.310 (8.1); 4.281 (6.7); 3.268 (6.4); 3.239 (8.1); 3.007 (7.7); 2.978 (6.4); 1.775 (4.0); 1.257 (2.0); 1.237 (0.7); 0.882 (0.6); 0.868 (0.4); 0.842 (0.4); 0.765 (1.8); 0.760 (1.9); 0.741 (6.9); 0.718 (10.6); 0.695 (3.8); 0.669 (3.8); 0.648 (16.0); 0.000 10.1)

Example I-10

$^1$H-NMR (499.9 MHz, $d_6$-DMSO): δ=8.363 (1.1); 8.308 (2.0); 8.304 (2.2); 8.299 (2.3); 8.295 (2.2); 8.157 (1.4); 8.154 (1.3); 8.142 (1.4); 7.586 (4.2); 7.445 (0.4); 7.399 (1.9); 7.390 (2.0); 7.384 (2.1); 7.374 (1.9); 6.847 (0.4); 6.572 (3.9); 4.382 (2.6); 4.352 (2.9); 3.835 (2.7); 3.806 (2.5); 3.317 (1.9); 3.289 (3.7); 3.257 (0.4); 3.233 (2.9); 3.205 (1.6); 2.893 (1.0); 2.733 (0.8); 2.507 (3.0); 2.504 (4.2); 2.500 (3.4); 2.279 (0.4); 2.111 (16.0); 2.087 (0.4); 2.073 (3.0); 2.063 (1.6); 1.987 (0.6); 1.234 (0.6); 1.176 (0.3); 1.036 (0.7); 1.032 (0.8); 1.021 (1.1); 1.008 (0.8); 0.679 (0.5); 0.664 (2.0); 0.660 (1.8); 0.650 (3.6); 0.630 (1.6); 0.610 (1.5); 0.594 (1.6); 0.582 (1.0); 0.000 (1.7)

Example I-11

$^1$H-NMR (499.9 MHz, CDCl$_3$): δ=8.238 (6.2); 8.227 (6.2); 8.142 (0.5); 8.131 (0.5); 7.673 (9.6); 7.620 (0.9); 7.359 (6.4); 7.349 (6.1); 7.272 (3.6); 6.901 (9.9); 6.889 (0.5); 6.657 (0.5); 6.646 (0.5); 4.694 (5.7); 4.664 (6.2); 4.596 (0.4); 4.566 (0.7); 4.448 (0.6); 4.418 (0.4); 4.125 (4.9); 4.095 (4.4); 3.691 (0.5); 3.661 (16.0); 3.641 (0.7); 3.631 (0.5); 3.237 (0.6); 3.203 (0.5); 2.651 (8.1); 1.878 (2.3); 1.359 (0.4); 1.346 (0.4); 1.114 (0.4); 1.096 (0.4); 0.996 (0.5); 0.984 (2.1); 0.975 (2.7); 0.968 (2.7); 0.962 (5.6); 0.954 (3.1); 0.947 (3.7); 0.941 (3.6); 0.928 (1.3); 0.879 (2.2); 0.866 (3.2); 0.857 (1.7); 0.853 (2.3); 0.845 (2.2); 0.831 (1.5); 0.745 (2.0); 0.733 (2.0); 0.729 (2.2); 0.725 (2.2); 0.718 (1.8); 0.713 (1.9); 0.709 (1.9); 0.697 (1.2); 0.000 (2.4)

Example I-12

$^1$H-NMR (499.9 MHz, CDCl$_3$): δ=9.532 (13.6); 8.008 (11.8); 7.826 (13.8); 7.506 (4.9); 7.503 (5.0); 7.491 (5.5); 7.488 (5.5); 7.416 (5.1); 7.401 (6.1); 7.400 (6.1); 7.313 (2.5); 7.300 (5.8); 7.299 (5.6); 7.286 (4.1); 7.273 (4.4); 7.269 (4.6); 7.261 (8.9); 7.255 (5.0); 7.242 (2.0); 7.239 (1.8); 4.806 (7.1); 4.776 (8.5); 4.480 (8.6); 4.450 (7.2); 4.041 (0.8); 3.904 (0.5); 3.897 (1.0); 3.827 (16.0); 3.702 (7.7); 3.674 (8.5); 3.132 (7.8); 3.104 (7.1); 2.837 (0.4); 1.663 (5.9); 0.908 (1.7); 0.897 (2.9); 0.894 (2.8); 0.887 (2.6); 0.882 (3.1); 0.875 (3.2); 0.873 (3.0); 0.861 (2.7);

0.817 (2.1); 0.803 (3.0); 0.796 (3.2); 0.791 (2.4); 0.782 (3.7); 0.770 (2.4); 0.682 (2.7); 0.671 (3.5); 0.668 (3.2); 0.661 (2.5); 0.657 (3.1); 0.650 (2.7); 0.635 (1.9); 0.530 (2.6); 0.518 (3.1); 0.516 (3.3); 0.508 (3.0); 0.505 (2.9); 0.497 (2.8); 0.494 (2.8); 0.483 (1.8); 0.000 (4.5)

Example I-13

$^1$H-NMR (499.9 MHz, d$_6$-DMSO): δ=7.944 (1.9); 7.929 (2.0); 7.817 (0.4); 7.814 (0.3); 7.665 (4.2); 7.519 (2.4); 7.503 (2.8); 7.462 (1.2); 7.447 (2.3); 7.432 (1.4); 7.420 (1.9); 7.418 (1.9); 7.404 (2.2); 7.390 (0.9); 6.928 (0.7); 6.620 (3.6); 6.379 (3.0); 6.360 (0.5); 6.290 (3.2); 6.284 (1.1); 6.271 (0.5); 6.179 (4.8); 4.712 (0.4); 4.682 (0.5); 4.650 (2.4); 4.620 (2.9); 4.399 (0.3); 4.365 (0.4); 4.356 (1.9); 4.354 (1.9); 4.339 (0.4); 4.335 (0.4); 4.326 (1.7); 3.299 (0.7); 2.890 (1.0); 2.732 (0.9); 2.503 (2.7); 2.500 (3.4); 2.496 (2.5); 2.278 (16.0); 2.163 (0.9); 2.092 (2.7); 1.236 (1.0); 0.877 (0.4); 0.436 (0.5); 0.426 (0.8); 0.414 (4.5); 0.410 (3.5); 0.396 (3.9); 0.384 (1.4); 0.373 (0.9); 0.268 (1.1); 0.260 (2.3); 0.246 (1.7); 0.236 (0.9); 0.229 (0.5); 0.164 (0.3); 0.000 (1.2)

Example I-14

$^1$H-NMR (499.9 MHz, CDCl$_3$): δ=7.901 (15.1); 7.518 (6.0); 7.514 (6.5); 7.503 (5.7); 7.499 (7.0); 7.417 (0.3); 7.402 (6.2); 7.399 (5.1); 7.387 (7.9); 7.383 (7.7); 7.370 (0.4); 7.291 (2.1); 7.288 (2.7); 7.277 (7.3); 7.273 (7.5); 7.265 (8.8); 7.263 (10.2); 7.260 (11.4); 7.258 (11.7); 7.250 (6.7); 7.246 (5.9); 7.235 (2.2); 7.231 (1.7); 7.137 (0.4); 7.120 (16.0); 7.011 (0.4); 7.008 (0.3); 6.944 (0.5); 5.201 (0.9); 4.464 (10.8); 4.434 (14.7); 4.280 (13.8); 4.250 (10.2); 3.387 (7.8); 3.358 (14.4); 3.295 (16.0); 3.267 (8.8); 2.368 (0.7); 2.199 (12.4); 2.178 (1.7); 1.615 (1.6); 1.257 (0.6); 0.854 (0.4); 0.842 (1.4); 0.836 (2.2); 0.825 (5.2); 0.819 (3.6); 0.810 (7.2); 0.800 (6.9); 0.793 (6.9); 0.790 (11.7); 0.784 (15.1); 0.775 (6.5); 0.768 (9.6); 0.758 (3.3); 0.755 (1.8); 0.724 (0.5); 0.700 (1.4); 0.688 (4.0); 0.684 (4.6); 0.674 (7.3); 0.667 (2.6); 0.659 (3.1); 0.655 (2.6); 0.648 (0.4); 0.639 (0.7); 0.069 (2.1); 0.006 (1.2); 0.000 (31.8); −0.007 (1.3)

Example I-15

$^1$H-NMR (499.9 MHz, CDCl$_3$): δ=7.925 (14.4); 7.616 (0.4); 7.517 (0.4); 7.508 (5.2); 7.502 (5.1); 7.493 (4.3); 7.489 (6.2); 7.458 (0.4); 7.442 (11.1); 7.421 (0.4); 7.393 (5.5); 7.389 (4.0); 7.387 (3.3); 7.379 (5.6); 7.374 (6.8); 7.365 (0.8); 7.301 (0.5); 7.299 (0.5); 7.293 (1.5); 7.289 (2.3); 7.278 (6.9); 7.274 (7.8); 7.272 (8.1); 7.266 (14.1); 7.260 (7.2); 7.257 (6.9); 7.253 (5.6); 7.242 (1.8); 7.238 (1.2); 4.593 (0.3); 4.500 (7.2); 4.470 (14.3); 4.414 (11.4); 4.384 (5.7); 3.999 (0.4); 3.971 (0.3); 3.433 (0.5); 3.394 (7.6); 3.382 (0.7); 3.365 (9.8); 3.354 (0.6); 3.174 (11.5); 3.145 (9.0); 2.451 (0.6); 2.322 (16.0); 1.643 (1.4); 1.255 (1.0); 0.903 (1.3); 0.892 (3.1); 0.887 (2.7); 0.877 (5.2); 0.872 (5.3); 0.866 (3.7); 0.858 (8.2); 0.853 (5.8); 0.840 (8.5); 0.832 (11.9); 0.824 (6.0); 0.818 (3.1); 0.814 (1.5); 0.809 (3.9); 0.804 (2.8); 0.800 (1.2); 0.789 (1.8); 0.684 (0.4); 0.665 (3.2); 0.657 (4.3); 0.655 (4.4); 0.646 (5.0); 0.637 (3.3); 0.633 (3.3); 0.622 (2.6); 0.071 (1.9); 0.006 (0.7); 0.000 (15.4); −0.007 (1.0)

Example I-16

$^1$H-NMR (499.9 MHz, CDCl$_3$): δ=7.511 (0.5); 7.503 (4.7); 7.497 (4.1); 7.491 (2.8); 7.488 (3.4); 7.484 (5.4); 7.476 (0.4); 7.422 (0.4); 7.414 (4.8); 7.410 (3.1); 7.407 (2.6); 7.400 (4.5); 7.395 (6.0); 7.386 (0.5); 7.298 (12.3); 7.283 (6.5); 7.279 (7.8); 7.278 (8.0); 0.271 (13.5); 7.263 (21.7); 7.259 (5.2); 7.248 (1.5); 7.244 (1.0); 6.532 (6.0); 6.531 (5.9); 6.517 (6.1); 6.515 (5.9); 4.444 (9.5); 4.415 (10.7); 3.999 (9.5); 3.969 (8.4); 3.422 (4.3); 3.394 (14.0); 3.371 (13.3); 3.342 (4.0); 2.396 (11.9); 1.722 (2.1); 1.255 (0.5); 0.784 (0.8); 0.776 (0.9); 0.774 (0.8); 0.766 (5.4); 0.756 (16.0); 0.747 (5.4); 0.741 (2.3); 0.738 (5.4); 0.730 (2.4); 0.726 (0.8); 0.717 (1.8); 0.712 (1.9); 0.704 (4.9); 0.696 (4.8); 0.694 (6.1); 0.689 (4.1); 0.675 (5.7); 0.666 (4.9); 0.654 (2.6); 0.650 (1.8); 0.632 (0.4); 0.070 (1.1); 0.006 (0.5); 0.000 (12.1); −0.007 (0.4)

Example I-17

$^1$H-NMR (499.9 MHz, CDCl$_3$): δ=8.368 (16.0); 7.711 (7.4); 7.561 (15.6); 7.262 (2.8); 6.973 (8.5); 4.459 (6.8); 4.429 (9.3); 4.278 (9.2); 4.248 (6.9); 3.386 (6.1); 3.358 (8.7); 3.236 (9.4); 3.208 (6.7); 2.537 (0.8); 2.043 (0.7); 1.258 (0.7); 1.255 (0.6); 0.895 (0.9); 0.889 (0.8); 0.884 (1.0); 0.882 (1.6); 0.869 (3.8); 0.863 (9.1); 0.859 (11.2); 0.844 (2.8); 0.839 (0.9); 0.836 (1.2); 0.830 (2.1); 0.824 (0.7); 0.794 (2.0); 0.788 (1.3); 0.776 (2.8); 0.764 (8.3); 0.756 (8.2); 0.751 (4.0); 0.742 (2.1); 0.735 (1.1); 0.730 (1.0); 0.724 (1.1); 0.070 (1.6); 0.006 (0.8); 0.000 (23.9); −0.007 (1.3)

Example I-18

$^1$H-NMR (499.9 MHz, CDCl$_3$): δ=8.198 (16.0); 7.687 (12.8); 7.266 (1.4); 7.215 (10.7); 7.210 (11.0); 6.921 (13.5); 4.451 (9.2); 4.421 (12.8); 4.278 (12.7); 4.249 (9.4); 3.423 (8.3); 3.395 (11.7); 3.266 (10.7); 3.238 (7.8); 3.221 (0.4); 3.183 (2.1); 2.006 (0.4); 0.879 (0.8); 0.876 (1.2); 0.873 (1.2); 0.865 (3.7); 0.861 (2.6); 0.857 (4.5); 0.852 (6.5); 0.847 (9.1); 0.843 (10.2); 0.831 (2.8); 0.828 (3.0); 0.825 (1.9); 0.821 (1.3); 0.813 (3.4); 0.807 (6.3); 0.796 (13.9); 0.792 (7.0); 0.783 (2.7); 0.779 (2.3); 0.773 (1.2); 0.763 (0.3); 0.071 (0.5); 0.006 (0.3); 0.000 (11.2); −0.007 (0.6)

Example I-19

$^1$H-NMR (499.9 MHz, CDCl$_3$): δ=7.975 (3.0); 7.827 (3.0); 7.528 (1.0); 7.525 (1.1); 7.513 (1.2); 7.509 (1.3); 7.408 (1.1); 7.406 (1.2); 7.392 (1.4); 7.390 (1.5); 7.315 (0.6); 7.312 (0.6); 7.300 (1.4); 7.297 (1.3); 7.285 (0.9); 7.282 (0.8); 7.262 (1.0); 7.258 (1.0); 7.246 (1.2); 7.243 (1.2); 7.231 (0.5); 7.228 (0.5); 4.761 (1.7); 4.732 (2.1); 4.478 (2.2); 4.468 (4.1); 4.449 (1.8); 3.729 (2.0); 3.702 (2.2); 3.090 (1.9); 3.062 (1.7); 2.420 (16.0); 0.930 (0.5); 0.919 (0.6); 0.915 (0.7); 0.908 (0.7); 0.904 (0.8); 0.897 (0.8); 0.894 (0.8); 0.882 (0.7); 0.811 (0.5); 0.799 (0.5); 0.796 (0.7); 0.789 (0.8); 0.785 (0.6); 0.778 (0.7); 0.775 (0.9); 0.764 (0.7); 0.687 (0.7); 0.676 (0.8); 0.672 (0.7); 0.666 (0.6); 0.661 (0.8); 0.655 (0.7); 0.651 (0.5); 0.640 (0.5); 0.521 (0.6); 0.510 (0.7); 0.506 (0.7); 0.499 (0.7); 0.495 (0.7); 0.488 (0.6); 0.485 (0.7); 0.474 (0.5); 0.000 (1.4)

Example I-20

$^1$H-NMR (400.1 MHz, CDCl$_3$): δ=7.822 (15.7); 7.820 (16.0); 7.585 (0.9); 7.582 (0.9); 7.545 (0.5); 7.542 (0.6); 7.537 (0.5); 7.534 (0.5); 7.498 (0.3); 7.475 (0.4); 7.426 (0.4); 7.409 (0.4); 7.403 (0.6); 7.380 (6.2); 7.375 (7.1); 7.365 (6.5); 7.361 (12.5); 7.357 (10.3); 7.348 (7.7); 7.342 (7.6); 7.327 (0.5); 7.313 (0.9); 7.305 (0.8); 7.300 (0.7);

7.293 (0.6); 7.287 (0.8); 7.282 (1.4); 7.277 (9.6); 7.274 (10.4); 7.264 (12.4); 7.260 (40.3); 7.248 (2.4); 7.242 (3.0); 7.229 (7.7); 7.224 (7.1); 7.214 (8.3); 7.212 (9.8); 7.209 (9.6); 7.205 (6.2); 7.196 (8.0); 7.192 (6.2); 7.178 (2.3); 7.174 (1.8); 7.164 (0.4); 7.146 (16.5); 7.143 (16.7); 7.131 (0.3); 6.970 (8.0); 6.961 (12.0); 6.957 (7.4); 6.948 (11.5); 6.926 (11.6); 6.923 (12.3); 6.917 (8.0); 6.914 (7.4); 4.600 (10.7); 4.563 (14.8); 4.386 (14.5); 4.349 (10.5); 4.003 (0.7); 3.967 (0.6); 3.494 (0.5); 3.458 (0.8); 3.366 (10.9); 3.330 (14.4); 3.138 (12.2); 3.102 (9.1); 2.000 (1.6); 1.954 (9.0); 1.690 (4.5); 1.257 (0.4); 0.834 (3.3); 0.827 (2.2); 0.821 (1.4); 0.818 (2.4); 0.814 (3.4); 0.801 (9.6); 0.793 (2.8); 0.779 (9.7); 0.776 (8.3); 0.771 (5.1); 0.764 (0.7); 0.751 (6.4); 0.747 (3.4); 0.739 (7.6); 0.731 (1.1); 0.727 (0.7); 0.719 (5.0); 0.713 (12.1); 0.710 (14.7); 0.706 (13.8); 0.694 (3.8); 0.689 (2.5); 0.681 (1.4); 0.674 (2.4); 0.664 (0.5); 0.655 (0.5); 0.651 (0.5); 0.645 (0.5); 0.640 (0.5); 0.635 (0.4); 0.070 (1.0); 0.008 (0.5); 0.000 (17.4); −0.009 (0.6)

Example I-21

$^1$H-NMR (499.9 MHz, d$_6$-DMSO): δ=7.658 (5.5); 7.654 (6.4); 7.649 (16.0); 7.647 (15.7); 7.643 (7.4); 7.639 (6.6); 7.471 (5.7); 7.468 (5.5); 7.456 (7.3); 7.453 (7.0); 7.367 (0.4); 7.357 (2.3); 7.354 (2.5); 7.342 (6.4); 7.339 (6.1); 7.328 (5.5); 7.324 (6.3); 7.322 (6.4); 7.318 (5.7); 7.307 (5.5); 7.303 (5.6); 7.292 (2.2); 7.288 (1.8); 6.836 (12.6); 6.835 (12.3); 5.283 (13.0); 4.524 (5.7); 4.494 (6.1); 3.972 (3.5); 3.971 (3.4); 3.935 (12.7); 3.910 (12.1); 3.909 (11.7); 3.873 (3.2); 3.871 (3.1); 3.819 (0.8); 3.818 (0.8); 3.712 (8.4); 3.682 (8.1); 3.625 (7.7); 3.597 (8.4); 3.324 (29.6); 3.043 (7.7); 3.014 (7.1); 2.505 (3.4); 2.502 (4.6); 2.498 (3.4); 2.072 (15.1); 1.067 (1.7); 1.053 (3.1); 1.046 (2.8); 1.041 (2.7); 1.033 (3.3); 1.032 (3.2); 1.019 (2.1); 0.755 (1.7); 0.740 (2.8); 0.734 (3.0); 0.728 (2.6); 0.721 (3.3); 0.719 (3.4); 0.707 (2.3); 0.586 (2.2); 0.575 (3.3); 0.572 (3.1); 0.565 (2.6); 0.561 (3.2); 0.553 (2.7); 0.551 (2.4); 0.539 (1.9); 0.441 (2.2); 0.429 (2.7); 0.426 (3.0); 0.420 (3.0); 0.415 (2.7); 0.408 (2.6); 0.405 (2.7); 0.393 (1.7); 0.000 (2.6)

Example I-22

$^1$H-NMR (400.1 MHz, d$_6$-DMSO): δ=7.811 (2.3); 7.808 (2.4); 7.616 (0.8); 7.609 (0.8); 7.600 (0.5); 7.597 (0.7); 7.592 (1.0); 7.430 (0.9); 7.426 (0.9); 7.423 (0.5); 7.413 (0.9); 7.407 (1.2); 7.307 (0.9); 7.293 (1.2); 7.288 (1.2); 7.285 (1.3); 7.277 (2.4); 7.270 (1.1); 7.267 (1.1); 7.261 (1.0); 7.248 (0.4); 7.071 (2.5); 7.069 (2.6); 5.108 (2.7); 4.471 (1.0); 4.435 (1.3); 4.176 (1.6); 4.140 (1.3); 3.266 (1.1); 3.230 (1.7); 3.130 (1.5); 3.095 (1.0); 2.511 (0.4); 2.506 (0.8); 2.502 (1.1); 2.497 (0.8); 2.493 (0.4); 2.210 (16.0); 0.956 (0.3); 0.951 (0.4); 0.938 (0.6); 0.931 (0.5); 0.925 (0.5); 0.918 (0.5); 0.811 (0.3); 0.805 (0.5); 0.801 (0.6); 0.795 (0.5); 0.790 (0.3); 0.774 (0.4); 0.765 (0.5); 0.743 (0.4); 0.718 (0.8); 0.706 (0.8); 0.703 (0.8); 0.695 (1.3); 0.689 (0.8); 0.681 (0.6); 0.672 (0.6); 0.000 (1.0)

Example I-23

$^1$H-NMR (499.9 MHz, d$_6$-DMSO): δ=7.932 (4.1); 7.918 (16.0); 7.674 (0.4); 7.521 (3.8); 7.505 (6.3); 7.464 (2.3); 7.450 (4.4); 7.434 (2.6); 7.419 (3.3); 7.417 (3.4); 7.402 (4.5); 7.389 (1.8); 7.004 (11.4); 6.932 (0.4); 6.399 (7.4); 6.310 (7.6); 6.300 (14.0); 4.712 (5.2); 4.682 (7.0); 4.510 (4.7); 4.482 (3.5); 4.481 (3.4); 3.317 (0.8); 2.506 (3.3); 2.502 (4.6); 2.499 (3.5); 2.073 (0.4); 0.858 (0.3); 0.542 (0.5); 0.532 (1.5); 0.520 (2.2); 0.510 (5.1); 0.505 (3.0); 0.493 (5.7); 0.484 (6.7); 0.478 (5.3); 0.470 (2.1); 0.468 (2.1); 0.462 (1.6); 0.449 (0.7); 0.308 (1.3); 0.296 (2.2); 0.290 (3.6); 0.286 (3.6); 0.272 (2.5); 0.263 (1.3); 0.000 (4.9)

Example I-24

$^1$H-NMR (499.9 MHz, d$_6$-DMSO): δ=8.428 (3.7); 8.097 (15.3); 7.882 (5.3); 7.880 (5.5); 7.872 (16.0); 7.867 (6.3); 7.864 (5.5); 7.523 (4.5); 7.508 (7.2); 7.467 (2.7); 7.452 (5.1); 7.437 (3.0); 7.422 (4.0); 7.421 (4.0); 7.407 (5.4); 7.392 (2.1); 6.735 (0.7); 6.446 (8.2); 6.357 (8.3); 4.861 (6.4); 4.831 (8.5); 4.665 (5.5); 4.637 (4.2); 3.172 (0.9); 2.507 (4.0); 2.503 (5.3); 2.500 (4.0); 0.427 (0.4); 0.417 (1.6); 0.399 (4.2); 0.390 (4.9); 0.383 (6.5); 0.372 (5.7); 0.367 (6.9); 0.361 (4.7); 0.346 (6.0); 0.340 (4.5); 0.329 (5.3); 0.321 (1.8); 0.311 (1.7); 0.301 (0.5); 0.000 (3.4)

Example I-25

$^1$H-NMR (499.9 MHz, CDCl$_3$): δ=8.330 (10.3); 8.327 (10.9); 8.321 (10.8); 8.318 (10.1); 8.174 (1.1); 7.982 (1.4); 7.929 (9.4); 7.927 (9.4); 7.914 (9.8); 7.842 (8.2); 7.276 (1.4); 7.260 (8.2); 7.250 (8.9); 7.245 (8.7); 7.235 (7.6); 7.001 (13.5); 6.939 (0.3); 4.465 (9.6); 4.436 (14.8); 4.340 (14.8); 4.311 (9.7); 4.294 (0.5); 4.276 (0.3); 4.249 (0.4); 4.220 (0.4); 4.079 (0.3); 4.066 (0.6); 4.052 (0.4); 4.037 (0.5); 3.417 (11.7); 3.389 (16.0); 3.270 (0.3); 3.247 (15.4); 3.218 (11.3); 2.957 (6.9); 2.870 (6.6); 2.670 (0.3); 1.459 (0.3); 1.441 (0.6); 1.427 (0.7); 1.256 (0.4); 0.856 (1.3); 0.845 (3.4); 0.839 (2.9); 0.830 (7.5); 0.823 (8.2); 0.818 (10.2); 0.809 (11.2); 0.797 (7.6); 0.787 (12.1); 0.778 (7.8); 0.765 (6.4); 0.757 (4.5); 0.744 (3.4); 0.733 (4.7); 0.723 (5.1); 0.718 (5.5); 0.715 (5.4); 0.709 (4.0); 0.705 (3.8); 0.699 (3.4); 0.688 (1.9); 0.000 (7.7)

Example I-26

$^1$H-NMR (499.9 MHz, d$_6$-DMSO): δ=8.340 (5.3); 8.337 (6.0); 8.331 (5.9); 8.327 (6.0); 8.040 (5.1); 8.037 (5.5); 8.025 (5.7); 8.022 (5.7); 7.943 (16.0); 7.812 (15.5); 7.434 (5.5); 7.425 (5.6); 7.419 (5.6); 7.409 (5.3); 5.753 (13.1); 5.512 (15.2); 4.652 (6.4); 4.622 (7.0); 4.029 (8.2); 4.000 (7.7); 3.436 (6.8); 3.407 (8.4); 3.315 (34.7); 3.196 (8.1); 3.167 (6.6); 2.506 (5.5); 2.502 (7.6); 2.499 (6.0); 0.954 (1.6); 0.940 (3.0); 0.933 (2.6); 0.928 (2.7); 0.919 (3.2); 0.906 (2.2); 0.753 (1.7); 0.739 (2.8); 0.732 (2.9); 0.727 (2.5); 0.717 (3.5); 0.705 (2.3); 0.598 (2.1); 0.587 (3.0); 0.584 (3.0); 0.577 (2.4); 0.572 (3.1); 0.566 (2.7); 0.563 (2.3); 0.551 (1.9); 0.498 (2.2); 0.487 (2.5); 0.484 (2.9); 0.477 (2.9); 0.473 (2.6); 0.466 (2.4); 0.462 (2.7); 0.451 (1.6); 0.000 (2.9)

Example I-27

$^1$H-NMR (499.9 MHz, d$_6$-DMSO): δ=7.741 (13.6); 7.528 (3.8); 7.512 (7.5); 7.496 (4.0); 7.364 (5.1); 7.361 (5.1); 7.345 (5.1); 7.341 (4.9); 7.245 (5.6); 7.241 (5.2); 7.228 (5.0); 7.225 (4.5); 6.952 (13.8); 5.750 (6.9); 5.274 (16.0); 4.375 (6.2); 4.346 (7.8); 4.138 (7.8); 4.109 (6.3); 3.303 (14.3); 3.152 (5.2); 3.124 (6.3); 2.901 (6.2); 2.873 (5.1); 2.501 (10.0); 1.236 (0.5); 0.726 (0.5); 0.710 (2.6); 0.705 (2.5); 0.701 (2.3); 0.696 (3.3); 0.684 (3.7); 0.679 (2.9); 0.648 (2.4); 0.639 (3.5); 0.636 (3.4); 0.626 (4.2); 0.616 (4.0); 0.596 (7.1); 0.583 (13.0); 0.571 (3.4); 0.550 (0.9); 0.000 (2.7)

Example I-28

¹H-NMR (499.9 MHz, d₆-DMSO): δ=7.628 (7.7); 7.543 (1.3); 7.529 (2.7); 7.515 (1.5); 7.290 (0.7); 7.276 (1.7); 7.262 (1.8); 7.248 (0.9); 7.061 (2.7); 7.047 (4.0); 7.034 (2.8); 7.019 (1.6); 6.756 (7.1); 6.124 (4.2); 6.048 (9.0); 6.034 (4.4); 4.543 (3.7); 4.513 (4.6); 4.248 (3.0); 4.220 (2.5); 3.108 (16.0); 2.295 (2.7); 2.292 (3.6); 2.289 (2.7); 1.778 (0.4); 0.233 (0.6); 0.222 (1.2); 0.219 (1.1); 0.211 (1.2); 0.207 (1.5); 0.200 (1.5); 0.197 (1.4); 0.185 (1.6); 0.182 (1.3); 0.166 (1.5); 0.160 (1.7); 0.155 (1.1); 0.146 (2.0); 0.135 (1.3); 0.080 (1.1); 0.069 (1.6); 0.059 (1.0); 0.054 (1.4); 0.049 (1.3); 0.033 (0.8); 0.014 (1.4); 0.003 (1.4); 0.000 (1.6); −0.007 (1.6); −0.011 (1.3); −0.018 (1.2); −0.022 (1.3); −0.033 (0.7); −0.21 1.4)

Example I-29

¹H-NMR (499.9 MHz, CDCl₃): δ=7.855 (6.9); 7.651 (7.3); 7.375 (1.8); 7.359 (3.8); 7.342 (2.2); 7.262 (5.2); 7.189 (2.3); 7.185 (3.0); 7.173 (1.8); 7.169 (3.2); 7.165 (3.5); 7.145 (2.5); 7.141 (2.3); 5.297 (16.0); 4.680 (3.8); 4.650 (4.3); 4.206 (4.2); 4.177 (3.7); 3.319 (2.2); 3.290 (3.2); 3.154 (3.3); 3.126 (2.3); 2.227 (2.1); 2.213 (2.1); 2.002 (0.9); 1.256 (1.4); 1.242 (0.5); 0.720 (0.6); 0.708 (0.9); 0.698 (1.6); 0.690 (1.9); 0.686 (2.1); 0.678 (2.3); 0.672 (2.1); 0.663 (2.5); 0.654 (1.7); 0.641 (1.0); 0.631 (1.1); 0.583 (1.1); 0.573 (1.0); 0.561 (1.7); 0.550 (2.5); 0.542 (1.7); 0.526 (1.8); 0.518 (1.9); 0.515 (2.0); 0.506 (1.8); 0.497 (0.9); 0.494 (0.9); 0.484 (0.7); 0.070 (1.6); 0.000 (5.4)

Example I-30

¹H-NMR (499.9 MHz, d₆-DMSO): δ=7.828 (13.6); 7.513 (3.6); 7.496 (7.4); 7.480 (4.1); 7.357 (4.4); 7.353 (4.7); 7.338 (4.4); 7.334 (4.7); 7.237 (5.0); 7.233 (4.9); 7.220 (4.5); 7.216 (4.5); 6.993 (13.1); 5.272 (16.0); 4.352 (5.6); 4.323 (8.3); 4.217 (8.4); 4.188 (5.8); 3.328 (12.3); 3.163 (5.1); 3.134 (5.9); 2.821 (5.8); 2.793 (5.0); 2.509 (2.5); 2.506 (3.4); 2.502 (2.6); 0.741 (0.7); 0.734 (0.7); 0.731 (0.7); 0.709 (13.7); 0.688 (1.6); 0.681 (1.7); 0.675 (1.0); 0.645 (2.2); 0.623 (8.5); 0.601 (6.0); 0.596 (5.1); 0.581 (1.4); 0.576 (1.4); 0.571 (1.2); 0.000 (1.5)

Example I-31

¹H-NMR (499.9 MHz, d₆-DMSO): δ=7.827 (10.4); 7.662 (0.6); 7.639 (10.3); 7.563 (0.4); 7.486 (1.7); 7.471 (3.3); 7.458 (1.7); 7.272 (0.9); 7.258 (2.0); 7.244 (2.1); 7.230 (1.1); 7.043 (3.6); 7.029 (5.0); 7.020 (3.3); 7.015 (3.1); 7.002 (2.0); 6.153 (16.0); 6.063 (5.5); 4.640 (4.8); 4.610 (6.1); 4.401 (3.8); 4.373 (3.0); 4.371 (3.0); 3.805 (0.5); 3.791 (0.5); 3.089 (4.1); 2.274 (1.9); 2.271 (2.7); 2.267 (2.0); 1.756 (2.0); 1.001 (0.4); 0.957 (0.6); 0.943 (1.1); 0.928 (0.6); 0.147 (0.7); 0.136 (1.1); 0.126 (1.5); 0.121 (1.7); 0.116 (1.8); 0.110 (1.8); 0.102 (1.7); 0.085 (1.0); 0.072 (1.7); 0.063 (2.1); 0.050 (2.6); 0.042 (5.5); 0.033 (2.6); 0.020 (2.1); 0.013 (2.3); 0.000 (2.5); −0.008 (1.8); −0.013 (2.1); −0.019 (1.7); −0.023 (1.5); −0.034 (1.2); −0.045 (0.6); −0.234 (1.8)

Example I-32

¹H-NMR (499.9 MHz, d₆-DMSO): δ=7.741 (11.9); 7.594 (0.3); 7.592 (0.4); 7.523 (2.4); 7.511 (4.3); 7.508 (4.6); 7.495 (2.5); 7.493 (2.4); 7.317 (1.1); 7.314 (1.2); 7.302 (2.8); 7.287 (3.1); 7.276 (1.6); 7.273 (1.5); 7.232 (0.4); 7.230 (0.4); 7.160 (3.6); 7.149 (4.3); 7.142 (4.9); 7.135 (7.3); 7.121 (4.6); 6.948 (11.7); 5.754 (0.4); 5.226 (16.0); 4.397 (6.1); 4.368 (7.4); 4.088 (7.6); 4.058 (6.5); 3.331 (1.1); 3.128 (4.2); 3.100 (6.4); 3.007 (6.5); 2.979 (4.2); 2.507 (2.6); 2.504 (3.5); 2.500 (2.7); 0.755 (0.5); 0.737 (2.6); 0.727 (3.1); 0.716 (3.1); 0.710 (2.3); 0.631 (1.1); 0.622 (2.3); 0.617 (2.4); 0.608 (3.8); 0.604 (2.5); 0.597 (3.1); 0.584 (5.3); 0.580 (4.8); 0.572 (13.9); 0.559 (3.1); 0.553 (1.0); 0.539 (0.7); 0.000 (1.9)

Example I-33

¹H-NMR (499.9 MHz, d₆-DMSO): δ=7.824 (13.1); 7.510 (2.3); 7.507 (2.4); 7.495 (4.4); 7.492 (4.6); 7.479 (2.5); 7.477 (2.4); 7.311 (1.1); 7.308 (1.2); 7.296 (2.8); 7.281 (3.3); 7.269 (1.6); 7.267 (1.5); 7.153 (3.6); 7.140 (4.7); 7.134 (5.0); 7.127 (7.2); 7.113 (4.1); 6.984 (12.7); 5.205 (16.0); 4.373 (6.0); 4.344 (7.8); 4.164 (8.1); 4.135 (6.4); 3.323 (1.9); 3.139 (4.8); 3.111 (6.1); 2.927 (6.2); 2.899 (4.8); 2.507 (3.1); 2.503 (4.1); 2.500 (3.1); 0.755 (0.6); 0.746 (1.4); 0.742 (1.5); 0.734 (2.6); 0.726 (2.8); 0.721 (3.7); 0.717 (3.5); 0.707 (3.9); 0.701 (3.9); 0.700 (3.9); 0.689 (3.3); 0.678 (2.0); 0.668 (0.9); 0.661 (0.3); 0.648 (0.4); 0.641 (0.4); 0.631 (1.3); 0.626 (1.3); 0.623 (1.2); 0.615 (3.3); 0.602 (5.3); 0.597 (3.5); 0.591 (3.2); 0.587 (4.6); 0.583 (3.4); 0.575 (2.7); 0.567 (1.3); 0.562 (1.2); 0.559 (1.0); 0.549 (0.3); 0.000 (1.8)

Example I-34

¹H-NMR (499.9 MHz, d₆-DMSO): δ=7.951 (16.0); 7.815 (15.2); 7.552 (2.6); 7.539 (4.8); 7.536 (5.1); 7.523 (2.7); 7.521 (2.7); 7.339 (1.2); 7.336 (1.3); 7.324 (3.1); 7.313 (3.0); 7.309 (3.5); 7.298 (1.9); 7.295 (1.7); 7.188 (3.8); 7.173 (7.7); 7.159 (7.5); 7.153 (3.7); 7.145 (3.5); 7.110 (0.3); 5.430 (15.9); 4.585 (6.5); 4.555 (7.2); 4.069 (8.0); 4.040 (7.3); 3.320 (5.6); 3.222 (4.9); 3.194 (7.2); 3.085 (6.7); 3.057 (4.5); 2.507 (2.9); 2.503 (4.0); 2.500 (3.1); 2.074 (3.3); 0.885 (0.5); 0.818 (1.6); 0.804 (2.8); 0.796 (2.6); 0.791 (2.7); 0.782 (3.1); 0.770 (2.3); 0.631 (1.6); 0.617 (2.7); 0.610 (2.9); 0.605 (2.3); 0.596 (3.4); 0.584 (2.4); 0.501 (2.2); 0.490 (3.1); 0.487 (2.9); 0.480 (2.2); 0.475 (3.1); 0.469 (2.6); 0.466 (2.1); 0.454 (1.9); 0.426 (2.4); 0.415 (2.5); 0.412 (2.9); 0.405 (3.0); 0.401 (2.5); 0.394 (2.4); 0.390 (2.6); 0.379 (1.5); 0.000 (1.8)

Example I-35

¹H-NMR (499.9 MHz, d₆-DMSO): δ=7.488 (0.7); 7.475 (1.3); 7.473 (1.4); 7.460 (0.7); 7.458 (0.7); 7.293 (0.3); 7.281 (0.8); 7.266 (1.0); 7.255 (0.5); 7.252 (0.5); 7.234 (3.7); 7.136 (1.1); 7.126 (1.3); 7.118 (1.5); 7.112 (2.3); 7.098 (1.6); 6.228 (3.7); 5.036 (3.7); 4.181 (1.8); 4.152 (2.3); 3.944 (2.3); 3.915 (1.9); 3.784 (16.0); 3.324 (0.6); 3.094 (1.4); 3.066 (1.9); 2.917 (1.9); 2.889 (1.4); 2.502 (1.4); 2.499 (1.1); 0.650 (3.8); 0.634 (0.4); 0.630 (0.4); 0.626 (0.4); 0.561 (0.6); 0.536 (2.0); 0.515 (1.9); 0.499 (0.5); 0.495 (0.4); 0.492 (0.4); 0.000 (0.6)

Example I-36

¹H-NMR (499.9 MHz, d₆-DMSO): δ=7.797 (11.6); 7.662 (0.5); 7.629 (1.2); 7.542 (2.3); 7.529 (4.0); 7.526 (4.5); 7.513 (2.3); 7.511 (2.4); 7.494 (0.7); 7.468 (1.2); 7.384 (0.3); 7.381 (0.3); 7.370 (0.5); 7.367 (0.5); 7.358 (1.3); 7.354 (1.5); 7.343 (2.6); 7.327 (3.4); 7.321 (12.2); 7.263 (0.5);

7.248 (0.4); 7.230 (0.6); 7.222 (0.6); 7.209 (1.1); 7.195 (3.6); 7.185 (4.0); 7.177 (4.4); 7.171 (6.6); 7.157 (4.3); 5.332 (1.5); 5.242 (13.2); 4.886 (0.4); 4.677 (16.0); 4.531 (0.6); 4.502 (0.7); 4.453 (4.7); 4.424 (7.1); 4.332 (0.6); 4.322 (7.2); 4.293 (4.9); 4.262 (0.4); 4.040 (0.8); 4.004 (0.7); 3.992 (1.8); 3.975 (0.6); 3.373 (12.7); 3.218 (4.3); 3.190 (5.1); 3.167 (0.3); 3.139 (0.8); 3.114 (0.8); 2.924 (5.3); 2.896 (4.3); 2.562 (5.6); 2.559 (7.7); 2.556 (5.9); 1.057 (0.4); 0.804 (0.8); 0.796 (0.8); 0.791 (1.3); 0.776 (3.1); 0.766 (5.4); 0.762 (4.6); 0.743 (1.5); 0.738 (1.3); 0.730 (1.6); 0.711 (0.4); 0.688 (0.4); 0.676 (1.7); 0.669 (1.2); 0.655 (2.3); 0.644 (4.3); 0.628 (4.0); 0.624 (3.6); 0.616 (2.0); 0.607 (1.4); 0.603 (1.4); 0.595 (1.2); 0.588 (0.5); 0.458 (0.4); 0.450 (0.4); 0.443 (0.4); 0.439 (0.5); 0.435 (0.5); 0.429 (0.4); 0.423 (0.3)

Example I-37

$^1$H-NMR (499.9 MHz, $d_6$-DMSO): δ=7.539 (10.7); 7.523 (4.1); 7.508 (2.1); 7.315 (0.9); 7.303 (2.3); 7.288 (2.6); 7.277 (1.4); 7.274 (1.3); 7.170 (2.8); 7.152 (6.6); 7.138 (5.9); 7.123 (2.6); 6.509 (8.4); 5.099 (11.1); 4.409 (4.5); 4.380 (5.5); 4.111 (5.6); 4.082 (4.8); 3.323 (1.4); 3.081 (16.0); 2.502 (4.1); 2.073 (2.8); 1.820 (0.6); 1.809 (1.4); 1.803 (1.6); 1.793 (2.8); 1.783 (1.8); 1.777 (1.6); 1.767 (0.8); 1.337 (0.4); 0.818 (0.8); 0.805 (2.9); 0.800 (3.6); 0.792 (4.7); 0.781 (4.4); 0.772 (3.1); 0.764 (1.3); 0.711 (1.0); 0.703 (1.2); 0.700 (1.4); 0.693 (2.2); 0.683 (2.1); 0.675 (2.2); 0.670 (1.0); 0.665 (1.1); 0.657 (1.5); 0.647 (1.8); 0.642 (1.9); 0.633 (4.4); 0.614 (4.6); 0.598 (9.0); 0.582 (2.1); 0.570 (0.5); 0.563 (0.8); 0.537 (0.8); 0.526 (1.6); 0.518 (2.5); 0.508 (2.8); 0.500 (2.1); 0.489 (1.0); 0.434 (1.1); 0.424 (2.1); 0.416 (2.7); 0.405 (2.5); 0.397 (1.5); 0.387 (0.8); 0.000 (1.0)

Example I-38

$^1$H-NMR (499.9 MHz, $d_6$-DMSO): δ=7.712 (13.6); 7.604 (4.0); 7.600 (4.3); 7.590 (3.9); 7.586 (4.8); 7.418 (4.0); 7.415 (3.6); 7.404 (4.8); 7.400 (5.4); 7.389 (0.4); 7.296 (1.7); 7.284 (4.7); 7.281 (5.0); 7.275 (5.0); 7.270 (8.5); 7.260 (4.9); 7.252 (13.7); 7.242 (1.6); 5.753 (2.3); 5.143 (13.6); 4.583 (16.0); 4.453 (5.9); 4.424 (7.0); 4.137 (7.4); 4.108 (6.4); 3.322 (7.1); 3.235 (3.3); 3.206 (9.8); 3.182 (9.5); 3.154 (3.2); 2.503 (4.2); 2.074 (0.5); 0.927 (1.4); 0.914 (2.1); 0.904 (3.4); 0.897 (2.4); 0.893 (2.6); 0.884 (2.1); 0.782 (1.6); 0.772 (2.8); 0.764 (3.4); 0.751 (2.1); 0.742 (2.4); 0.719 (2.0); 0.710 (1.5); 0.699 (3.2); 0.687 (3.8); 0.677 (3.7); 0.674 (4.0); 0.666 (3.1); 0.661 (2.9); 0.652 (2.8); 0.645 (1.3); 0.641 (1.3); 0.632 (1.0); 0.000 (1.1)

Example I-39

$^1$H-NMR (300.2 MHz, $d_6$-DMSO): δ=8.157 (0.4); 7.760 (12.3); 7.395 (8.1); 7.373 (12.7); 7.319 (6.1); 7.297 (12.0); 7.272 (11.5); 7.243 (4.4); 7.220 (1.3); 6.981 (12.1); 5.798 (0.6); 5.779 (1.4); 5.257 (16.0); 4.516 (0.8); 4.395 (5.4); 4.372 (0.7); 4.347 (8.3); 4.181 (8.2); 4.132 (5.4); 3.346 (23.0); 3.193 (5.8); 3.147 (7.2); 2.816 (6.9); 2.770 (5.6); 2.525 (15.7); 1.317 (0.5); 1.293 (0.4); 1.258 (0.4); 0.617 (1.7); 0.582 (4.7); 0.571 (7.1); 0.554 (8.0); 0.536 (13.1); 0.513 (3.7); 0.499 (2.7); 0.478 (1.5); 0.456 (2.3); 0.438 (3.7); 0.421 (3.5); 0.396 (2.2); 0.379 (1.2); 0.023 (12.2)

Example I-40

$^1$H-NMR (300.2 MHz, CDCl$_3$): δ=7.892 (14.7); 7.731 (0.3); 7.682 (15.1); 7.662 (0.5); 7.648 (6.0); 7.644 (6.2); 7.621 (7.2); 7.617 (7.2); 7.600 (2.3); 7.552 (4.9); 7.547 (5.3); 7.527 (6.9); 7.521 (7.0); 7.409 (3.4); 7.405 (3.5); 7.384 (6.7); 7.380 (6.6); 7.359 (3.8); 7.355 (3.5); 7.298 (16.2); 7.265 (4.1); 7.259 (4.4); 7.239 (5.5); 7.234 (5.8); 7.214 (2.7); 7.208 (2.8); 7.146 (0.7); 7.116 (0.5); 5.486 (0.8); 4.760 (9.4); 4.711 (11.3); 4.696 (1.1); 4.651 (1.2); 4.377 (0.8); 4.332 (0.6); 4.263 (11.0); 4.215 (9.2); 4.190 (0.4); 4.166 (1.0); 4.142 (1.0); 4.119 (0.3); 3.825 (0.4); 3.538 (2.4); 3.490 (15.1); 3.473 (16.0); 3.425 (2.6); 3.395 (1.2); 3.346 (1.1); 2.488 (12.9); 2.078 (4.3); 2.041 (12.4); 1.696 (12.8); 1.603 (0.3); 1.316 (1.1); 1.292 (2.3); 1.269 (1.2); 1.166 (0.4); 1.149 (0.5); 1.128 (0.9); 1.106 (0.4); 1.058 (0.3); 1.031 (0.6); 1.024 (0.4); 1.016 (0.4); 1.006 (0.4); 0.990 (0.4); 0.879 (0.7); 0.850 (2.2); 0.840 (2.8); 0.832 (3.3); 0.827 (2.4); 0.808 (3.9); 0.804 (3.1); 0.796 (4.0); 0.762 (0.8); 0.752 (3.0); 0.740 (2.5); 0.732 (4.6); 0.718 (5.6); 0.713 (4.9); 0.705 (4.4); 0.700 (5.1); 0.693 (5.0); 0.687 (5.1); 0.673 (4.9); 0.666 (2.6); 0.653 (3.9); 0.620 (4.2); 0.612 (3.5); 0.609 (4.2); 0.589 (2.7); 0.586 (3.3); 0.576 (2.7); 0.571 (1.6); 0.566 (2.2); 0.537 (0.7); 0.044 (0.5); 0.033 (15.3); 0.022 (0.6)

Example I-41

$^1$H-NMR (300.2 MHz, CDCl$_3$): δ=7.868 (6.3); 7.659 (5.2); 7.605 (5.1); 7.468 (0.8); 7.465 (0.8); 7.430 (9.9); 7.403 (1.4); 7.300 (2.1); 4.731 (3.9); 4.682 (4.7); 4.232 (3.1); 4.183 (2.6); 3.389 (16.0); 2.987 (1.3); 2.891 (0.8); 2.677 (1.1); 2.661 (1.5); 2.033 (3.1); 0.853 (0.3); 0.823 (1.2); 0.814 (1.3); 0.805 (1.9); 0.800 (1.5); 0.782 (2.0); 0.778 (1.8); 0.770 (2.1); 0.733 (1.3); 0.713 (1.8); 0.695 (3.2); 0.688 (2.6); 0.680 (2.4); 0.670 (3.4); 0.655 (2.0); 0.649 (1.5); 0.635 (1.3); 0.588 (1.4); 0.577 (1.9); 0.552 (1.8); 0.544 (1.6); 0.534 (1.1); 0.024 (1.0)

Example I-42

$^1$H-NMR (300.2 MHz, CDCl$_3$): δ=7.977 (0.5); 7.886 (8.8); 7.690 (4.6); 7.677 (5.5); 7.597 (0.4); 7.588 (0.4); 7.381 (0.8); 7.373 (0.9); 7.352 (16.0); 7.333 (8.0); 7.321 (3.3); 7.314 (3.4); 7.306 (3.0); 7.300 (10.2); 7.099 (0.4); 7.072 (0.4); 4.930 (1.2); 4.873 (0.4); 4.823 (0.5); 4.724 (5.7); 4.675 (7.0); 4.560 (0.5); 4.511 (0.4); 4.247 (5.3); 4.198 (4.4); 3.353 (2.8); 3.305 (4.9); 3.188 (7.1); 3.140 (4.0); 2.458 (0.7); 2.437 (0.7); 2.268 (0.9); 2.244 (0.7); 2.042 (1.6); 1.673 (0.5); 1.021 (0.3); 0.921 (0.4); 0.754 (0.9); 0.747 (1.7); 0.726 (4.3); 0.711 (4.4); 0.702 (5.5); 0.698 (5.2); 0.675 (1.7); 0.663 (1.1); 0.653 (1.8); 0.646 (1.9); 0.626 (2.5); 0.623 (2.5); 0.613 (1.1); 0.605 (0.5); 0.595 (2.2); 0.592 (2.4); 0.577 (4.6); 0.573 (4.7); 0.553 (4.2); 0.539 (2.6); 0.526 (2.2); 0.512 (1.1); 0.505 (1.0); 0.495 (1.2); 0.104 (0.3); 0.034 (4.9)

Example I-43

$^1$H-NMR (300.2 MHz, CDCl$_3$): δ=7.765 (6.1); 7.601 (6.7); 7.448 (16.0); 7.444 (15.3); 7.300 (50.8); 7.021 (6.9); 5.339 (3.6); 4.471 (3.9); 4.422 (7.1); 4.317 (7.0); 4.267 (3.8); 3.402 (3.4); 3.354 (7.2); 3.274 (7.5); 3.226 (3.6); 2.358 (0.5); 2.154 (3.2); 2.128 (0.6); 2.085 (0.4); 1.633 (3.1); 1.322 (0.4); 1.292 (4.0); 1.261 (0.4); 0.888 (0.7); 0.865 (1.6); 0.842 (5.5); 0.838 (5.0); 0.831 (3.3); 0.820 (5.9); 0.811 (1.6); 0.802 (2.0); 0.786 (2.7); 0.779 (2.0); 0.776 (1.9); 0.755 (0.5); 0.738 (0.5); 0.718 (3.2); 0.703 (1.4); 0.698 (2.0); 0.687 (1.0); 0.675 (1.1); 0.049 (1.7); 0.038 (49.4); 0.028 (1.7)

Example I-44

¹H-NMR (300.2 MHz, CDCl₃): δ=7.722 (14.8); 7.719 (16.0); 7.391 (3.6); 7.377 (1.1); 7.362 (8.5); 7.338 (8.5); 7.318 (8.5); 7.312 (13.6); 7.305 (9.2); 7.300 (12.0); 7.289 (4.7); 7.285 (4.1); 7.272 (7.3); 7.267 (5.5); 6.940 (12.8); 6.937 (14.2); 4.446 (7.8); 4.397 (15.7); 4.312 (15.1); 4.263 (7.6); 3.322 (5.4); 3.318 (5.6); 3.274 (7.3); 3.271 (7.8); 3.040 (8.0); 3.037 (8.1); 2.993 (6.1); 2.990 (6.2); 2.075 (0.6); 2.037 (1.8); 0.826 (2.5); 0.812 (3.5); 0.794 (6.5); 0.789 (6.9); 0.778 (8.1); 0.761 (11.4); 0.750 (9.6); 0.736 (7.4); 0.715 (5.6); 0.704 (7.0); 0.693 (2.8); 0.688 (3.8); 0.682 (3.7); 0.676 (4.2); 0.659 (2.4); 0.657 (2.3); 0.644 (2.1); 0.626 (0.9); 0.032 (5.8)

Example I-45

¹H-NMR (300.2 MHz, d₆-DMSO): δ=7.977 (4.5); 7.975 (4.5); 7.862 (4.6); 7.860 (4.3); 7.631 (2.9); 7.483 (1.3); 7.457 (1.7); 7.434 (1.4); 7.408 (2.0); 7.312 (2.5); 7.286 (3.3); 7.260 (1.2); 5.776 (16.0); 5.557 (5.7); 5.451 (0.5); 4.594 (2.0); 4.545 (2.4); 4.184 (2.4); 4.135 (2.0); 4.061 (0.6); 4.037 (0.6); 3.343 (87.6); 3.194 (1.6); 3.148 (2.4); 2.994 (2.3); 2.948 (1.5); 2.653 (0.4); 2.620 (0.4); 2.533 (2.8); 2.527 (5.8); 2.521 (7.9); 2.515 (5.8); 2.510 (2.8); 2.094 (0.5); 2.008 (2.7); 1.218 (0.7); 1.194 (1.5); 1.171 (0.7); 0.572 (0.5); 0.566 (0.5); 0.557 (0.7); 0.541 (0.7); 0.529 (1.5); 0.505 (0.8); 0.496 (0.9); 0.479 (2.0); 0.474 (2.4); 0.468 (2.5); 0.460 (2.4); 0.446 (1.0); 0.435 (0.9); 0.414 (1.4); 0.402 (0.8); 0.385 (0.8); 0.370 (0.5); 0.020 (5.3)

Example I-46

¹H-NMR (300.2 MHz, CDCl₃): δ=8.765 (15.1); 8.753 (4.7); 8.545 (8.1); 8.529 (9.9); 8.515 (2.6); 7.887 (16.0); 7.699 (13.4); 7.691 (4.9); 7.646 (0.4); 7.551 (12.1); 7.535 (11.8); 7.300 (19.5); 5.334 (2.7); 4.751 (10.8); 4.702 (13.2); 4.307 (8.7); 4.297 (3.1); 4.258 (7.2); 4.249 (2.5); 3.555 (5.0); 3.546 (1.9); 3.508 (9.5); 3.499 (3.9); 3.411 (10.1); 3.364 (5.3); 2.993 (0.5); 2.791 (0.5); 2.716 (0.5); 2.600 (5.1); 2.042 (5.0); 1.887 (0.9); 1.771 (6.2); 1.284 (0.6); 0.875 (1.9); 0.863 (2.2); 0.856 (2.4); 0.843 (4.4); 0.832 (3.5); 0.821 (4.7); 0.809 (5.5); 0.783 (4.4); 0.772 (4.6); 0.767 (5.9); 0.753 (4.6); 0.741 (1.2); 0.732 (2.8); 0.720 (4.9); 0.710 (1.6); 0.698 (3.2); 0.685 (2.2); 0.680 (1.8); 0.663 (3.9); 0.649 (4.7); 0.646 (4.3); 0.634 (3.6); 0.623 (5.9); 0.612 (5.1); 0.601 (3.7); 0.592 (5.0); 0.577 (2.6); 0.569 (2.3); 0.557 (1.8); 0.102 (1.0); 0.042 (0.5); 0.031 (14.8); 0.020 (0.7)

Example I-47

¹H-NMR (300.2 MHz, CDCl₃): δ=8.513 (15.9); 7.869 (12.0); 7.738 (16.0); 7.683 (12.1); 7.681 (11.8); 7.653 (0.4); 7.300 (4.6); 4.750 (6.4); 4.701 (7.8); 4.582 (0.4); 4.448 (0.4); 4.292 (7.9); 4.243 (6.6); 4.153 (0.5); 4.129 (0.5); 3.510 (4.5); 3.463 (8.6); 3.427 (0.4); 3.375 (9.7); 3.328 (5.0); 2.921 (15.9); 2.072 (2.0); 1.941 (5.3); 1.310 (0.6); 1.286 (1.2); 1.262 (0.6); 1.139 (0.3); 0.947 (0.5); 0.915 (2.4); 0.908 (1.9); 0.899 (2.8); 0.892 (2.0); 0.875 (2.6); 0.868 (1.9); 0.859 (2.8); 0.804 (2.0); 0.788 (2.0); 0.782 (3.0); 0.766 (3.4); 0.758 (0.9); 0.749 (5.4); 0.741 (5.5); 0.724 (3.7); 0.707 (2.9); 0.701 (2.1); 0.685 (1.9); 0.623 (2.7); 0.614 (1.8); 0.608 (2.5); 0.589 (2.0); 0.583 (2.9); 0.573 (1.8); 0.566 (2.3); 0.534 (0.5); 0.097 (1.5); 0.025 (3.1)

Example I-48

¹H-NMR (300.2 MHz, CDCl₃): δ=8.282 (1.7); 8.267 (6.1); 8.251 (5.0); 7.847 (9.1); 7.635 (2.5); 7.618 (7.4); 7.600 (0.4); 7.512 (10.3); 7.496 (10.0); 7.300 (2.6); 5.483 (0.6); 4.724 (4.9); 4.675 (5.9); 4.252 (4.2); 4.203 (3.5); 4.148 (0.7); 4.132 (0.9); 4.124 (1.9); 4.108 (0.9); 4.100 (1.9); 4.076 (0.7); 3.606 (0.6); 3.596 (0.5); 3.544 (16.0); 3.496 (1.2); 3.393 (3.6); 3.328 (0.5); 2.373 (0.4); 2.053 (4.1); 2.047 (8.5); 1.503 (1.3); 1.287 (3.9); 1.270 (6.4); 1.264 (7.4); 1.246 (1.7); 1.240 (2.6); 0.908 (1.6); 0.899 (2.2); 0.887 (3.9); 0.864 (3.8); 0.857 (2.8); 0.845 (3.1); 0.840 (3.4); 0.813 (2.8); 0.794 (1.9); 0.781 (2.5); 0.775 (2.8); 0.754 (8.3); 0.731 (2.6); 0.714 (1.8); 0.692 (0.9); 0.630 (1.4); 0.604 (2.6); 0.599 (2.7); 0.586 (2.5); 0.580 (2.1); 0.562 (1.8); 0.544 (0.8); 0.013 (0.6); 0.007 (0.8)

Example I-49

¹H-NMR (300.2 MHz, CDCl₃): δ=7.861 (15.8); 7.631 (13.3); 7.478 (7.3); 7.470 (8.6); 7.452 (10.1); 7.444 (12.2); 7.301 (2.8); 7.276 (6.5); 7.250 (9.8); 7.224 (4.1); 4.750 (8.5); 4.702 (10.1); 4.206 (9.2); 4.157 (7.8); 3.562 (4.9); 3.514 (15.1); 3.474 (11.9); 3.426 (3.8); 2.836 (1.4); 2.806 (2.9); 2.791 (2.9); 2.043 (0.4); 2.027 (16.0); 0.851 (1.4); 0.836 (2.6); 0.819 (3.2); 0.812 (4.0); 0.804 (3.8); 0.794 (4.9); 0.778 (0.8); 0.767 (3.1); 0.744 (1.7); 0.722 (4.2); 0.707 (10.5); 0.689 (8.1); 0.685 (9.6); 0.671 (3.6); 0.663 (2.6); 0.649 (1.5); 0.599 (2.2); 0.573 (4.1); 0.563 (3.7); 0.555 (4.4); 0.550 (3.7); 0.530 (2.8); 0.517 (1.4); 0.020 (1.9)

Example I-50

¹H-NMR (300.2 MHz, CDCl₃): δ=8.313 (5.9); 8.297 (6.2); 7.877 (10.0); 7.680 (9.7); 7.616 (0.4); 7.509 (6.2); 7.493 (5.9); 7.302 (3.8); 7.300 (3.2); 4.756 (4.8); 4.707 (5.8); 4.286 (5.8); 4.237 (4.8); 4.155 (0.4); 4.131 (0.4); 3.559 (2.0); 3.513 (8.3); 3.488 (8.3); 3.442 (1.9); 2.776 (3.0); 2.072 (1.6); 2.042 (16.0); 1.843 (0.8); 1.312 (0.4); 1.288 (0.9); 1.264 (0.4); 0.865 (1.5); 0.857 (1.3); 0.843 (2.6); 0.822 (2.0); 0.809 (2.8); 0.784 (1.9); 0.765 (2.8); 0.749 (2.7); 0.729 (3.6); 0.718 (3.6); 0.697 (2.4); 0.679 (2.4); 0.663 (1.6); 0.609 (2.3); 0.597 (2.0); 0.574 (2.9); 0.562 (1.4); 0.553 (1.7); 0.029 (3.5)

Example I-51

¹H-NMR (300.2 MHz, CDCl₃): δ=7.891 (5.0); 7.677 (4.7); 7.675 (4.8); 7.300 (3.9); 7.201 (2.0); 7.176 (2.9); 7.152 (0.5); 7.144 (0.6); 7.078 (4.7); 7.049 (1.4); 4.698 (2.8); 4.650 (3.5); 4.279 (3.4); 4.259 (0.3); 4.231 (2.7); 3.454 (2.4); 3.407 (2.9); 3.051 (3.0); 3.004 (2.4); 2.397 (0.4); 2.376 (0.4); 2.347 (15.1); 2.295 (16.0); 2.082 (0.4); 2.072 (0.4); 2.016 (0.5); 1.939 (0.3); 1.911 (0.3); 0.925 (0.6); 0.917 (0.8); 0.911 (0.8); 0.897 (1.3); 0.893 (1.5); 0.876 (1.1); 0.862 (1.3); 0.756 (1.1); 0.744 (1.0); 0.738 (1.3); 0.725 (1.5); 0.703 (1.2); 0.698 (1.7); 0.690 (1.7); 0.683 (1.0); 0.665 (1.5); 0.647 (1.7); 0.629 (1.4); 0.615 (2.0); 0.603 (1.3); 0.580 (1.4); 0.569 (0.6); 0.560 (0.7); 0.555 (0.5); 0.037 (3.5)

Example I-52

¹H-NMR (300.2 MHz, CDCl₃): δ=7.884 (11.5); 7.683 (11.5); 7.666 (0.6); 7.617 (1.3); 7.505 (7.3); 7.477 (16.0); 7.469 (8.5); 7.375 (0.6); 7.335 (5.3); 7.328 (4.7); 7.307 (4.0); 7.300 (11.4); 7.210 (0.6); 7.203 (0.6); 7.182 (0.4); 7.175 (0.4); 7.138 (0.4); 5.333 (2.5); 4.740 (7.0); 4.691 (8.4); 4.571 (0.4); 4.398 (0.5); 4.252 (7.2); 4.204 (6.0); 3.464 (1.8); 3.416 (10.9); 3.400 (12.7); 3.352 (2.9); 3.304 (0.8); 2.502 (3.2); 2.498 (3.2); 2.473 (1.8); 1.765 (0.8);

1.742 (0.5); 1.119 (0.6); 1.100 (0.5); 1.022 (0.5); 1.006 (0.4); 0.832 (1.2); 0.828 (1.6); 0.820 (1.7); 0.810 (2.7); 0.805 (2.2); 0.786 (3.1); 0.773 (4.5); 0.745 (2.7); 0.733 (2.7); 0.727 (3.3); 0.711 (3.1); 0.692 (2.6); 0.689 (4.1); 0.679 (4.1); 0.674 (2.5); 0.662 (1.6); 0.653 (3.1); 0.640 (3.6); 0.635 (3.3); 0.622 (3.1); 0.600 (4.5); 0.588 (3.0); 0.568 (3.8); 0.558 (1.0); 0.554 (1.6); 0.545 (1.5); 0.541 (1.4); 0.032 (7.1)

Example I-53

$^1$H-NMR (300.2 MHz, CDCl$_3$): δ=7.885 (13.4); 7.662 (10.7); 7.599 (0.8); 7.486 (8.0); 7.458 (8.9); 7.389 (1.4); 7.378 (13.0); 7.371 (4.4); 7.355 (5.7); 7.349 (15.0); 7.337 (2.2); 7.300 (3.2); 7.060 (8.7); 7.051 (9.9); 7.028 (1.9); 7.017 (16.0); 7.009 (4.8); 6.994 (5.2); 6.987 (13.5); 6.975 (6.7); 6.966 (4.6); 6.947 (5.2); 6.938 (4.3); 4.755 (7.1); 4.706 (8.4); 4.562 (0.4); 4.455 (0.6); 4.410 (0.3); 4.221 (7.1); 4.172 (6.0); 3.457 (1.7); 3.409 (10.9); 3.393 (10.9); 3.344 (1.8); 3.307 (0.4); 3.258 (0.3); 2.579 (2.7); 2.528 (0.9); 2.033 (2.9); 1.913 (0.4); 0.864 (0.9); 0.849 (1.8); 0.831 (2.7); 0.825 (2.9); 0.817 (2.8); 0.807 (3.5); 0.792 (0.7); 0.780 (2.3); 0.766 (1.2); 0.752 (2.3); 0.744 (2.8); 0.729 (8.1); 0.712 (5.6); 0.707 (6.6); 0.694 (2.8); 0.686 (1.5); 0.672 (1.1); 0.622 (1.7); 0.612 (0.7); 0.596 (3.3); 0.585 (2.7); 0.578 (3.2); 0.573 (2.6); 0.553 (2.2); 0.540 (1.0); 0.029 (2.7)

Example I-54

$^1$H-NMR (300.2 MHz, d$_6$-DMSO): δ=8.042 (0.3); 8.039 (0.3); 7.958 (4.6); 7.893 (0.4); 7.837 (4.5); 7.479 (1.1); 7.465 (1.3); 7.463 (1.4); 7.451 (1.3); 7.208 (0.4); 7.191 (1.0); 7.169 (6.6); 7.159 (3.3); 7.150 (2.4); 7.138 (1.8); 5.677 (0.8); 5.570 (0.4); 5.237 (4.5); 5.204 (0.4); 4.567 (1.7); 4.553 (0.4); 4.519 (2.1); 4.060 (2.7); 4.011 (2.2); 3.359 (6.0); 3.214 (1.6); 3.166 (2.9); 3.139 (0.3); 3.076 (2.7); 3.028 (1.4); 2.533 (3.9); 2.527 (8.2); 2.521 (11.1); 2.515 (8.0); 2.509 (3.8); 2.340 (1.3); 2.318 (16.0); 2.249 (0.6); 2.009 (0.8); 1.195 (0.4); 0.959 (0.4); 0.938 (0.8); 0.934 (0.8); 0.923 (0.8); 0.914 (0.8); 0.903 (0.9); 0.899 (0.9); 0.879 (0.7); 0.761 (0.5); 0.736 (0.8); 0.726 (0.9); 0.716 (0.7); 0.707 (0.8); 0.701 (1.1); 0.682 (0.8); 0.604 (0.6); 0.587 (1.0); 0.570 (0.5); 0.562 (1.1); 0.550 (1.4); 0.525 (1.2); 0.514 (1.0); 0.506 (0.7); 0.495 (0.7); 0.489 (0.8); 0.471 (0.4); 0.031 (0.5); 0.020 (13.0); 0.009 (0.5)

Example I-55

$^1$H-NMR (300.2 MHz, d$_6$-DMSO): δ=7.916 (3.6); 7.914 (3.6); 7.802 (3.8); 7.799 (3.6); 7.440 (1.2); 7.435 (1.3); 7.416 (1.4); 7.410 (1.4); 7.315 (0.6); 7.310 (0.6); 7.288 (1.2); 7.263 (0.9); 7.258 (0.8); 7.049 (1.8); 7.024 (1.4); 6.975 (1.0); 6.972 (0.9); 6.951 (1.7); 6.947 (1.6); 6.926 (0.8); 6.922 (0.7); 5.138 (3.0); 5.136 (3.0); 4.640 (1.2); 4.591 (1.4); 4.084 (1.0); 4.061 (3.1); 4.037 (3.1); 4.013 (1.0); 3.896 (2.0); 3.847 (2.6); 3.838 (16.0); 3.528 (1.6); 3.481 (1.8); 3.340 (8.9); 2.866 (1.7); 2.820 (1.5); 2.533 (1.5); 2.527 (3.2); 2.521 (4.3); 2.515 (3.1); 2.509 (1.5); 2.009 (13.8); 1.218 (3.8); 1.194 (7.5); 1.171 (3.7); 1.004 (0.4); 0.980 (0.6); 0.968 (0.6); 0.960 (0.6); 0.948 (0.7); 0.925 (0.5); 0.727 (0.4); 0.702 (0.6); 0.692 (0.7); 0.683 (0.5); 0.672 (0.7); 0.667 (0.8); 0.648 (0.6); 0.541 (0.5); 0.523 (0.7); 0.518 (0.6); 0.506 (0.5); 0.499 (0.8); 0.488 (0.6); 0.482 (0.4); 0.464 (0.4); 0.428 (0.6); 0.410 (0.6); 0.403 (0.7); 0.392 (0.7); 0.386 (0.6); 0.374 (0.5); 0.368 (0.5); 0.350 (0.3); 0.020 (5.8)

Example I-56

$^1$H-NMR (300.2 MHz, CDCl$_3$): δ=8.420 (11.8); 7.879 (11.9); 7.686 (9.7); 7.580 (16.0); 7.300 (6.9); 4.763 (6.7); 4.714 (8.0); 4.282 (5.7); 4.233 (4.7); 4.156 (0.3); 4.132 (0.3); 3.487 (3.0); 3.440 (7.7); 3.387 (9.0); 3.340 (3.6); 2.844 (1.3); 2.074 (1.7); 2.043 (8.1); 1.892 (1.3); 1.311 (0.4); 1.288 (0.9); 1.264 (0.4); 0.886 (1.7); 0.879 (1.7); 0.868 (2.7); 0.862 (2.9); 0.844 (2.7); 0.829 (3.3); 0.788 (2.0); 0.767 (2.8); 0.751 (2.8); 0.732 (2.3); 0.726 (3.9); 0.719 (3.9); 0.693 (2.4); 0.675 (2.4); 0.656 (1.5); 0.602 (3.2); 0.587 (2.5); 0.568 (2.8); 0.563 (2.7); 0.552 (1.7); 0.545 (1.7); 0.538 (1.1); 0.027 (5.5)

Example I-57

$^1$H-NMR (300.2 MHz, CDCl$_3$): δ=8.646 (16.0); 8.525 (7.0); 8.509 (7.2); 8.484 (0.6); 7.892 (9.9); 7.698 (14.7); 7.658 (0.4); 7.646 (0.4); 7.534 (7.0); 7.518 (6.7); 7.479 (0.4); 7.462 (0.4); 7.300 (15.2); 6.882 (0.4); 4.762 (7.0); 4.713 (8.5); 4.291 (8.1); 4.242 (6.7); 4.187 (0.6); 4.163 (1.9); 4.139 (1.9); 4.126 (0.3); 4.116 (0.7); 3.511 (3.7); 3.465 (10.4); 3.420 (10.9); 3.373 (3.9); 2.996 (0.4); 2.650 (1.9); 2.619 (4.5); 2.077 (8.6); 2.043 (3.7); 1.814 (0.7); 1.315 (2.4); 1.291 (4.6); 1.267 (2.3); 0.852 (1.2); 0.838 (1.3); 0.832 (1.5); 0.821 (2.2); 0.807 (3.3); 0.797 (3.2); 0.786 (3.3); 0.768 (3.0); 0.758 (3.9); 0.754 (3.9); 0.737 (2.8); 0.726 (0.8); 0.719 (1.6); 0.706 (2.5); 0.677 (2.3); 0.663 (1.5); 0.651 (1.7); 0.638 (2.1); 0.628 (4.0); 0.613 (3.3); 0.602 (3.5); 0.592 (3.1); 0.582 (2.7); 0.575 (2.3); 0.562 (1.2); 0.557 (1.4); 0.549 (1.2); 0.537 (1.1); 0.042 (0.4); 0.031 (10.0); 0.020 (0.4)

Example I-58

$^1$H-NMR (300.2 MHz, CDCl$_3$): δ=7.884 (15.4); 7.703 (16.0); 7.668 (0.4); 7.654 (0.7); 7.380 (5.6); 7.374 (10.5); 7.368 (6.7); 7.336 (0.3); 7.298 (11.8); 7.286 (22.8); 7.280 (20.5); 7.145 (0.4); 7.139 (0.3); 4.666 (6.8); 4.617 (9.2); 4.362 (9.6); 4.313 (7.0); 3.537 (7.6); 3.491 (8.4); 3.100 (0.5); 2.765 (8.2); 2.719 (7.3); 2.343 (15.8); 2.044 (3.7); 1.728 (7.6); 0.807 (1.2); 0.785 (1.6); 0.772 (3.2); 0.749 (4.8); 0.738 (9.4); 0.725 (5.8); 0.705 (3.7); 0.690 (1.6); 0.670 (1.9); 0.602 (0.6); 0.567 (1.9); 0.554 (2.3); 0.537 (4.2); 0.518 (3.8); 0.497 (2.8); 0.434 (3.3); 0.416 (4.2); 0.395 (3.6); 0.380 (2.7); 0.366 (1.5); 0.044 (0.6); 0.033 (11.3)

Example I-59

$^1$H-NMR (300.2 MHz, d$_6$-DMSO): δ=8.025 (0.3); 8.021 (0.3); 7.957 (4.9); 7.955 (4.9); 7.848 (5.1); 7.845 (4.7); 7.800 (0.5); 7.223 (3.0); 7.207 (4.5); 7.190 (4.3); 7.165 (0.6); 7.089 (1.2); 7.073 (1.4); 7.061 (0.9); 5.570 (0.6); 5.396 (5.9); 5.329 (0.4); 4.567 (2.1); 4.518 (2.6); 4.480 (0.3); 4.137 (2.8); 4.088 (2.4); 4.061 (1.6); 4.037 (1.6); 4.014 (0.5); 3.341 (42.9); 3.135 (1.7); 3.089 (2.8); 2.980 (2.8); 2.934 (1.6); 2.533 (4.3); 2.527 (9.2); 2.521 (12.8); 2.515 (9.2); 2.509 (4.3); 2.307 (16.0); 2.009 (7.0); 1.218 (1.8); 1.195 (3.7); 1.171 (1.8); 0.674 (0.4); 0.657 (0.7); 0.651 (0.7); 0.634 (1.0); 0.621 (1.0); 0.616 (1.0); 0.608 (0.8); 0.579 (0.4); 0.546 (0.4); 0.523 (0.6); 0.513 (1.0); 0.497 (0.9); 0.482 (2.7); 0.454 (1.6); 0.444 (0.8); 0.423 (1.2); 0.406 (0.8); 0.397 (1.1); 0.381 (0.7); 0.372 (0.7); 0.031 (0.5); 0.020 (13.7); 0.009 (0.5)

Example I-60

$^1$H-NMR (300.2 MHz, d$_6$-DMSO): δ=7.988 (4.9); 7.877 (4.9); 7.344 (3.9); 7.310 (3.8); 5.786 (16.0); 5.699 (5.9);

4.603 (1.9); 4.554 (2.4); 4.222 (2.4); 4.173 (2.0); 4.067 (0.9); 4.043 (0.9); 3.354 (56.6); 3.333 (0.6); 3.194 (1.6); 3.149 (2.4); 3.002 (2.3); 2.956 (1.6); 2.534 (15.6); 2.528 (21.2); 2.522 (15.4); 2.489 (0.4); 2.459 (15.3); 2.420 (0.8); 2.309 (1.0); 2.015 (3.9); 1.355 (1.8); 1.261 (0.7); 1.224 (1.2); 1.200 (2.2); 1.177 (1.0); 1.081 (0.4); 0.640 (0.6); 0.620 (0.7); 0.606 (1.0); 0.598 (1.3); 0.583 (0.5); 0.562 (1.0); 0.550 (1.1); 0.529 (4.4); 0.508 (1.1); 0.497 (0.7); 0.475 (0.8); 0.441 (1.2); 0.435 (1.2); 0.420 (0.7); 0.400 (0.7); 0.387 (0.4); 0.037 (0.7); 0.026 (25.7); 0.015 (1.1)

Example I-61

$^1$H-NMR (300.2 MHz, CDCl$_3$): δ=7.886 (5.9); 7.713 (6.2); 7.378 (16.0); 7.351 (0.4); 7.320 (0.4); 7.300 (5.1); 7.236 (0.7); 7.226 (1.1); 4.678 (2.5); 4.630 (3.5); 4.611 (0.4); 4.401 (3.5); 4.383 (0.3); 4.352 (2.6); 3.530 (2.7); 3.485 (3.1); 3.312 (3.6); 3.020 (1.1); 2.919 (1.0); 2.843 (2.9); 2.798 (2.6); 2.050 (5.3); 1.841 (0.5); 0.757 (0.8); 0.732 (4.6); 0.724 (3.0); 0.712 (1.2); 0.692 (0.4); 0.569 (0.6); 0.540 (2.9); 0.531 (2.6); 0.521 (2.0); 0.509 (2.5); 0.484 (0.4); 0.478 (0.4); 0.033 (4.2)

Example I-62

$^1$H-NMR (300.2 MHz, CDCl$_3$): δ=8.425 (1.9); 8.408 (1.9); 7.889 (3.1); 7.730 (3.1); 7.728 (2.8); 7.390 (2.3); 7.300 (16.2); 7.286 (1.6); 7.281 (1.3); 4.689 (1.6); 4.641 (2.2); 4.401 (2.2); 4.352 (1.6); 3.580 (1.8); 3.535 (2.0); 2.795 (1.9); 2.750 (1.7); 2.111 (4.1); 1.625 (16.0); 0.760 (1.6); 0.749 (2.8); 0.740 (2.1); 0.704 (0.6); 0.560 (0.5); 0.554 (0.6); 0.549 (0.5); 0.544 (0.4); 0.528 (0.7); 0.518 (0.9); 0.513 (0.9); 0.504 (0.6); 0.417 (0.7); 0.409 (1.0); 0.406 (0.9); 0.397 (0.6); 0.382 (0.4); 0.373 (0.6); 0.370 (0.6); 0.361 (0.4); 0.048 (0.6); 0.037 (14.4); 0.026 (0.6)

Example I-63

$^1$H-NMR (400.1 MHz, d$_6$-DMSO): δ=8.032 (0.9); 7.972 (14.7); 7.844 (15.4); 7.813 (1.0); 7.698 (11.1); 7.679 (13.2); 7.634 (12.3); 7.614 (16.0); 7.500 (15.0); 7.480 (15.2); 7.464 (14.0); 7.444 (8.2); 7.372 (4.8); 7.354 (6.7); 7.336 (2.5); 5.758 (1.1); 5.492 (14.2); 5.416 (0.9); 4.592 (6.0); 4.555 (7.0); 4.181 (7.1); 4.145 (6.1); 4.071 (0.4); 4.036 (0.4); 3.325 (141.0); 3.209 (5.0); 3.174 (7.1); 3.149 (0.4); 3.114 (0.5); 3.045 (7.0); 3.025 (0.9); 3.011 (4.8); 2.991 (0.4); 2.676 (0.6); 2.511 (71.8); 2.507 (87.8); 2.334 (0.5); 0.681 (1.3); 0.666 (2.5); 0.652 (3.4); 0.640 (3.1); 0.626 (2.2); 0.547 (1.2); 0.529 (2.2); 0.522 (3.0); 0.504 (4.0); 0.491 (4.5); 0.476 (3.9); 0.459 (3.3); 0.451 (2.3); 0.432 (3.7); 0.421 (2.8); 0.415 (2.8); 0.407 (3.4); 0.394 (2.1); 0.389 (2.1); 0.376 (1.1)

Example I-64

$^1$H-NMR (300.2 MHz, CDCl$_3$): δ=7.860 (16.0); 7.659 (13.3); 7.657 (12.8); 7.368 (7.5); 7.340 (20.5); 7.308 (26.9); 7.300 (9.4); 7.286 (4.3); 7.280 (9.4); 5.325 (0.9); 4.646 (7.4); 4.597 (9.9); 4.332 (9.3); 4.284 (7.0); 3.531 (6.4); 3.485 (7.2); 2.800 (8.4); 2.754 (7.5); 2.648 (1.3); 2.567 (1.7); 2.544 (1.7); 2.067 (0.6); 2.050 (0.5); 2.032 (0.6); 0.740 (1.0); 0.719 (1.2); 0.705 (2.7); 0.677 (9.5); 0.649 (3.4); 0.634 (1.2); 0.631 (1.2); 0.614 (1.6); 0.571 (0.9); 0.536 (2.0); 0.529 (2.5); 0.523 (2.2); 0.510 (4.0); 0.493 (3.9); 0.488 (3.8); 0.472 (2.9); 0.408 (3.4); 0.392 (4.1); 0.372 (2.9); 0.364 (2.0); 0.356 (2.8); 0.346 (1.6); 0.311 (0.4); 0.026 (2.5)

Example I-65

$^1$H-NMR (300.2 MHz, CDCl$_3$): δ=7.879 (11.1); 7.671 (12.0); 7.440 (1.0); 7.430 (1.5); 7.424 (1.0); 7.418 (1.4); 7.411 (6.1); 7.400 (2.9); 7.393 (6.5); 7.387 (16.0); 7.380 (6.9); 7.367 (4.0); 7.346 (10.0); 7.338 (7.5); 7.320 (5.1); 7.314 (3.8); 7.300 (4.1); 4.675 (5.7); 4.626 (7.5); 4.326 (7.6); 4.278 (5.9); 3.556 (6.3); 3.510 (7.1); 2.845 (6.9); 2.799 (6.1); 2.198 (10.1); 1.866 (0.5); 0.770 (1.1); 0.752 (1.1); 0.748 (1.4); 0.735 (2.7); 0.717 (3.1); 0.712 (3.6); 0.697 (4.8); 0.694 (4.4); 0.679 (3.7); 0.675 (3.6); 0.657 (3.3); 0.644 (1.3); 0.640 (1.3); 0.622 (1.8); 0.583 (0.3); 0.544 (1.8); 0.529 (1.8); 0.524 (1.7); 0.511 (3.7); 0.494 (2.7); 0.488 (2.8); 0.471 (2.2); 0.391 (2.9); 0.373 (3.0); 0.369 (2.9); 0.352 (3.6); 0.337 (2.0); 0.334 (2.0); 0.319 (1.3); 0.033 (3.3)

Example I-66

$^1$H-NMR (300.2 MHz, CDCl$_3$): δ=7.757 (12.4); 7.494 (5.9); 7.484 (5.8); 7.479 (5.2); 7.469 (7.8); 7.457 (7.7); 7.301 (14.4); 7.276 (5.8); 7.249 (8.1); 7.223 (3.7); 7.004 (12.6); 5.320 (0.4); 4.496 (6.5); 4.447 (10.5); 4.298 (10.2); 4.249 (6.3); 3.491 (3.2); 3.443 (12.3); 3.412 (12.9); 3.365 (3.4); 2.280 (11.4); 2.083 (0.6); 1.690 (5.5); 1.321 (0.6); 1.293 (1.9); 1.274 (0.4); 0.941 (0.4); 0.919 (1.1); 0.908 (0.5); 0.894 (0.7); 0.886 (1.0); 0.860 (2.7); 0.838 (16.0); 0.824 (6.5); 0.817 (6.4); 0.810 (3.4); 0.807 (3.3); 0.794 (3.6); 0.784 (6.2); 0.757 (0.6); 0.735 (5.4); 0.725 (2.3); 0.712 (2.3); 0.704 (1.8); 0.693 (1.9); 0.666 (0.3); 0.038 (12.5)

Example I-67

$^1$H-NMR (300.2 MHz, CDCl$_3$): δ=8.306 (8.6); 8.290 (8.9); 7.752 (10.9); 7.718 (0.5); 7.695 (0.5); 7.690 (0.5); 7.678 (0.4); 7.655 (0.5); 7.649 (0.4); 7.594 (0.3); 7.575 (0.4); 7.570 (0.3); 7.515 (9.0); 7.499 (8.9); 7.300 (30.1); 7.021 (11.1); 7.019 (11.0); 4.511 (6.1); 4.462 (10.0); 4.321 (9.9); 4.272 (6.1); 3.509 (4.8); 3.463 (10.2); 3.387 (10.5); 3.341 (5.0); 2.381 (14.8); 2.083 (0.4); 1.641 (16.0); 1.291 (3.1); 0.928 (1.6); 0.920 (2.0); 0.913 (2.8); 0.901 (1.5); 0.887 (7.2); 0.874 (8.6); 0.854 (3.5); 0.839 (3.8); 0.821 (3.8); 0.810 (3.4); 0.786 (11.1); 0.778 (8.2); 0.759 (1.1); 0.748 (2.0); 0.736 (1.3); 0.702 (0.3); 0.048 (1.2); 0.037 (27.6); 0.026 (1.7)

Example I-68

$^1$H-NMR (300.2 MHz, CDCl$_3$): δ=7.769 (4.2); 7.300 (5.9); 7.224 (2.0); 7.198 (2.5); 7.125 (0.4); 7.114 (0.5); 7.048 (6.2); 7.023 (1.7); 6.996 (4.5); 6.994 (4.5); 5.337 (2.3); 4.413 (0.8); 4.364 (5.6); 4.350 (5.4); 4.301 (0.8); 3.416 (2.4); 3.368 (2.9); 2.916 (3.0); 2.869 (2.5); 2.340 (15.4); 2.282 (0.4); 2.215 (16.0); 1.722 (1.0); 1.323 (0.6); 1.293 (3.2); 1.248 (0.3); 0.953 (0.6); 0.938 (0.7); 0.929 (1.0); 0.920 (1.4); 0.909 (1.0); 0.896 (2.1); 0.884 (3.4); 0.870 (2.4); 0.855 (2.1); 0.848 (2.7); 0.824 (2.3); 0.817 (1.7); 0.807 (1.3); 0.800 (1.5); 0.783 (0.7); 0.724 (1.4); 0.710 (1.2); 0.695 (1.5); 0.688 (1.1); 0.676 (0.9); 0.669 (0.8); 0.658 (0.6); 0.109 (0.5); 0.039 (5.1)

Example I-69

$^1$H-NMR (300.2 MHz, CDCl$_3$): δ=7.722 (10.8); 7.719 (10.5); 7.526 (7.5); 7.498 (9.4); 7.432 (8.6); 7.425 (9.1); 7.300 (3.6); 7.287 (5.8); 7.280 (5.3); 7.259 (4.6); 7.252

(4.2); 6.951 (10.9); 6.948 (10.3); 4.465 (6.2); 4.416 (10.0); 4.275 (9.5); 4.226 (5.9); 3.389 (3.5); 3.341 (10.1); 3.296 (11.1); 3.248 (4.0); 2.807 (5.2); 2.063 (0.8); 2.034 (2.8); 0.865 (0.5); 0.856 (0.6); 0.833 (3.6); 0.815 (16.0); 0.810 (10.4); 0.800 (4.9); 0.793 (7.3); 0.784 (6.0); 0.778 (4.6); 0.771 (2.3); 0.756 (5.2); 0.750 (2.9); 0.737 (2.0); 0.735 (2.0); 0.729 (1.2); 0.718 (0.7); 0.710 (1.2); 0.702 (0.7); 0.029 (2.4)

Example I-70

$^1$H-NMR (300.2 MHz, d$_6$-DMSO): δ=7.732 (11.0); 7.729 (10.3); 7.655 (6.6); 7.627 (7.3); 7.509 (1.3); 7.497 (13.3); 7.489 (4.3); 7.475 (4.7); 7.467 (15.2); 7.456 (1.6); 7.136 (8.6); 7.128 (10.4); 7.118 (16.0); 7.111 (4.8); 7.096 (4.5); 7.088 (13.0); 7.077 (1.3); 7.045 (4.9); 7.037 (4.1); 7.017 (4.5); 7.008 (4.0); 6.965 (11.3); 6.961 (10.5); 5.779 (1.9); 5.253 (3.9); 4.467 (4.9); 4.418 (5.9); 4.012 (5.7); 3.964 (4.9); 3.351 (20.3); 3.302 (6.0); 3.153 (5.6); 3.106 (3.7); 2.537 (3.1); 2.531 (6.5); 2.525 (8.7); 2.519 (6.4); 2.513 (3.0); 1.027 (0.8); 1.011 (1.5); 0.992 (1.7); 0.985 (2.1); 0.970 (1.8); 0.961 (1.2); 0.947 (0.7); 0.793 (0.7); 0.772 (1.2); 0.756 (2.2); 0.725 (5.2); 0.702 (4.0); 0.688 (4.2); 0.667 (2.5); 0.646 (1.4); 0.629 (0.4); 0.032 (0.4); 0.021 (9.6); 0.010 (0.4)

Example I-71

$^1$H-NMR (300.2 MHz, CDCl$_3$): δ=7.761 (3.9); 7.365 (0.8); 7.359 (1.0); 7.352 (1.1); 7.343 (1.5); 7.333 (1.4); 7.321 (0.4); 7.300 (3.8); 7.239 (8.2); 7.230 (5.4); 7.190 (0.5); 6.991 (3.8); 6.989 (3.9); 4.423 (0.7); 4.374 (5.2); 4.360 (5.1); 4.311 (0.7); 3.453 (2.4); 3.406 (2.9); 2.968 (3.1); 2.921 (2.6); 2.370 (0.6); 2.261 (16.0); 2.196 (0.6); 1.781 (0.8); 1.293 (0.5); 0.959 (0.4); 0.943 (0.5); 0.934 (0.7); 0.926 (1.0); 0.920 (1.1); 0.901 (1.6); 0.891 (2.9); 0.885 (1.5); 0.880 (2.0); 0.858 (2.3); 0.850 (0.8); 0.832 (2.0); 0.826 (1.4); 0.815 (1.0); 0.808 (1.2); 0.791 (0.5); 0.711 (1.1); 0.696 (1.0); 0.681 (1.4); 0.675 (1.0); 0.662 (0.8); 0.656 (0.7); 0.645 (0.6); 0.038 (3.0)

Example I-72

$^1$H-NMR (300.2 MHz, CDCl$_3$): δ=8.630 (16.0); 8.509 (10.1); 8.492 (10.4); 7.760 (11.4); 7.757 (11.1); 7.545 (8.5); 7.528 (8.2); 7.300 (39.8); 7.021 (12.0); 7.018 (11.5); 5.338 (4.2); 4.498 (6.9); 4.449 (12.1); 4.331 (11.9); 4.282 (6.8); 3.453 (5.6); 3.407 (10.6); 3.313 (11.4); 3.266 (6.0); 2.341 (10.1); 1.666 (7.6); 1.291 (3.9); 1.258 (0.5); 0.939 (0.5); 0.913 (1.8); 0.900 (1.5); 0.891 (3.1); 0.866 (7.2); 0.858 (5.6); 0.852 (4.3); 0.846 (5.2); 0.835 (7.1); 0.824 (3.9); 0.815 (3.4); 0.805 (4.3); 0.798 (3.9); 0.792 (4.2); 0.784 (3.3); 0.780 (3.6); 0.770 (0.9); 0.742 (5.3); 0.736 (4.1); 0.716 (3.4); 0.709 (1.8); 0.704 (1.9); 0.693 (2.0); 0.665 (0.5); 0.106 (0.6); 0.047 (1.3); 0.036 (33.4); 0.025 (1.3)

Example I-73

$^1$H-NMR (300.2 MHz, CDCl$_3$): δ=7.750 (4.6); 7.301 (7.1); 7.276 (2.7); 7.251 (2.1); 7.171 (2.1); 7.134 (2.3); 7.100 (3.5); 6.992 (4.7); 4.426 (0.8); 4.377 (4.7); 4.359 (5.4); 4.310 (0.9); 3.504 (2.9); 3.459 (3.0); 2.626 (3.0); 2.580 (2.7); 2.382 (16.0); 1.945 (4.4); 1.708 (2.4); 1.294 (0.5); 1.247 (0.4); 0.921 (0.8); 0.835 (0.7); 0.814 (1.4); 0.797 (2.9); 0.794 (3.1); 0.775 (4.1); 0.767 (3.9); 0.746 (1.3); 0.736 (0.4); 0.729 (0.7); 0.709 (0.4); 0.459 (0.7); 0.445 (1.1); 0.436 (1.3); 0.430 (1.9); 0.406 (1.3); 0.390 (0.8); 0.038 (5.3)

Example I-74

$^1$H-NMR (300.2 MHz, CDCl$_3$): δ=7.645 (4.5); 7.403 (16.0); 7.300 (34.9); 6.949 (0.3); 6.929 (4.8); 6.926 (4.7); 5.339 (0.7); 4.519 (2.5); 4.469 (4.2); 4.338 (3.9); 4.288 (2.4); 3.668 (1.1); 3.484 (2.8); 3.438 (3.2); 2.738 (2.8); 2.693 (2.5); 1.617 (8.1); 1.292 (2.1); 0.918 (1.1); 0.911 (0.6); 0.892 (1.5); 0.882 (1.7); 0.873 (2.1); 0.861 (1.7); 0.856 (1.9); 0.838 (1.7); 0.820 (0.9); 0.784 (1.3); 0.765 (1.6); 0.748 (0.8); 0.742 (1.3); 0.730 (1.0); 0.706 (0.7); 0.673 (1.1); 0.654 (1.0); 0.647 (1.1); 0.639 (1.2); 0.628 (0.9); 0.619 (0.9); 0.613 (0.9); 0.593 (0.5); 0.107 (0.5); 0.049 (1.0); 0.038 (30.0); 0.027 (1.2)

Example I-75

$^1$H-NMR (300.2 MHz, CDCl$_3$): δ=8.360 (9.8); 8.343 (10.1); 7.648 (13.7); 7.646 (13.8); 7.457 (12.2); 7.362 (6.9); 7.357 (6.5); 7.345 (6.7); 7.340 (6.3); 7.300 (37.5); 6.906 (14.4); 6.903 (14.1); 5.322 (0.6); 4.539 (8.2); 4.490 (12.4); 4.314 (11.7); 4.265 (7.9); 3.870 (7.2); 3.506 (8.5); 3.460 (9.5); 2.743 (8.5); 2.698 (7.7); 1.666 (16.0); 1.291 (9.9); 0.927 (0.9); 0.917 (0.8); 0.908 (3.5); 0.896 (3.9); 0.881 (4.8); 0.870 (6.8); 0.863 (6.8); 0.844 (7.2); 0.839 (6.4); 0.820 (1.7); 0.740 (3.2); 0.720 (4.0); 0.710 (3.6); 0.693 (3.4); 0.688 (3.6); 0.681 (1.8); 0.661 (2.2); 0.627 (3.4); 0.607 (3.3); 0.603 (4.0); 0.591 (3.1); 0.581 (2.8); 0.573 (2.4); 0.567 (2.8); 0.547 (1.6); 0.106 (0.7); 0.048 (0.9); 0.037 (28.3); 0.026 (1.2)

Example I-76

$^1$H-NMR (300.2 MHz, CDCl$_3$): δ=7.746 (3.5); 7.301 (7.4); 7.189 (23.7); 6.991 (3.6); 4.419 (0.5); 4.370 (3.8); 4.356 (4.4); 4.307 (0.6); 3.503 (2.3); 3.457 (2.5); 2.622 (2.5); 2.576 (2.3); 2.385 (16.0); 2.360 (0.3); 1.875 (2.8); 1.673 (2.6); 1.293 (0.6); 0.921 (0.6); 0.832 (0.5); 0.809 (0.6); 0.803 (1.1); 0.795 (1.7); 0.784 (2.4); 0.781 (2.4); 0.771 (3.9); 0.769 (4.0); 0.756 (1.5); 0.749 (1.6); 0.741 (0.6); 0.732 (0.6); 0.457 (0.5); 0.445 (0.8); 0.433 (1.3); 0.430 (1.2); 0.406 (1.1); 0.394 (0.6); 0.039 (6.2)

Example I-77

$^1$H-NMR (300.2 MHz, d$_6$-DMSO): δ=7.759 (7.9); 7.411 (3.1); 7.403 (1.8); 7.381 (14.9); 7.366 (16.0); 7.345 (1.8); 7.337 (3.1); 6.988 (7.9); 6.985 (7.5); 5.334 (11.6); 4.388 (3.4); 4.339 (5.5); 4.203 (5.5); 4.154 (3.5); 3.346 (31.1); 3.202 (3.8); 3.156 (4.6); 2.775 (4.3); 2.729 (3.6); 2.530 (10.1); 2.524 (13.3); 2.518 (9.8); 2.097 (0.7); 2.012 (1.1); 1.197 (0.5); 0.624 (1.0); 0.605 (1.6); 0.597 (2.1); 0.590 (2.7); 0.583 (3.0); 0.571 (2.8); 0.563 (3.1); 0.551 (2.8); 0.535 (3.5); 0.519 (2.5); 0.497 (2.2); 0.484 (1.7); 0.473 (2.3); 0.459 (2.0); 0.444 (2.3); 0.432 (1.2); 0.415 (1.1); 0.397 (0.5); 0.023 (8.8)

Example I-78

$^1$H-NMR (499.9 MHz, CDCl$_3$): δ=7.681 (0.4); 7.672 (3.4); 7.667 (3.3); 7.657 (3.0); 7.653 (4.3); 7.646 (8.7); 7.645 (8.5); 7.554 (0.7); 7.551 (0.8); 7.540 (0.7); 7.536 (0.7); 7.390 (3.5); 7.386 (2.6); 7.376 (3.8); 7.372 (4.3); 7.362 (0.7); 7.354 (0.5); 7.343 (1.0); 7.340 (0.9); 7.328

(1.1); 7.325 (1.0); 7.301 (1.3); 7.278 (11.1); 7.251 (0.9); 7.247 (1.4); 7.236 (4.0); 7.232 (4.4); 7.230 (4.5); 7.224 (7.9); 7.218 (4.1); 7.215 (4.2); 7.210 (3.5); 7.200 (1.7); 7.196 (1.4); 7.191 (1.0); 7.177 (1.3); 7.174 (1.3); 7.162 (1.1); 7.159 (1.4); 7.155 (1.2); 7.144 (0.8); 7.140 (0.8); 7.130 (0.4); 7.126 (0.3); 6.538 (8.6); 6.537 (8.3); 6.208 (1.2); 6.206 (1.2); 5.301 (2.1); 4.609 (5.9); 4.579 (6.4); 4.463 (0.3); 4.189 (0.4); 4.178 (0.4); 4.140 (0.4); 4.126 (0.5); 4.112 (0.5); 4.097 (0.4); 4.075 (0.3); 4.061 (0.4); 4.046 (0.4); 4.035 (0.4); 4.027 (0.4); 4.017 (0.4); 4.007 (0.4); 3.996 (0.4); 3.987 (0.4); 3.975 (0.4); 3.964 (0.4); 3.958 (0.4); 3.946 (0.4); 3.935 (0.4); 3.925 (0.4); 3.915 (0.4); 3.906 (0.4); 3.877 (6.3); 3.847 (6.0); 3.825 (0.6); 3.807 (0.5); 3.793 (0.6); 3.780 (0.5); 3.764 (0.5); 3.754 (0.4); 3.725 (1.6); 3.720 (6.2); 3.704 (0.8); 3.698 (1.8); 3.691 (7.2); 3.679 (4.0); 3.666 (8.9); 3.653 (11.9); 3.639 (9.2); 3.626 (4.0); 3.613 (1.1); 3.598 (0.4); 3.587 (0.5); 3.580 (0.3); 3.567 (1.1); 3.553 (0.4); 3.539 (1.2); 3.525 (0.4); 3.204 (5.7); 3.176 (5.1); 3.117 (5.6); 3.102 (15.1); 3.087 (16.0); 3.072 (5.5); 3.056 (1.1); 3.045 (0.4); 2.347 (0.5); 2.041 (0.9); 1.600 (0.3); 1.557 (15.8); 1.542 (31.8); 1.527 (16.3); 1.486 (37.3); 1.474 (38.6); 1.411 (0.8); 1.396 (0.5); 1.358 (0.4); 1.344 (0.4); 1.257 (0.6); 1.243 (0.4); 1.236 (0.4); 1.228 (0.4); 1.225 (0.4); 1.217 (0.4); 1.215 (0.4); 1.207 (0.4); 1.204 (0.4); 1.194 (0.4); 1.088 (1.3); 1.074 (2.0); 1.067 (2.0); 1.061 (1.9); 1.052 (2.3); 1.040 (1.7); 0.972 (0.4); 0.961 (0.5); 0.958 (0.5); 0.948 (0.6); 0.941 (0.4); 0.937 (0.5); 0.927 (0.6); 0.887 (0.4); 0.876 (0.4); 0.873 (0.3); 0.866 (0.6); 0.855 (0.6); 0.852 (0.6); 0.842 (0.5); 0.809 (0.7); 0.804 (1.5); 0.799 (0.8); 0.789 (2.3); 0.783 (2.3); 0.777 (2.3); 0.768 (2.7); 0.756 (2.1); 0.645 (1.5); 0.633 (2.5); 0.624 (1.5); 0.619 (2.5); 0.612 (2.3); 0.600 (2.6); 0.589 (2.1); 0.586 (2.5); 0.579 (2.4); 0.574 (1.7); 0.567 (1.8); 0.544 (2.2); 0.553 (1.2); 0.006 (0.5); 0.000 (11.6); −0.006 (0.8)

Example I-79

$^1$H-NMR (300.2 MHz, CDCl$_3$): δ=7.730 (4.5); 7.656 (4.9); 7.654 (4.6); 7.469 (1.3); 7.462 (0.8); 7.453 (1.7); 7.450 (1.3); 7.440 (1.9); 7.429 (0.4); 7.425 (0.4); 7.358 (0.4); 7.347 (0.7); 7.344 (1.0); 7.335 (1.5); 7.326 (3.4); 7.316 (5.2); 7.307 (3.0); 7.298 (5.2); 7.293 (2.2); 7.284 (1.8); 7.270 (0.4); 4.494 (2.5); 4.445 (3.2); 4.108 (3.4); 4.060 (2.7); 3.320 (1.4); 3.272 (4.9); 3.237 (4.7); 3.189 (1.4); 1.920 (5.7); 1.721 (1.9); 1.399 (16.0); 1.340 (0.5); 0.447 (0.4); 0.432 (0.7); 0.417 (1.2); 0.405 (0.8); 0.400 (0.9); 0.386 (0.8); 0.263 (0.6); 0.247 (1.1); 0.234 (1.1); 0.221 (0.4); 0.214 (0.7); 0.203 (0.9); 0.181 (1.1); 0.169 (0.8); 0.163 (0.4); 0.153 (1.6); 0.139 (1.4); 0.135 (1.3); 0.122 (1.2); 0.095 (1.4); 0.084 (1.2); 0.076 (1.2); 0.065 (1.6); 0.054 (0.7); 0.047 (0.7); 0.033 (3.4)

Example I-80

$^1$H-NMR (300.2 MHz, CDCl$_3$): δ=7.714 (15.7); 7.684 (2.1); 7.668 (16.0); 7.648 (0.3); 7.501 (0.4); 7.498 (0.3); 7.478 (0.7); 7.467 (4.7); 7.455 (5.2); 7.449 (3.8); 7.446 (3.2); 7.436 (6.4); 7.423 (1.5); 7.368 (0.8); 7.357 (3.5); 7.345 (4.6); 7.338 (4.9); 7.326 (9.1); 7.309 (4.1); 7.299 (16.1); 7.297 (16.8); 7.285 (11.5); 7.277 (9.4); 7.265 (8.1); 7.253 (1.1); 7.236 (0.4); 7.188 (0.7); 7.175 (0.4); 7.170 (0.4); 7.157 (0.5); 4.588 (0.6); 4.454 (0.4); 4.445 (0.4); 4.369 (0.4); 4.321 (0.4); 4.301 (0.4); 4.253 (12.9); 4.208 (15.0); 4.189 (0.5); 4.160 (5.3); 4.142 (0.4); 4.119 (0.7); 4.087 (0.4); 3.287 (8.3); 3.241 (13.0); 3.136 (0.6); 3.089 (13.4); 3.043 (8.5); 2.078 (3.9); 1.901 (3.0); 1.879 (2.0); 1.842 (2.0); 1.781 (1.0); 1.766 (0.9); 1.742 (0.9); 1.341 (0.6); 1.316 (1.9); 1.300 (3.7); 1.293 (4.8); 1.269 (1.3); 1.056 (1.1); 1.038 (2.5); 1.029 (2.6); 1.021 (1.7); 1.011 (5.0); 1.001 (1.8); 0.993 (2.8); 0.983 (2.9); 0.965 (1.5); 0.937 (1.3); 0.916 (4.0); 0.892 (1.6); 0.395 (1.1); 0.380 (1.5); 0.377 (1.4); 0.364 (2.9); 0.349 (3.8); 0.335 (3.4); 0.321 (2.4); 0.318 (2.3); 0.304 (2.0); 0.287 (1.9); 0.274 (2.5); 0.270 (2.3); 0.257 (3.3); 0.246 (2.9); 0.243 (3.5); 0.229 (3.0); 0.216 (1.3); 0.212 (1.3); 0.198 (1.4); 0.165 (0.5); 0.105 (0.6); 0.045 (0.4); 0.034 (7.7); 0.026 (1.3); 0.010 (2.2); −0.007 (3.5); 0.024 (4.5); −0.039 (4.1); −0.056 (2.0); −0.065 (2.4); −0.078 (2.7); −0.082 (4.4); −0.095 (4.8); −0.114 (3.6); −0.128 (2.1); −0.146 (1.0)

Example I-81

$^1$H-NMR (300.2 MHz, CDCl$_3$): δ=7.772 (14.8); 7.655 (16.0); 7.653 (15.7); 7.457 (1.0); 7.448 (4.3); 7.440 (2.7); 7.433 (4.7); 7.430 (4.8); 7.418 (6.0); 7.408 (1.3); 7.404 (0.9); 7.331 (1.8); 7.320 (2.6); 7.316 (4.0); 7.308 (4.8); 7.298 (43.1); 7.285 (17.8); 7.276 (9.2); 7.270 (5.8); 7.268 (5.9); 7.263 (6.9); 7.253 (8.1); 7.240 (1.2); 7.230 (0.5); 4.241 (0.4); 4.177 (6.3); 4.128 (10.6); 3.995 (11.8); 3.947 (7.1); 3.132 (9.2); 3.085 (12.5); 2.844 (12.4); 2.797 (9.2); 2.751 (0.7); 2.723 (2.7); 2.711 (1.1); 2.692 (2.9); 2.675 (1.6); 2.665 (1.9); 2.653 (0.7); 2.637 (0.8); 2.183 (11.7); 2.044 (13.5); 1.924 (0.6); 1.891 (1.9); 1.873 (8.0); 1.868 (10.1); 1.860 (11.8); 1.852 (9.2); 1.847 (9.2); 1.840 (7.9); 1.834 (7.6); 1.814 (3.1); 1.804 (3.6); 1.774 (1.6); 1.754 (0.4); 1.743 (0.4); 1.721 (1.1); 1.709 (1.3); 1.696 (1.7); 1.688 (2.1); 1.677 (2.9); 1.661 (1.9); 1.653 (1.7); 1.630 (14.7); 1.610 (1.5); 1.603 (1.8); 1.590 (2.3); 1.582 (2.2); 1.559 (2.1); 1.535 (0.6); 1.531 (0.5); 0.106 (1.4); 0.047 (1.2); 0.036 (32.4); 0.025 (1.1)

Example I-82

$^1$H-NMR (300.2 MHz, CDCl$_3$): δ=7.764 (4.5); 7.624 (4.7); 7.622 (4.1); 7.461 (1.3); 7.454 (0.8); 7.447 (0.8); 7.442 (1.2); 7.439 (1.1); 7.430 (1.9); 7.362 (0.8); 7.352 (0.8); 7.349 (0.9); 7.345 (0.9); 7.338 (1.3); 7.330 (2.6); 7.317 (1.0); 7.301 (3.5); 7.298 (4.4); 7.294 (2.6); 7.283 (3.0); 7.274 (1.8); 7.270 (1.5); 7.265 (1.4); 7.250 (0.4); 4.380 (2.2); 4.332 (2.8); 3.961 (3.0); 3.913 (2.4); 3.148 (1.9); 3.101 (3.6); 3.008 (4.1); 2.961 (2.1); 2.381 (1.7); 2.374 (1.9); 1.802 (0.6); 1.797 (0.7); 1.782 (0.5); 1.759 (1.0); 1.736 (1.5); 1.713 (1.2); 1.690 (0.5); 1.153 (16.0); 1.130 (14.0); 0.031 (1.7)

Example I-83

$^1$H-NMR (300.2 MHz, d$_6$-DMSO): δ=8.029 (1.8); 7.855 (1.9); 7.852 (1.7); 7.581 (0.5); 7.572 (0.5); 7.556 (0.4); 7.549 (0.6); 7.471 (0.6); 7.465 (0.4); 7.449 (0.6); 7.440 (0.8); 7.312 (0.7); 7.305 (0.9); 7.292 (1.4); 7.281 (0.7); 7.271 (0.5); 4.761 (2.5); 4.317 (0.7); 4.269 (0.9); 4.047 (0.9); 4.040 (0.4); 4.000 (0.7); 3.349 (6.5); 3.221 (0.7); 3.175 (0.9); 2.828 (0.8); 2.781 (0.7); 2.536 (0.7); 2.531 (1.5); 2.525 (2.0); 2.519 (1.4); 2.513 (0.7); 2.012 (1.3); 1.521 (0.5); 1.471 (1.1); 1.407 (1.1); 1.357 (0.5); 1.221 (0.4); 1.197 (0.7); 1.173 (0.4); 0.973 (16.0); 0.022 (1.6)

Example I-84

$^1$H-NMR (300.2 MHz, CDCl$_3$): δ=7.806 (14.6); 7.695 (0.4); 7.658 (16.0); 7.656 (13.1); 7.501 (0.6); 7.462 (0.5); 7.452 (4.6); 7.444 (2.9); 7.438 (3.2); 7.433 (3.8); 7.430

(3.6); 7.421 (6.4); 7.409 (1.0); 7.400 (0.5); 7.389 (0.4); 7.377 (3.5); 7.368 (3.0); 7.365 (3.3); 7.360 (2.8); 7.353 (3.8); 7.346 (7.5); 7.335 (1.5); 7.313 (1.1); 7.305 (2.8); 7.300 (7.9); 7.289 (8.9); 7.284 (9.7); 7.281 (7.9); 7.271 (11.6); 7.261 (6.4); 7.258 (5.7); 7.253 (5.1); 7.237 (1.4); 7.229 (0.8); 5.094 (0.3); 4.885 (0.3); 4.458 (0.6); 4.410 (0.7); 4.359 (6.4); 4.311 (9.2); 4.109 (10.5); 4.061 (7.4); 3.291 (8.0); 3.245 (11.0); 3.010 (11.0); 2.963 (8.1); 2.555 (5.8); 2.076 (0.6); 2.039 (3.8); 1.787 (4.3); 1.759 (0.4); 1.673 (3.5); 1.653 (3.7); 1.625 (4.5); 1.605 (4.7); 1.341 (0.9); 1.314 (4.7); 1.289 (5.3); 1.266 (3.7); 1.241 (4.1); 0.875 (0.6); 0.867 (0.7); 0.849 (1.7); 0.839 (1.4); 0.830 (2.0); 0.824 (2.2); 0.815 (1.5); 0.804 (2.0); 0.786 (1.0); 0.779 (0.9); 0.762 (0.4); 0.652 (2.2); 0.637 (8.0); 0.626 (4.2); 0.615 (6.9); 0.599 (2.1); 0.183 (0.4); 0.168 (0.5); 0.147 (3.1); 0.133 (7.2); 0.128 (6.6); 0.117 (7.9); 0.102 (2.6); 0.086 (0.5); 0.080 (0.5); 0.032 (5.4)

Example I-85

$^1$H-NMR (300.2 MHz, CDCl$_3$): δ=7.761 (15.4); 7.636 (16.0); 7.442 (5.2); 7.436 (5.6); 7.416 (6.4); 7.410 (6.7); 7.298 (6.3); 7.273 (3.5); 7.266 (4.4); 7.247 (10.1); 7.241 (8.4); 7.218 (10.0); 7.206 (0.4); 7.193 (11.0); 7.167 (3.6); 4.163 (6.1); 4.135 (0.4); 4.114 (10.2); 3.984 (11.3); 3.936 (6.8); 3.179 (8.2); 3.133 (11.1); 2.890 (11.5); 2.843 (8.6); 2.749 (0.7); 2.722 (2.5); 2.713 (1.0); 2.694 (3.0); 2.675 (1.5); 2.668 (1.7); 2.663 (1.9); 2.642 (0.5); 2.635 (0.6); 2.486 (2.7); 2.473 (2.3); 2.461 (2.5); 2.447 (2.7); 2.073 (1.4); 1.927 (0.6); 1.897 (1.3); 1.885 (1.3); 1.860 (8.6); 1.854 (9.0); 1.845 (8.8); 1.836 (7.4); 1.828 (7.5); 1.823 (7.2); 1.816 (5.7); 1.799 (4.0); 1.771 (1.6); 1.755 (0.4); 1.717 (1.1); 1.705 (1.1); 1.687 (1.9); 1.680 (2.0); 1.671 (2.4); 1.659 (2.1); 1.649 (2.0); 1.632 (1.5); 1.627 (1.4); 1.609 (2.6); 1.601 (2.1); 1.582 (2.2); 1.576 (1.9); 1.547 (0.5); 1.334 (0.6); 1.311 (1.2); 1.294 (3.4); 1.287 (3.5); 1.263 (0.6); 0.931 (1.3); 0.909 (4.0); 0.886 (1.5); 0.100 (0.3); 0.028 (5.9)

Example I-86

$^1$H-NMR (300.2 MHz, CDCl$_3$): δ=7.836 (1.2); 7.705 (1.2); 7.363 (1.2); 7.357 (0.4); 7.342 (0.5); 7.335 (1.6); 7.302 (2.8); 7.152 (1.5); 7.130 (0.4); 7.125 (1.1); 4.394 (0.7); 4.346 (0.9); 4.006 (0.6); 3.958 (0.5); 2.980 (0.6); 2.935 (0.8); 2.561 (0.8); 2.515 (0.6); 1.741 (1.1); 1.626 (2.4); 1.613 (0.6); 1.563 (1.1); 1.460 (1.0); 1.410 (0.5); 1.084 (16.0); 0.039 (2.2)

Example I-87

$^1$H-NMR (499.9 MHz, CDCl$_3$): δ=7.806 (2.0); 7.741 (0.7); 7.725 (0.7); 7.657 (1.7); 7.493 (0.5); 7.478 (0.6); 7.386 (0.4); 7.383 (0.4); 7.371 (0.9); 7.369 (0.8); 7.356 (0.6); 7.353 (0.5); 7.315 (0.6); 7.312 (0.6); 7.300 (0.9); 7.297 (0.8); 7.285 (0.4); 7.282 (0.4); 7.259 (5.0); 4.554 (0.5); 4.525 (0.8); 4.415 (0.6); 4.386 (0.4); 3.537 (0.8); 1.558 (2.2); 1.422 (1.4); 1.370 (0.6); 1.336 (1.4); 1.332 (0.9); 1.284 (2.0); 1.256 (16.0); 1.177 (0.7); 1.162 (0.6); 1.157 (0.6); 1.142 (0.5); 1.107 (1.1); 1.087 (0.9); 1.074 (0.8); 1.048 (0.7); 1.041 (0.8); 1.036 (0.7); 1.029 (0.6); 1.021 (0.6); 1.006 (0.4); 0.902 (0.6); 0.894 (1.3); 0.889 (1.2); 0.881 (2.1); 0.869 (1.7); 0.856 (1.5); 0.848 (1.7); 0.842 (1.5); 0.834 (1.5); 0.818 (0.7); 0.754 (0.3); 0.731 (0.4); 0.716 (0.5); 0.683 (0.5); 0.673 (0.4); 0.669 (0.4); 0.659 (0.4); 0.000 (5.0)

Example I-88

$^1$H-NMR (300.2 MHz, CDCl$_3$): δ=7.887 (16.0); 7.686 (10.0); 7.663 (12.5); 7.626 (4.0); 7.599 (9.3); 7.572 (7.1); 7.523 (5.5); 7.497 (5.9); 7.472 (2.0); 7.301 (2.9); 4.683 (7.1); 4.635 (9.3); 4.372 (8.8); 4.323 (6.6); 3.634 (5.7); 3.588 (6.4); 3.071 (0.9); 3.023 (1.3); 2.996 (0.8); 2.957 (0.6); 2.910 (6.1); 2.864 (5.0); 2.034 (0.9); 0.695 (0.8); 0.648 (11.4); 0.603 (1.9); 0.570 (0.9); 0.530 (2.9); 0.525 (3.0); 0.519 (2.3); 0.512 (1.9); 0.496 (2.7); 0.489 (3.7); 0.484 (3.7); 0.477 (2.7); 0.442 (0.5); 0.374 (0.6); 0.330 (4.0); 0.326 (4.0); 0.305 (1.5); 0.294 (2.3); 0.290 (2.3); 0.028 (2.1)

Example I-89

$^1$H-NMR (300.2 MHz, CDCl$_3$): δ=7.707 (16.0); 7.646 (0.4); 7.614 (3.2); 7.587 (6.6); 7.558 (5.1); 7.503 (4.2); 7.478 (4.7); 7.452 (1.8); 7.300 (10.5); 6.952 (10.0); 5.320 (0.4); 4.500 (4.3); 4.451 (8.4); 4.359 (8.5); 4.310 (4.4); 3.609 (5.6); 3.563 (6.2); 3.529 (0.4); 3.505 (0.4); 2.950 (4.7); 2.768 (5.9); 2.722 (5.3); 1.727 (2.8); 1.292 (0.6); 1.269 (0.4); 1.246 (0.6); 1.223 (0.3); 0.920 (0.5); 0.851 (3.4); 0.848 (3.4); 0.820 (8.7); 0.790 (7.1); 0.710 (2.6); 0.690 (3.2); 0.675 (1.7); 0.662 (2.8); 0.651 (1.5); 0.631 (1.4); 0.442 (2.1); 0.421 (2.4); 0.414 (2.9); 0.391 (2.7); 0.382 (2.0); 0.361 (1.4); 0.037 (9.6)

Example I-90

$^1$H-NMR (300.2 MHz, CDCl$_3$): δ=7.891 (8.6); 7.869 (5.7); 7.687 (8.8); 7.576 (16.0); 7.572 (14.3); 7.300 (4.7); 4.765 (5.1); 4.716 (6.3); 4.311 (6.0); 4.263 (5.0); 3.578 (2.9); 3.530 (7.1); 3.471 (8.1); 3.423 (3.3); 2.543 (5.3); 1.759 (0.4); 1.291 (0.5); 0.914 (0.5); 0.808 (1.3); 0.802 (1.0); 0.780 (2.3); 0.774 (2.5); 0.766 (4.4); 0.743 (2.9); 0.739 (3.3); 0.735 (3.0); 0.724 (2.7); 0.704 (0.8); 0.699 (1.6); 0.688 (0.4); 0.659 (0.6); 0.596 (1.1); 0.580 (1.0); 0.569 (3.0); 0.557 (9.5); 0.542 (2.7); 0.529 (0.6); 0.514 (0.6); 0.105 (0.7); 0.033 (3.8)

Example I-91

$^1$H-NMR (300.2 MHz, CDCl$_3$): δ=7.908 (6.6); 7.734 (8.1); 7.527 (16.0); 7.494 (0.7); 7.301 (2.0); 6.953 (8.2); 4.483 (3.8); 4.434 (6.8); 4.322 (6.7); 4.273 (3.8); 4.160 (0.7); 4.136 (0.7); 3.488 (3.0); 3.440 (7.0); 3.379 (7.3); 3.331 (3.1); 3.015 (0.9); 2.087 (0.6); 2.073 (3.1); 1.364 (0.3); 1.312 (1.8); 1.288 (4.5); 1.265 (1.4); 0.973 (0.6); 0.963 (0.4); 0.951 (0.7); 0.912 (1.3); 0.889 (1.1); 0.876 (1.4); 0.854 (2.0); 0.841 (4.4); 0.824 (6.8); 0.814 (9.1); 0.796 (4.8); 0.781 (2.5); 0.776 (2.3); 0.756 (1.8); 0.720 (2.0); 0.707 (2.4); 0.690 (3.3); 0.666 (1.5); 0.653 (1.0); 0.031 (1.4)

Example I-92

$^1$H-NMR (300.2 MHz, CDCl$_3$): δ=8.908 (10.2); 8.773 (6.5); 8.756 (6.8); 7.851 (12.2); 7.784 (5.7); 7.767 (5.5); 7.640 (12.8); 7.638 (12.0); 7.300 (5.7); 4.703 (5.9); 4.654 (6.9); 4.136 (7.6); 4.087 (6.6); 3.493 (16.0); 2.978 (5.6); 2.974 (5.6); 2.037 (7.0); 2.009 (0.6); 1.283 (0.6); 1.022 (1.1); 1.003 (1.8); 0.986 (2.4); 0.978 (2.3); 0.967 (2.8); 0.961 (3.0); 0.933 (1.7); 0.902 (1.5); 0.879 (2.7); 0.867 (2.2); 0.860 (2.8); 0.839 (8.8); 0.819 (2.7); 0.813 (2.2);

0.801 (2.3); 0.777 (1.2); 0.651 (1.3); 0.624 (2.8); 0.617 (2.4); 0.607 (2.6); 0.599 (2.3); 0.582 (2.1); 0.564 (1.2); 0.099 (0.6); 0.026 (4.7)

Example I-93

$^1$H-NMR (400.1 MHz, d$_6$-DMSO): δ=7.920 (0.9); 7.881 (15.0); 7.844 (0.8); 7.812 (16.0); 7.810 (15.3); 7.776 (0.8); 7.733 (0.7); 7.304 (0.8); 7.301 (0.8); 7.281 (6.7); 7.268 (8.6); 7.254 (5.2); 7.245 (4.0); 7.221 (0.7); 5.505 (12.5); 4.716 (0.8); 4.557 (1.5); 4.480 (4.2); 4.477 (4.1); 4.443 (5.3); 4.441 (5.2); 4.210 (6.2); 4.173 (4.9); 3.305 (189.7); 3.195 (0.5); 3.182 (0.6); 3.161 (3.6); 3.126 (5.5); 3.011 (5.3); 2.976 (3.4); 2.664 (0.5); 2.659 (0.7); 2.655 (0.5); 2.494 (85.6); 2.490 (110.7); 2.486 (80.5); 2.321 (0.5); 2.317 (0.6); 2.313 (0.5); 0.818 (0.3); 0.808 (0.4); 0.785 (0.4); 0.780 (0.4); 0.759 (0.4); 0.613 (0.6); 0.594 (1.0); 0.583 (1.4); 0.564 (1.8); 0.549 (1.9); 0.532 (1.5); 0.517 (1.5); 0.513 (1.6); 0.497 (1.6); 0.479 (1.5); 0.475 (1.6); 0.460 (1.7); 0.445 (2.0); 0.430 (2.2); 0.411 (1.6); 0.396 (1.1); 0.382 (1.0); 0.353 (1.1); 0.333 (1.4); 0.325 (2.3); 0.319 (1.5); 0.310 (2.4); 0.299 (1.9); 0.292 (1.7); 0.284 (1.6); 0.266 (0.8); 0.045 (1.1); 0.030 (1.4); 0.025 (1.6); 0.018 (2.1); 0.011 (1.7); 0.000 (2.4); −0.008 (1.6); −0.015 (1.8); −0.023 (1.3); −0.027 (1.2); −0.042 (0.8)

Example I-94

$^1$H-NMR (300.2 MHz, CDCl$_3$): δ=7.757 (15.2); 7.693 (16.0); 7.690 (14.9); 7.663 (1.6); 7.646 (0.4); 7.460 (3.0); 7.454 (3.2); 7.434 (5.0); 7.429 (5.1); 7.410 (3.6); 7.404 (3.7); 7.363 (0.3); 7.300 (48.5); 7.263 (2.3); 7.258 (2.4); 7.237 (5.3); 7.217 (4.0); 7.211 (3.4); 7.174 (6.2); 7.171 (5.9); 7.148 (7.7); 7.145 (7.6); 7.122 (2.8); 7.119 (2.9); 5.426 (1.8); 5.418 (1.8); 4.617 (4.7); 4.611 (4.7); 4.569 (6.0); 4.562 (5.9); 4.392 (0.3); 4.233 (6.4); 4.230 (6.4); 4.185 (5.0); 4.181 (5.0); 3.333 (3.2); 3.286 (7.1); 3.216 (7.3); 3.168 (3.2); 2.997 (1.2); 2.919 (1.0); 2.211 (0.5); 2.129 (4.2); 2.116 (4.3); 1.683 (0.4); 1.672 (0.6); 1.660 (0.8); 1.627 (5.8); 1.610 (2.0); 1.604 (1.4); 1.589 (0.8); 1.582 (1.0); 1.569 (0.6); 0.857 (1.0); 0.838 (0.9); 0.833 (1.1); 0.813 (1.7); 0.798 (2.5); 0.793 (2.8); 0.779 (2.8); 0.770 (3.3); 0.756 (2.9); 0.753 (3.0); 0.747 (2.2); 0.738 (2.3); 0.731 (2.6); 0.726 (2.7); 0.713 (3.6); 0.703 (2.8); 0.690 (2.9); 0.687 (2.9); 0.671 (2.0); 0.650 (1.0); 0.646 (1.1); 0.628 (1.2); 0.423 (1.2); 0.401 (1.2); 0.389 (1.5); 0.384 (2.3); 0.366 (3.7); 0.349 (4.1); 0.332 (3.1); 0.322 (2.7); 0.315 (2.6); 0.309 (2.6); 0.304 (2.9); 0.287 (4.0); 0.274 (2.7); 0.269 (3.4); 0.252 (2.3); 0.236 (1.2); 0.231 (1.1); 0.212 (0.9); 0.107 (0.8); 0.048 (1.9); 0.037 (47.9); 0.027 (2.1)

Example I-95

$^1$H-NMR (300.2 MHz, CDCl$_3$): δ=7.756 (15.5); 7.729 (0.4); 7.688 (16.0); 7.661 (0.5); 7.300 (36.2); 7.249 (1.0); 7.242 (1.1); 7.222 (2.4); 7.216 (3.1); 7.209 (1.3); 7.198 (2.7); 7.191 (4.2); 7.182 (3.8); 7.167 (3.0); 7.162 (4.7); 7.159 (4.5); 7.156 (4.5); 7.138 (5.2); 7.126 (2.5); 7.112 (6.1); 7.106 (4.0); 7.085 (3.8); 7.072 (1.5); 7.066 (1.8); 7.045 (0.5); 4.620 (4.8); 4.614 (4.8); 4.572 (6.1); 4.565 (6.1); 4.230 (6.6); 4.227 (6.6); 4.194 (0.7); 4.182 (5.2); 4.178 (5.3); 4.170 (2.2); 4.146 (1.6); 4.123 (0.6); 3.347 (3.3); 3.299 (7.1); 3.222 (7.5); 3.174 (3.5); 2.161 (3.5); 2.118 (0.4); 2.083 (7.3); 1.640 (14.9); 1.321 (2.0); 1.297 (4.0); 1.273 (1.9); 0.865 (0.8); 0.842 (1.0); 0.823 (2.1); 0.805 (2.5); 0.801 (2.8); 0.786 (2.6); 0.774 (3.3); 0.756 (4.5); 0.738 (4.1); 0.719 (3.5); 0.707 (2.6); 0.693 (2.9); 0.672 (2.0); 0.649 (1.2); 0.630 (1.1); 0.437 (1.2); 0.417 (1.3); 0.415 (1.3); 0.403 (1.5); 0.397 (2.6); 0.380 (3.6); 0.363 (3.7); 0.343 (2.9); 0.327 (3.8); 0.312 (2.5); 0.307 (2.3); 0.291 (3.7); 0.277 (2.8); 0.272 (3.1); 0.255 (2.4); 0.239 (1.3); 0.234 (1.3); 0.215 (1.0); 0.107 (4.3); 0.048 (1.0); 0.037 (33.4); 0.026 (1.4)

Example I-96

$^1$H-NMR (300.2 MHz, CDCl$_3$): δ=7.730 (15.9); 7.677 (0.4); 7.654 (16.0); 7.640 (0.8); 7.504 (0.4); 7.500 (0.4); 7.312 (2.8); 7.300 (7.8); 7.284 (7.5); 7.258 (6.1); 7.190 (18.8); 7.159 (9.5); 7.153 (3.9); 4.640 (0.5); 4.635 (0.4); 4.626 (0.5); 4.621 (0.5); 4.584 (4.7); 4.578 (4.7); 4.535 (6.0); 4.529 (6.1); 4.218 (6.7); 4.215 (6.5); 4.170 (5.2); 4.166 (5.1); 3.270 (3.3); 3.222 (7.4); 3.150 (7.7); 3.103 (3.5); 2.682 (2.7); 2.039 (7.0); 1.926 (3.0); 1.917 (2.8); 0.829 (0.8); 0.809 (0.9); 0.804 (0.9); 0.788 (2.1); 0.769 (2.4); 0.764 (2.7); 0.748 (2.6); 0.738 (3.1); 0.721 (4.4); 0.700 (3.9); 0.682 (3.3); 0.671 (2.4); 0.656 (2.8); 0.653 (2.5); 0.634 (2.0); 0.616 (0.9); 0.612 (0.9); 0.593 (1.0); 0.436 (1.1); 0.416 (1.2); 0.413 (1.4); 0.402 (1.4); 0.395 (2.5); 0.378 (3.3); 0.360 (3.6); 0.344 (2.3); 0.341 (2.4); 0.325 (1.7); 0.301 (1.8); 0.285 (2.0); 0.280 (2.0); 0.265 (3.6); 0.250 (2.5); 0.246 (2.8); 0.230 (2.3); 0.223 (1.2); 0.213 (1.3); 0.208 (1.1); 0.188 (0.9); 0.029 (4.4)

Example I-97

$^1$H-NMR (300.2 MHz, CDCl$_3$): δ=7.744 (14.8); 7.669 (16.0); 7.352 (1.6); 7.344 (0.7); 7.330 (2.3); 7.322 (4.2); 7.300 (11.4); 7.273 (2.5); 6.969 (1.9); 6.960 (2.9); 6.942 (5.0); 6.935 (8.5); 6.914 (3.7); 6.908 (9.9); 6.900 (2.7); 6.879 (3.1); 6.871 (2.2); 5.424 (0.4); 5.417 (0.4); 4.589 (4.5); 4.583 (4.4); 4.540 (5.8); 4.534 (5.7); 4.221 (6.4); 4.217 (6.2); 4.172 (4.9); 4.169 (4.9); 3.272 (3.0); 3.224 (6.8); 3.150 (7.0); 3.102 (3.1); 2.482 (3.7); 2.477 (4.1); 2.465 (4.3); 2.460 (4.4); 2.041 (12.2); 1.822 (4.9); 1.803 (0.6); 1.290 (0.3); 0.830 (0.7); 0.810 (0.8); 0.806 (0.8); 0.788 (1.7); 0.770 (2.3); 0.765 (2.5); 0.752 (2.8); 0.744 (3.1); 0.731 (2.8); 0.728 (2.7); 0.721 (2.1); 0.710 (2.3); 0.703 (2.4); 0.699 (2.5); 0.685 (3.1); 0.678 (2.8); 0.665 (2.8); 0.661 (2.7); 0.644 (2.0); 0.624 (0.8); 0.621 (0.9); 0.602 (1.0); 0.423 (1.2); 0.404 (1.2); 0.401 (1.2); 0.389 (1.4); 0.382 (2.2); 0.366 (3.3); 0.348 (3.7); 0.332 (2.5); 0.329 (2.4); 0.315 (2.0); 0.308 (2.1); 0.294 (2.1); 0.289 (2.1); 0.273 (3.9); 0.259 (2.5); 0.255 (2.7); 0.239 (2.3); 0.233 (1.2); 0.222 (1.2); 0.216 (1.0); 0.198 (0.9); 0.103 (1.1); 0.031 (6.5)

Example I-98

$^1$H-NMR (300.2 MHz, CDCl$_3$): δ=7.748 (10.0); 7.666 (10.6); 7.587 (0.4); 7.561 (0.4); 7.488 (0.4); 7.477 (3.0); 7.464 (2.8); 7.458 (3.6); 7.446 (4.6); 7.433 (1.4); 7.427 (2.6); 7.415 (3.1); 7.410 (2.7); 7.406 (2.4); 7.396 (4.8); 7.384 (0.9); 7.345 (1.7); 7.332 (10.5); 7.321 (6.5); 7.313 (5.9); 7.300 (12.2); 7.288 (0.8); 5.028 (0.3); 4.632 (3.4); 4.625 (3.4); 4.583 (4.3); 4.577 (4.3); 4.232 (4.5); 4.228 (4.3); 4.183 (3.6); 4.179 (3.4); 3.382 (16.0); 3.379 (15.8); 2.566 (2.9); 2.040 (8.5); 0.879 (0.6); 0.858 (0.8); 0.854 (0.8); 0.838 (1.3); 0.818 (1.5); 0.813 (1.9); 0.795 (1.8); 0.787 (0.9); 0.771 (1.5); 0.768 (1.2); 0.763 (1.5); 0.752 (1.7); 0.746 (2.6); 0.741 (1.7); 0.728 (1.7); 0.722 (1.7); 0.705 (0.9); 0.697 (1.6); 0.679 (2.0); 0.675 (1.6); 0.656 (1.5); 0.639 (0.7); 0.634 (0.8); 0.615 (0.8); 0.473 (0.9); 0.452 (0.9); 0.449 (0.9); 0.439 (1.1); 0.434 (1.6); 0.414

(2.3); 0.411 (1.9); 0.400 (1.7); 0.392 (1.5); 0.380 (1.6); 0.377 (1.6); 0.358 (1.2); 0.335 (1.3); 0.317 (1.4); 0.311 (1.4); 0.300 (1.8); 0.293 (1.4); 0.282 (1.7); 0.277 (1.9); 0.263 (1.0); 0.258 (1.4); 0.244 (0.9); 0.239 (0.8); 0.219 (0.7); 0.033 (5.9)

Example I-99

$^1$H-NMR (499.9 MHz, CDCl$_3$): δ=7.709 (15.3); 7.626 (16.0); 7.350 (1.3); 7.347 (1.6); 7.339 (1.7); 7.335 (3.4); 7.332 (3.2); 7.319 (4.0); 7.315 (2.6); 7.305 (4.4); 7.291 (5.7); 7.288 (5.2); 7.276 (3.5); 7.273 (3.1); 7.265 (7.5); 7.179 (4.3); 7.177 (4.8); 7.164 (6.8); 7.162 (7.5); 7.149 (3.0); 7.147 (3.3); 7.136 (3.8); 7.117 (5.0); 7.099 (3.1); 7.098 (3.1); 4.554 (5.1); 4.551 (5.0); 4.525 (5.8); 4.521 (5.8); 4.160 (6.6); 4.131 (5.8); 3.499 (0.4); 3.485 (1.3); 3.471 (1.3); 3.457 (0.4); 3.252 (3.5); 3.223 (7.9); 3.181 (8.0); 3.153 (3.5); 2.416 (5.5); 2.413 (5.8); 2.403 (5.5); 2.400 (5.5); 1.722 (10.7); 1.311 (0.4); 1.297 (0.5); 1.284 (0.3); 1.220 (1.4); 1.206 (2.7); 1.192 (1.3); 0.896 (0.9); 0.882 (2.0); 0.867 (1.0); 0.766 (0.9); 0.753 (1.2); 0.751 (1.3); 0.742 (1.7); 0.739 (1.2); 0.727 (2.9); 0.714 (2.6); 0.701 (1.8); 0.699 (1.3); 0.686 (3.9); 0.674 (3.9); 0.660 (2.1); 0.647 (2.6); 0.635 (3.0); 0.633 (2.6); 0.620 (2.0); 0.610 (1.1); 0.608 (1.3); 0.596 (1.1); 0.387 (1.2); 0.372 (1.7); 0.366 (1.7); 0.363 (2.2); 0.359 (1.4); 0.351 (3.5); 0.343 (2.1); 0.337 (2.1); 0.330 (2.3); 0.329 (2.3); 0.316 (1.5); 0.269 (1.6); 0.257 (1.9); 0.254 (2.1); 0.247 (2.5); 0.242 (1.9); 0.234 (3.2); 0.226 (1.5); 0.222 (2.0); 0.213 (1.4); 0.211 (1.4); 0.198 (1.0); 0.006 (0.4); 0.000 (7.0)

Example I-100

$^1$H-NMR (400.1 MHz, d$_6$-DMSO): δ=7.859 (1.6); 7.845 (15.2); 7.797 (16.0); 7.796 (15.4); 7.743 (0.9); 7.741 (0.9); 7.357 (6.5); 7.343 (8.2); 7.336 (8.9); 7.321 (7.4); 7.277 (0.4); 7.263 (0.5); 7.256 (0.6); 7.242 (0.5); 7.138 (0.9); 7.119 (8.6); 7.097 (14.1); 7.075 (6.9); 5.738 (1.3); 5.393 (9.9); 5.388 (9.8); 4.475 (1.1); 4.465 (1.3); 4.453 (4.4); 4.416 (5.3); 4.095 (6.3); 4.058 (5.3); 3.306 (97.7); 3.111 (0.7); 3.088 (0.8); 3.057 (3.2); 3.022 (6.1); 2.955 (6.2); 2.920 (3.2); 2.656 (0.4); 2.496 (23.8); 2.492 (44.4); 2.487 (57.6); 2.483 (41.8); 2.314 (0.4); 0.765 (0.3); 0.759 (0.6); 0.547 (0.3); 0.532 (0.7); 0.519 (0.9); 0.515 (0.9); 0.503 (1.7); 0.489 (1.9); 0.485 (2.1); 0.473 (2.4); 0.468 (2.7); 0.452 (3.2); 0.438 (3.2); 0.433 (2.4); 0.423 (2.9); 0.418 (2.5); 0.408 (2.3); 0.404 (2.2); 0.390 (1.6); 0.374 (0.8); 0.360 (0.8); 0.312 (1.1); 0.298 (1.3); 0.295 (1.4); 0.282 (2.2); 0.271 (2.5); 0.256 (2.7); 0.245 (1.6); 0.231 (0.9); 0.025 (1.1); 0.014 (1.4); 0.010 (1.6); 0.000 (2.8); −0.013 (2.3); −0.016 (2.3); −0.025 (2.2); −0.038 (1.3); −0.043 (1.1); −0.057 (0.8)

Example I-101

$^1$H-NMR (300.2 MHz, CDCl$_3$): δ=7.897 (16.0); 7.686 (16.0); 7.405 (2.4); 7.385 (2.7); 7.377 (4.3); 7.357 (4.4); 7.350 (3.2); 7.330 (2.8); 7.300 (10.0); 7.081 (3.5); 7.075 (3.6); 7.053 (5.3); 7.048 (5.5); 7.025 (3.0); 7.019 (3.0); 4.744 (9.1); 4.695 (11.0); 4.258 (11.0); 4.209 (9.2); 4.163 (0.4); 4.139 (0.3); 3.402 (3.7); 3.397 (3.7); 3.354 (6.1); 3.349 (6.3); 3.215 (6.3); 3.212 (6.3); 3.167 (3.8); 3.164 (3.8); 2.395 (6.3); 2.379 (6.0); 2.078 (1.5); 1.790 (9.0); 1.338 (0.6); 1.315 (1.3); 1.298 (3.8); 1.292 (3.9); 1.268 (0.7); 0.935 (1.4); 0.914 (4.5); 0.890 (1.7); 0.778 (1.4); 0.766 (1.4); 0.759 (1.8); 0.756 (1.6); 0.735 (4.0); 0.724 (5.0); 0.717 (5.9); 0.710 (5.8); 0.702 (5.6); 0.699 (5.7); 0.692 (3.0); 0.675 (2.5); 0.663 (2.0); 0.652 (3.3); 0.642 (0.5); 0.621 (3.5); 0.609 (1.9); 0.603 (0.8); 0.590 (3.8); 0.573 (6.0); 0.563 (4.7); 0.548 (5.1); 0.541 (4.8); 0.530 (4.7); 0.518 (2.8); 0.505 (1.8); 0.498 (1.6); 0.486 (1.6); 0.032 (10.1); 0.021 (0.4)

Example I-102

$^1$H-NMR (400.1 MHz, d$_6$-DMSO): δ=8.172 (1.8); 8.038 (1.9); 7.549 (0.4); 7.530 (0.4); 7.477 (0.4); 7.456 (0.4); 5.982 (0.4); 4.872 (2.2); 4.636 (0.8); 4.599 (1.0); 4.337 (0.9); 4.301 (0.8); 3.547 (16.0); 3.306 (0.5); 3.271 (0.7); (0.9); 3.101 (0.7); 3.065 (0.5); 2.736 (8.0); 2.732 (9.9); 2.728 (7.4); 1.443 (5.2); 0.437 (0.4); 0.213 (0.4); 0.017 (0.5); 0.000 (1.1); −0.017 (0.4)

Example I-103

$^1$H-NMR (300.2 MHz, CDCl$_3$): δ=7.900 (15.1); 7.692 (16.0); 7.300 (13.8); 7.224 (1.1); 7.216 (1.1); 7.206 (1.3); 7.196 (2.6); 7.187 (2.0); 7.170 (3.1); 7.163 (1.9); 7.152 (1.5); 7.144 (1.6); 7.090 (1.8); 7.084 (1.8); 7.067 (1.9); 7.060 (4.1); 7.053 (2.8); 7.036 (2.6); 7.030 (3.5); 7.023 (1.4); 7.006 (1.1); 7.000 (1.2); 4.751 (9.0); 4.702 (10.9); 4.249 (10.3); 4.200 (8.6); 3.402 (3.4); 3.398 (3.6); 3.354 (5.7); 3.349 (6.0); 3.208 (6.2); 3.164 (3.6); 3.160 (3.8); 2.245 (2.7); 2.080 (0.5); 2.045 (14.9); 1.729 (1.7); 0.789 (1.3); 0.777 (1.2); 0.769 (2.0); 0.751 (2.7); 0.745 (3.6); 0.734 (4.6); 0.727 (5.7); 0.721 (5.8); 0.713 (5.3); 0.710 (5.6); 0.701 (3.3); 0.682 (2.1); 0.675 (1.9); 0.663 (3.1); 0.648 (0.4); 0.631 (3.6); 0.619 (1.9); 0.613 (0.9); 0.598 (3.6); 0.583 (5.2); 0.580 (5.4); 0.572 (4.2); 0.553 (4.4); 0.546 (4.5); 0.536 (4.0); 0.525 (2.8); 0.511 (1.7); 0.503 (1.6); 0.491 (1.6); 0.046 (0.3); 0.035 (11.5); 0.024 (0.5)

Example I-104

$^1$H-NMR (300.2 MHz, CDCl$_3$): δ=7.792 (15.1); 7.664 (15.8); 7.661 (16.0); 7.644 (0.4); 7.298 (18.4); 7.029 (0.9); 7.009 (0.6); 6.996 (4.1); 6.984 (6.2); 6.980 (4.2); 6.968 (9.8); 6.955 (4.1); 6.951 (6.1); 6.938 (1.0); 6.926 (0.5); 6.918 (0.6); 4.112 (5.2); 4.063 (11.4); 3.988 (11.5); 3.940 (5.3); 2.946 (4.2); 2.941 (4.2); 2.899 (5.7); 2.893 (5.6); 2.688 (0.6); 2.651 (6.6); 2.645 (6.1); 2.632 (3.4); 2.616 (2.0); 2.603 (6.0); 2.598 (5.6); 2.580 (0.7); 2.573 (0.8); 2.133 (10.6); 2.044 (4.6); 1.948 (0.7); 1.920 (1.6); 1.884 (7.3); 1.875 (9.8); 1.868 (8.2); 1.853 (8.6); 1.841 (6.6); 1.833 (4.1); 1.826 (3.6); 1.812 (2.5); 1.798 (3.3); 1.772 (1.3); 1.748 (0.8); 1.740 (1.1); 1.728 (1.7); 1.716 (1.8); 1.704 (2.5); 1.695 (2.9); 1.675 (11.6); 1.660 (2.5); 1.652 (3.0); 1.641 (2.3); 1.624 (1.9); 1.618 (2.1); 1.607 (1.3); 1.587 (0.6); 0.044 (0.6); 0.034 (16.7); 0.023 (0.6)

Example I-105

$^1$H-NMR (300.2 MHz, CDCl$_3$): δ=7.805 (6.7); 7.732 (0.6); 7.728 (0.9); 7.723 (0.5); 7.712 (0.3); 7.705 (1.2); 7.700 (1.1); 7.692 (0.8); 7.688 (1.1); 7.683 (0.7); 7.672 (7.9); 7.670 (7.5); 7.660 (1.2); 7.593 (0.6); 7.587 (0.6); 7.573 (0.4); 7.568 (0.8); 7.563 (0.7); 7.529 (0.9); 7.519 (0.9); 7.515 (0.5); 7.509 (0.7); 7.504 (1.1); 7.499 (0.9); 7.494 (1.1); 7.481 (0.5); 7.476 (0.5); 7.471 (0.4); 7.298 (12.5); 7.034 (0.4); 7.003 (3.1); 6.991 (1.9); 6.986 (2.7); 6.977 (4.6); 6.961 (4.8); 6.932 (0.4); 4.306 (3.1); 4.257 (4.4); 4.024 (4.4); 3.975 (3.1); 3.074 (2.0); 3.068 (2.0); 3.026 (2.5); 3.021 (2.5); 2.670 (2.5); 2.665 (2.5); 2.622 (2.0); 2.617 (2.0); 2.080 (1.1); 2.028 (4.9); 2.026 (4.9); 2.024 (5.0); 1.744 (0.6); 1.721 (1.5); 1.699 (2.2); 1.675

(1.8); 1.653 (8.3); 1.318 (0.5); 1.294 (1.3); 1.288 (1.9); 1.271 (0.6); 1.139 (14.8); 1.131 (16.0); 1.116 (14.0); 1.108 (14.7); 0.046 (0.5); 0.035 (12.5); 0.024 (0.5)

Example I-106

$^1$H-NMR (400.1 MHz, CDCl$_3$): δ=7.788 (15.0); 7.677 (0.5); 7.653 (16.0); 7.261 (27.0); 6.996 (0.7); 6.991 (0.5); 6.972 (6.2); 6.959 (9.2); 6.946 (5.8); 6.937 (3.9); 6.914 (0.9); 5.298 (1.5); 4.257 (5.7); 4.221 (8.9); 4.147 (0.4); 4.129 (1.1); 4.112 (1.3); 4.099 (9.8); 4.063 (6.3); 3.074 (4.2); 3.071 (4.4); 3.039 (5.1); 3.036 (5.3); 2.726 (4.9); 2.722 (5.1); 2.690 (4.0); 2.686 (4.2); 2.223 (14.5); 2.042 (4.5); 2.004 (1.5); 1.801 (0.3); 1.576 (29.5); 1.546 (3.2); 1.530 (3.3); 1.509 (4.1); 1.494 (4.2); 1.303 (0.7); 1.275 (5.0); 1.258 (6.4); 1.239 (3.9); 1.221 (3.4); 0.776 (0.7); 0.763 (1.7); 0.756 (1.5); 0.745 (2.4); 0.728 (2.1); 0.714 (1.1); 0.710 (1.0); 0.697 (0.4); 0.633 (3.2); 0.621 (7.8); 0.611 (4.8); 0.603 (6.3); 0.591 (2.6); 0.108 (3.0); 0.096 (8.4); 0.085 (9.0); 0.008 (1.2); 0.000 (25.3)

Example I-107

$^1$H-NMR (300.2 MHz, CDCl$_3$): δ=7.893 (4.9); 7.674 (4.9); 7.300 (5.1); 7.269 (2.8); 7.242 (1.6); 7.030 (2.0); 7.004 (1.8); 6.992 (1.9); 6.953 (1.7); 4.730 (3.0); 4.682 (3.6); 4.201 (3.3); 4.152 (2.7); 3.311 (0.7); 3.263 (3.3); 3.240 (3.4); 3.191 (0.7); 2.401 (16.0); 2.357 (0.7); 2.349 (0.8); 2.334 (0.4); 2.317 (0.4); 0.767 (0.8); 0.755 (0.6); 0.749 (1.4); 0.724 (1.6); 0.722 (1.5); 0.716 (1.5); 0.701 (1.4); 0.691 (1.3); 0.684 (2.0); 0.671 (2.9); 0.663 (1.6); 0.653 (1.4); 0.644 (1.6); 0.641 (1.7); 0.631 (1.5); 0.623 (1.0); 0.613 (1.0); 0.559 (1.3); 0.554 (1.1); 0.550 (1.3); 0.528 (1.4); 0.518 (0.8); 0.507 (0.9); 0.036 (3.0)

Example I-108

$^1$H-NMR (300.2 MHz, CDCl$_3$): δ=7.755 (4.5); 7.467 (0.4); 7.311 (1.4); 7.301 (7.1); 7.285 (2.8); 7.259 (1.6); 7.032 (0.5); 7.001 (2.1); 6.984 (5.1); 6.957 (1.8); 6.918 (1.7); 5.338 (1.9); 5.321 (1.2); 4.454 (2.4); 4.405 (4.3); 4.291 (4.0); 4.242 (2.2); 4.171 (0.9); 4.147 (0.9); 3.295 (1.6); 3.247 (2.5); 3.075 (2.5); 3.028 (1.6); 2.393 (16.0); 2.231 (1.2); 2.207 (1.2); 2.083 (4.1); 1.827 (0.4); 1.815 (0.5); 1.711 (1.7); 1.561 (0.4); 1.549 (0.4); 1.321 (1.1); 1.297 (2.5); 1.273 (1.2); 0.827 (0.7); 0.804 (1.4); 0.792 (1.8); 0.782 (2.5); 0.768 (1.8); 0.763 (2.9); 0.748 (4.6); 0.733 (0.5); 0.725 (1.5); 0.710 (1.0); 0.688 (1.5); 0.669 (1.3); 0.658 (1.1); 0.654 (1.2); 0.645 (1.0); 0.627 (0.8); 0.610 (0.4); 0.038 (6.1)

Example I-109

$^1$H-NMR (300.2 MHz, CDCl$_3$): δ=7.875 (16.0); 7.682 (11.3); 7.300 (5.9); 7.274 (2.8); 7.268 (2.9); 7.249 (3.0); 7.242 (3.8); 7.238 (3.6); 7.230 (3.6); 7.212 (3.0); 7.205 (3.6); 7.199 (4.1); 7.193 (3.8); 7.165 (4.8); 7.138 (2.6); 7.100 (3.5); 7.091 (3.8); 7.066 (2.1); 4.651 (7.1); 4.603 (9.5); 4.353 (9.0); 4.305 (6.6); 3.530 (5.3); 3.484 (5.9); 2.781 (5.5); 2.735 (5.0); 2.655 (0.7); 2.633 (0.7); 2.565 (0.8); 2.532 (0.9); 2.481 (0.9); 2.075 (0.9); 2.042 (13.0); 1.862 (0.4); 1.290 (0.5); 0.765 (0.7); 0.743 (0.9); 0.731 (2.1); 0.706 (10.6); 0.701 (10.2); 0.684 (3.0); 0.677 (2.1); 0.648 (1.3); 0.588 (1.0); 0.575 (0.4); 0.548 (3.2); 0.542 (3.0); 0.528 (3.5); 0.512 (3.7); 0.508 (4.1); 0.492 (2.7); 0.463 (0.4); 0.414 (2.5); 0.399 (3.7); 0.387 (1.7); 0.380 (2.0); 0.365 (3.3); 0.030 (4.7)

Example I-110

$^1$H-NMR (300.2 MHz, CDCl$_3$): δ=7.832 (0.4); 7.793 (0.4); 7.674 (15.3); 7.624 (0.3); 7.612 (0.4); 7.321 (4.0); 7.300 (11.0); 7.257 (4.1); 7.185 (1.7); 7.157 (4.9); 7.126 (11.5); 7.106 (12.2); 7.017 (0.4); 6.994 (0.3); 6.908 (16.0); 5.321 (0.4); 4.494 (7.0); 4.445 (11.6); 4.306 (11.4); 4.257 (7.0); 3.526 (0.6); 3.484 (9.1); 3.438 (14.4); 2.677 (9.0); 2.630 (8.1); 1.823 (1.1); 1.813 (1.1); 1.351 (0.4); 1.327 (0.7); 1.294 (1.4); 1.268 (0.7); 1.244 (0.9); 1.221 (0.5); 0.940 (0.9); 0.918 (1.8); 0.901 (1.6); 0.883 (3.7); 0.858 (7.4); 0.848 (5.8); 0.824 (8.7); 0.803 (6.0); 0.783 (3.0); 0.736 (4.0); 0.716 (5.1); 0.690 (4.4); 0.683 (3.9); 0.657 (2.2); 0.551 (3.3); 0.530 (5.1); 0.515 (4.1); 0.507 (3.7); 0.496 (4.2); 0.472 (2.1); 0.035 (7.2)

Example I-111

$^1$H-NMR (499.9 MHz, d$_6$-DMSO): δ=7.955 (12.1); 7.821 (11.6); 7.560 (3.0); 7.544 (6.3); 7.527 (3.5); 7.397 (3.6); 7.393 (3.8); 7.377 (3.8); 7.373 (3.9); 7.272 (4.0); 7.268 (3.9); 7.255 (3.7); 7.251 (3.5); 5.749 (12.8); 5.463 (12.7); 4.567 (5.0); 4.538 (5.7); 4.120 (6.1); 4.091 (5.6); 3.301 (29.2); 3.106 (16.0); 2.504 (4.5); 2.501 (5.9); 2.498 (4.3); 0.778 (1.2); 0.766 (2.0); 0.764 (2.0); 0.757 (2.0); 0.752 (2.1); 0.745 (2.4); 0.743 (2.3); 0.731 (1.8); 0.633 (1.2); 0.618 (2.0); 0.612 (2.2); 0.606 (1.8); 0.597 (2.6); 0.585 (1.9); 0.512 (1.7); 0.501 (2.5); 0.498 (2.1); 0.491 (1.7); 0.486 (2.4); 0.480 (2.0); 0.477 (1.6); 0.465 (1.4); 0.439 (1.9); 0.427 (2.0); 0.424 (2.2); 0.417 (2.3); 0.413 (2.0); 0.406 (1.9); 0.403 (2.0); 0.392 (1.2); 0.000 (3.1)

Example I-112

$^1$H-NMR (499.9 MHz, d$_6$-DMSO): δ=7.955 (12.0); 7.821 (11.5); 7.561 (3.0); 7.544 (6.2); 7.527 (3.4); 7.396 (3.6); 7.392 (3.9); 7.377 (3.8); 7.373 (3.9); 7.272 (4.0); 7.268 (3.9); 7.255 (3.7); 7.251 (3.5); 5.749 (15.4); 5.464 (12.8); 4.567 (5.0); 4.538 (5.7); 4.120 (6.0); 4.091 (5.5); 3.303 (25.0); 3.106 (16.0); 2.505 (3.7); 2.501 (4.9); 2.498 (3.6); 0.779 (1.2); 0.766 (2.0); 0.765 (2.0); 0.757 (2.0); 0.753 (2.1); 0.745 (2.4); 0.743 (2.3); 0.731 (1.8); 0.633 (1.2); 0.618 (2.0); 0.612 (2.2); 0.606 (1.8); 0.597 (2.6); 0.585 (1.9); 0.512 (1.7); 0.501 (2.5); 0.498 (2.2); 0.491 (1.7); 0.487 (2.4); 0.480 (2.0); 0.465 (1.4); 0.439 (1.8); 0.428 (2.0); 0.425 (2.2); 0.418 (2.3); 0.414 (1.9); 0.407 (1.8); 0.403 (2.0); 0.392 (1.1); 0.000 (2.2)

Example I-113

$^1$H-NMR (499.9 MHz, d$_6$-DMSO): δ=7.742 (12.1); 7.529 (3.4); 7.512 (7.0); 7.496 (3.9); 7.363 (4.0); 7.359 (4.3); 7.344 (4.2); 7.339 (4.4); 7.244 (4.4); 7.240 (4.3); 7.228 (4.1); 7.224 (3.9); 6.952 (11.3); 5.275 (16.0); 4.375 (5.8); 4.346 (7.4); 4.139 (7.4); 4.109 (6.1); 3.307 (7.5); 3.152 (4.5); 3.124 (5.5); 2.902 (5.4); 2.874 (4.4); 2.506 (2.4); 2.503 (3.3); 2.499 (2.4); 0.728 (0.4); 0.711 (2.1); 0.706 (1.9); 0.703 (1.6); 0.697 (2.6); 0.686 (3.1); 0.680 (2.6); 0.671 (0.7); 0.649 (1.9); 0.640 (2.7); 0.637 (2.7); 0.627 (3.5); 0.616 (3.5); 0.597 (6.0); 0.583 (11.8); 0.570 (3.0); 0.563 (1.2); 0.557 (0.7); 0.550 (0.8); 0.000 (3.1)

Example I-114

$^1$H-NMR (499.9 MHz, d$_6$-DMSO): δ=7.742 (12.7); 7.529 (3.5); 7.512 (7.2); 7.496 (4.0); 7.363 (4.1); 7.359 (4.3);

7.344 (4.2); 7.340 (4.4); 7.244 (4.6); 7.241 (4.4); 7.228 (4.2); 7.224 (4.0); 6.952 (11.8); 5.275 (16.0); 4.375 (6.0); 4.346 (7.6); 4.139 (7.6); 4.109 (6.2); 3.307 (8.6); 3.153 (4.7); 3.124 (5.8); 2.902 (5.7); 2.874 (4.6); 2.506 (2.7); 2.502 (3.6); 2.499 (2.7); 0.728 (0.4); 0.711 (2.2); 0.706 (2.0); 0.703 (1.7); 0.697 (2.7); 0.686 (3.3); 0.680 (2.7); 0.671 (0.7); 0.649 (2.0); 0.640 (2.8); 0.637 (2.8); 0.627 (3.7); 0.616 (3.6); 0.597 (6.2); 0.583 (12.2); 0.571 (3.2); 0.563 (1.2); 0.557 (0.7); 0.550 (0.8); 0.000 (2.8)

Example I-115

$^1$H-NMR (499.9 MHz, CDCl$_3$): δ=7.656 (4.8); 7.627 (5.2); 7.626 (4.9); 7.263 (4.6); 7.187 (1.1); 7.172 (2.4); 7.160 (0.6); 7.155 (2.1); 7.143 (1.4); 7.139 (2.6); 7.135 (2.8); 7.133 (2.6); 7.124 (1.9); 7.119 (3.8); 7.115 (1.2); 5.297 (16.0); 4.196 (1.7); 4.167 (4.4); 4.133 (4.3); 4.104 (1.8); 3.053 (1.6); 3.051 (1.6); 3.025 (2.0); 3.023 (2.1); 2.826 (1.9); 2.824 (2.0); 2.799 (1.5); 2.796 (1.6); 1.602 (0.9); 0.933 (0.3); 0.922 (0.7); 0.916 (0.8); 0.911 (0.6); 0.905 (1.5); 0.900 (0.6); 0.895 (0.9); 0.889 (0.9); 0.878 (0.5); 0.340 (0.3); 0.330 (0.5); 0.329 (0.5); 0.321 (0.7); 0.312 (1.2); 0.304 (0.8); 0.301 (0.9); 0.294 (0.8); 0.293 (0.8); 0.283 (0.6); 0.259 (0.6); 0.250 (0.8); 0.248 (0.8); 0.242 (0.8); 0.239 (0.9); 0.232 (1.2); 0.223 (0.9); 0.220 (0.7); 0.215 (0.6); 0.213 (0.6); 0.204 (0.5); 0.000 (4.8); −0.028 (0.4); −0.038 (0.9); −0.048 (1.2); −0.058 (1.5); −0.068 (1.4); −0.078 (0.6); −0.110 (0.6); −0.121 (1.2); −0.130 (1.3); −0.141 (1.1); −0.150 (0.8); −0.161 (0.4)

Example I-116

$^1$H-NMR (499.9 MHz, d$_6$-DMSO): δ=8.144 (5.6); 7.865 (1.9); 7.737 (15.8); 7.575 (16.0); 7.354 (4.6); 7.338 (10.3); 7.332 (7.8); 7.328 (8.1); 7.321 (7.9); 7.313 (8.0); 7.309 (8.0); 7.191 (6.3); 7.187 (6.3); 7.174 (5.4); 7.170 (5.4); 5.153 (3.4); 4.658 (7.0); 4.630 (8.2); 4.327 (8.0); 4.299 (7.1); 3.311 (0.5); 2.910 (5.3); 2.883 (6.6); 2.687 (5.9); 2.660 (4.7); 2.509 (3.2); 2.505 (6.5); 2.502 (9.0); 2.498 (6.8); 2.495 (3.6); 0.810 (0.9); 0.799 (2.0); 0.793 (2.4); 0.789 (2.1); 0.782 (4.1); 0.772 (2.7); 0.766 (2.4); 0.755 (1.2); 0.000 (4.5); −0.011 (0.9); −0.017 (1.1); −0.021 (1.2); −0.028 (3.0); −0.034 (2.7); −0.039 (2.9); −0.045 (3.8); −0.056 (2.1); −0.062 (1.8); −0.071 (1.6); −0.078 (1.9); −0.082 (2.2); −0.089 (3.4); −0.095 (2.5); −0.099 (3.2); −0.106 (3.5); −0.116 (1.7); −0.123 (2.7); −0.130 (2.0); −0.135 (2.6); −0.141 (3.7); −0.152 (3.9); −0.159 (2.8); −0.170 (1.3); −0.303 (1.2); −0.314 (2.5); −0.321 (3.7); −0.332 (3.6); −0.339 (2.3); −0.349 (1.2)

Example I-117

$^1$H-NMR (300.2 MHz, CDCl$_3$): δ=7.784 (7.2); 7.628 (7.6); 7.298 (2.3); 7.216 (1.1); 7.189 (3.0); 7.164 (2.8); 7.140 (8.0); 7.111 (4.6); 4.091 (2.4); 4.043 (4.9); 3.963 (4.9); 3.914 (2.4); 2.912 (2.1); 2.908 (2.0); 2.866 (2.9); 2.862 (2.9); 2.646 (3.0); 2.642 (3.0); 2.626 (0.9); 2.600 (3.2); 2.595 (3.1); 2.562 (2.0); 2.556 (2.1); 2.539 (1.2); 2.517 (0.7); 2.067 (0.9); 2.032 (16.0); 1.925 (0.6); 1.916 (0.6); 1.892 (1.3); 1.887 (1.5); 1.867 (3.1); 1.853 (4.4); 1.846 (3.7); 1.835 (2.7); 1.827 (2.5); 1.799 (0.8); 1.790 (1.1); 1.762 (0.6); 1.712 (0.6); 1.696 (0.6); 1.671 (1.5); 1.661 (0.9); 1.652 (0.9); 1.646 (0.8); 1.618 (0.6); 1.608 (0.8); 1.599 (1.0); 1.592 (1.0); 1.587 (1.0); 1.576 (0.8); 1.567 (1.1); 1.539 (0.3); 1.282 (0.5); 0.023 (1.8)

Example I-118

$^1$H-NMR (300.2 MHz, CDCl$_3$): δ=7.811 (6.8); 7.676 (7.6); 7.673 (7.2); 7.298 (14.6); 7.222 (1.0); 7.195 (3.1); 7.171 (11.6); 7.166 (5.3); 7.148 (3.1); 7.142 (3.9); 4.306 (3.2); 4.257 (4.4); 4.012 (4.4); 3.964 (3.2); 3.044 (2.2); 3.040 (2.3); 2.997 (2.8); 2.993 (3.0); 2.668 (2.8); 2.664 (3.1); 2.621 (2.2); 2.617 (2.5); 1.960 (4.5); 1.952 (4.5); 1.735 (0.6); 1.712 (1.6); 1.689 (2.2); 1.666 (1.8); 1.643 (0.9); 1.627 (11.5); 1.130 (14.8); 1.120 (16.0); 1.107 (14.0); 1.097 (14.5); 0.047 (0.5); 0.036 (15.0); 0.025 (0.6)

Example I-119

$^1$H-NMR (300.2 MHz, d$_6$-DMSO): δ=8.022 (1.8); 7.854 (1.9); 7.852 (1.7); 7.493 (1.9); 7.466 (1.0); 7.438 (0.6); 7.423 (0.6); 7.416 (0.7); 7.390 (0.6); 7.383 (0.7); 7.273 (0.7); 7.266 (0.6); 7.246 (0.5); 7.238 (0.5); 4.756 (2.5); 4.277 (0.6); 4.229 (0.9); 4.076 (0.9); 4.029 (0.6); 3.348 (6.6); 3.036 (0.5); 2.990 (0.6); 2.638 (0.6); 2.592 (0.5); 2.537 (0.7); 2.531 (1.5); 2.525 (2.1); 2.519 (1.5); 2.513 (0.7); 2.098 (0.5); 1.451 (0.4); 1.402 (1.0); 1.358 (1.0); 1.308 (0.4); 0.965 (16.0); 0.022 (1.6)

Example I-120

$^1$H-NMR (300.2 MHz, CDCl$_3$): δ=7.828 (11.7); 7.713 (0.4); 7.688 (12.3); 7.320 (0.3); 7.300 (15.9); 7.248 (2.1); 7.222 (5.2); 7.197 (4.4); 7.172 (12.6); 7.143 (8.3); 5.338 (2.5); 4.300 (4.3); 4.251 (7.5); 4.193 (0.5); 4.169 (1.3); 4.146 (1.5); 4.129 (8.0); 4.081 (4.5); 3.101 (4.3); 3.055 (5.5); 2.760 (5.4); 2.714 (4.1); 2.283 (11.7); 2.082 (5.6); 2.045 (1.8); 1.638 (16.0); 1.594 (2.4); 1.573 (2.6); 1.546 (3.3); 1.525 (3.5); 1.320 (2.2); 1.296 (5.2); 1.272 (3.4); 1.267 (3.9); 1.243 (2.5); 1.219 (2.7); 0.918 (0.6); 0.835 (0.7); 0.817 (1.5); 0.794 (2.1); 0.773 (1.9); 0.753 (1.0); 0.729 (0.4); 0.664 (2.5); 0.648 (7.1); 0.632 (3.9); 0.624 (6.0); 0.607 (1.9); 0.141 (2.4); 0.126 (8.0); 0.110 (8.9); 0.095 (2.0); 0.036 (15.2)

Example I-121

$^1$H-NMR (300.2 MHz, CDCl$_3$): δ=7.678 (2.9); 7.638 (2.9); 7.300 (2.1); 7.264 (0.7); 7.235 (1.5); 7.210 (1.4); 7.184 (1.5); 7.177 (2.3); 7.169 (1.5); 7.162 (1.2); 7.154 (0.9); 7.150 (0.8); 7.136 (1.3); 7.129 (0.9); 5.334 (2.3); 4.046 (1.0); 4.044 (1.0); 3.998 (2.0); 3.904 (2.1); 3.856 (1.1); 3.471 (16.0); 2.907 (0.9); 2.902 (0.9); 2.860 (1.1); 2.854 (1.1); 2.418 (1.3); 2.415 (1.3); 2.371 (1.1); 2.368 (1.1); 1.712 (0.5); 0.652 (0.4); 0.638 (0.4); 0.628 (0.6); 0.621 (0.7); 0.615 (0.5); 0.605 (1.5); 0.599 (0.9); 0.587 (1.0); 0.581 (1.5); 0.560 (1.9); 0.547 (0.4); 0.537 (0.9); 0.476 (1.4); 0.465 (0.7); 0.453 (2.0); 0.431 (1.1); 0.409 (0.4); 0.034 (2.2)

Example I-122

$^1$H-NMR (300.2 MHz, CDCl$_3$): δ=7.746 (8.2); 7.443 (2.2); 7.415 (4.8); 7.389 (2.9); 7.300 (30.4); 7.164 (4.8); 7.142 (6.7); 7.113 (4.3); 6.996 (9.0); 4.459 (4.2); 4.409 (5.7); 4.129 (5.6); 4.078 (4.2); 3.915 (0.5); 3.893 (2.2); 3.868 (3.6); 3.845 (2.8); 3.821 (1.0); 3.797 (0.9); 3.774 (2.8); 3.750 (3.7); 3.726 (2.2); 3.700 (0.7); 3.178 (3.3); 3.128 (5.8); 3.008 (5.9); 2.958 (3.4); 2.179 (0.5); 2.061 (1.1); 1.989 (1.0); 1.295 (6.4); 1.259 (8.9); 1.236 (16.0); 1.214 (8.3); 1.142 (0.6); 1.061 (0.4); 1.007 (2.3); 0.995 (2.3); 0.972 (3.0); 0.920 (1.2); 0.868 (4.1); 0.827 (13.3); 0.798 (2.0); 0.704 (0.3); 0.038 (24.4)

Example I-123

$^1$H-NMR (300.2 MHz, CDCl$_3$): δ=7.679 (10.8); 7.452 (3.5); 7.440 (1.0); 7.423 (7.2); 7.396 (4.4); 7.300 (36.5);

7.155 (3.9); 7.147 (7.3); 7.142 (6.9); 7.135 (5.3); 7.124 (5.0); 7.122 (4.8); 7.108 (6.2); 7.101 (4.0); 6.972 (11.6); 6.969 (11.5); 6.949 (0.4); 5.957 (1.0); 5.941 (1.9); 5.923 (1.5); 5.906 (2.2); 5.900 (1.5); 5.890 (1.4); 5.884 (2.4); 5.866 (1.8); 5.849 (2.5); 5.833 (1.3); 5.287 (1.7); 5.281 (4.6); 5.276 (5.1); 5.271 (2.2); 5.240 (2.2); 5.235 (5.4); 5.230 (6.2); 5.224 (5.4); 5.219 (4.5); 5.213 (2.1); 5.205 (2.0); 5.200 (4.8); 5.195 (4.4); 4.490 (7.4); 4.439 (10.1); 4.417 (1.3); 4.412 (2.0); 4.406 (1.4); 4.402 (1.4); 4.396 (2.0); 4.391 (1.2); 4.377 (1.9); 4.371 (3.3); 4.366 (2.3); 4.362 (2.3); 4.356 (3.2); 4.351 (1.9); 4.271 (3.2); 4.259 (2.1); 4.254 (3.3); 4.231 (2.0); 4.219 (1.2); 4.214 (1.8); 4.167 (9.7); 4.117 (7.3); 3.987 (0.5); 3.224 (3.7); 3.174 (6.5); 3.050 (7.5); 2.999 (4.4); 1.741 (1.6); 1.667 (0.6); 1.292 (1.4); 1.034 (0.4); 1.009 (1.6); 1.001 (2.6); 0.984 (4.1); 0.967 (3.8); 0.960 (3.8); 0.946 (1.1); 0.924 (2.6); 0.911 (4.0); 0.906 (3.8); 0.891 (4.4); 0.871 (4.9); 0.855 (1.1); 0.848 (3.5); 0.840 (8.6); 0.823 (16.0); 0.802 (4.8); 0.789 (1.1); 0.771 (1.0); 0.048 (0.6); 0.037 (26.6); 0.026 (1.3)

Example I-124

$^1$H-NMR (300.2 MHz, CDCl$_3$): δ=7.750 (4.7); 7.646 (5.0); 7.298 (1.7); 7.265 (0.6); 7.244 (0.8); 7.235 (1.4); 7.214 (1.5); 7.208 (1.0); 7.186 (0.8); 6.929 (0.6); 6.919 (1.2); 6.913 (1.1); 6.903 (1.3); 6.893 (1.9); 6.884 (1.2); 6.877 (1.9); 6.869 (1.6); 6.849 (1.1); 6.841 (0.7); 4.417 (2.3); 4.368 (3.3); 4.143 (3.2); 4.095 (2.3); 3.159 (1.4); 3.156 (1.3); 3.112 (2.0); 3.108 (2.0); 2.924 (2.0); 2.877 (1.4); 2.874 (1.4); 2.031 (5.8); 1.899 (2.4); 1.346 (16.0); 0.259 (0.6); 0.234 (4.2); 0.213 (0.8); 0.189 (0.5); 0.098 (0.7); 0.090 (0.5); 0.072 (1.2); 0.056 (3.4); 0.046 (3.5); 0.039 (1.7); 0.027 (1.0); 0.023 (1.7); 0.015 (0.4); 0.009 (0.4); 0.001 (0.4)

Example I-125

$^1$H-NMR (300.2 MHz, CDCl$_3$): δ=7.887 (15.3); 7.886 (15.3); 7.672 (16.0); 7.670 (15.5); 7.646 (0.4); 7.465 (2.2); 7.444 (2.7); 7.437 (5.0); 7.416 (5.1); 7.409 (3.1); 7.387 (2.7); 7.300 (6.4); 6.984 (2.0); 6.982 (2.0); 6.976 (2.6); 6.973 (2.7); 6.955 (3.7); 6.946 (5.7); 6.938 (4.1); 6.930 (3.5); 6.919 (3.3); 6.910 (4.1); 6.904 (4.4); 6.896 (2.9); 6.876 (3.2); 6.867 (2.5); 4.727 (9.5); 4.678 (11.4); 4.235 (11.2); 4.186 (9.3); 4.160 (0.3); 3.350 (3.7); 3.348 (3.7); 3.302 (7.2); 3.299 (7.3); 3.205 (7.6); 3.157 (3.9); 2.446 (7.7); 2.424 (7.6); 2.073 (1.3); 2.038 (5.2); 1.855 (2.6); 1.312 (0.4); 1.288 (0.8); 1.264 (0.3); 0.759 (1.6); 0.750 (1.6); 0.743 (2.1); 0.724 (4.2); 0.708 (5.4); 0.700 (6.7); 0.695 (6.7); 0.687 (7.0); 0.684 (6.6); 0.675 (3.9); 0.656 (2.2); 0.649 (2.6); 0.641 (4.5); 0.624 (4.5); 0.615 (2.5); 0.605 (0.6); 0.593 (4.5); 0.580 (5.7); 0.576 (5.5); 0.569 (4.8); 0.564 (2.0); 0.549 (5.1); 0.542 (5.1); 0.535 (2.0); 0.528 (3.3); 0.521 (3.4); 0.507 (2.0); 0.499 (1.8); 0.491 (1.7); 0.101 (0.4); 0.029 (4.2)

Example I-126

$^1$H-NMR (300.2 MHz, d$_6$-DMSO): δ=10.098 (0.4); 7.969 (0.4); 7.946 (0.5); 7.863 (0.3); 7.838 (0.4); 7.765 (12.2); 7.675 (0.4); 7.638 (0.4); 7.587 (1.9); 7.559 (4.4); 7.535 (4.5); 7.506 (2.0); 7.421 (0.4); 7.228 (2.5); 7.221 (2.6); 7.196 (4.5); 7.188 (4.5); 7.163 (2.5); 7.155 (2.5); 7.090 (2.7); 7.061 (4.7); 7.034 (2.4); 6.978 (12.1); 6.934 (0.5); 5.781 (1.5); 5.430 (1.5); 5.328 (0.5); 5.283 (14.6); 4.654 (0.4); 4.641 (0.4); 4.411 (5.2); 4.362 (7.5); 4.151 (7.6); 4.102 (5.2); 4.039 (0.3); 4.028 (0.4); 3.429 (0.4); 3.345 (58.4); 3.168 (4.4); 3.120 (6.3); 3.078 (0.4); 2.935 (6.3); 2.887 (4.3); 2.751 (0.6); 2.662 (0.4); 2.525 (49.8); 2.385 (0.4); 2.297 (0.4); 0.720 (2.5); 0.704 (3.1); 0.688 (5.3); 0.639 (6.9); 0.613 (8.0); 0.598 (16.0); 0.503 (0.5); 0.377 (0.3); 0.219 (0.3); 0.023 (37.8); −0.078 (0.6); −0.221 (0.4); −0.271 (0.4); −3.211 (0.3)

Example I-127

$^1$H-NMR (300.2 MHz, CDCl$_3$): δ=7.796 (15.7); 7.646 (16.0); 7.298 (8.7); 7.249 (1.8); 7.240 (0.6); 7.228 (2.4); 7.220 (4.7); 7.198 (4.3); 7.192 (3.2); 7.170 (2.7); 6.922 (1.9); 6.913 (2.9); 6.896 (4.5); 6.888 (7.3); 6.862 (8.6); 6.834 (3.1); 6.826 (2.1); 4.101 (5.2); 4.053 (10.9); 3.970 (11.1); 3.922 (5.4); 2.916 (4.4); 2.912 (4.3); 2.869 (6.1); 2.865 (6.1); 2.665 (0.7); 2.646 (6.5); 2.641 (7.5); 2.624 (1.4); 2.610 (2.9); 2.599 (5.9); 2.580 (2.0); 2.567 (0.7); 2.550 (0.8); 2.292 (2.7); 2.244 (1.2); 2.039 (6.4); 1.923 (0.7); 1.914 (0.8); 1.893 (2.5); 1.873 (8.6); 1.861 (9.7); 1.852 (10.0); 1.845 (8.6); 1.831 (4.5); 1.828 (4.5); 1.825 (4.5); 1.813 (2.8); 1.796 (3.0); 1.782 (1.6); 1.768 (2.3); 1.750 (0.9); 1.733 (0.6); 1.721 (1.3); 1.714 (1.0); 1.708 (1.1); 1.695 (1.7); 1.681 (3.1); 1.668 (2.0); 1.655 (1.9); 1.644 (0.9); 1.622 (1.6); 1.610 (2.0); 1.600 (2.5); 1.586 (1.8); 1.578 (2.1); 1.564 (1.0); 1.549 (0.6); 0.030 (7.2)

Example I-128

$^1$H-NMR (300.2 MHz, CDCl$_3$): δ=7.792 (7.2); 7.636 (7.8); 7.634 (7.5); 7.298 (3.4); 7.271 (0.9); 7.250 (1.0); 7.241 (2.1); 7.231 (0.4); 7.220 (2.1); 7.214 (1.5); 7.192 (1.2); 6.929 (0.9); 6.919 (1.6); 6.910 (1.5); 6.902 (2.7); 6.893 (2.7); 6.880 (1.6); 6.874 (3.1); 6.869 (2.4); 6.867 (2.4); 6.846 (1.6); 6.838 (1.0); 4.301 (3.5); 4.253 (4.6); 3.996 (4.4); 3.947 (3.3); 3.027 (2.1); 3.024 (2.1); 2.980 (2.7); 2.976 (2.7); 2.671 (2.9); 2.624 (2.2); 2.252 (4.2); 2.245 (4.7); 1.786 (3.4); 1.735 (0.6); 1.712 (1.6); 1.689 (2.3); 1.666 (1.9); 1.644 (0.8); 1.328 (0.3); 1.306 (0.4); 1.128 (15.0); 1.118 (16.0); 1.105 (14.3); 1.095 (14.4); 0.030 (2.9)

Example I-129

$^1$H-NMR (300.2 MHz, d$_6$-DMSO): δ=8.024 (1.7); 8.022 (1.7); 7.853 (1.8); 7.850 (1.7); 7.491 (0.5); 7.468 (0.5); 7.462 (0.3); 7.211 (0.4); 7.205 (0.4); 7.056 (0.5); 7.049 (0.4); 4.734 (2.6); 4.266 (0.6); 4.219 (0.9); 4.069 (0.9); 4.022 (0.6); 3.349 (4.6); 3.022 (0.5); 2.976 (0.6); 2.640 (0.6); 2.594 (0.5); 2.537 (0.5); 2.531 (1.0); 2.525 (1.4); 2.519 (1.0); 2.513 (0.5); 1.453 (0.4); 1.403 (1.0); 1.349 (1.0); 1.300 (0.4); 0.961 (16.0); 0.873 (0.4); 0.784 (0.5); 0.022 (0.9)

Example I-130

$^1$H-NMR (300.2 MHz, CDCl$_3$): δ=7.821 (14.5); 7.688 (0.5); 7.666 (15.4); 7.664 (14.7); 7.520 (0.4); 7.475 (0.4); 7.300 (8.5); 7.291 (1.9); 7.279 (0.6); 7.270 (2.1); 7.261 (4.4); 7.248 (0.9); 7.239 (4.1); 7.233 (3.0); 7.212 (2.5); 7.017 (0.3); 6.932 (1.7); 6.922 (2.9); 6.910 (2.9); 6.903 (5.2); 6.898 (5.7); 6.873 (6.2); 6.847 (3.2); 6.839 (2.1); 4.444 (0.4); 4.392 (0.4); 4.295 (5.4); 4.247 (9.3); 4.121 (10.1); 4.072 (6.0); 3.098 (4.2); 3.094 (4.3); 3.051 (5.5); 3.047 (5.6); 2.763 (5.3); 2.760 (5.4); 2.716 (4.1); 2.713 (4.2); 2.473 (12.1); 2.041 (1.5); 1.814 (0.5); 1.764 (16.0); 1.586 (3.1); 1.565 (3.3); 1.538 (4.3); 1.527 (1.8); 1.517 (4.5); 1.312 (0.7); 1.292 (4.3); 1.268 (4.7); 1.244 (3.2);

1.220 (3.5); 0.853 (0.6); 0.845 (0.7); 0.827 (1.6); 0.817 (1.4); 0.803 (2.2); 0.793 (1.5); 0.780 (1.9); 0.763 (1.0); 0.756 (0.9); 0.740 (0.4); 0.658 (3.1); 0.641 (7.5); 0.627 (4.4); 0.617 (6.3); 0.600 (2.7); 0.139 (3.0); 0.124 (8.0); 0.108 (8.7); 0.093 (2.2); 0.042 (0.4); 0.031 (5.9)

Example I-131

$^1$H-NMR (300.2 MHz, CDCl$_3$): δ=7.763 (4.7); 7.666 (5.0); 7.380 (0.4); 7.373 (0.4); 7.362 (0.5); 7.355 (1.1); 7.348 (0.9); 7.329 (1.2); 7.322 (0.7); 7.311 (0.6); 7.300 (4.2); 7.270 (0.6); 7.264 (0.7); 7.246 (1.5); 7.239 (1.5); 7.221 (1.4); 7.214 (1.1); 7.199 (1.8); 7.197 (1.8); 7.172 (2.3); 7.150 (0.8); 7.147 (0.8); 7.140 (1.1); 7.134 (1.5); 7.105 (1.0); 4.446 (2.4); 4.397 (3.3); 4.150 (3.1); 4.102 (2.2); 3.194 (1.3); 3.147 (2.2); 3.007 (2.3); 2.959 (1.4); 1.819 (1.6); 1.803 (1.6); 1.696 (1.5); 1.690 (2.2); 1.679 (0.9); 1.370 (16.0); 1.343 (0.7); 0.310 (0.3); 0.297 (0.4); 0.281 (0.7); 0.262 (2.4); 0.251 (2.7); 0.234 (0.9); 0.215 (0.4); 0.205 (0.5); 0.104 (0.7); 0.093 (0.4); 0.080 (0.9); 0.062 (2.7); 0.059 (2.8); 0.050 (3.0); 0.043 (2.1); 0.036 (4.1); 0.027 (0.7); 0.018 (0.4); 0.012 (0.4); 0.004 (0.4)

Example I-132

$^1$H-NMR (499.9 MHz, CDCl$_3$): δ=7.857 (10.6); 7.638 (10.7); 7.404 (1.8); 7.401 (2.0); 7.389 (3.8); 7.385 (4.2); 7.373 (2.2); 7.370 (2.4); 7.356 (1.2); 7.352 (1.1); 7.345 (1.3); 7.341 (2.7); 7.337 (2.1); 7.329 (2.3); 7.325 (2.9); 7.321 (1.6); 7.313 (1.6); 7.310 (1.4); 7.262 (9.3); 7.196 (3.1); 7.195 (3.2); 7.181 (5.2); 7.180 (5.2); 7.166 (2.4); 7.165 (2.4); 7.136 (2.8); 7.116 (3.4); 7.098 (2.5); 5.297 (16.0); 4.697 (6.9); 4.668 (7.8); 4.183 (7.4); 4.154 (6.8); 3.317 (2.8); 3.289 (6.0); 3.242 (6.3); 3.213 (3.0); 2.340 (6.6); 2.324 (6.7); 1.637 (4.8); 1.255 (0.3); 1.241 (0.3); 0.719 (1.3); 0.710 (1.5); 0.706 (1.5); 0.699 (2.7); 0.690 (2.9); 0.685 (3.2); 0.676 (3.7); 0.664 (3.2); 0.655 (3.4); 0.653 (3.7); 0.643 (3.8); 0.636 (1.0); 0.632 (2.0); 0.623 (2.9); 0.616 (0.5); 0.604 (2.9); 0.595 (2.1); 0.591 (1.2); 0.583 (3.9); 0.573 (3.6); 0.571 (3.3); 0.562 (2.8); 0.550 (0.4); 0.532 (3.3); 0.523 (3.0); 0.518 (2.9); 0.510 (3.2); 0.502 (2.0); 0.498 (1.9); 0.489 (1.6); 0.006 (0.3); 0.000 (9.1); −0.007 (0.5)

Example I-133

$^1$H-NMR (499.9 MHz, CDCl$_3$): δ=7.858 (11.5); 7.639 (11.6); 7.403 (1.9); 7.400 (2.2); 7.388 (4.0); 7.385 (4.5); 7.373 (2.3); 7.370 (2.5); 7.356 (1.1); 7.353 (1.1); 7.345 (1.3); 7.341 (2.8); 7.338 (2.2); 7.329 (2.3); 7.325 (3.1); 7.321 (1.7); 7.314 (1.6); 7.310 (1.4); 7.262 (10.6); 7.197 (3.2); 7.195 (3.5); 7.182 (5.4); 7.180 (5.7); 7.167 (2.4); 7.165 (2.5); 7.136 (2.9); 7.116 (3.6); 7.099 (2.5); 5.297 (16.0); 4.697 (7.4); 4.668 (8.3); 4.183 (7.9); 4.154 (7.1); 3.317 (3.0); 3.289 (6.5); 3.242 (6.8); 3.213 (3.1); 2.330 (7.0); 2.314 (7.1); 1.626 (5.0); 1.255 (0.4); 1.241 (0.4); 0.719 (1.3); 0.710 (1.5); 0.706 (1.6); 0.699 (2.9); 0.690 (3.1); 0.685 (3.4); 0.676 (3.9); 0.665 (3.4); 0.656 (3.6); 0.653 (3.9); 0.644 (3.8); 0.636 (1.0); 0.632 (1.9); 0.623 (2.8); 0.615 (0.4); 0.604 (2.8); 0.594 (2.1); 0.591 (1.2); 0.583 (4.0); 0.573 (3.6); 0.571 (3.5); 0.562 (2.8); 0.532 (3.3); 0.524 (3.1); 0.518 (3.0); 0.511 (3.4); 0.502 (1.9); 0.498 (1.9); 0.489 (1.5); 0.006 (0.4); 0.000 (10.3); −0.007 (0.7)

Example I-134

$^1$H-NMR (300.2 MHz, CDCl$_3$): δ=8.441 (0.5); 8.030 (16.0); 7.698 (1.0); 7.695 (1.0); 7.663 (1.1); 7.466 (0.8); 7.460 (0.9); 7.441 (1.9); 7.435 (2.1); 7.416 (1.3); 7.410 (1.4); 7.390 (0.4); 7.385 (0.4); 7.330 (0.4); 7.323 (0.7); 7.315 (0.6); 7.313 (0.6); 7.300 (4.4); 7.289 (1.5); 7.279 (2.2); 7.272 (2.0); 7.263 (1.2); 7.261 (1.2); 7.253 (1.9); 7.247 (1.0); 7.232 (1.9); 7.226 (1.7); 7.215 (0.5); 7.207 (1.5); 7.201 (1.2); 7.190 (0.6); 7.187 (0.7); 7.164 (2.1); 7.160 (2.1); 7.147 (1.9); 7.143 (2.9); 7.139 (3.1); 7.135 (3.1); 7.122 (2.2); 7.118 (3.6); 7.111 (2.2); 7.105 (1.9); 7.101 (1.5); 7.097 (1.4); 7.093 (1.6); 7.088 (1.5); 7.083 (2.1); 7.078 (2.3); 7.072 (2.3); 7.067 (2.0); 7.055 (1.2); 7.052 (1.1); 7.044 (1.3); 7.041 (1.2); 7.033 (0.5); 4.758 (0.5); 4.749 (1.2); 4.700 (4.7); 4.670 (4.6); 4.621 (1.2); 4.570 (0.6); 4.521 (0.4); 4.192 (0.5); 4.169 (1.7); 4.150 (9.5); 4.141 (5.4); 4.121 (0.7); 4.006 (0.5); 3.950 (0.5); 3.396 (0.4); 3.351 (0.5); 3.327 (1.5); 3.280 (2.6); 3.166 (2.2); 3.162 (2.2); 3.120 (1.3); 3.115 (1.3); 3.064 (0.4); 3.059 (0.4); 2.080 (7.3); 2.033 (8.3); 1.806 (1.6); 1.318 (1.9); 1.294 (3.8); 1.271 (1.9); 0.807 (0.4); 0.771 (0.4); 0.753 (1.0); 0.746 (0.8); 0.735 (0.6); 0.728 (2.2); 0.719 (1.7); 0.716 (1.8); 0.709 (1.5); 0.705 (1.7); 0.696 (2.3); 0.693 (2.6); 0.679 (1.2); 0.674 (2.0); 0.658 (1.4); 0.646 (1.9); 0.631 (1.7); 0.620 (0.9); 0.616 (0.8); 0.605 (1.3); 0.598 (1.1); 0.589 (0.4); 0.572 (0.6); 0.519 (1.2); 0.503 (1.1); 0.498 (1.3); 0.484 (1.2); 0.480 (1.2); 0.469 (0.8); 0.461 (0.9); 0.444 (0.6); 0.037 (2.9)

Example I-135

$^1$H-NMR (499.9 MHz, CDCl$_3$): δ=8.328 (1.3); 8.065 (0.9); 7.919 (5.3); 7.746 (5.4); 7.425 (1.2); 7.423 (1.2); 7.410 (2.3); 7.407 (2.3); 7.395 (1.4); 7.392 (1.4); 7.292 (0.5); 7.289 (0.6); 7.282 (0.6); 7.278 (1.4); 7.274 (1.3); 7.260 (10.2); 7.251 (0.9); 7.247 (0.9); 7.144 (1.5); 7.143 (1.6); 7.129 (2.8); 7.128 (2.9); 7.115 (1.6); 7.113 (1.6); 7.081 (1.5); 7.074 (0.6); 7.072 (0.6); 7.063 (2.2); 7.046 (1.3); 7.044 (1.3); 7.016 (0.3); 5.296 (1.3); 4.886 (0.8); 4.716 (2.5); 4.687 (4.0); 4.601 (3.9); 4.571 (2.4); 4.462 (0.5); 4.427 (0.6); 4.267 (1.0); 4.256 (2.1); 4.249 (0.7); 4.241 (6.5); 4.234 (1.6); 4.227 (6.8); 4.219 (1.0); 4.213 (2.5); 4.205 (0.8); 4.201 (0.8); 4.197 (0.7); 4.161 (0.4); 4.119 (4.7); 4.093 (0.6); 3.965 (0.8); 3.936 (0.4); 3.931 (0.7); 3.906 (0.4); 3.487 (0.5); 3.457 (0.4); 3.359 (2.8); 3.330 (3.0); 3.292 (0.9); 3.284 (0.6); 3.263 (0.4); 3.238 (0.3); 3.209 (0.6); 3.135 (0.5); 3.114 (2.2); 3.111 (2.3); 3.086 (1.8); 3.083 (1.8); 2.954 (0.3); 1.612 (10.0); 1.319 (7.9); 1.305 (16.0); 1.291 (8.3); 1.278 (2.9); 1.264 (1.6); 1.256 (0.4); 1.228 (0.4); 0.909 (0.5); 0.894 (0.4); 0.891 (0.4); 0.879 (0.3); 0.775 (0.8); 0.764 (1.3); 0.760 (1.2); 0.753 (1.6); 0.749 (1.9); 0.742 (1.5); 0.739 (1.5); 0.734 (1.2); 0.732 (1.2); 0.728 (1.6); 0.719 (1.1); 0.715 (0.7); 0.708 (0.7); 0.705 (1.2); 0.698 (1.5); 0.694 (0.7); 0.687 (1.3); 0.684 (1.8); 0.673 (1.3); 0.647 (1.5); 0.636 (1.6); 0.633 (1.3); 0.626 (0.9); 0.622 (1.4); 0.616 (1.1); 0.612 (0.7); 0.601 (0.8); 0.504 (1.2); 0.494 (1.3); 0.491 (1.3); 0.483 (1.3); 0.480 (1.3); 0.472 (1.1); 0.469 (1.1); 0.458 (0.8); 0.000 (7.3); −0.007 (0.4)

Example I-136

$^1$H-NMR (300.2 MHz, CDCl$_3$): δ=7.708 (15.0); 7.660 (0.6); 7.656 (0.6); 7.641 (15.5); 7.357 (1.3); 7.351 (1.5); 7.339 (1.5); 7.332 (3.3); 7.325 (2.7); 7.306 (3.8); 7.300 (6.2); 7.287 (3.5); 7.282 (4.1); 7.263 (4.8); 7.258 (4.9); 7.238 (3.9); 7.232 (3.0); 7.174 (4.8); 7.170 (5.2); 7.146 (11.4); 7.120 (6.3); 7.114 (4.8); 7.086 (3.0); 4.448 (0.3); 4.438 (0.4); 4.250 (3.1); 4.202 (12.3); 4.173 (12.9); 4.125 (3.3); 3.137 (4.4); 3.134 (4.2); 3.091 (6.6); 3.088 (6.4);

2.927 (6.3); 2.923 (6.3); 2.882 (4.1); 2.877 (4.2); 2.113 (3.7); 2.069 (1.1); 2.047 (0.4); 2.031 (16.0); 1.987 (1.2); 1.966 (0.6); 1.284 (0.9); 0.981 (0.9); 0.963 (2.0); 0.953 (2.2); 0.945 (1.5); 0.936 (4.1); 0.926 (1.6); 0.918 (2.4); 0.908 (2.4); 0.890 (1.2); 0.368 (1.0); 0.353 (1.4); 0.349 (1.3); 0.337 (2.5); 0.322 (3.3); 0.308 (2.6); 0.305 (2.8); 0.294 (2.1); 0.290 (2.0); 0.275 (1.8); 0.259 (1.7); 0.245 (2.2); 0.241 (2.1); 0.231 (2.5); 0.227 (2.8); 0.214 (3.1); 0.200 (2.7); 0.187 (1.2); 0.183 (1.2); 0.169 (1.2); 0.054 (1.3); 0.037 (2.6); 0.027 (3.9); 0.022 (3.9); 0.004 (4.6); −0.011 (3.6); −0.028 (1.6); −0.083 (1.6); −0.101 (3.2); −0.115 (3.9); −0.133 (3.2); −0.147 (2.0); −0.165 (0.9)

Example I-137

$^1$H-NMR (300.2 MHz, CDCl$_3$): δ=7.796 (14.3); 7.644 (0.5); 7.632 (16.0); 7.629 (15.4); 7.446 (0.4); 7.443 (0.5); 7.397 (0.4); 7.341 (1.2); 7.334 (1.5); 7.323 (1.5); 7.316 (3.2); 7.309 (2.8); 7.298 (8.0); 7.290 (3.9); 7.283 (2.6); 7.272 (2.2); 7.265 (2.4); 7.254 (2.0); 7.248 (2.2); 7.229 (5.0); 7.222 (4.7); 7.204 (4.0); 7.197 (3.1); 7.169 (5.0); 7.165 (5.9); 7.144 (5.6); 7.140 (6.9); 7.131 (4.4); 7.119 (2.5); 7.115 (2.7); 7.104 (3.4); 7.098 (4.7); 7.094 (3.6); 7.070 (2.9); 7.066 (2.6); 4.291 (0.4); 4.234 (0.4); 4.112 (5.2); 4.064 (10.5); 3.976 (10.1); 3.928 (5.1); 2.960 (4.3); 2.956 (4.3); 2.913 (6.0); 2.909 (6.2); 2.698 (6.1); 2.694 (6.2); 2.667 (0.8); 2.652 (4.8); 2.647 (5.1); 2.634 (1.6); 2.617 (2.1); 2.611 (2.2); 2.602 (1.8); 2.583 (2.1); 2.563 (0.5); 2.553 (0.9); 2.412 (8.9); 2.403 (9.1); 2.035 (0.5); 1.953 (0.4); 1.943 (1.1); 1.913 (1.9); 1.898 (2.4); 1.882 (5.1); 1.874 (6.7); 1.864 (7.1); 1.857 (8.5); 1.850 (13.3); 1.837 (6.0); 1.827 (4.1); 1.812 (2.7); 1.801 (2.5); 1.791 (1.0); 1.777 (1.2); 1.744 (0.5); 1.730 (0.5); 1.713 (0.9); 1.699 (0.9); 1.683 (1.7); 1.672 (3.3); 1.661 (2.1); 1.652 (1.7); 1.633 (0.9); 1.623 (0.7); 1.618 (0.7); 1.610 (0.6); 1.594 (1.1); 1.590 (1.0); 1.580 (1.4); 1.570 (1.9); 1.564 (1.9); 1.557 (2.2); 1.544 (1.8); 1.537 (2.3); 1.523 (0.7); 1.513 (1.1); 0.102 (0.7); 0.029 (5.6)

Example I-138

$^1$H-NMR (300.2 MHz, CDCl$_3$): δ=7.694 (1.1); 7.583 (1.3); 7.580 (1.2); 7.300 (0.9); 7.239 (0.3); 7.082 (0.4); 7.057 (0.7); 7.053 (0.9); 7.034 (0.6); 7.031 (0.6); 7.028 (0.7); 7.011 (0.3); 7.005 (0.3); 4.358 (0.5); 4.310 (0.8); 4.144 (0.6); 4.142 (0.6); 4.096 (0.4); 4.093 (0.4); 3.253 (0.4); 3.249 (0.4); 3.204 (0.4); 3.200 (0.4); 2.786 (0.5); 2.738 (0.4); 2.403 (0.5); 2.381 (0.5); 1.094 (16.0); 0.035 (0.9)

Example I-139

$^1$H-NMR (300.2 MHz, CDCl$_3$): δ=7.801 (4.4); 7.631 (4.7); 7.351 (0.3); 7.344 (0.4); 7.333 (0.4); 7.326 (0.9); 7.319 (0.9); 7.308 (0.7); 7.298 (2.5); 7.293 (0.8); 7.282 (0.6); 7.275 (0.7); 7.270 (0.6); 7.264 (0.7); 7.245 (1.5); 7.239 (1.4); 7.220 (1.2); 7.214 (0.9); 7.180 (1.4); 7.176 (1.7); 7.155 (1.7); 7.151 (2.3); 7.130 (0.7); 7.126 (0.8); 7.120 (1.0); 7.114 (1.4); 7.086 (0.9); 7.083 (0.8); 4.320 (2.1); 4.271 (2.9); 4.001 (2.7); 3.953 (2.0); 3.063 (1.3); 3.059 (1.3); 3.016 (1.8); 3.012 (1.8); 2.729 (1.9); 2.682 (1.5); 2.299 (1.3); 2.289 (1.8); 1.844 (0.6); 1.746 (0.4); 1.723 (1.0); 1.700 (1.4); 1.677 (1.2); 1.654 (0.5); 1.342 (0.5); 1.320 (0.5); 1.134 (9.0); 1.112 (16.0); 1.089 (8.6); 0.030 (1.4)

Example I-140

$^1$H-NMR (300.2 MHz, d$_6$-DMSO): δ=8.035 (1.8); 8.033 (1.8); 7.853 (1.8); 7.851 (1.7); 7.446 (0.5); 7.440 (0.7); 7.415 (0.4); 7.324 (0.4); 7.320 (0.4); 7.304 (0.4); 7.296 (0.5); 7.212 (0.5); 7.183 (1.0); 7.161 (0.8); 7.157 (0.8); 7.136 (0.4); 4.743 (2.4); 4.248 (0.6); 4.201 (1.0); 4.078 (0.9); 4.030 (0.6); 3.351 (11.6); 3.054 (0.5); 3.008 (0.7); 2.697 (0.6); 2.650 (0.5); 2.537 (0.7); 2.531 (1.3); 2.525 (1.8); 2.519 (1.3); 2.513 (0.6); 1.478 (0.5); 1.429 (0.9); 1.333 (0.9); 1.283 (0.5); 0.961 (16.0); 0.889 (1.3); 0.763 (0.7); 0.022 (0.8)

Example I-141

$^1$H-NMR (300.2 MHz, CDCl$_3$): δ=7.834 (14.4); 7.701 (0.5); 7.699 (0.4); 7.670 (16.0); 7.668 (13.6); 7.507 (0.6); 7.446 (0.7); 7.443 (0.6); 7.355 (1.2); 7.349 (1.6); 7.337 (2.0); 7.330 (3.2); 7.323 (2.9); 7.310 (2.7); 7.300 (13.2); 7.286 (3.8); 7.280 (3.9); 7.263 (5.1); 7.256 (4.5); 7.237 (3.8); 7.231 (2.9); 7.185 (4.7); 7.182 (5.4); 7.161 (5.7); 7.157 (7.2); 7.151 (4.7); 7.136 (2.5); 7.132 (2.8); 7.124 (3.7); 7.118 (5.0); 7.090 (3.0); 7.087 (2.6); 5.096 (0.4); 4.889 (0.4); 4.461 (0.7); 4.413 (0.7); 4.314 (5.5); 4.266 (9.3); 4.134 (9.8); 4.086 (5.9); 3.154 (4.6); 3.150 (4.5); 3.107 (5.9); 3.104 (5.9); 2.823 (5.8); 2.819 (5.8); 2.776 (4.4); 2.773 (4.4); 2.392 (8.0); 2.079 (0.4); 2.042 (13.0); 1.724 (11.6); 1.622 (3.2); 1.601 (3.4); 1.574 (4.2); 1.553 (4.4); 1.326 (0.8); 1.293 (0.3); 1.275 (4.3); 1.251 (4.8); 1.227 (3.3); 1.203 (3.7); 0.881 (0.6); 0.873 (0.8); 0.855 (1.8); 0.845 (1.4); 0.835 (2.1); 0.830 (2.2); 0.820 (1.4); 0.811 (2.0); 0.792 (1.0); 0.785 (0.9); 0.768 (0.4); 0.670 (0.4); 0.653 (2.7); 0.636 (7.8); 0.625 (4.4); 0.614 (6.8); 0.597 (2.5); 0.161 (0.3); 0.140 (3.1); 0.126 (7.7); 0.122 (6.7); 0.110 (8.3); 0.095 (2.4); 0.079 (0.4); 0.074 (0.5); 0.044 (0.5); 0.034 (8.8); 0.023 (0.4)

Example I-142

$^1$H-NMR (300.2 MHz, CDCl$_3$): δ=7.885 (8.5); 7.658 (7.7); 7.300 (2.6); 7.238 (1.5); 7.214 (3.7); 7.197 (3.8); 7.175 (2.2); 7.109 (3.7); 7.084 (4.4); 7.059 (1.7); 4.737 (4.8); 4.689 (5.7); 4.195 (5.3); 4.146 (4.5); 3.329 (0.4); 3.281 (11.9); 3.233 (0.3); 2.539 (1.1); 2.528 (1.4); 2.514 (2.5); 2.502 (1.2); 2.488 (1.7); 2.325 (16.0); 2.319 (16.0); 2.036 (2.7); 0.766 (1.1); 0.753 (1.1); 0.747 (2.3); 0.724 (2.5); 0.720 (2.4); 0.716 (2.6); 0.694 (2.3); 0.688 (2.6); 0.676 (2.6); 0.665 (4.4); 0.660 (3.5); 0.646 (2.8); 0.638 (4.7); 0.629 (2.7); 0.619 (1.4); 0.611 (1.8); 0.585 (0.5); 0.559 (2.1); 0.556 (2.2); 0.550 (2.2); 0.528 (3.0); 0.519 (1.3); 0.507 (1.4); 0.478 (0.3); 0.030 (2.3)

Example I-143

$^1$H-NMR (300.2 MHz, CDCl$_3$): δ=7.732 (7.7); 7.729 (8.0); 7.300 (1.2); 7.265 (1.4); 7.240 (2.8); 7.221 (1.6); 7.216 (1.6); 7.175 (1.2); 7.153 (2.7); 7.128 (1.8); 7.063 (3.8); 7.038 (5.2); 7.013 (2.0); 6.933 (7.9); 6.930 (8.1); 5.318 (0.9); 4.460 (4.2); 4.411 (6.7); 4.262 (6.4); 4.213 (4.0); 3.300 (2.2); 3.296 (2.3); 3.253 (3.9); 3.249 (4.0); 3.136 (4.2); 3.091 (2.3); 3.088 (2.3); 2.887 (2.6); 2.865 (2.6); 2.301 (15.6); 2.294 (16.0); 2.066 (1.3); 1.307 (0.7); 1.292 (1.2); 1.283 (1.6); 1.259 (0.4); 0.930 (0.4); 0.909 (1.3); 0.885 (0.5); 0.807 (0.9); 0.792 (1.5); 0.780 (2.3); 0.767 (3.1); 0.760 (3.4); 0.745 (12.9); 0.735 (5.4); 0.713 (3.0); 0.707 (4.7); 0.697 (2.7); 0.689 (2.4); 0.682 (1.5); 0.668 (1.6); 0.651 (0.9); 0.634 (0.4); 0.028 (1.0)

Example I-144

$^1$H-NMR (300.2 MHz, CDCl$_3$): δ=7.759 (4.9); 7.655 (4.5); 7.300 (2.1); 7.199 (0.3); 7.176 (0.8); 7.172 (1.0);

7.153 (0.8); 7.146 (1.2); 7.139 (0.8); 7.131 (0.9); 7.122 (0.8); 7.114 (1.6); 7.106 (1.1); 7.103 (1.1); 7.089 (1.2); 7.079 (0.6); 7.076 (0.6); 7.060 (0.6); 7.030 (0.8); 7.025 (1.2); 7.010 (0.9); 7.005 (1.4); 7.000 (1.4); 6.987 (0.5); 6.980 (0.7); 6.975 (0.4); 4.441 (2.4); 4.393 (3.3); 4.167 (3.2); 4.119 (2.3); 3.246 (1.4); 3.241 (1.4); 3.199 (2.0); 3.194 (2.0); 2.983 (2.1); 2.978 (2.1); 2.936 (1.5); 2.931 (1.5); 1.853 (1.1); 1.846 (1.1); 1.369 (16.0); 0.270 (0.4); 0.243 (5.9); 0.220 (0.6); 0.203 (0.4); 0.124 (0.8); 0.089 (3.1); 0.061 (2.6); 0.030 (2.2)

Example I-145

$^1$H-NMR (300.2 MHz, CDCl$_3$): δ=7.897 (8.2); 7.683 (8.5); 7.453 (1.4); 7.448 (1.5); 7.426 (2.6); 7.423 (2.7); 7.402 (1.7); 7.397 (1.9); 7.376 (1.4); 7.371 (1.4); 7.350 (3.0); 7.329 (2.0); 7.323 (1.6); 7.300 (7.0); 7.180 (2.7); 7.177 (2.4); 7.154 (4.0); 7.128 (1.7); 7.125 (1.5); 4.753 (4.7); 4.704 (5.6); 4.241 (5.5); 4.192 (4.7); 4.165 (0.7); 4.141 (0.7); 3.406 (1.7); 3.401 (1.7); 3.359 (3.7); 3.354 (3.7); 3.280 (3.8); 3.275 (3.8); 3.232 (1.8); 3.227 (1.8); 2.353 (2.4); 2.333 (2.8); 2.078 (3.2); 2.043 (16.0); 1.739 (0.7); 1.316 (0.9); 1.292 (1.7); 1.269 (0.8); 0.782 (0.7); 0.773 (0.8); 0.765 (1.0); 0.762 (0.8); 0.747 (2.0); 0.731 (2.3); 0.721 (2.7); 0.711 (2.8); 0.702 (2.6); 0.698 (2.6); 0.689 (1.4); 0.675 (1.2); 0.663 (1.1); 0.654 (2.1); 0.648 (0.5); 0.638 (2.3); 0.628 (1.2); 0.609 (2.2); 0.601 (0.6); 0.593 (2.8); 0.589 (2.6); 0.580 (2.5); 0.563 (2.6); 0.554 (2.3); 0.541 (1.9); 0.530 (1.5); 0.519 (0.9); 0.511 (0.9); 0.502 (0.8); 0.033 (6.5)

Example I-146

$^1$H-NMR (300.2 MHz, CDCl$_3$): δ=7.894 (13.3); 7.668 (16.0); 7.298 (7.4); 7.237 (1.0); 7.230 (1.3); 7.225 (1.3); 7.214 (2.6); 7.205 (4.7); 7.194 (6.9); 7.177 (9.3); 7.170 (9.4); 7.153 (8.2); 7.145 (3.5); 7.131 (2.6); 7.125 (1.5); 7.118 (0.9); 7.102 (0.7); 4.755 (8.5); 4.706 (10.1); 4.231 (9.6); 4.182 (8.1); 3.409 (3.0); 3.404 (3.0); 3.361 (6.6); 3.357 (6.7); 3.289 (7.2); 3.285 (7.3); 3.242 (3.2); 3.237 (3.3); 2.424 (3.7); 2.038 (9.5); 0.778 (2.3); 0.769 (1.7); 0.757 (5.0); 0.735 (3.9); 0.725 (6.1); 0.712 (4.2); 0.700 (4.0); 0.695 (4.6); 0.682 (4.3); 0.669 (1.2); 0.660 (6.1); 0.648 (5.4); 0.625 (4.3); 0.612 (4.3); 0.607 (4.0); 0.595 (3.2); 0.563 (5.1); 0.552 (4.1); 0.530 (5.5); 0.518 (2.0); 0.508 (2.5); 0.476 (0.4); 0.029 (7.2)

Example I-147

$^1$H-NMR (300.2 MHz, CDCl$_3$): δ=7.752 (15.2); 7.461 (0.7); 7.367 (1.0); 7.348 (0.5); 7.339 (0.4); 7.321 (0.5); 7.300 (14.9); 7.234 (3.0); 7.209 (7.0); 7.184 (5.1); 7.181 (5.2); 7.157 (4.7); 7.148 (6.2); 7.141 (8.2); 7.127 (6.1); 7.122 (9.1); 7.118 (6.8); 7.099 (3.8); 7.097 (3.8); 7.086 (1.8); 7.069 (1.5); 7.036 (0.6); 7.020 (1.0); 6.979 (15.9); 6.935 (0.6); 6.910 (0.4); 6.782 (0.6); 5.319 (2.3); 5.058 (0.4); 4.828 (0.4); 4.761 (0.3); 4.712 (0.7); 4.645 (0.7); 4.488 (9.2); 4.439 (15.7); 4.393 (0.4); 4.355 (0.4); 4.312 (15.1); 4.263 (8.8); 3.526 (0.6); 3.503 (0.4); 3.480 (0.4); 3.402 (5.7); 3.398 (5.7); 3.355 (8.0); 3.350 (8.0); 3.132 (8.5); 3.127 (8.4); 3.084 (6.0); 3.080 (6.0); 2.419 (3.4); 1.842 (0.6); 1.824 (1.3); 1.812 (1.7); 1.796 (1.8); 1.785 (1.8); 1.575 (0.4); 1.560 (0.9); 1.548 (0.8); 1.331 (0.4); 1.290 (1.4); 1.267 (0.7); 1.244 (1.0); 1.220 (0.5); 1.133 (2.6); 0.940 (0.5); 0.917 (1.2); 0.894 (0.6); 0.863 (1.0); 0.846 (2.7); 0.826 (3.2); 0.823 (3.3); 0.811 (8.1); 0.801 (6.0); 0.793 (7.0); 0.782 (12.0); 0.778 (9.6); 0.761 (16.0); 0.742 (7.3); 0.727 (4.3); 0.706 (3.2); 0.698 (4.9); 0.679 (4.9); 0.674 (3.5); 0.669 (5.1); 0.662 (4.9); 0.656 (3.7); 0.637 (3.2); 0.620 (1.7); 0.035 (12.0)

Example I-148

$^1$H-NMR (300.2 MHz, CDCl$_3$): δ=7.801 (15.8); 7.659 (16.0); 7.657 (15.8); 7.298 (18.4); 7.186 (1.0); 7.180 (1.1); 7.159 (2.6); 7.153 (3.1); 7.148 (1.5); 7.135 (2.8); 7.127 (4.3); 7.120 (5.1); 7.103 (5.7); 7.097 (6.1); 7.078 (4.2); 7.070 (1.7); 7.066 (1.9); 7.050 (1.8); 7.016 (2.4); 7.011 (3.5); 6.991 (3.7); 6.986 (4.4); 6.974 (1.5); 6.966 (2.0); 4.168 (0.5); 4.144 (0.6); 4.125 (5.4); 4.077 (11.5); 3.997 (11.5); 3.949 (5.5); 2.995 (4.7); 2.990 (4.8); 2.949 (6.3); 2.943 (6.5); 2.702 (6.4); 2.697 (7.0); 2.667 (2.8); 2.656 (5.7); 2.650 (5.8); 2.641 (3.1); 2.619 (1.4); 2.610 (2.3); 2.581 (0.8); 2.147 (3.6); 2.138 (3.8); 2.080 (2.3); 1.935 (0.6); 1.907 (1.9); 1.884 (9.6); 1.874 (10.0); 1.869 (9.1); 1.859 (12.9); 1.834 (4.5); 1.804 (3.3); 1.776 (1.5); 1.731 (1.2); 1.721 (1.6); 1.709 (1.8); 1.689 (3.1); 1.673 (5.9); 1.665 (5.6); 1.660 (3.8); 1.645 (1.7); 1.633 (2.1); 1.618 (2.7); 1.612 (2.8); 1.593 (2.4); 1.587 (2.4); 1.555 (1.0); 1.538 (0.5); 1.452 (0.6); 1.439 (1.2); 1.327 (2.3); 1.318 (2.8); 1.294 (8.1); 1.270 (2.4); 1.208 (0.7); 1.097 (0.7); 1.068 (0.7); 1.012 (0.4); 0.937 (1.8); 0.916 (5.1); 0.889 (5.5); 0.863 (5.1); 0.299 (0.3); 0.121 (1.4); 0.117 (3.3); 0.105 (85.0); 0.092 (3.4); 0.080 (0.9); 0.045 (0.7); 0.034 (17.3); 0.024 (0.8); −0.094 (0.3)

Example I-149

$^1$H-NMR (300.2 MHz, CDCl$_3$): δ=7.821 (5.2); 7.685 (5.6); 7.682 (5.7); 7.298 (22.5); 7.203 (0.3); 7.197 (0.4); 7.175 (0.9); 7.169 (1.1); 7.164 (0.5); 7.152 (1.0); 7.144 (1.5); 7.137 (1.8); 7.121 (1.3); 7.118 (1.9); 7.113 (2.2); 7.109 (1.5); 7.095 (1.3); 7.092 (1.4); 7.085 (0.6); 7.081 (0.6); 7.065 (0.6); 7.016 (1.2); 6.997 (1.3); 6.991 (1.5); 6.979 (0.5); 6.972 (0.7); 4.327 (2.5); 4.279 (3.4); 4.035 (3.3); 3.987 (2.4); 3.120 (1.6); 3.115 (1.7); 3.073 (2.0); 3.068 (2.1); 2.727 (2.0); 2.722 (2.1); 2.680 (1.6); 2.675 (1.7); 1.897 (3.4); 1.890 (3.5); 1.757 (0.4); 1.735 (1.2); 1.712 (1.7); 1.689 (1.4); 1.666 (0.6); 1.602 (16.0); 1.147 (11.2); 1.132 (12.6); 1.125 (11.4); 1.109 (10.9); 0.048 (0.8); 0.037 (23.6); 0.026 (0.9)

Example I-150

$^1$H-NMR (300.2 MHz, d$_6$-DMSO): δ=8.024 (1.7); 8.022 (1.6); 7.853 (1.8); 7.850 (1.7); 7.708 (0.5); 7.327 (0.4); 7.300 (0.3); 7.292 (0.4); 7.265 (0.4); 7.258 (0.5); 7.254 (0.5); 7.234 (0.4); 7.171 (0.4); 7.166 (0.4); 7.162 (0.4); 7.145 (0.4); 4.783 (2.5); 4.288 (0.6); 4.240 (0.9); 4.092 (0.9); 4.044 (0.6); 3.349 (4.5); 3.103 (0.5); 3.058 (0.6); 2.728 (0.6); 2.683 (0.4); 2.537 (0.4); 2.531 (0.8); 2.525 (1.1); 2.519 (0.8); 2.513 (0.4); 2.098 (0.4); 1.482 (0.4); 1.432 (1.0); 1.374 (1.0); 1.325 (0.4); 0.973 (16.0); 0.787 (1.4); 0.021 (0.6)

Example I-151

$^1$H-NMR (300.2 MHz, CDCl$_3$): δ=7.837 (3.9); 7.691 (4.3); 7.688 (4.1); 7.300 (8.6); 7.169 (0.6); 7.163 (0.8); 7.157 (0.4); 7.146 (0.7); 7.138 (1.1); 7.130 (1.3); 7.114 (1.4); 7.107 (1.6); 7.090 (1.2); 7.081 (0.5); 7.078 (0.6); 7.062 (0.7); 7.050 (0.7); 7.045 (0.9); 7.026 (0.9); 7.020 (1.0); 7.008 (0.4); 7.001 (0.4); 4.317 (1.4); 4.269 (2.5); 4.151 (2.8); 4.103 (1.6); 3.181 (1.2); 3.175 (1.2); 3.134 (1.6);

3.129 (1.6); 2.825 (1.5); 2.820 (1.5); 2.779 (1.2); 2.773 (1.2); 2.284 (3.5); 2.047 (1.0); 1.641 (16.0); 1.632 (1.1); 1.611 (1.0); 1.583 (1.2); 1.563 (1.2); 1.292 (1.2); 1.268 (1.3); 1.244 (0.9); 1.220 (1.0); 0.837 (0.5); 0.828 (0.4); 0.812 (0.6); 0.803 (0.4); 0.792 (0.5); 0.671 (0.9); 0.654 (2.2); 0.645 (1.0); 0.640 (1.2); 0.631 (1.9); 0.626 (1.5); 0.614 (0.7); 0.152 (0.8); 0.136 (2.2); 0.121 (2.4); 0.106 (0.6); 0.036 (6.3)

Example I-152

$^1$H-NMR (300.2 MHz, CDCl$_3$): δ=8.204 (8.7); 8.188 (9.1); 7.886 (16.0); 7.689 (0.6); 7.668 (14.8); 7.464 (5.4); 7.448 (10.4); 7.431 (5.2); 7.300 (5.1); 4.745 (7.6); 4.696 (9.4); 4.324 (9.6); 4.275 (7.9); 3.477 (4.9); 3.430 (7.2); 3.409 (0.3); 3.283 (1.9); 3.249 (7.9); 3.202 (4.9); 2.136 (0.7); 2.039 (15.8); 1.017 (0.4); 0.767 (1.1); 0.763 (1.2); 0.754 (1.2); 0.741 (3.5); 0.719 (4.8); 0.712 (7.5); 0.704 (6.5); 0.686 (3.6); 0.659 (3.9); 0.646 (4.4); 0.613 (3.0); 0.605 (3.9); 0.601 (3.8); 0.595 (3.1); 0.585 (1.1); 0.557 (1.5); 0.549 (3.4); 0.542 (3.4); 0.525 (3.9); 0.507 (1.8); 0.499 (1.8); 0.493 (1.6); 0.021 (4.0)

Example I-153

$^1$H-NMR (300.2 MHz, CDCl$_3$): δ=7.878 (4.4); 7.677 (4.3); 7.345 (0.8); 7.326 (1.0); 7.317 (1.3); 7.300 (3.4); 6.983 (2.8); 6.954 (3.1); 6.931 (0.8); 6.922 (0.4); 4.680 (2.4); 4.631 (3.0); 4.310 (2.9); 4.262 (2.2); 4.164 (0.5); 4.140 (0.6); 3.480 (2.2); 3.433 (2.6); 3.012 (2.8); 2.964 (2.4); 2.313 (16.0); 2.077 (2.5); 1.849 (0.8); 1.835 (1.0); 1.813 (0.4); 1.719 (0.4); 1.316 (0.7); 1.292 (1.4); 1.268 (0.7); 0.927 (0.7); 0.918 (0.8); 0.914 (0.8); 0.905 (0.6); 0.889 (0.9); 0.884 (1.2); 0.878 (1.3); 0.873 (1.1); 0.772 (0.7); 0.763 (1.1); 0.759 (1.2); 0.750 (1.0); 0.734 (0.5); 0.729 (0.6); 0.723 (0.8); 0.717 (0.8); 0.647 (1.0); 0.611 (3.3); 0.603 (3.8); 0.596 (2.3); 0.591 (2.8); 0.556 (0.4); 0.033 (2.8)

Example I-154

$^1$H-NMR (300.2 MHz, CDCl$_3$): δ=7.881 (12.7); 7.671 (13.0); 7.553 (4.4); 7.533 (4.6); 7.524 (5.2); 7.504 (4.8); 7.300 (4.6); 7.224 (4.6); 7.215 (5.2); 7.196 (4.6); 7.188 (5.1); 7.097 (3.0); 7.089 (2.7); 7.071 (3.9); 7.069 (4.0); 7.062 (3.6); 7.061 (3.5); 7.043 (2.7); 7.034 (2.3); 4.741 (7.7); 4.692 (9.3); 4.242 (9.1); 4.193 (7.6); 3.456 (1.2); 3.408 (14.2); 3.401 (15.3); 3.352 (1.2); 2.504 (16.0); 2.037 (1.5); 1.835 (0.9); 0.859 (0.4); 0.829 (1.5); 0.824 (1.9); 0.816 (2.0); 0.806 (3.2); 0.803 (3.1); 0.793 (1.1); 0.782 (3.5); 0.770 (4.7); 0.739 (3.1); 0.727 (3.2); 0.721 (4.0); 0.706 (4.1); 0.683 (4.8); 0.674 (4.7); 0.670 (3.2); 0.659 (1.6); 0.649 (3.9); 0.635 (4.2); 0.630 (3.7); 0.617 (3.5); 0.595 (4.9); 0.583 (3.5); 0.563 (4.5); 0.549 (1.9); 0.540 (1.9); 0.537 (1.7); 0.506 (0.3); 0.029 (3.8)

Example I-155

$^1$H-NMR (300.2 MHz, CDCl$_3$): δ=7.759 (4.0); 7.757 (3.9); 7.362 (1.0); 7.354 (0.5); 7.342 (1.4); 7.331 (1.5); 7.312 (1.4); 7.300 (10.8); 7.007 (4.4); 7.004 (4.2); 6.960 (2.8); 6.930 (2.5); 6.921 (1.3); 6.910 (1.0); 6.900 (0.4); 5.338 (6.6); 4.363 (11.2); 3.427 (2.4); 3.380 (2.8); 2.896 (3.1); 2.848 (2.6); 2.238 (16.0); 2.083 (0.8); 1.653 (0.6); 1.592 (2.3); 1.297 (0.9); 1.292 (0.8); 0.960 (0.4); 0.937 (0.5); 0.927 (1.1); 0.920 (0.8); 0.900 (4.1); 0.894 (2.7); 0.884 (1.7); 0.875 (2.4); 0.868 (0.9); 0.858 (1.1); 0.852 (0.9); 0.842 (1.3); 0.834 (1.9); 0.817 (1.1); 0.810 (1.3); 0.794 (0.7); 0.686 (1.2); 0.673 (1.3); 0.660 (0.9); 0.653 (1.1); 0.649 (0.8); 0.638 (1.0); 0.632 (1.0); 0.629 (0.7); 0.049 (0.4); 0.038 (10.2); 0.027 (0.5)

Example I-156

$^1$H-NMR (300.2 MHz, CDCl$_3$): δ=7.880 (16.0); 7.701 (0.4); 7.677 (14.3); 7.300 (5.3); 6.980 (0.6); 6.973 (1.3); 6.957 (6.1); 6.950 (8.5); 6.930 (8.1); 6.923 (6.8); 6.908 (1.4); 6.900 (0.7); 6.848 (1.7); 6.841 (2.5); 6.833 (1.3); 6.818 (3.4); 6.811 (4.9); 6.803 (2.3); 6.789 (1.8); 6.781 (2.5); 6.774 (1.2); 4.656 (7.2); 4.607 (9.8); 4.355 (9.7); 4.306 (7.2); 3.533 (6.4); 3.487 (7.3); 2.828 (8.1); 2.782 (7.1); 2.733 (0.7); 2.041 (3.0); 1.990 (0.4); 1.961 (0.4); 0.777 (0.9); 0.762 (1.0); 0.757 (1.1); 0.743 (2.4); 0.727 (4.1); 0.714 (7.5); 0.704 (5.4); 0.684 (3.2); 0.669 (1.4); 0.650 (1.6); 0.604 (0.8); 0.570 (1.9); 0.560 (2.1); 0.554 (1.9); 0.541 (4.0); 0.524 (4.2); 0.519 (4.1); 0.504 (3.3); 0.464 (3.2); 0.449 (3.7); 0.429 (2.6); 0.422 (1.8); 0.413 (2.2); 0.400 (1.3); 0.029 (4.8)

Example I-157

$^1$H-NMR (300.2 MHz, CDCl$_3$): δ=7.878 (15.2); 7.681 (16.0); 7.345 (6.9); 7.338 (3.3); 7.327 (7.9); 7.316 (9.4); 7.299 (13.4); 7.129 (1.3); 7.120 (9.2); 7.113 (3.0); 7.091 (16.0); 7.069 (2.8); 7.062 (7.1); 7.052 (0.9); 4.659 (7.9); 4.645 (0.5); 4.611 (10.6); 4.343 (10.7); 4.295 (8.1); 3.557 (7.9); 3.510 (8.8); 2.788 (8.7); 2.741 (7.8); 2.209 (9.6); 2.039 (2.8); 1.285 (1.0); 0.763 (1.4); 0.746 (1.1); 0.740 (1.5); 0.727 (3.6); 0.711 (4.8); 0.705 (5.9); 0.697 (11.9); 0.689 (6.5); 0.668 (4.5); 0.654 (1.5); 0.650 (1.4); 0.633 (2.2); 0.578 (0.9); 0.543 (2.2); 0.535 (2.7); 0.529 (2.5); 0.516 (4.1); 0.499 (3.8); 0.494 (3.8); 0.477 (2.9); 0.378 (3.5); 0.361 (4.1); 0.357 (3.9); 0.340 (3.2); 0.334 (2.3); 0.325 (3.1); 0.322 (2.9); 0.313 (1.8); 0.279 (0.4); 0.031 (5.4)

Example I-158

$^1$H-NMR (300.2 MHz, d$_6$-DMSO): δ=7.757 (12.7); 7.421 (6.1); 7.402 (8.3); 7.393 (8.9); 7.374 (7.3); 7.312 (0.6); 7.296 (0.6); 7.286 (0.6); 7.274 (0.7); 7.245 (0.7); 7.148 (7.6); 7.118 (12.4); 7.089 (6.0); 6.986 (11.9); 5.298 (16.0); 5.254 (0.6); 5.215 (0.4); 4.388 (5.2); 4.339 (8.3); 4.194 (8.2); 4.145 (5.3); 3.930 (0.4); 3.346 (27.3); 3.196 (5.6); 3.150 (6.8); 2.913 (1.9); 2.882 (0.6); 2.868 (0.6); 2.853 (0.3); 2.781 (6.8); 2.754 (2.4); 2.734 (5.3); 2.525 (20.5); 0.617 (2.1); 0.575 (5.7); 0.564 (5.3); 0.556 (5.8); 0.543 (5.2); 0.522 (4.6); 0.505 (4.2); 0.484 (3.7); 0.472 (3.1); 0.459 (4.1); 0.444 (3.5); 0.431 (4.0); 0.417 (2.3); 0.401 (1.9); 0.382 (1.0); 0.062 (0.3); 0.023 (20.6)

Example I-159

$^1$H-NMR (499.9 MHz, CDCl$_3$): δ=7.838 (1.2); 7.799 (5.3); 7.655 (1.5); 7.635 (5.8); 7.622 (2.8); 7.606 (2.6); 7.467 (0.3); 7.260 (52.3); 7.215 (3.2); 7.204 (3.9); 7.198 (4.3); 7.187 (3.8); 7.143 (0.8); 7.132 (1.0); 7.126 (1.2); 7.114 (1.7); 7.102 (1.6); 7.096 (1.9); 7.085 (1.7); 7.070 (3.9); 7.053 (6.7); 7.036 (3.5); 7.015 (3.3); 6.998 (3.5); 6.980 (1.3); 5.299 (0.7); 4.742 (5.7); 4.478 (4.5); 4.460 (3.7); 4.431 (4.3); 4.180 (0.7); 4.173 (0.4); 4.152 (1.1); 4.141 (4.0); 4.112 (3.4); 4.022 (1.0); 3.994 (0.7); 3.656 (0.7); 3.164 (3.4); 3.135 (3.9); 2.963 (0.9); 2.945 (2.1); 2.928 (2.1); 2.911 (1.2); 2.875 (0.8); 2.847 (0.9); 2.745 (3.8); 2.717 (3.4); 2.555 (1.4); 2.538 (1.7); 2.530 (1.1); 2.526 (1.1); 2.513 (1.8); 2.494 (1.0); 2.392 (0.7); 2.374 (1.6); 2.367 (1.0);

2.354 (1.2); 2.348 (1.9); 2.330 (1.3); 2.300 (0.6); 2.279 (4.6); 2.264 (2.0); 2.242 (1.9); 2.224 (1.2); 2.205 (0.5); 2.106 (0.6); 2.089 (1.5); 2.074 (2.2); 2.058 (1.5); 2.042 (0.6); 2.006 (0.3); 1.975 (0.5); 1.958 (1.2); 1.950 (1.1); 1.941 (1.6); 1.932 (1.4); 1.925 (1.5); 1.916 (1.1); 1.908 (0.8); 1.811 (0.9); 1.801 (1.0); 1.794 (1.3); 1.786 (1.4); 1.776 (1.2); 1.769 (1.1); 1.759 (1.0); 1.751 (0.7); 1.742 (0.7); 1.733 (0.6); 1.717 (0.5); 1.703 (0.9); 1.697 (0.7); 1.685 (1.9); 1.681 (1.6); 1.663 (2.3); 1.657 (2.0); 1.645 (1.6); 1.626 (1.0); 1.569 (6.6); 1.493 (1.0); 1.481 (0.9); 1.474 (0.9); 1.333 (0.5); 1.255 (16.0); 1.158 (0.7); 1.146 (0.7); 1.103 (0.6); 0.894 (1.1); 0.880 (1.6); 0.867 (0.9); 0.859 (0.5); 0.841 (0.6); 0.831 (0.6); 0.730 (0.3); 0.715 (0.5); 0.000 (51.3)

Example I-160

$^1$H-NMR (400.1 MHz, d$_6$-DMSO): δ=7.920 (13.7); 7.771 (14.5); 7.311 (5.8); 7.297 (7.3); 7.290 (8.0); 7.275 (6.6); 7.122 (7.4); 7.100 (12.3); 7.078 (5.8); 5.006 (16.0); 3.978 (3.5); 3.942 (9.0); 3.905 (9.5); 3.869 (3.7); 3.323 (118.5); 2.712 (3.9); 2.677 (8.0); 2.618 (7.7); 2.584 (4.2); 2.512 (52.4); 2.507 (66.9); 2.503 (47.9); 2.436 (0.6); 2.414 (1.7); 2.395 (2.4); 2.372 (1.8); 2.350 (0.7); 2.334 (0.5); 2.006 (1.6); 1.984 (2.6); 1.961 (1.2); 1.949 (0.9); 1.748 (0.5); 1.726 (1.7); 1.703 (3.0); 1.687 (3.6); 1.680 (3.9); 1.671 (4.6); 1.654 (4.6); 1.639 (3.8); 1.619 (1.6); 1.558 (0.5); 1.536 (1.4); 1.515 (2.4); 1.497 (1.8); 1.475 (0.6); 1.350 (0.7); 1.336 (1.3); 1.324 (2.1); 1.311 (1.9); 1.298 (1.8); 1.280 (0.5)

Example I-161

$^1$H-NMR (499.9 MHz, CDCl$_3$): δ=7.829 (12.7); 7.647 (12.8); 7.261 (15.7); 7.223 (0.7); 7.144 (7.9); 7.128 (11.0); 7.117 (8.6); 7.030 (8.6); 7.013 (12.8); 6.996 (5.9); 6.969 (0.8); 4.178 (6.1); 4.149 (8.3); 4.129 (0.8); 4.114 (0.6); 4.100 (0.4); 4.020 (7.9); 3.992 (5.5); 2.976 (0.7); 2.963 (0.7); 2.875 (6.4); 2.847 (7.2); 2.554 (7.4); 2.526 (6.1); 2.043 (1.4); 1.992 (1.8); 1.975 (3.8); 1.958 (5.5); 1.940 (4.2); 1.923 (1.7); 1.878 (0.7); 1.756 (7.7); 1.742 (8.2); 1.704 (16.0); 1.671 (6.6); 1.657 (7.1); 1.647 (6.9); 1.633 (5.6); 1.615 (5.6); 1.581 (27.9); 1.480 (6.4); 1.474 (6.5); 1.272 (1.0); 1.258 (2.0); 0.882 (0.4); 0.000 (14.9)

Example I-162

$^1$H-NMR (400.1 MHz, d$_6$-DMSO): δ=7.948 (6.6); 7.809 (6.9); 7.808 (6.9); 7.335 (2.9); 7.330 (1.5); 7.321 (3.6); 7.314 (3.9); 7.305 (1.7); 7.299 (3.3); 7.101 (3.7); 7.079 (6.2); 7.062 (1.3); 7.057 (3.0); 4.806 (9.3); 4.222 (2.8); 4.186 (3.6); 3.941 (3.7); 3.905 (3.0); 3.323 (54.8); 2.843 (2.5); 2.809 (3.1); 2.554 (3.3); 2.516 (13.3); 2.512 (23.1); 2.507 (29.9); 2.503 (21.7); 2.499 (10.8); 2.079 (0.5); 1.994 (0.4); 1.525 (0.5); 1.508 (1.3); 1.491 (1.9); 1.473 (1.5); 1.456 (0.6); 0.946 (16.0); 0.929 (14.8)

Example I-163

$^1$H-NMR (300.2 MHz, d$_6$-DMSO): δ=8.552 (2.6); 8.546 (2.6); 8.400 (1.7); 8.384 (1.7); 8.005 (3.5); 8.003 (3.4); 7.871 (3.6); 7.868 (3.3); 7.610 (1.0); 7.593 (1.2); 7.589 (1.2); 7.572 (1.0); 5.786 (16.0); 5.693 (3.7); 4.630 (1.4); 4.581 (1.8); 4.226 (1.8); 4.177 (1.5); 3.355 (7.3); 3.265 (0.8); 3.218 (1.9); 3.162 (1.8); 3.116 (0.9); 2.540 (1.7); 2.534 (3.6); 2.528 (4.9); 2.522 (3.6); 2.516 (1.7); 2.015 (0.4); 1.081 (0.4); 0.750 (0.5); 0.745 (0.5); 0.731 (0.6); 0.726 (0.6); 0.714 (0.6); 0.709 (0.6); 0.692 (0.6); 0.655 (0.4); 0.630 (0.6); 0.620 (0.7); 0.613 (0.4); 0.596 (0.9); 0.579 (0.8); 0.560 (0.7); 0.544 (0.8); 0.538 (0.7); 0.520 (0.8); 0.510 (0.6); 0.486 (0.4); 0.477 (0.7); 0.460 (0.6); 0.454 (0.7); 0.442 (0.7); 0.425 (0.5); 0.418 (0.5); 0.026 (5.8)

Example I-164

$^1$H-NMR (300.2 MHz, CDCl$_3$): δ=8.203 (8.1); 8.186 (8.3); 7.680 (10.6); 7.646 (0.5); 7.300 (62.7); 7.284 (3.8); 7.280 (4.9); 7.056 (9.5); 6.949 (0.8); 6.929 (11.4); 4.527 (7.3); 4.478 (11.9); 4.340 (11.3); 4.290 (7.0); 3.548 (7.9); 3.503 (11.0); 2.784 (8.0); 2.739 (7.2); 1.638 (15.4); 1.592 (1.6); 1.291 (16.0); 1.186 (0.4); 1.166 (0.4); 1.139 (0.5); 0.918 (1.1); 0.894 (4.5); 0.889 (4.5); 0.862 (10.9); 0.832 (8.8); 0.775 (0.4); 0.742 (3.2); 0.722 (4.1); 0.718 (3.3); 0.707 (1.9); 0.693 (4.2); 0.683 (1.7); 0.663 (2.0); 0.608 (3.2); 0.588 (2.9); 0.580 (3.6); 0.575 (2.8); 0.557 (3.9); 0.547 (2.4); 0.527 (1.6); 0.048 (1.5); 0.037 (42.1); 0.026 (1.6)

Example I-165

$^1$H-NMR (300.2 MHz, CDCl$_3$): δ=8.268 (8.9); 7.884 (9.2); 7.691 (8.7); 7.300 (5.0); 7.226 (6.2); 7.218 (6.2); 4.766 (5.1); 4.717 (6.2); 4.291 (5.2); 4.243 (4.3); 4.158 (0.4); 4.134 (0.4); 3.526 (2.8); 3.479 (6.8); 3.421 (6.0); 3.374 (2.4); 2.773 (1.1); 2.762 (1.6); 2.722 (1.9); 2.074 (1.8); 2.042 (16.0); 1.313 (0.5); 1.289 (0.9); 1.265 (0.5); 0.892 (0.9); 0.882 (1.3); 0.875 (1.4); 0.863 (0.9); 0.858 (2.1); 0.840 (2.3); 0.825 (2.9); 0.795 (2.0); 0.779 (2.3); 0.775 (2.7); 0.759 (2.7); 0.740 (1.8); 0.731 (2.9); 0.721 (2.4); 0.714 (1.4); 0.710 (1.3); 0.691 (2.0); 0.674 (2.5); 0.658 (1.3); 0.655 (1.3); 0.612 (2.7); 0.597 (2.2); 0.582 (1.7); 0.574 (2.2); 0.562 (1.4); 0.555 (1.4); 0.545 (0.9); 0.029 (4.8)

Example I-166

$^1$H-NMR (300.2 MHz, CDCl$_3$): δ=7.916 (6.8); 7.894 (16.0); 7.683 (12.5); 7.558 (4.8); 7.553 (5.2); 7.533 (7.2); 7.528 (7.4); 7.438 (3.9); 7.413 (6.7); 7.388 (3.2); 7.300 (9.4); 7.081 (3.4); 7.076 (3.0); 7.055 (5.6); 7.030 (2.9); 7.025 (2.4); 4.742 (8.3); 4.694 (10.2); 4.295 (8.2); 4.247 (6.7); 3.634 (5.6); 3.586 (8.4); 3.408 (12.1); 3.360 (8.1); 2.289 (7.1); 2.260 (1.5); 2.219 (0.8); 2.041 (2.7); 1.736 (0.5); 1.289 (0.8); 0.924 (0.7); 0.894 (0.9); 0.883 (2.4); 0.875 (4.3); 0.870 (3.0); 0.852 (3.7); 0.847 (2.9); 0.840 (3.9); 0.812 (0.8); 0.777 (2.4); 0.767 (2.5); 0.757 (3.7); 0.746 (8.5); 0.738 (5.1); 0.726 (5.2); 0.720 (9.7); 0.707 (4.7); 0.699 (3.2); 0.686 (4.0); 0.654 (3.6); 0.647 (4.1); 0.620 (4.7); 0.613 (2.4); 0.600 (2.4); 0.584 (0.3); 0.572 (0.6); 0.106 (1.4); 0.034 (6.8)

Example I-167

$^1$H-NMR (300.2 MHz, CDCl$_3$): δ=7.892 (3.7); 7.889 (3.6); 7.866 (3.9); 7.862 (3.8); 7.778 (5.3); 7.631 (0.5); 7.593 (3.1); 7.588 (3.3); 7.568 (4.0); 7.563 (3.8); 7.511 (0.4); 7.484 (0.4); 7.413 (2.2); 7.410 (2.2); 7.388 (4.0); 7.385 (3.9); 7.363 (2.1); 7.359 (2.0); 7.329 (1.2); 7.315 (1.9); 7.300 (19.1); 7.290 (1.9); 7.265 (0.4); 7.253 (0.5); 7.241 (0.4); 7.229 (0.7); 7.211 (0.4); 7.204 (0.5); 7.185 (0.8); 7.175 (0.5); 7.162 (0.5); 7.054 (2.2); 7.048 (2.2); 7.021 (8.0); 7.003 (2.3); 6.997 (2.0); 6.973 (0.4); 6.947 (0.3); 6.910 (0.5); 6.890 (0.7); 5.338 (3.0); 4.558 (0.5); 4.521 (0.6); 4.472 (0.4); 4.459 (3.0); 4.410 (7.9); 4.356 (7.7); 4.307

(2.9); 3.615 (4.4); 3.567 (5.8); 3.346 (0.4); 3.271 (6.1); 3.223 (4.6); 3.012 (0.3); 2.994 (0.4); 2.074 (1.7); 1.825 (0.4); 1.806 (0.5); 1.763 (0.8); 1.755 (0.8); 1.744 (0.8); 1.733 (0.8); 1.520 (0.9); 1.498 (0.8); 1.471 (0.5); 1.464 (0.5); 1.293 (2.4); 1.262 (0.5); 1.215 (0.5); 1.191 (0.8); 1.172 (0.5); 1.006 (0.8); 0.918 (0.7); 0.890 (1.5); 0.867 (16.0); 0.854 (4.6); 0.837 (3.6); 0.826 (3.5); 0.813 (2.2); 0.803 (1.3); 0.755 (3.0); 0.739 (1.8); 0.721 (2.0); 0.712 (1.2); 0.038 (14.1)

Example I-168

$^1$H-NMR (300.2 MHz, d$_6$-DMSO): δ=9.221 (3.3); 9.204 (3.4); 8.065 (0.3); 7.997 (4.5); 7.937 (2.9); 7.920 (2.8); 7.870 (4.7); 7.845 (0.3); 5.786 (16.0); 5.762 (4.8); 4.668 (1.7); 4.619 (2.1); 4.213 (2.3); 4.164 (1.9); 3.354 (41.8); 3.333 (7.9); 3.290 (0.5); 2.534 (12.3); 2.528 (16.7); 2.522 (12.1); 1.355 (1.0); 1.262 (0.6); 1.081 (0.5); 0.929 (0.4); 0.907 (0.7); 0.886 (0.8); 0.872 (0.9); 0.850 (0.7); 0.790 (0.4); 0.765 (0.7); 0.755 (0.8); 0.731 (1.0); 0.712 (0.8); 0.658 (0.7); 0.640 (0.9); 0.616 (0.9); 0.606 (0.8); 0.581 (0.5); 0.564 (0.8); 0.540 (0.8); 0.528 (0.8); 0.522 (0.7); 0.505 (0.7); 0.485 (0.4); 0.037 (0.8); 0.026 (22.4); 0.015 (1.0)

Example I-169

$^1$H-NMR (300.2 MHz, CDCl$_3$): δ=8.012 (9.3); 7.997 (8.8); 7.387 (2.5); 7.382 (3.5); 7.360 (16.0); 7.354 (7.3); 7.345 (9.8); 7.342 (10.7); 7.335 (10.0); 7.326 (7.1); 7.319 (8.7); 7.306 (2.3); 7.300 (13.9); 7.281 (7.3); 7.275 (7.1); 7.254 (4.1); 4.718 (0.9); 4.669 (10.3); 4.661 (10.1); 4.612 (0.9); 4.200 (13.8); 4.175 (0.9); 4.126 (9.8); 4.117 (9.8); 4.068 (0.8); 3.310 (5.0); 3.265 (6.4); 2.969 (6.0); 2.924 (4.7); 1.671 (4.9); 0.623 (0.4); 0.618 (0.4); 0.608 (0.6); 0.595 (2.5); 0.580 (9.2); 0.575 (5.3); 0.567 (3.2); 0.562 (2.0); 0.557 (1.7); 0.552 (1.6); 0.547 (2.1); 0.533 (2.8); 0.524 (3.4); 0.518 (2.8); 0.512 (1.8); 0.491 (1.3); 0.485 (3.4); 0.475 (1.9); 0.453 (2.0); 0.442 (0.8); 0.042 (8.0)

Example XVII-1

$^1$H-NMR (499.9 MHz, CDCl$_3$): δ=7.427 (4.1); 7.263 (4.5); 6.995 (4.4); 6.993 (4.5); 5.278 (16.0); 1.792 (2.0); 1.782 (6.0); 1.775 (6.1); 1.765 (2.5); 1.673 (0.5); 1.526 (2.4); 1.516 (6.0); 1.509 (6.2); 1.498 (2.1); 0.000 (4.3)

Example XVII-2

$^1$H-NMR (499.9 MHz, CDCl$_3$): δ=7.701 (5.1); 7.699 (5.3); 7.587 (4.7); 7.266 (3.7); 5.451 (16.0); 2.004 (2.6); 1.841 (2.1); 1.830 (6.2); 1.823 (6.0); 1.813 (2.5); 1.643 (2.5); 1.575 (2.5); 1.565 (6.0); 1.558 (6.3); 1.547 (2.1); 0.000 (3.9)

Example XVII-3

$^1$H-NMR (499.9 MHz, CDCl$_3$): δ=7.688 (6.2); 7.627 (5.8); 7.267 (2.5); 5.299 (0.7); 5.067 (16.0); 1.998 (0.5); 1.989 (1.1); 1.982 (1.3); 1.973 (2.2); 1.965 (1.4); 1.958 (1.2); 1.949 (0.7); 1.259 (1.0); 1.251 (3.5); 1.243 (5.3); 1.235 (4.2); 1.228 (1.6); 1.207 (0.4); 1.134 (1.3); 1.127 (3.5); 1.120 (3.8); 1.112 (4.3); 1.105 (3.0); 1.097 (1.2); 0.000 (2.5)

Example XVII-4

$^1$H-NMR (499.9 MHz, CDCl$_3$): δ=7.715 (9.8); 7.622 (9.1); 7.264 (6.3); 5.383 (15.1); 5.378 (16.0); 1.641 (1.2); 1.634 (1.3); 1.623 (6.9); 1.620 (5.1); 1.610 (3.1); 1.606 (2.0); 1.599 (1.5); 1.590 (3.0); 1.583 (4.4); 1.575 (5.0); 1.566 (3.0); 1.557 (4.4); 1.549 (6.8); 1.542 (5.2); 1.535 (4.0); 1.519 (1.5); 0.006 (0.3); 0.000 (6.5)

Example XVII-5

$^1$H-NMR (300.2 MHz, CDCl$_3$): δ=7.742 (0.9); 7.738 (1.3); 7.733 (0.6); 7.722 (0.4); 7.715 (1.7); 7.710 (1.5); 7.702 (0.9); 7.698 (1.3); 7.693 (0.6); 7.682 (0.4); 7.675 (1.7); 7.670 (1.5); 7.613 (0.3); 7.608 (0.4); 7.588 (0.9); 7.583 (0.9); 7.569 (0.5); 7.564 (1.1); 7.558 (1.0); 7.553 (0.4); 7.527 (1.3); 7.522 (0.9); 7.517 (1.4); 7.513 (0.7); 7.507 (1.0); 7.502 (1.6); 7.497 (1.3); 7.492 (1.6); 7.487 (0.5); 7.479 (0.7); 7.474 (0.6); 7.469 (0.6); 7.464 (0.4); 7.300 (4.6); 7.114 (3.8); 7.112 (3.8); 6.623 (2.1); 6.620 (2.1); 6.598 (2.1); 6.595 (2.1); 5.245 (16.0); 1.845 (2.0); 1.827 (4.9); 1.815 (5.6); 1.800 (2.7); 1.744 (0.4); 1.630 (0.4); 1.574 (2.6); 1.559 (5.5); 1.547 (5.0); 1.529 (2.0); 0.033 (4.7)

Example XVII-6

$^1$H-NMR (300.2 MHz, CDCl$_3$): δ=7.796 (2.6); 7.793 (2.5); 7.567 (2.4); 7.300 (3.7); 5.647 (8.2); 3.847 (16.0); 3.521 (2.3); 1.828 (1.2); 1.810 (2.9); 1.798 (3.2); 1.782 (1.8); 1.727 (0.5); 1.560 (1.5); 1.545 (3.0); 1.533 (2.7); 1.515 (1.1); 0.105 (0.4); 0.033 (3.1)

Example XVII-7

$^1$H-NMR (300.2 MHz, CDCl$_3$): δ=7.713 (1.2); 7.615 (1.3); 7.300 (1.2); 5.082 (5.5); 2.080 (0.4); 2.074 (0.8); 1.341 (7.2); 1.334 (16.0); 1.317 (0.5); 1.314 (0.4); 1.289 (0.5); 0.035 (0.5); 0.030 (0.7)

Example XVII-8

$^1$H-NMR (300.2 MHz, CDCl$_3$): δ=7.704 (1.9); 7.647 (1.8); 5.411 (5.6); 1.821 (16.0)

Example XVII-9

$^1$H-NMR (300.2 MHz, CDCl$_3$): δ=7.739 (8.8); 7.710 (9.5); 7.691 (0.5); 7.686 (0.4); 7.679 (0.5); 7.674 (0.4); 7.652 (0.3); 7.550 (0.9); 7.546 (0.9); 7.512 (0.3); 7.503 (1.3); 7.499 (1.0); 7.488 (0.4); 7.482 (0.4); 7.478 (0.4); 7.300 (2.7); 5.424 (0.5); 5.422 (0.4); 5.390 (0.4); 5.323 (1.4); 5.308 (0.5); 5.251 (0.6); 5.249 (0.6); 4.989 (16.0); 4.669 (6.5); 4.655 (0.5); 4.637 (12.1); 4.604 (7.1); 3.755 (0.8); 3.740 (1.0); 3.724 (0.8); 3.063 (4.1); 3.050 (0.5); 3.031 (7.3); 2.998 (3.9); 2.483 (0.5); 2.469 (0.6); 2.454 (0.5); 2.060 (0.8); 1.275 (0.5); 0.016 (2.2)

Example XVII-10

$^1$H-NMR (499.9 MHz, CDCl$_3$): δ=7.612 (2.6); 7.466 (0.6); 7.259 (116.3); 7.180 (3.6); 7.047 (0.7); 5.288 (16.0); 4.868 (0.8); 1.808 (2.1); 1.797 (6.5); 1.790 (6.9); 1.781 (2.9); 1.747 (0.4); 1.552 (48.1); 1.536 (13.2); 1.525 (11.4); 1.518 (9.8); 1.508 (4.2); 1.476 (0.9); 1.436 (0.5); 1.255 (4.5); 1.186 (0.4); 1.178 (0.5); 1.170 (0.4); 1.161 (0.3); 1.140 (0.5); 1.035 (0.4); 0.894 (0.4); 0.880 (0.7); 0.866 (0.5); 0.856 (0.4); 0.837 (0.4); 0.116 (0.4); 0.069 (1.0); 0.000 (93.5); −0.120 (0.5)

Example XVII-11

$^1$H-NMR (400.1 MHz, d$_6$-DMSO): δ=7.962 (3.7); 7.891 (4.0); 5.646 (5.5); 5.641 (5.5); 3.314 (4.0); 2.513 (8.3); 2.509 (10.9); 2.505 (8.2); 1.579 (16.0); 1.524 (16.0)

Example XVII-13

$^1$H-NMR (300.2 MHz, CDCl$_3$): δ=7.724 (1.2); 7.609 (1.0); 7.299 (1.0); 4.882 (3.1); 2.480 (3.0); 2.078 (0.8); 1.292 (0.5); 1.124 (16.0); 0.033 (1.0)

Example XVII-14

$^1$H-NMR (400.1 MHz, d$_6$-DMSO): δ=7.918 (3.0); 7.860 (3.2); 7.858 (3.0); 5.381 (8.2); 3.331 (14.0); 2.867 (0.4); 2.850 (1.1); 2.833 (1.4); 2.816 (1.1); 2.798 (0.4); 2.516 (2.1); 2.512 (3.9); 2.507 (5.1); 2.503 (3.7); 2.499 (1.8); 1.129 (16.0); 1.112 (15.7)

Example XVII-15

$^1$H-NMR (300.2 MHz, d$_6$-DMSO): δ=7.945 (5.5); 7.943 (5.5); 7.876 (6.1); 7.873 (5.4); 5.359 (16.0); 3.345 (1.2); 3.171 (0.5); 3.147 (1.1); 3.142 (1.1); 3.119 (2.2); 3.095 (1.3); 3.090 (1.2); 3.066 (0.6); 2.533 (1.1); 2.527 (2.2); 2.521 (3.1); 2.515 (2.2); 2.509 (1.0); 2.106 (9.6); 2.099 (0.5); 2.094 (2.3); 1.930 (0.4); 1.917 (1.0); 1.906 (0.6); 1.899 (1.0); 1.888 (1.5); 1.877 (1.5); 1.871 (1.6); 1.856 (1.3); 1.849 (1.4); 1.844 (1.3); 1.826 (0.7); 1.809 (0.5); 1.794 (0.6); 1.784 (1.8); 1.768 (1.1); 1.760 (2.1); 1.742 (1.2); 1.735 (1.3); 1.717 (1.1); 1.700 (0.5); 1.693 (0.6); 1.659 (0.4); 1.646 (1.0); 1.626 (4.9); 1.614 (4.4); 1.601 (6.3); 1.590 (3.5); 1.579 (2.1); 1.561 (0.6); 0.020 (3.3)

Example XVII-16

$^1$H-NMR (499.9 MHz, CDCl$_3$): δ=7.709 (10.1); 7.708 (10.5); 7.599 (9.6); 7.263 (8.7); 5.299 (0.4); 5.260 (15.5); 5.256 (16.0); 2.177 (3.0); 2.165 (6.5); 2.154 (3.9); 2.150 (4.1); 2.135 (0.5); 2.122 (3.3); 2.118 (2.9); 2.107 (6.3); 2.099 (2.8); 2.095 (3.9); 1.968 (0.4); 1.959 (0.7); 1.950 (1.2); 1.943 (2.0); 1.937 (2.7); 1.934 (2.5); 1.926 (3.3); 1.921 (2.4); 1.918 (2.5); 1.912 (2.8); 1.902 (1.1); 1.891 (1.6); 1.879 (1.4); 1.874 (1.3); 1.860 (3.2); 1.847 (3.7); 1.838 (2.4); 1.832 (1.8); 1.813 (0.5); 1.607 (2.8); 0.006 (0.4); 0.000 (9.5); −0.007 (0.6)

Example XVII-17

$^1$H-NMR (300.2 MHz, CDCl$_3$): δ=7.716 (4.8); 7.631 (4.3); 7.298 (1.8); 5.326 (0.7); 4.875 (16.0); 3.462 (1.1); 3.434 (1.7); 3.406 (1.2); 3.379 (0.4); 3.376 (0.3); 2.458 (0.4); 2.430 (0.9); 2.426 (0.9); 2.421 (1.0); 2.416 (0.7); 2.395 (1.7); 2.389 (2.1); 2.361 (1.9); 2.360 (1.8); 2.339 (1.1); 2.332 (1.2); 2.325 (1.0); 2.310 (1.4); 2.303 (1.2); 2.296 (1.8); 2.288 (1.0); 2.281 (1.2); 2.275 (1.0); 2.267 (1.5); 2.261 (0.9); 2.247 (0.5); 2.240 (0.4); 2.233 (0.3); 2.231 (0.3); 2.227 (0.4); 2.173 (0.4); 2.147 (0.6); 2.142 (0.5); 2.136 (0.5); 2.116 (1.0); 2.109 (1.1); 2.106 (0.9); 2.088 (0.4); 2.079 (1.8); 2.051 (0.7); 2.022 (0.5); 2.012 (0.5); 2.009 (0.5); 1.997 (0.6); 1.994 (0.7); 1.985 (0.3); 1.980 (0.9); 1.977 (0.9); 1.971 (0.4); 1.964 (0.7); 1.961 (0.6); 1.957 (0.5); 1.944 (0.6); 1.940 (0.5); 1.927 (0.4); 1.790 (0.8); 0.024 (1.9)

Example XVII-18

$^1$H-NMR (300.2 MHz, d$_6$-DMSO): δ=8.103 (0.9); 8.099 (0.9); 8.040 (5.5); 8.038 (5.5); 7.952 (0.7); 7.926 (5.9); 7.923 (5.5); 7.876 (0.8); 7.873 (0.8); 7.854 (0.6); 7.819 (0.5); 5.710 (16.0); 5.572 (2.5); 4.238 (0.7); 4.183 (1.1); 3.499 (4.5); 2.972 (1.3); 2.962 (0.9); 2.954 (1.5); 2.948 (1.0); 2.943 (2.0); 2.933 (1.7); 2.926 (2.8); 2.915 (1.5); 2.908 (2.2); 2.897 (2.0); 2.891 (1.1); 2.885 (1.0); 2.879 (1.6); 2.607 (1.2); 2.596 (0.5); 2.582 (1.7); 2.575 (2.4); 2.562 (1.6); 2.549 (2.1); 2.533 (6.0); 2.527 (11.9); 2.521 (15.1); 2.515 (11.4); 2.509 (5.8); 2.360 (0.4); 2.334 (0.3); 2.237 (0.4); 2.219 (0.6); 2.202 (0.9); 2.186 (1.2); 2.183 (1.0); 2.166 (1.1); 2.150 (1.4); 2.134 (0.9); 2.117 (0.6); 2.109 (0.4); 2.099 (0.4); 1.911 (0.4); 1.903 (0.4); 1.866 (0.5); 1.840 (0.9); 1.828 (0.5); 1.811 (1.5); 1.803 (0.9); 1.799 (0.9); 1.786 (1.0); 1.781 (0.9); 1.774 (1.3); 1.756 (0.6); 1.748 (0.7); 0.031 (0.7); 0.020 (21.4); 0.009 (0.9)

Example XVII-19

$^1$H-NMR (300.2 MHz, CDCl$_3$): δ=7.705 (5.6); 7.703 (5.5); 7.621 (5.1); 7.300 (1.3); 4.919 (16.0); 2.601 (3.8); 2.577 (6.6); 2.552 (4.3); 1.727 (0.9); 1.703 (2.7); 1.695 (0.9); 1.678 (3.4); 1.671 (1.4); 1.652 (2.5); 1.627 (1.2); 1.453 (0.6); 1.429 (1.9); 1.403 (2.7); 1.384 (1.3); 1.378 (2.9); 1.361 (0.6); 1.354 (1.8); 1.330 (0.6); 0.977 (6.9); 0.953 (13.5); 0.929 (5.4); 0.017 (1.3)

Use Examples

Example A: In Vivo Preventive Test on *Alternaria brassicae* (Leaf Spot on Radish)

Solvent: 5% by volume of Dimethyl sulfoxide
10% by volume of Acetone

Emulsifier: 1 µl of Tween® 80 per mg of active ingredient

The active ingredients are made soluble and homogenized in a mixture of Dimethyl sulfoxide/Acetone/Tween® 80 and then diluted in water to the desired concentration.

The young plants of radish are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Alternaria brassicae* spores. The contaminated radish plants are incubated for 6 days at 20° C. and at 100% relative humidity.

The test is evaluated 6 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-04; I-13; I-18; I-53; I-66; I-69; I-70; I-112; I-155.

In this test the following compounds according to the invention showed efficacy between 80% and 89% at a concentration of 500 ppm of active ingredient: I-01; I-03; I-19; I-20; I-22; I-23; I-40; I-54; I-55; I-99.

In this test the following compounds according to the invention showed efficacy between 90% and 100% at a concentration of 500 ppm of active ingredient: I-02; I-15; I-16; I-17; I-27; I-32; I-33; I-34; I-114.

Example B: In Vivo Preventive Test on *Botrytis Cinerea* (Grey Mould)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone/Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Botrytis cinerea* spores. The contaminated gherkin plants are incubated for 4 to 5 days at 17° C. and at 90% relative humidity.

The test is evaluated 4 to 5 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-15; I-66; I-72; I-98; I-131; I-137; I-149.

In this test the following compounds according to the invention showed efficacy between 80% and 89% at a concentration of 500 ppm of active ingredient: I-13; I-17; I-42; I-45; I-69; I-75; I-125; I-138; I-142; I-154.

In this test the following compounds according to the invention showed efficacy between 90% and 100% at a concentration of 500 ppm of active ingredient: I-02; I-04; I-05; I-06; I-08; I-14; I-16; I-18; I-21; I-25; I-27; I-29; I-30; I-32; I-33; I-34; I-36; I-38; I-39; I-40; I-43; I-44; I-54; I-55; I-59; I-65; I-71; I-73; I-76; I-77; I-79; I-82; I-99; I-107; I-108; I-110; I-112; I-114; I-118; I-124; I-126; I-128; I-130; I-133; I-139; I-144; I-146; I-147; I-155; I-157; I-158; I-164; I-167.

Example C: In Vivo Preventive Test on *Puccinia recondita* (Brown Rust on Wheat)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone/Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-61; I-68; I-75; I-105; I-132; I-169.

In this test the following compounds according to the invention showed efficacy between 80% and 89% at a concentration of 500 ppm of active ingredient: I-02; I-03; I-05; I-07; I-10; I-11; I-12; I-13; I-14; I-15; I-16; I-17; I-20; I-21; I-24; I-25; I-28; I-33; I-37; I-38; I-40; I-44; I-47; I-48; I-50; I-52; I-54; I-56; I-58; I-59; I-67; I-69; I-70; I-72; I-73; I-77; I-80; I-89; I-90; I-92; I-106; I-107; I-110; I-113; I-121; I-122; I-123; I-127; I-137; I-142; I-151; I-155; I-158; I-164; I-167.

In this test the following compounds according to the invention showed efficacy between 90% and 100% at a concentration of 500 ppm of active ingredient: I-01; I-04; I-06; I-08; I-18; I-19; I-22; I-23; I-26; I-27; I-29; I-30; I-31; I-32; I-34; I-36; I-39; I-41; I-42; I-43; I-45; I-46; I-49; I-51; I-53; I-55; I-57; I-62; I-64; I-65; I-66; I-71; I-76; I-79; I-81; I-82; I-84; I-85; I-88; I-91; I-95; I-96; I-97; I-98; I-99; I-101; I-103; I-104; I-108; I-109; I-111; I-112; I-114; I-115; I-117; I-118; I-120; I-124; I-125; I-126; I-128; I-130; I-131; I-133; I-136; I-138; I-139; I-141; I-143; I-144; I-146; I-147; I-148; I-149; I-152; I-153; I-154; I-156; I-157; I-165; I-166.

Example D: In Vivo Preventive Test on *Pyrenophora Teres* (Net Blotch on Barley)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone/Tween® 80 and then diluted in water to the desired concentration.

The young plants of barley are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Pyrenophora teres* spores. The contaminated barley plants are incubated for 48 hours at 20° C. and at 100% relative humidity and then for 12 days at 20° C. and at 70-80% relative humidity.

The test is evaluated 14 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-07; I-40; I-42; I-48; I-53; I-56; I-118; I-120; I-121; I-130; I-139; I-143; I-151; I-152; I-155.

In this test the following compounds according to the invention showed efficacy between 80% and 89% at a concentration of 500 ppm of active ingredient: I-08; I-11; I-13; I-14; I-19; I-22; I-23; I-25; I-29; I-32; I-33; I-38; I-45; I-50; I-54; I-55; I-69; I-72; I-73; I-75; I-77; I-80; I-82; I-84; I-85; I-89; I-95; I-97; I-103; I-112; I-131; I-142; I-148; I-153; I-156; I-164; I-166; I-167.

In this test the following compounds according to the invention showed efficacy between 90% and 100% at a concentration of 500 ppm of active ingredient: I-01; I-02; I-04; I-06; I-12; I-15; I-16; I-17; I-18; I-27; I-30; I-34; I-36; I-39; I-43; I-44; I-49; I-51; I-62; I-65; I-66; I-71; I-76; I-79; I-88; I-98; I-99; I-101; I-107; I-108; I-109; I-110; I-114; I-124; I-126; I-133; I-144; I-146; I-147; I-157; I-158.

Example E: In Vivo Preventive Test on *Septoria tritici* (Leaf Spot on Wheat)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone/Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-09; I-21; I-90; I-105; I-118; I-120; I-134; I-142; I-166; I-169.

In this test the following compounds according to the invention showed efficacy between 80% and 89% at a concentration of 500 ppm of active ingredient: I-05; I-20; I-28; I-58; I-65; I-69; I-73; I-78; I-87; I-110; I-149.

In this test the following compounds according to the invention showed efficacy between 90% and 100% at a concentration of 500 ppm of active ingredient: I-01; I-02; I-03; I-04; I-06; I-07; I-08; I-11; I-12; I-13; I-14; I-15; I-16; I-17; I-18; I-19; I-22; I-23; I-24; I-25; I-26; I-27; I-29; I-30; I-31; I-32; I-33; I-34; I-35; I-36; I-37; I-38; I-39; I-40; I-41; I-42; I-43; I-44; I-45; I-48; I-49; I-50; I-51; I-52; I-53; I-54; I-55; I-56; I-57; I-59; I-61; I-62; I-64; I-66; I-70; I-71; I-72; I-74; I-75; I-76; I-77; I-79; I-80; I-81; I-82; I-84; I-85; I-88; I-91; I-92; I-95; I-96; I-97; I-98; I-99; I-101; I-103; I-104; I-106; I-107; I-108; I-109; I-111; I-112; I-113; I-115; I-116; I-117; I-121; I-122; I-123; I-124; I-125; I-126; I-127; I-128; I-130; I-131; I-132; I-133; I-136; I-137; I-138; I-139; I-141; I-143; I-144; I-146; I-147; I-148; I-151; I-152; I-153; I-154; I-155; I-156; I-157; I-158; I-164; I-165.

Example F: In Vivo Preventive Test on *Sphaerotheca Fuliginea* (Powdery Mildew on Cucurbits)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone/Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Sphaerotheca fuliginea* spores. The contaminated gherkin plants are incubated for 72 hours at 18° C. and at 100% relative humidity and then for 12 days at 20° C. and at 70-80% relative humidity.

The test is evaluated 15 days after the inoculation. 0% means an efficacy which corresponds to that of the control plants while an efficacy of 100% means that no disease is observed.

In this test the following compounds according to the invention showed efficacy between 80% and 89% at a concentration of 500 ppm of active ingredient: I-78.

In this test the following compounds according to the invention showed efficacy between 90% and 100% at a concentration of 500 ppm of active ingredient: I-01; I-02; I-03; I-04; I-05; I-06; I-07; I-08; I-09; I-11; I-12; I-13; I-14; I-15; I-16; I-17; I-18; I-19; I-20; I-21; I-22; I-23; I-24; I-25; I-26; I-27; I-28; I-29; I-30; I-31; I-32; I-33; I-34; I-36; I-38; I-39; I-40; I-41; I-42; I-43; I-44; I-45; I-46; I-47; I-48; I-49; I-50; I-51; I-52; I-53; I-54; I-55; I-56; I-57; I-58; I-59; I-61; I-62; I-64; I-65; I-66; I-67; I-69; I-70; I-71; I-72; I-73; I-74; I-75; I-76; I-77; I-79; I-80; I-81; I-82; I-84; I-85; I-87; I-88; I-89; I-90; I-91; I-92; I-95; I-96; I-97; I-98; I-99; I-101; I-103; I-104; I-105; I-106; I-107; I-108; I-109; I-110; I-111; I-112; I-113; I-114; I-115; I-116; I-117; I-118; I-120; I-121; I-122; I-123; I-124; I-125; I-126; I-127; I-128; I-130; I-131; I-132; I-133; I-134; I-136; I-137; I-138; I-139; I-141; I-142; I-143; I-144; I-146; I-147; I-149; I-151; I-152; I-153; I-154; I-155; I-156; I-157; I-158; I-164; I-165; I-166; I-167; I-169.

Example G: In Vivo Preventive Test on *Uromyces appendiculatus* (Bean Rust)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone/Tween® 80 and then diluted in water to the desired concentration.

The young plants of bean are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-21; I-28; I-134; I-169.

In this test the following compounds according to the invention showed efficacy between 80% and 89% at a concentration of 500 ppm of active ingredient: I-51; I-107; I-114; I-123.

In this test the following compounds according to the invention showed efficacy between 90% and 100% at a concentration of 500 ppm of active ingredient: I-01; I-02; I-03; I-04; I-05; I-06; I-07; I-08; I-09; I-10; I-11; I-12; I-14; I-15; I-16; I-17; I-18; I-20; I-22; I-23; I-24; I-25; I-26; I-27; I-29; I-30; I-31; I-32; I-33; I-34; I-36; I-38; I-39; I-40; I-41; I-42; I-43; I-44; I-45; I-46; I-47; I-48; I-49; I-50; I-52; I-53; I-54; I-55; I-56; I-57; I-58; I-59; I-61; I-62; I-64; I-65; I-66; I-67; I-68; I-69; I-70; I-71; I-72; I-74; I-75; I-77; I-79; I-80; I-81; I-82; I-84; I-85; I-88; I-89; I-90; I-91; I-92; I-95; I-96; I-97; I-98; I-99; I-101; I-103; I-104; I-106; I-109; I-110;

I-111; I-112; I-113; I-115; I-117; I-118; I-120; I-121; I-122; I-124; I-125; I-126; I-127; I-128; I-130; I-131; I-132; I-133; I-136; I-137; I-138; I-139; I-141; I-142; I-144; I-146; I-147; I-148; I-149; I-151; I-152; I-153; I-154; I-155; I-156; I-157; I-158; I-164; I-165; I-166; I-167.

Example H: In Vivo Preventive Test on *Alternaria* Test (Tomatoes)

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Alternaria solani*. The plants are then placed in an incubation cabinet at approximately 20° C. and a relative atmospheric humidity of 100%.

The test is evaluated 3 days after the inoculation. 0% means an efficacy which corresponds to that of the untreated control while an efficacy of 100% means that no disease is observed.

In this test the following compounds according to the invention showed efficacy between 70% and 79% at a concentration of 100 ppm of active ingredient: I-05; I-42; I-50; I-96.

In this test the following compounds according to the invention showed efficacy between 80% and 89% at a concentration of 100 ppm of active ingredient: I-26; I-43; I-97; I-103; I-133; I-157.

In this test the following compounds according to the invention showed efficacy between 90% and 100% at a concentration of 100 ppm of active ingredient: I-04; I-06; I-08; I-16; I-17; I-18; I-27; I-29; I-30; I-32; I-33; I-34; I-36; I-38; I-39; I-40; I-44; I-65; I-69; I-95; I-98; I-99; I-101; I-107; I-112; I-114; I-125; I-126; I-146; I-147; I-153; I-155; I-158.

Example I: In Vivo Preventive Test on *Phakopsora* Test (Soybeans)

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of soybean rust (Phakopsorapachyrhizi) and stay for 24 h without light in an incubation cabinet at approximately 24° C. and a relative atmospheric humidity of 95%.

The plants remain in the incubation cabinet at approximately 24° C. and a relative atmospheric humidity of approximately 80% and a day/night interval of 12 h.

The test is evaluated 7 days after the inoculation. 0% means an efficacy which corresponds to that of the untreated control, while an efficacy of 100% means that no disease is observed.

In this test the following compounds according to the invention showed efficacy between 70% and 79% at a concentration of 100 ppm of active ingredient: I-26.

In this test the following compounds according to the invention showed efficacy between 80% and 89% at a concentration of 100 ppm of active ingredient: I-50; I-96; I-107; I-133.

In this test the following compounds according to the invention showed efficacy between 90% and 100% at a concentration of 100 ppm of active ingredient: I-04; I-05; I-06; I-08; I-16; I-17; I-18; I-23; I-27; I-29; I-30; I-32; I-33; I-34; I-36; I-38; I-39; I-40; I-42; I-43; I-44; I-65; I-69; I-95; I-97; I-98; I-99; I-101; I-103; I-112; I-114; I-125; I-126; I-138; I-146; I-147; I-153; I-155; I-157; I-158.

Example J: In Vivo Preventive Test on *Venturia* Test (Apples)

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

In this test the following compounds according to the invention showed efficacy between 70% and 79% at a concentration of 100 ppm of active ingredient: I-133; I-138.

In this test the following compounds according to the invention showed efficacy between 80% and 89% at a concentration of 100 ppm of active ingredient: I-06; I-40; I-42; I-50; I-65; I-95; I-96; I-97; I-99; I-101; I-103; I-107; I-112; I-114; I-153.

In this test the following compounds according to the invention showed efficacy between 90% and 100% at a concentration of 100 ppm of active ingredient: I-04; I-08; I-16; I-17; I-18; I-26; I-27; I-29; I-30; I-32; I-33; I-34; I-36; I-38; I-44; I-69; I-98; I-125; I-146; I-147; I-155; I-157.

Example K: In Vivo Preventive *Blumeria* Test (Barley)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are dusted with spores of *Blumeria graminis* fsp. *hordei*.

The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the untreated control, while an efficacy of 100% means that no disease is observed.

In this test the following compounds according to the invention showed efficacy between 70% and 79% at a concentration of 500 ppm of active ingredient: I-17; I-25.

In this test the following compounds according to the invention showed efficacy between 80% and 89% at a concentration of 500 ppm of active ingredient: I-43.

In this test the following compounds according to the invention showed efficacy between 90% and 100% at a concentration of 500 ppm of active ingredient: I-01; I-02; I-04; I-06; I-08; I-16; I-18; I-22; I-26; I-27; I-29; I-30; I-32; I-33; I-34; I-36; I-38; I-39; I-40; I-41; I-42; I-44; I-49; I-50; I-62; I-64; I-65; I-72; I-75; I-80; I-84; I-88; I-92; I-95; I-96; I-97; I-98; I-99; I-101; I-103; I-109; I-112; I-114; I-125; I-126; I-133; I-136; I-138; I-144; I-146; I-147; I-152; I-154; I-156; I-157; –164; I-165.

Example L: In Vivo Preventive *Fusarium culmorum* Test (Wheat)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application. After the spray coating has been dried, the plants are slightly injured by using a sandblast and afterwards they are sprayed with a conidia suspension of *Fusarium culmorum*.

The plants are placed in the greenhouse under a translucent incubation cabinet at a temperature of approximately 22° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed efficacy between 70% and 79% at a concentration of 500 ppm of active ingredient: I-02.

In this test the following compounds according to the invention showed efficacy between 80% and 89% at a concentration of 500 ppm of active ingredient: I-18; I-29; I-36; I-38.

In this test the following compounds according to the invention showed efficacy between 90% and 100% at a concentration of 500 ppm of active ingredient: I-06; I-16; I-26; I-34; I-39; I-65; I-95; I-97; I-133; I-157.

Example M: In Vivo Preventive *Fusarium graminearum* Test (Barley)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium graminearum*.

The plants are placed in the greenhouse under a translucent incubation cabinet at a temperature of approximately 25° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed efficacy between 70% and 79% at a concentration of 500 ppm of active ingredient: I-04; I-08; I-32; I-44; I-49; I-72; I-112; I-114; I-152.

In this test the following compounds according to the invention showed efficacy between 80% and 89% at a concentration of 500 ppm of active ingredient: I-02; I-16; I-42; I-64; I-156.

In this test the following compounds according to the invention showed efficacy between 90% and 100% at a concentration of 500 ppm of active ingredient: I-06; I-18; I-29; I-34; I-39; I-41; I-65; I-88; I-95; I-96; I-97; I-98; I-99; I-103; I-109; I-125; I-126; I-133; I-138; I-144; I-146; I-147; I-154; I-157.

Example N: In Vivo Preventive *Leptosphaeria nodorum* Test (Wheat)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Leptosphaeria nodorum*. The plants remain for 48 hours in an incubation cabinet at approximately 20° C. and a relative atmospheric humidity of approximately 100%.

The plants are placed in the greenhouse at a temperature of approximately 25° C. and a relative atmospheric humidity of approximately 80%.

The test is evaluated 8 days after the inoculation. 0% means an efficacy which corresponds to that of the untreated control, while an efficacy of 100% means that no disease is observed.

In this test the following compounds according to the invention showed efficacy between 70% and 79% at a concentration of 500 ppm of active ingredient: I-26; I-39; I-41; I-152.

In this test the following compounds according to the invention showed efficacy between 80% and 89% at a concentration of 500 ppm of active ingredient: I-11; I-32; I-36; I-38; I-44; I-49; I-65; I-95; I-125; I-157.

In this test the following compounds according to the invention showed efficacy between 90% and 100% at a concentration of 500 ppm of active ingredient: I-02; I-04; I-06; I-08; I-16; I-18; I-27; I-29; I-30; I-33; I-34; I-42; I-72; I-99; –133; I-146; I-147; I-154.

Example O: In Vivo Preventive *Fusarium nivale* (Var. *Majus*) Test (Wheat)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium nivale* (var. *majus*).

The plants are placed in the greenhouse under a translucent incubation cabinet at a temperature of approximately 10° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed efficacy between 70% and 79% at a concentration of 500 ppm of active ingredient: I-01; I-39.

In this test the following compounds according to the invention showed efficacy between 80% and 89% at a concentration of 500 ppm of active ingredient: I-11; I-32; I-41; I-42; I-49; I-88; I-109; I-157; I-164.

In this test the following compounds according to the invention showed efficacy between 90% and 100% at a concentration of 500 ppm of active ingredient: I-02; I-04; I-06; I-08; I-16; I-18; I-26; I-29; I-34; I-36; I-38; I-50; I-65; I-72; I-95; I-97; I-99; I-125; I-133; I-146; I-147; I-152; I-154.

Example P: In Vivo Preventive *Pyricularia Oryzae* Test (Rice)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Pyricularia oryzae*. The plants remain for 48 hours in an incubation cabinet at approximately 25° C. and a relative atmospheric humidity of approximately 100%.

The plants are placed in the greenhouse under a translucent incubations cabinet at a temperature of approximately 25° C. and a relative atmospheric humidity of approximately 100%.

The test is evaluated 8 days after the inoculation. 0% means an efficacy which corresponds to that of the control, while an efficacy of 100% means that no disease is observed.

In this test the following compounds according to the invention showed efficacy between 70% and 79% at a concentration of 500 ppm of active ingredient: I-02; I-08; I-25; I-39; I-40; I-44; I-50; I-84; I-95; I-97; I-112; I-114; I-144; I-146; I-154; I-164.

In this test the following compounds according to the invention showed efficacy between 80% and 89% at a concentration of 500 ppm of active ingredient: I-11; I-22; I-26; I-42; I-49; I-92; I-99; I-125; I-138; I-147.

In this test the following compounds according to the invention showed efficacy between 90% and 100% at a concentration of 500 ppm of active ingredient: I-04; I-06; I-16; I-17; I-18; I-27; I-30; I-36; I-38; I-65; I-72; I-98; I-126; I-133; I-157; I-165.

Examples Q

The following examples Q1 to Q4 provide comparative data of the efficacy of 5-substituted imidazolylmethyl compounds according to the invention vs. an unsubstituted imidazolylmethyl compound against several pathogens. The data clearly demonstrate the superior properties of compounds according to the invention.

Example Q1: In Vivo Preventive Test on *Botrytis cinerea* (Grev Mould)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone/Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Botrytis cinerea* spores. The contaminated gherkin plants are incubated for 4 to 5 days at 17° C. and at 90% relative humidity.

The test is evaluated 4 to 5 days after the inoculation. 0% means an efficacy which corresponds to that of the control plants while an efficacy of 100% means that no disease is observed.

TABLE results

| Active compound | | Rate of application of active compound in ppm | Efficacy in % |
|---|---|---|---|
| Comparison compound | (structure: dichlorophenyl with OH, cyclopropyl-Cl, CH₂-imidazole, F) | 500<br>100 | 100<br>70 |
| *According to the invention:* | | | |
| I-27 | (structure shown) | 500<br>100 | 100<br>99 |
| I-29 | (structure shown) | 500<br>100 | 99<br>86 |
| I-30 | (structure shown) | 500<br>100 | 100<br>100 |

Example Q2: In Vivo Preventive Test on *Pyrenophora Teres* (Net Blotch on Barley)

Solvent: 5% by volume of Dimethyl sulfoxide
  10% by volume of Acetone
Emulsifier: 1 µl of Tween® 80 per mg of active ingredient The active ingredients are made soluble and homogenized in a mixture of Dimethyl sulfoxide/Acetone/Tween® 80 and then diluted in water to the desired concentration.

The young plants of barley are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Pyrenophora teres* spores. The contaminated barley plants are incubated for 48 hours at 20° C. and at 100% relative humidity and then for 12 days at 20° C. and at 70-80% relative humidity.

The test is evaluated 14 days after the inoculation. 0% means an efficacy which corresponds to that of the control plants while an efficacy of 100% means that no disease is observed.

TABLE results

| Active compound | | Rate of application of active compound in ppm | Efficacy in % |
|---|---|---|---|
| Comparison compound | 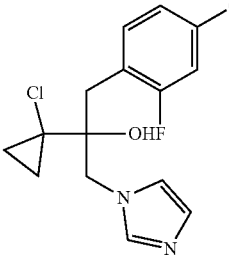 | 500<br>100 | 0<br>0 |

According to the invention:

| I-27 | 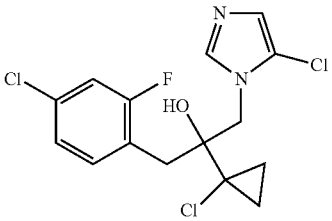 [SMILES: OC(Cc1ccc(Cl)cc1F)(Cn1cncc1Cl)C1(Cl)CC1] | 500<br>100 | 98<br>94 |
|---|---|---|---|
| I-29 | 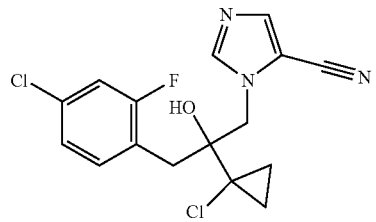 [SMILES: N#Cc1cncn1CC(O)(Cc1ccc(Cl)cc1F)C1(Cl)CC1] | 500<br>100 | 89<br>83 |
| I-30 | 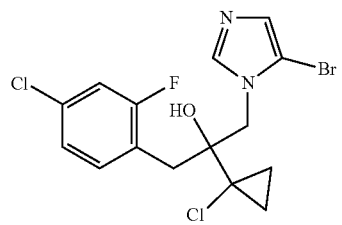 [SMILES: OC(Cc1ccc(Cl)cc1F)(Cn1cncc1Br)C1(Cl)CC1] | 500<br>100 | 94<br>91 |

Example Q3: In Vivo Preventive Test on *Septoria tritici* (Leaf Spot on Wheat)

Solvent: 5% by volume of Dimethyl sulfoxide
10% by volume of Acetone
Emulsifier: 1 μl of Tween® 80 per mg of active ingredient The active ingredients are made soluble and homogenized in a mixture of Dimethyl sulfoxide/Acetone/Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

TABLE results

| Active compound | | Rate of application of active compound in ppm | Efficacy in % |
|---|---|---|---|
| Comparison compound | 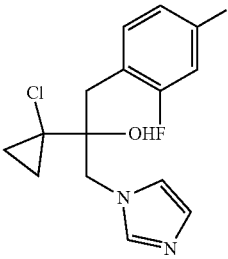 | 500<br>100 | 100<br>0 |

According to the invention:

| | | | |
|---|---|---|---|
| I-27 | 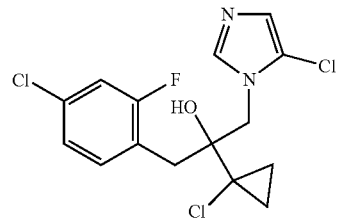 [SMILES: OC(Cc1ccc(Cl)cc1F)(Cn1cncc1Cl)C1(Cl)CC1] | 500<br>100 | 94<br>81 |
| I-29 | 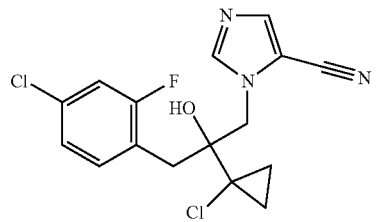 [SMILES: N#Cc1cncn1CC(O)(Cc1ccc(Cl)cc1F)C1(Cl)CC1] | 500<br>100 | 100<br>100 |
| I-30 | 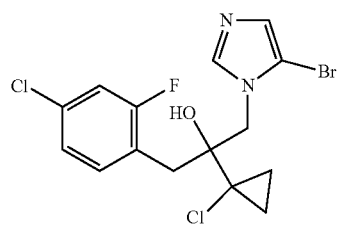 [SMILES: OC(Cc1ccc(Cl)cc1F)(Cn1cncc1Br)C1(Cl)CC1] | 500<br>100 | 98<br>94 |

Example Q4: In Vitro Test for the Calculation of the ED50-Value with Microorganisms Solvent: Dimethyl sulfoxide
Culture medium: 14.6 g anhydrous D-glucose (VWR), 7.1 g Mycological Peptone (Oxoid), 1.4 g granulated Yeast Extract (Merck), QSP liter
Inoculum: Spore suspension Fungicides were solubilized in DMSO and the solution used to prepare the required range of concentrations. The final concentration of DMSO used in the assay was ≤1%.

A spore suspension was prepared and diluted to the desired spore density.

Fungicides were evaluated for their ability to inhibit spore germination and mycelium growth in liquid culture assay. The compounds were added in the desired concentration to the culture medium with spores. After 4 to 7 days incubation, fungi-toxicity of compounds was determined by spectrometric measurement of mycelium growth. Inhibition of fungal growth was determined by comparing the absorbance values in wells containing the fungicides with the absorbance in control wells without fungicides.

TABLE results

| Active compound | Botrytis cinerea ED50 value in ppm | Leptosphaeria nodorum ED50 value in ppm | Septoria tritici ED50 value in ppm | Fusarium culmorum ED50 value in ppm |
|---|---|---|---|---|
| Comparison compound (structure) | 0.53 | 0.04 | 0.02 | 0.04 |
| According to the invention: | | | | |
| I-27 (structure) | 0.02 | <0.006 | <0.006 | <0.006 |
| I-29 (structure) | 0.26 | 0.02 | <0.006 | 0.01 |
| I-30 (structure) | 0.08 | 0.01 | <0.006 | 0.01 |

Examples R

The following examples R1 to R7 provide comparative data of the efficacy of 5-substituted imidazolylmethyl compounds according to the invention vs. substituted imidazolylmethyl derivatives bearing the substituent in another position against several pathogens. The data clearly demonstrate the superior properties of compounds according to the invention.

Example R1: In Vivo Preventive Test on *Alternaria brassicae* (Leaf Spot on Radish)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone/Tween® 80 and then diluted in water to the desired concentration.

The young plants of radish are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Alternaria brassicae* spores. The contaminated radish plants are incubated for 6 days at 20° C. and at 100% relative humidity.

The test is evaluated 6 days after the inoculation. 0% means an efficacy which corresponds to that of the control plants while an efficacy of 100% means that no disease is observed.

Results:
| Active compound | | Rate of application of active compound in ppm | Efficacy in % |
|---|---|---|---|
| Comparison compound | 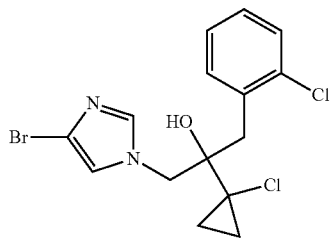 [SMILES: OC(Cc1ccccc1Cl)(Cn1cnc(Br)c1)C1(Cl)CC1] | 500<br>100 | 40<br>0 |
| According to the invention: | | | |
| I-04 | 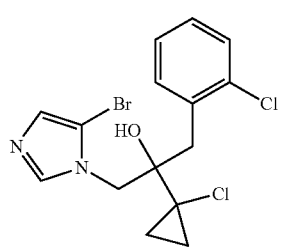 [SMILES: OC(Cc1ccccc1Cl)(Cn1cncc1Br)C1(Cl)CC1] | 500<br>100 | 70<br>20 |
| Comparison compound | 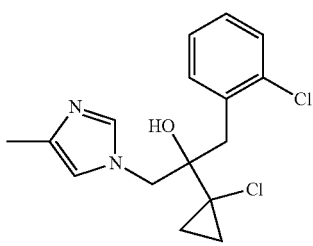 [SMILES: Cc1cn(CC(O)(Cc2ccccc2Cl)C2(Cl)CC2)cn1] | 500<br>100 | 0<br>0 |
| According to the invention: | | | |
| I-03 | 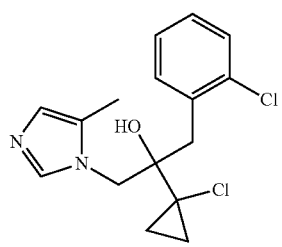 [SMILES: Cc1cncn1CC(O)(Cc1ccccc1Cl)C1(Cl)CC1] | 500<br>100 | 83<br>0 |
| Comparison compound | 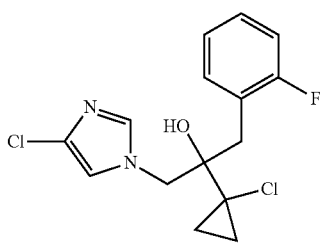 [SMILES: OC(Cc1ccccc1F)(Cn1cnc(Cl)c1)C1(Cl)CC1] | 500<br>100 | 0<br>0 |

-continued
| Active compound | | Rate of application of active compound in ppm | Efficacy in % |
|---|---|---|---|
| Comparison compound | 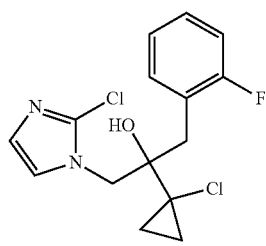 [SMILES: OC(Cc1ccccc1F)(Cn1ccnc1Cl)C1(Cl)CC1] | 500<br>100 | 0<br>0 |
| According to the invention: | | | |
| I-32 | 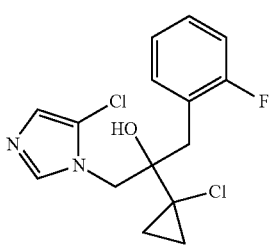 [SMILES: OC(Cc1ccccc1F)(Cn1cncc1Cl)C1(Cl)CC1] | 500<br>100 | 92<br>50 |
| Comparison compound | 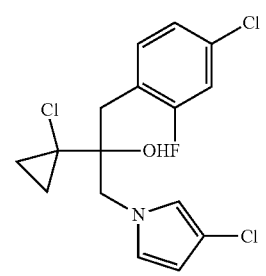 | 500<br>100 | 0<br>0 |
| According to the invention: | | | |
| I-27 | 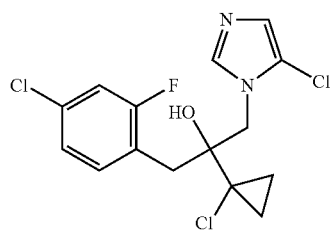 [SMILES: OC(Cc1ccc(Cl)cc1F)(Cn1cncc1Cl)C1(Cl)CC1] | 500<br>100 | 92<br>50 |
| Comparison compound | 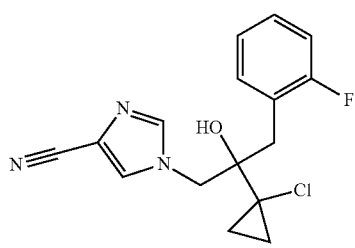 [SMILES: N#Cc1cn(CC(O)(Cc2ccccc2F)C2(Cl)CC2)cn1] | 500<br>100 | 0<br>0 |

| Active compound | Rate of application of active compound in ppm | Efficacy in % |
|---|---|---|
| According to the invention: | | |
| I-34 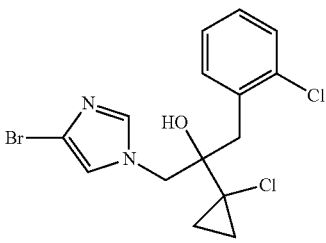 [SMILES: OC(Cc1ccccc1Cl)(Cn1cnc(Br)c1)C1(Cl)CC1] | 500<br>100 | 92<br>58 |

Example R2: In Vivo Preventive Test on *Botrytis cinerea* (Grey Mould)

The tested active ingredients are prepared by homogenization in a mixture of acetone/Dimethyl sulfoxide/Tween® as disclosed above, and then diluted with water to obtain the desired active material concentration.

The young plants of gherkin are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Botrytis cinerea* spores. The contaminated gherkin plants are incubated for 4 to 5 days at 17° C. and at 90% relative humidity.

The test is evaluated 4 to 5 days after the inoculation. 0% means an efficacy which corresponds to that of the control plants while an efficacy of 100% means that no disease is observed.

Results:

| | Active compound | Rate of application of active compound in ppm | Efficacy in % |
|---|---|---|---|
| Comparison compound | 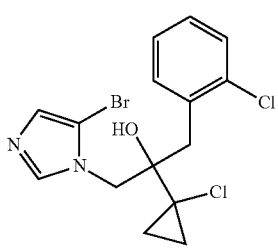 [SMILES: OC(Cc1ccccc1Cl)(Cn1cncc1Br)C1(Cl)CC1] | 500<br>100 | 0<br>5 |
| According to the invention: | | | |
| I-04 | 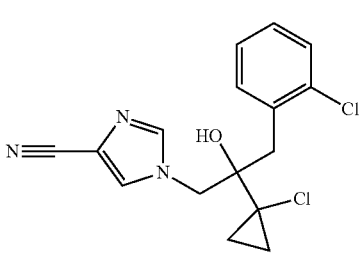 [SMILES: N#Cc1cn(CC(O)(Cc2ccccc2Cl)C2(Cl)CC2)cn1] | 500<br>100 | 100<br>90 |
| Comparison compound | | 500<br>100 | 0<br>0 |

-continued
| Active compound | | Rate of application of active compound in ppm | Efficacy in % |
|---|---|---|---|
| According to the invention: | | | |
| I-06 | 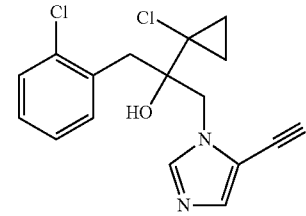 | 500<br>100 | 97<br>80 |
| Comparison compound | 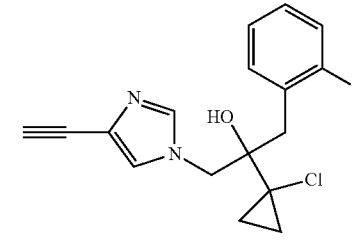 | 500<br>100 | 0<br>0 |
| According to the invention: | | | |
| I-36 | 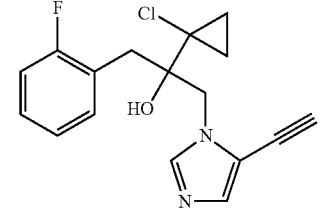 [SMILES: C#Cc1cncn1CC(O)(Cc1ccccc1F)C1(Cl)CC1] | 500<br>100 | 100<br>100 |
| Comparison compound | 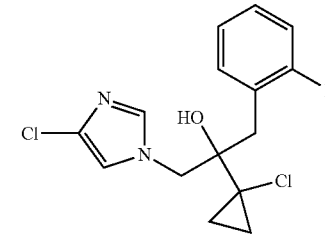 | 500<br>100 | 0<br>0 |
| Comparison compound | 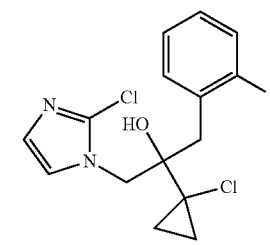 | 500<br>100 | 0<br>0 |

-continued
| | Active compound | Rate of application of active compound in ppm | Efficacy in % |
|---|---|---|---|
| According to the invention: | | | |
| I-32 | 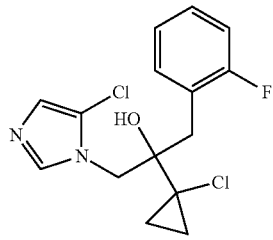 [SMILES: OC(Cc1ccccc1F)(Cn1cncc1Cl)C1(Cl)CC1] | 500<br>100 | 100<br>99 |
| Comparison compound | 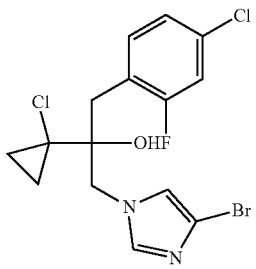 | 500<br>100 | 19<br>0 |
| According to the invention: | | | |
| I-30 | 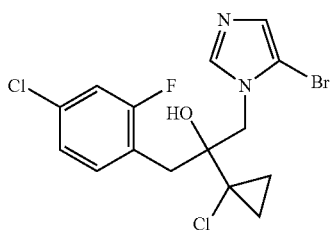 [SMILES: OC(Cc1ccc(Cl)cc1F)(Cn1cncc1Br)C1(Cl)CC1] | 500<br>100 | 100<br>100 |
| Comparison compound | 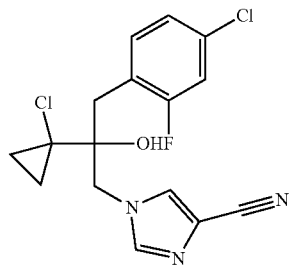 | 500<br>100 | 0<br>0 |
| According to the invention: | | | |
| I-29 | 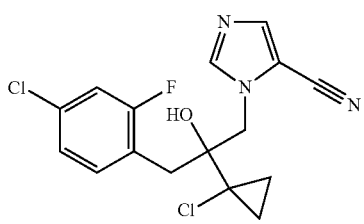 [SMILES: N#Cc1cncn1CC(O)(Cc1ccc(Cl)cc1F)C1(Cl)CC1] | 500<br>100 | 99<br>86 |

| Active compound | Rate of application of active compound in ppm | Efficacy in % |
|---|---|---|
| Comparison compound (structure) | 500<br>100 | 0<br>0 |
| According to the invention:<br>I-27 (structure) | 500<br>100 | 100<br>99 |
| Comparison compound (structure) | 500<br>100 | 0<br>0 |
| According to the invention:<br>I-34 (structure) | 500<br>100 | 100<br>94 |

Example R3: In Vivo Preventive Test on *Puccinia recondita* (Brown Rust on Wheat)

The tested active ingredients are prepared by homogenization in a mixture of acetone/Dimethyl sulfoxide/Tween® as disclosed above, and then diluted with water to obtain the desired active material concentration.

The young plants of wheat are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

Results:
| Active compound | | Rate of application of active compound in ppm | Efficacy in % |
|---|---|---|---|
| Comparison compound | 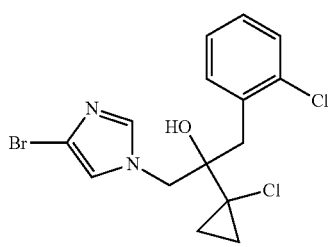 | 500<br>100 | 81<br>75 |
| According to the invention: | | | |
| I-04 | 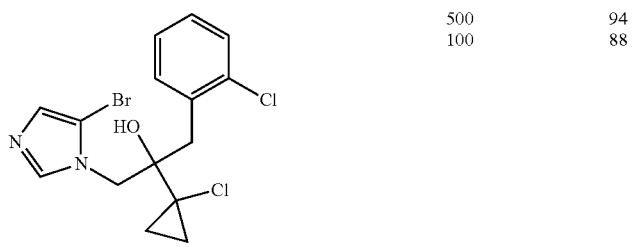 | 500<br>100 | 94<br>88 |
| Comparison compound | 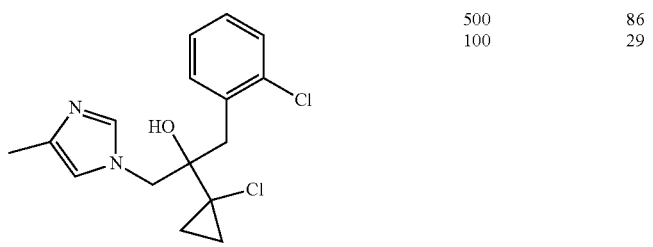 | 500<br>100 | 86<br>29 |
| According to the invention: | | | |
| I-03 | 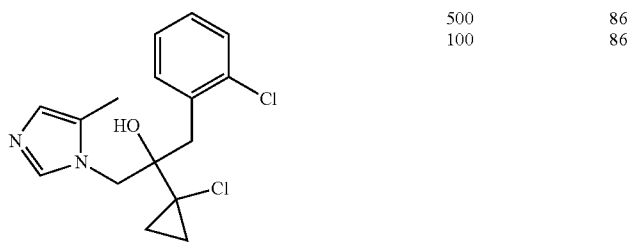 | 500<br>100 | 86<br>86 |
| Comparison compound | 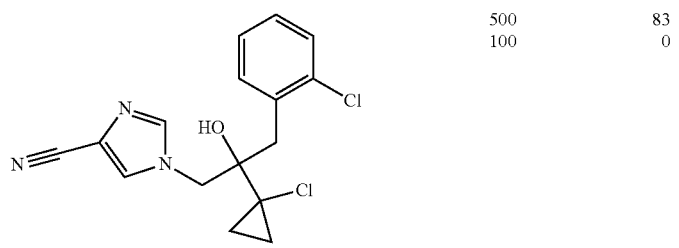 | 500<br>100 | 83<br>0 |

-continued
| | Active compound | Rate of application of active compound in ppm | Efficacy in % |
|---|---|---|---|
| According to the invention: | | | |
| I-06 | 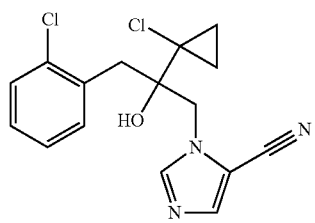 [SMILES: N#Cc1cncn1CC(O)(Cc1ccccc1F)C1(Cl)CC1] | 500<br>100 | 94<br>89 |
| Comparison compound | 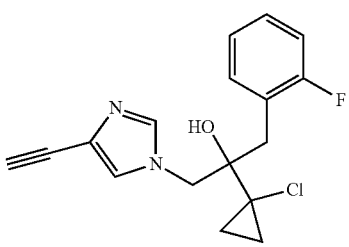 [SMILES: C#Cc1cn(CC(O)(Cc2ccccc2F)C2(Cl)CC2)cn1] | 500<br>100 | 13<br>0 |
| According to the invention: | | | |
| I-36 | 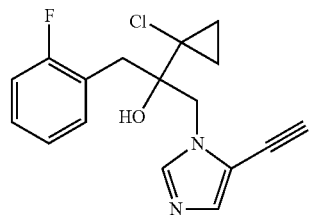 [SMILES: C#Cc1cncn1CC(O)(Cc1ccccc1F)C1(Cl)CC1] | 500<br>100 | 94<br>89 |
| Comparison compound | 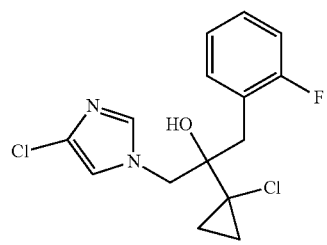 [SMILES: OC(Cc1ccccc1F)(Cn1cnc(Cl)c1)C1(Cl)CC1] | 500<br>100 | 33<br>0 |
| Comparison compound | 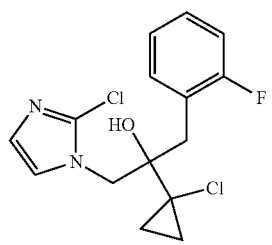 [SMILES: OC(Cc1ccccc1F)(Cn1ccnc1Cl)C1(Cl)CC1] | 500<br>100 | 0<br>0 |

-continued
| | Active compound | Rate of application of active compound in ppm | Efficacy in % |
|---|---|---|---|
| According to the invention: | | | |
| I-32 | 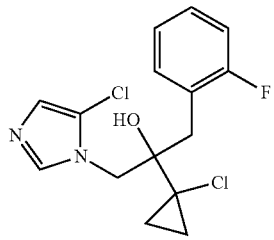 [SMILES: OC(Cc1ccccc1F)(Cn1cncc1Cl)C1(Cl)CC1] | 500<br>100 | 94<br>78 |
| Comparison compound | 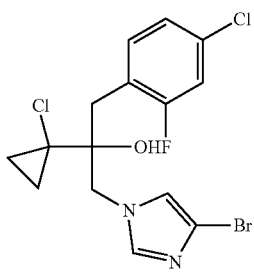 | 500<br>100 | 94<br>0 |
| According to the invention: | | | |
| I-30 | 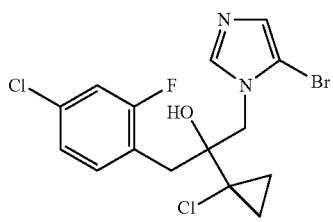 [SMILES: OC(Cc1ccc(Cl)cc1F)(Cn1cncc1Br)C1(Cl)CC1] | 500<br>100 | 94<br>88 |
| Comparison compound | 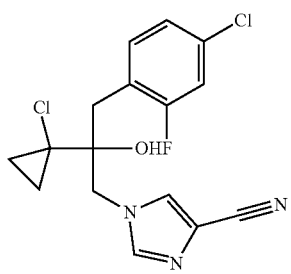 | 500<br>100 | 94<br>81 |
| According to the invention: | | | |
| I-29 | 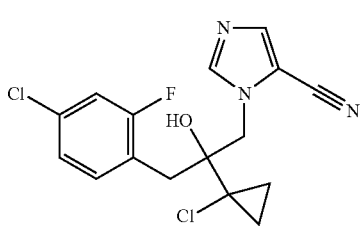 [SMILES: N#Cc1cncn1CC(O)(Cc1ccc(Cl)cc1F)C1(Cl)CC1] | 500<br>100 | 98<br>94 |

| Active compound | Rate of application of active compound in ppm | Efficacy in % |
|---|---|---|
| Comparison compound (structure) | 500<br>100 | 67<br>0 |

According to the invention:

| | | |
|---|---|---|
| I-27 (structure) | 500<br>100 | 98<br>89 |

| Comparison compound (structure) | 500<br>100 | 78<br>11 |
|---|---|---|

According to the invention:

| | | |
|---|---|---|
| I-34 (structure) | 500<br>100 | 100<br>94 |

Example R4: In Vivo Preventive Test on *Pyrenophora teres* (Net Blotch on Barley)

The tested active ingredients are prepared by homogenization in a mixture of acetone/Dimethyl sulfoxide/Tween® as disclosed above, and then diluted with water to obtain the desired active material concentration.

The young plants of barley are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Pyrenophora teres* spores. The contaminated barley plants are incubated for 48 hours at 20° C. and at 100% relative humidity and then for 12 days at 20° C. and at 70-80% relative humidity.

The test is evaluated 14 days after the inoculation. 0% means an efficacy which corresponds to that of the control plants while an efficacy of 100% means that no disease is observed.

Results:
| | Active compound | Rate of application of active compound in ppm | Efficacy in % |
|---|---|---|---|
| Comparison compound | 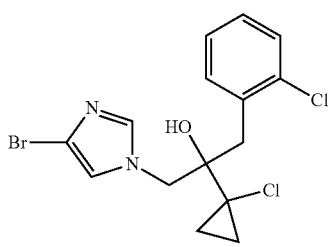 [SMILES: OC(Cc1ccccc1Cl)(Cn1cnc(Br)c1)C1(Cl)CC1] | 500<br>100 | 0<br>0 |
| According to the invention: | | | |
| I-04 | 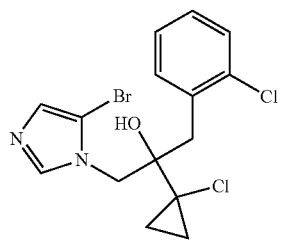 | 500<br>100 | 93<br>71 |
| Comparison compound | 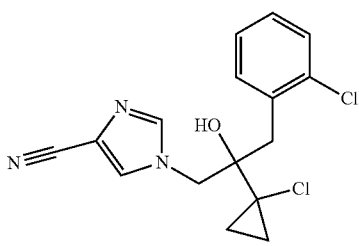 [SMILES: N#Cc1cn(CC(O)(Cc2ccccc2Cl)C2(Cl)CC2)cn1] | 500<br>100 | 0<br>0 |
| According to the invention: | | | |
| I-06 | 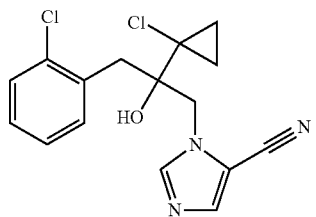 | 500<br>100 | 93<br>86 |
| Comparison compound | 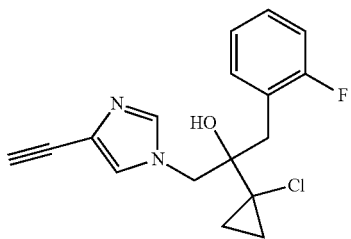 [SMILES: C#Cc1cn(CC(O)(Cc2ccccc2F)C2(Cl)CC2)cn1] | 500<br>100 | 0<br>0 |

-continued
| Active compound | | Rate of application of active compound in ppm | Efficacy in % |
|---|---|---|---|
| According to the invention: | | | |
| I-36 | 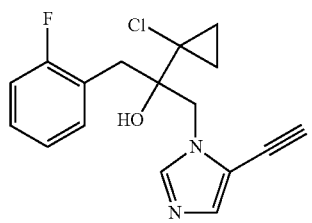 [SMILES: C#Cc1cncn1CC(O)(Cc1ccccc1F)C1(Cl)CC1] | 500<br>100 | 93<br>57 |
| Comparison compound | 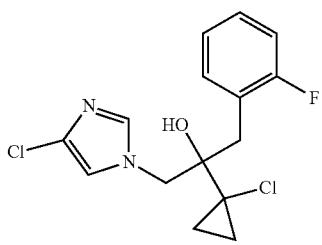 [SMILES: OC(Cc1ccccc1F)(Cn1cnc(Cl)c1)C1(Cl)CC1] | 500<br>100 | 0<br>0 |
| Comparison compound | 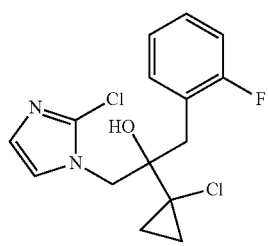 [SMILES: OC(Cc1ccccc1F)(Cn1ccnc1Cl)C1(Cl)CC1] | 500<br>100 | 0<br>0 |
| According to the invention: | | | |
| I-32 | 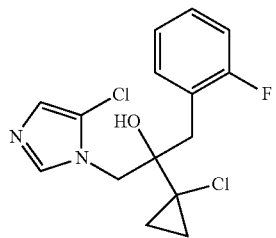 [SMILES: OC(Cc1ccccc1F)(Cn1cncc1Cl)C1(Cl)CC1] | 500<br>100 | 89<br>78 |
| Comparison compound | 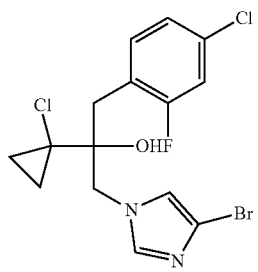 | 500<br>100 | 38<br>0 |

-continued
| Active compound | | Rate of application of active compound in ppm | Efficacy in % |
|---|---|---|---|
| According to the invention: | | | |
| I-30 | 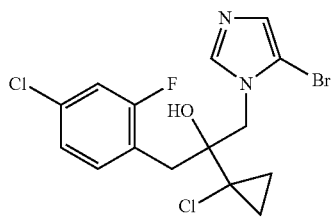 [SMILES: OC(Cc1ccc(Cl)cc1F)(Cn1cncc1Br)C1(Cl)CC1] | 500<br>100 | 94<br>81 |
| Comparison compound | 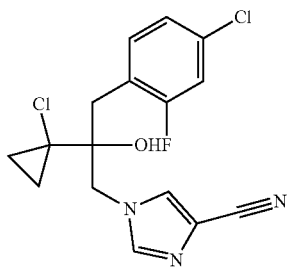 | 500<br>100 | 25<br>0 |
| According to the invention: | | | |
| I-29 | 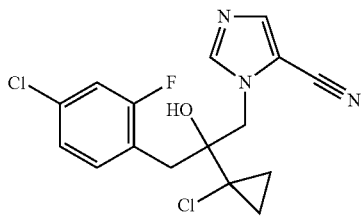 [SMILES: N#Cc1cncn1CC(O)(Cc1ccc(Cl)cc1F)C1(Cl)CC1] | 500<br>100 | 89<br>83 |
| Comparison compound | 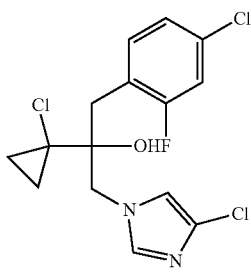 | 500<br>100 | 0<br>0 |
| According to the invention: | | | |
| I-27 | 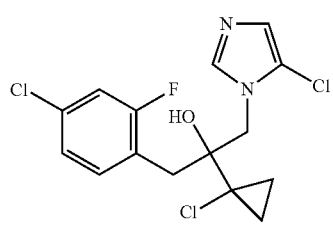 [SMILES: OC(Cc1ccc(Cl)cc1F)(Cn1cncc1Cl)C1(Cl)CC1] | 500<br>100 | 98<br>94 |

| Active compound | Rate of application of active compound in ppm | Efficacy in % |
|---|---|---|
| Comparison compound 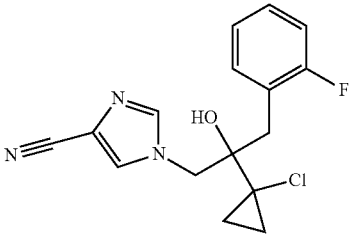 [SMILES: N#Cc1cn(CC(O)(Cc2ccccc2F)C2(Cl)CC2)cn1] | 500<br>100 | 0<br>0 |
| According to the invention:<br>I-34 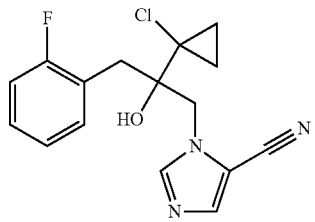 [SMILES: N#Cc1cncn1CC(O)(Cc1ccccc1F)C1(Cl)CC1] | 500<br>100 | 98<br>83 |

Example R5: In Vivo Preventive Test on *Septoria tritici* (Leaf Spot on Wheat)

The tested active ingredients are prepared by homogenization in a mixture of acetone/Dimethyl sulfoxide/Tween® as disclosed above, and then diluted with water to obtain the desired active material concentration.

The young plants of wheat are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

Results:

| Active compound | Rate of application of active compound in ppm | Efficacy in % |
|---|---|---|
| Comparison compound 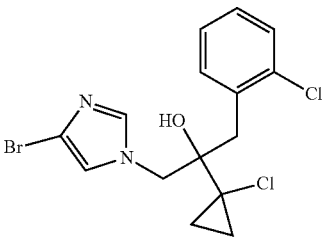 [SMILES: OC(Cc1ccccc1Cl)(Cn1cnc(Br)c1)C1(Cl)CC1] | 500<br>100 | 83<br>75 |
| According to the invention:<br>I-04 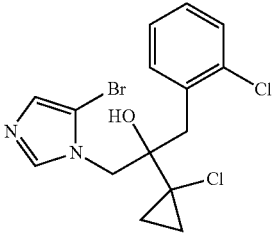 [SMILES: OC(Cc1ccccc1Cl)(Cn1cncc1Br)C1(Cl)CC1] | 500<br>100 | 100<br>97 |

-continued
| Active compound | | Rate of application of active compound in ppm | Efficacy in % |
|---|---|---|---|
| Comparison compound | 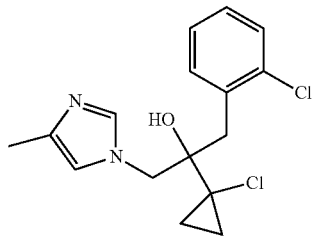 [SMILES: Cc1cn(CC(O)(Cc2ccccc2Cl)C2(Cl)CC2)cn1] | 500<br>100 | 33<br>17 |
| According to the invention: | | | |
| I-03 | 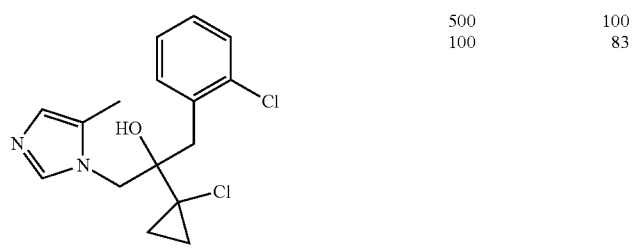 | 500<br>100 | 100<br>83 |
| Comparison compound | 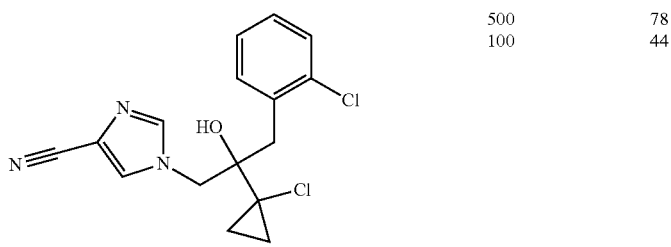 | 500<br>100 | 78<br>44 |
| According to the invention: | | | |
| I-06 | 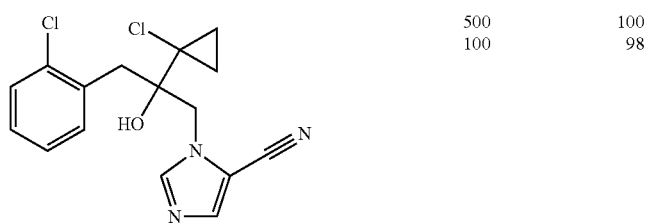 | 500<br>100 | 100<br>98 |
| Comparison compound | 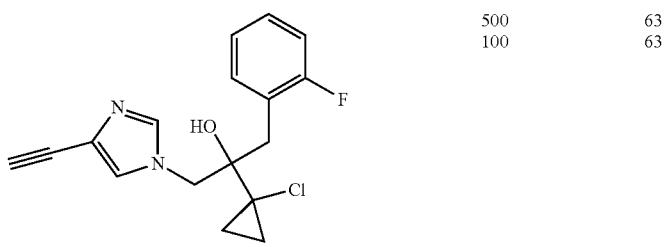 | 500<br>100 | 63<br>63 |

-continued
| Active compound | | Rate of application of active compound in ppm | Efficacy in % |
|---|---|---|---|
According to the invention:
I-36 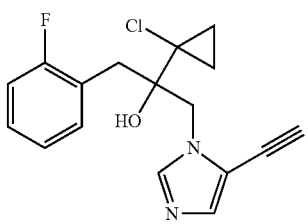 [SMILES: C#Cc1cncn1CC(O)(Cc1ccccc1F)C1(Cl)CC1] | 500 | 75 |
| | 100 | 83 |
Comparison compound 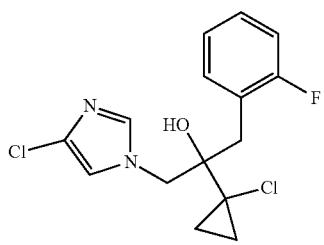 [SMILES: OC(Cc1ccccc1F)(Cn1cnc(Cl)c1)C1(Cl)CC1] | 500 | 93 |
| | 100 | 0 |
Comparison compound 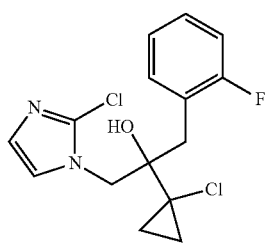 [SMILES: OC(Cc1ccccc1F)(Cn1ccnc1Cl)C1(Cl)CC1] | 500 | 96 |
| | 100 | 20 |
According to the invention:
I-32 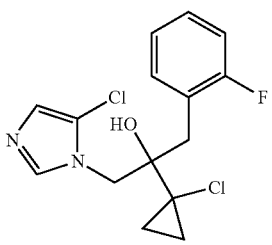 | 500 | 100 |
| | 100 | 71 |
Comparison compound 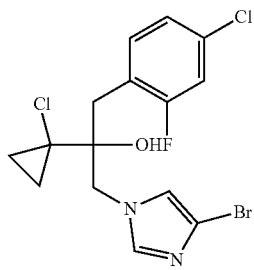 | 500 | 94 |
| | 100 | 38 |

-continued
| Active compound | | Rate of application of active compound in ppm | Efficacy in % |
|---|---|---|---|
| According to the invention: | | | |
| I-30 | 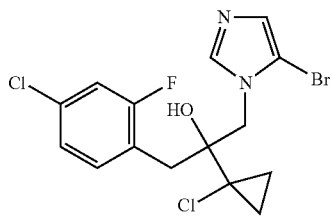 [SMILES: OC(Cc1ccc(Cl)cc1F)(Cn1cncc1Br)C1(Cl)CC1] | 500<br>100 | 98<br>94 |
| Comparison compound | 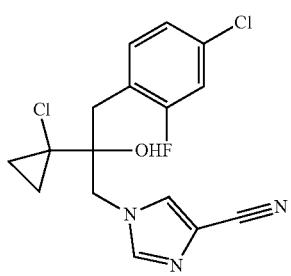 | 500<br>100 | 100<br>63 |
| According to the invention: | | | |
| I-29 | 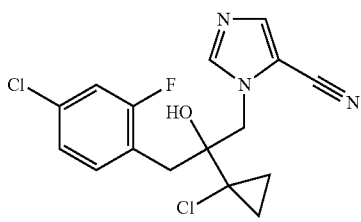 [SMILES: N#Cc1cncn1CC(O)(Cc1ccc(Cl)cc1F)C1(Cl)CC1] | 500<br>100 | 100<br>100 |
| Comparison compound | 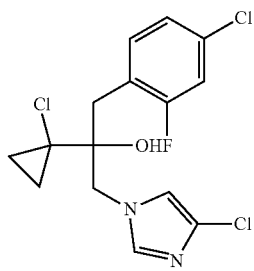 | 500<br>100 | 75<br>0 |
| According to the invention: | | | |
| I-27 | 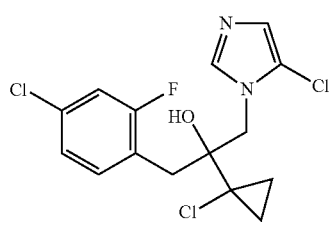 [SMILES: OC(Cc1ccc(Cl)cc1F)(Cn1cncc1Cl)C1(Cl)CC1] | 500<br>100 | 81<br>94 |

-continued

| Active compound | | Rate of application of active compound in ppm | Efficacy in % |
|---|---|---|---|
| Comparison compound | [structure: 4-cyano-imidazole-CH2-C(OH)(cyclopropyl-Cl)-CH2-(2-F-phenyl)] | 500<br>100 | 86<br>14 |
| According to the invention: | | | |
| I-34 | [structure: (2-F-phenyl)-CH2-C(OH)(cyclopropyl-Cl)-CH2-N(imidazole-5-CN)] | 500<br>100 | 100<br>100 |

Example R6: In Vivo Preventive Test on *Sphaerotheca fuliginea* (Powdery Mildew on Cucurbits)

The tested active ingredients are prepared by homogenization in a mixture of acetone/Dimethyl sulfoxide/Tween® as disclosed above, and then diluted with water to obtain the desired active material concentration.

The young plants of gherkin are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Sphaerotheca fuliginea* spores. The contaminated gherkin plants are incubated for 72 hours at 18° C. and at 100% relative humidity and then for 12 days at 20° C. and at 70-80% relative humidity.

The test is evaluated 15 days after the inoculation. 0% means an efficacy which corresponds to that of the control plants while an efficacy of 100% means that no disease is observed.

Results:

| Active compound | | Rate of application of active compound in ppm | Efficacy in % |
|---|---|---|---|
| Comparison compound | [structure: 4-Br-imidazole-CH2-C(OH)(cyclopropyl-Cl)-CH2-(2-Cl-phenyl)] | 500<br>100 | 30<br>20 |
| According to the invention: | | | |
| I-04 | [structure: 5-Br-imidazole-N-CH2-C(OH)(cyclopropyl-Cl)-CH2-(2-Cl-phenyl)] | 500<br>100 | 100<br>100 |

-continued

| Active compound | Rate of application of active compound in ppm | Efficacy in % |
|---|---|---|
| Comparison compound | 500<br>100 | 30<br>0 |
| According to the invention: | | |
| I-03 | 500<br>100 | 100<br>85 |
| Comparison compound | 500<br>100 | 60<br>0 |
| According to the invention: | | |
| I-36 | 500<br>100 | 100<br>100 |
| Comparison compound | 500<br>100 | 98<br>60 |
| Comparison compound | 500<br>100 | 78<br>0 |

|  | Active compound | Rate of application of active compound in ppm | Efficacy in % |
|---|---|---|---|
| According to the invention: | | | |
| I-32 | 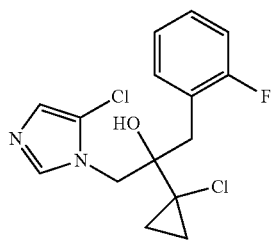 [SMILES: OC(Cc1ccccc1F)(Cn1cncc1Cl)C1(Cl)CC1] | 500<br>100 | 100<br>100 |
| Comparison compound | 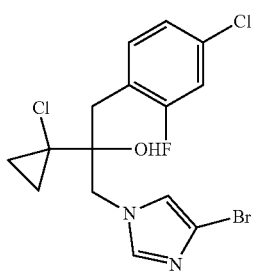 | 500<br>100 | 100<br>60 |
| According to the invention: | | | |
| I-30 | 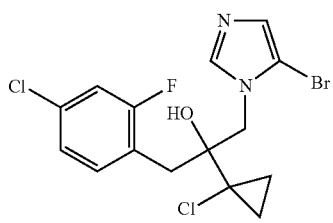 [SMILES: OC(Cc1ccc(Cl)cc1F)(Cn1cncc1Br)C1(Cl)CC1] | 500<br>100 | 100<br>100 |
| Comparison compound | 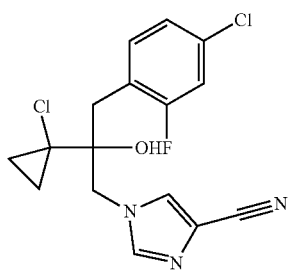 | 500<br>100 | 90<br>90 |
| According to the invention: | | | |
| I-29 | 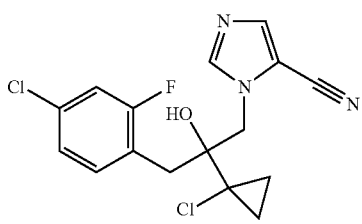 [SMILES: N#Cc1cncn1CC(O)(Cc1ccc(Cl)cc1F)C1(Cl)CC1] | 500<br>100 | 100<br>100 |

| Active compound | Rate of application of active compound in ppm | Efficacy in % |
|---|---|---|
| Comparison compound 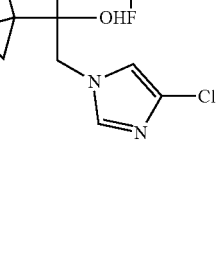 | 500<br>100 | 80<br>0 |
| According to the invention: | | |
| I-27 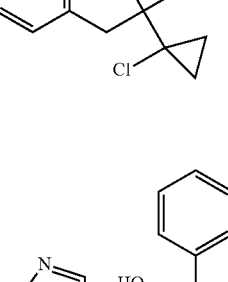 | 500<br>100 | 100<br>100 |
| Comparison compound 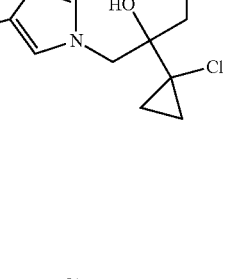 | 500<br>100 | 95<br>95 |
| According to the invention: | | |
| I-34 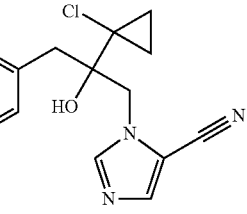 | 500<br>100 | 100<br>100 |

Example R7: In Vivo Preventive Test on *Uromyces appendiculatus* (Bean Rust)

The tested active ingredients are prepared by homogenization in a mixture of acetone/Dimethyl sulfoxide/Tween® as disclosed above, and then diluted with water to obtain the desired active material concentration.

The young plants of bean are treated by spraying the active ingredient prepared as described above. Control plants are treated only with an aqueous solution of acetone/Dimethyl sulfoxide/Tween®.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

Results:
| Active compound | Rate of application of active compound in ppm | Efficacy in % |
|---|---|---|
| Comparison compound 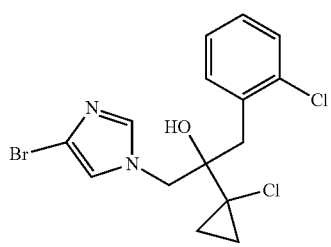 [SMILES: OC(Cc1ccccc1Cl)(Cn1cnc(Br)c1)C1(Cl)CC1] | 500<br>100 | 47<br>56 |
| According to the invention: | | |
| I-04 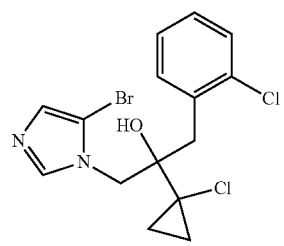 [SMILES: OC(Cc1ccccc1Cl)(Cn1cncc1Br)C1(Cl)CC1] | 500<br>100 | 100<br>100 |
| Comparison compound 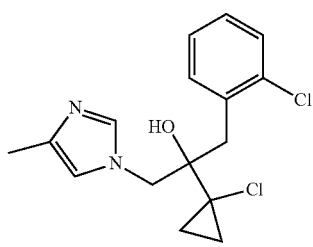 [SMILES: Cc1cn(CC(O)(Cc2ccccc2Cl)C2(Cl)CC2)cn1] | 500<br>100 | 100<br>0 |
| According to the invention: | | |
| I-03 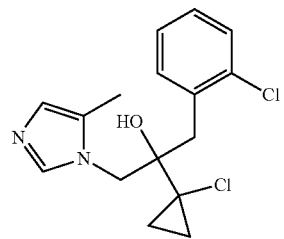 [SMILES: Cc1cncn1CC(O)(Cc1ccccc1Cl)C1(Cl)CC1] | 500<br>100 | 100<br>81 |
| Comparison compound 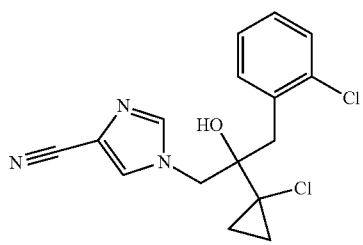 [SMILES: N#Cc1cn(CC(O)(Cc2ccccc2Cl)C2(Cl)CC2)cn1] | 500<br>100 | 50<br>25 |

-continued
| | Active compound | Rate of application of active compound in ppm | Efficacy in % |
|---|---|---|---|
| According to the invention: | | | |
| I-06 | 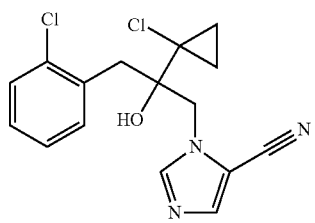 | 500<br>100 | 100<br>100 |
| Comparison compound | 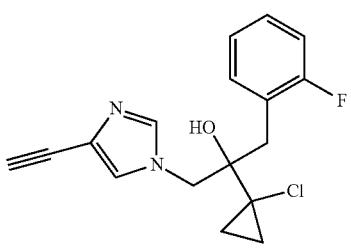 [SMILES: C#Cc1cn(CC(O)(Cc2ccccc2F)C2(Cl)CC2)cn1] | 500<br>100 | 0<br>0 |
| According to the invention: | | | |
| I-36 | 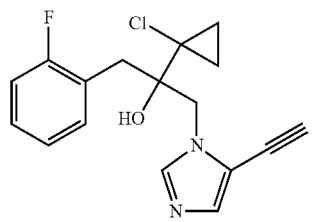 [SMILES: C#Cc1cncn1CC(O)(Cc1ccccc1F)C1(Cl)CC1] | 500<br>100 | 100<br>100 |
| Comparison compound | 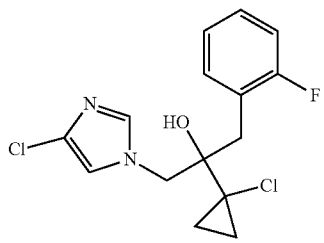 [SMILES: OC(Cc1ccccc1F)(Cn1cnc(Cl)c1)C1(Cl)CC1] | 500<br>100 | 0<br>0 |
| Comparison compound | 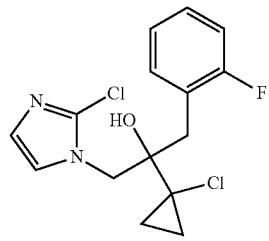 [SMILES: OC(Cc1ccccc1F)(Cn1ccnc1Cl)C1(Cl)CC1] | 500<br>100 | 0<br>0 |

| | Active compound | Rate of application of active compound in ppm | Efficacy in % |
|---|---|---|---|
| According to the invention: | | | |
| I-32 | 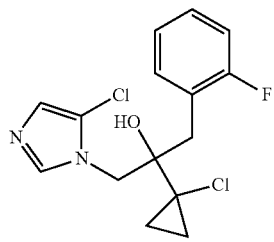 [SMILES: OC(Cc1ccccc1F)(Cn1cncc1Cl)C1(Cl)CC1] | 500<br>100 | 100<br>81 |
| Comparison compound | 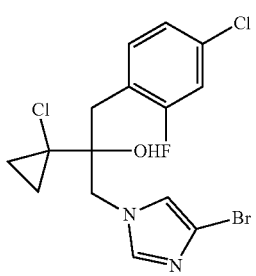 | 500<br>100 | 38<br>0 |
| According to the invention: | | | |
| I-30 | 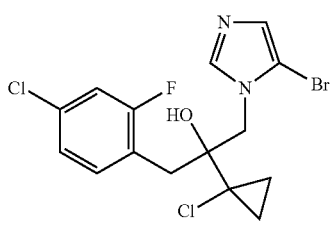 [SMILES: OC(Cc1ccc(Cl)cc1F)(Cn1cncc1Br)C1(Cl)CC1] | 500<br>100 | 100<br>88 |
| Comparison compound | 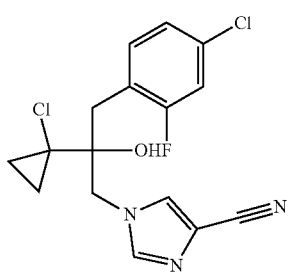 | 500<br>100 | 94<br>31 |
| According to the invention: | | | |
| I-29 | 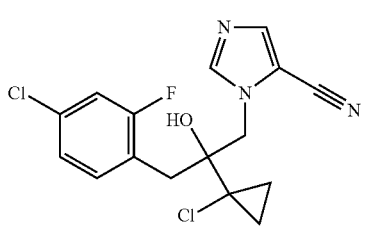 [SMILES: N#Cc1cncn1CC(O)(Cc1ccc(Cl)cc1F)C1(Cl)CC1] | 500<br>100 | 100<br>100 |

| Active compound | Rate of application of active compound in ppm | Efficacy in % |
|---|---|---|
| Comparison compound 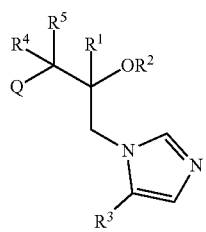 | 500<br>100 | 0<br>0 |

According to the invention:

I-27

500  100
100  20

Comparison compound 500  56
100  25

According to the invention:

I-34

500  100
100  100

The invention claimed is:
1. Imidazole derivative of the formula (I)

(I)

wherein
R¹ represents hydrogen, in each case optionally branched $C_1$-$C_8$-alkyl, $C_1$-$C_8$-haloalkyl, $C_2$-$C_7$-alkenyl, $C_2$-$C_7$-haloalkenyl, $C_2$-$C_8$-alkynyl, $C_2$-$C_8$-haloalkynyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted bicycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_8$-cycloalkylalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-halocycloalkyl-$C_1$-$C_4$-alkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-halocycloalkyl-$C_1$-$C_4$-haloalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl-$C_1$-$C_4$-haloalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl-$C_3$-$C_7$-cycloalkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkenyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted tri($C_1$-$C_8$-alkyl)silyl-$C_1$-$C_4$-alkyl; optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted tri($C_1$-$C_8$-alkyl)silyl-$C_3$-$C_7$-cycloalkyl;

$R^2$ represents H, $C_1$-$C_8$-alkyl, —Si($R^{3a}$)($R^{3b}$)($R^{3c}$), —P(O)(OH)$_2$, —CH$_2$—O—P(O)(OH)$_2$, —C(O)—$C_1$-$C_8$-alkyl, —C(O)—$C_3$-$C_7$-cycloalkyl, —C(O)NH—$C_1$-$C_8$-alkyl; —C(O)N-di-$C_1$-$C_8$-alkyl; —C(O)O—$C_1$-$C_8$-alkyl; wherein the —C(O)—$C_1$-$C_8$-alkyl, —C(O)—$C_3$-$C_7$-cycloalkyl, —C(O)NH—$C_1$-$C_8$-alkyl; —C(O)N-di-$C_1$-$C_8$-alkyl or —C(O)O—$C_1$-$C_8$-alkyl may be non-substituted or substituted by one or more group(s) selected from halogen or $C_1$-$C_8$-alkoxy; wherein $R^{3a}$, $R^{3b}$, $R^{3c}$ represent independent from each other a phenyl or $C_1$-$C_8$-alkyl;

$R^3$ represents halogen; hydroxyl; cyano; isocyano; nitro; amino; sulfanyl; pentafluoro-$\lambda^6$-sulfanyl; carboxaldehyde, hydroxycarbonyl, $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; tri($C_1$-$C_8$-alkyl)silyl; tri($C_1$-$C_8$-alkyl)silyl-$C_1$-$C_8$-alkyl; $C_3$-$C_7$-cycloalkyl; $C_3$-$C_7$-halogencycloalkyl; $C_3$-$C_7$-cycloalkenyl; $C_3$-$C_7$-halogencycloalkenyl; $C_4$-$C_{10}$-cycloalkylalkyl; $C_4$-$C_{10}$-halocycloalkylalkyl; $C_6$-$C_{12}$-cycloalkylcycloalkyl; $C_1$-$C_8$-alkyl-$C_3$-$C_7$-cycloalkyl; $C_1$-$C_8$-alkoxy-$C_3$-$C_7$-cycloalkyl; tri($C_1$-$C_8$-alkyl)silyl-$C_3$-$C_7$-cycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_1$-$C_8$-alkylamino; $C_1$-$C_8$-halogenalkylamino; $C_1$-$C_8$-cyanoalkoxy; $C_4$-$C_8$-cycloalkylalkoxy; $C_3$-$C_6$-cycloalkoxy; $C_1$-$C_8$-alkylsulfanyl; $C_1$-$C_8$-halogenoalkylsulfanyl; $C_1$-$C_8$-alkylcarbonyl; $C_1$-$C_8$-halogenoalkylcarbonyl; arylcarbonyl; aryl-$C_1$-$C_6$-alkylcarbonyl; $C_3$-$C_8$-cycloalkylcarbonyl; $C_3$-$C_8$-halogenocycloalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_6$-alkoxycarbamoyl; aminothiocarbonyl; $C_1$-$C_8$-alkoxycarbonyl; $C_1$-$C_8$-halogenoalkoxycarbonyl; $C_3$-$C_8$-cycloalkoxycarbonyl; $C_2$-$C_8$-alkoxyalkylcarbonyl; $C_2$-$C_8$-halogenoalkoxyalkylcarbonyl; $C_3$-$C_{10}$-cycloalkoxyalkylcarbonyl; $C_1$-$C_8$-alkylaminocarbonyl; di-$C_1$-$C_8$-alkylaminocarbonyl; $C_3$-$C_8$-cycloalkylaminocarbonyl; $C_1$-$C_8$-alkylcarbonyloxy; $C_1$-$C_8$-halogenoalkylcarbonyloxy; $C_3$-$C_8$-cycloalkylcarbonyloxy; $C_1$-$C_8$-alkylcarbonylamino; $C_1$-$C_8$-halogenoalkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfinyl; $C_1$-$C_8$-halogenoalkylsulfinyl; $C_1$-$C_8$-alkylsulfonyl; $C_1$-$C_8$-halogenoalkylsulfonyl; $C_1$-$C_8$-alkylsulfonyloxy; $C_1$-$C_8$-halogenoalkylsulfonyloxy; $C_1$-$C_8$-alkylaminosulfamoyl; di-$C_1$-$C_8$-alkylaminosulfamoyl; ($C_1$-$C_8$-alkoxyimino)-$C_1$-$C_8$-alkyl; ($C_3$-$C_7$-cycloalkoxyimino)-$C_1$-$C_8$-alkyl; hydroxyimino-$C_1$-$C_8$-alkyl; ($C_1$-$C_8$-alkoxyimino)-$C_3$-$C_7$-cycloalkyl; hydroxyimino-$C_3$-$C_7$-cycloalkyl; ($C_1$-$C_8$-alkylimino)-oxy; ($C_1$-$C_8$-alkylimino)-oxy-$C_1$-$C_8$-alkyl; ($C_3$-$C_7$-cycloalkylimino)-oxy-$C_1$-$C_8$-alkyl; ($C_1$-$C_6$-alkylimino)-oxy-$C_3$-$C_7$-cycloalkyl; ($C_1$-$C_8$-alkenyloxyimino)-$C_1$-$C_8$-alkyl; ($C_1$-$C_8$-alkynyloxyimino)-$C_1$-$C_8$-alkyl; (benzyloxyimino)-$C_1$-$C_8$-alkyl; $C_1$-$C_8$-alkoxyalkyl; $C_1$-$C_8$-alkylthioalkyl; $C_1$-$C_8$-alkoxyalkoxyalkyl; $C_1$-$C_8$-halogenoalkoxyalkyl; benzyl; phenyl; 5-membered heteroaryl; 6-membered heteroaryl; benzyloxy; phenyloxy; benzylsulfanyl; benzylamino; phenylsulfanyl; or phenylamino; wherein the benzyl, phenyl, 5-membered heteroaryl, 6-membered heteroaryl, benzyloxy or phenyloxy may be optionally substituted by one or more group(s) selected from halogen; hydroxyl; cyano; isocyano; amino; sulfanyl; pentafluoro-$\lambda^6$-sulfanyl; carboxaldehyde, hydroxycarbonyl, $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; tri($C_1$-$C_8$-alkyl)silyl; tri($C_1$-$C_8$-alkyl)silyl-$C_1$-$C_8$-alkyl; $C_3$-$C_7$-cycloalkyl; $C_3$-$C_7$-halogencycloalkyl; $C_3$-$C_7$-cycloalkenyl; $C_3$-$C_7$-halogencycloalkenyl; $C_4$-$C_{10}$-cycloalkylalkyl; $C_4$-$C_{10}$-halocycloalkylalkyl; $C_6$-$C_{12}$-cycloalkylcycloalkyl; $C_1$-$C_8$-alkyl-$C_3$-$C_7$-cycloalkyl; $C_1$-$C_8$-alkoxy-$C_3$-$C_7$-cycloalkyl; tri($C_1$-$C_8$-alkyl)silyl-$C_3$-$C_7$-cycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_1$-$C_8$-alkylamino; $C_1$-$C_8$-halogenalkylamino; $C_1$-$C_8$-cyanoalkoxy; $C_4$-$C_8$-cycloalkylalkoxy; $C_3$-$C_6$-cycloalkoxy; $C_1$-$C_8$-alkylsulfanyl; $C_1$-$C_8$-halogenoalkylsulfanyl; $C_1$-$C_8$-alkylcarbonyl; $C_1$-$C_8$-halogenoalkylcarbonyl; arylcarbonyl; aryl-$C_1$-$C_6$-alkylcarbonyl; $C_3$-$C_8$-cycloalkylcarbonyl; $C_3$-$C_8$-halogenocycloalkylcarbonyl; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_6$-alkoxycarbamoyl; aminothiocarbonyl; $C_1$-$C_8$-alkoxycarbonyl; $C_1$-$C_8$-halogenoalkoxycarbonyl; $C_3$-$C_8$-cycloalkoxycarbonyl; $C_2$-$C_8$-alkoxyalkylcarbonyl; $C_2$-$C_8$-halogenoalkoxyalkylcarbonyl; $C_3$-$C_{10}$-cycloalkoxyalkylcarbonyl; $C_1$-$C_8$-alkylaminocarbonyl; di-$C_1$-$C_8$-alkylaminocarbonyl; $C_3$-$C_8$-cycloalkylaminocarbonyl; $C_1$-$C_8$-alkylcarbonyloxy; $C_1$-$C_8$-halogenoalkylcarbonyloxy; $C_3$-$C_8$-cycloalkylcarbonyloxy; $C_1$-$C_8$-alkylcarbonylamino; $C_1$-$C_8$-halogenoalkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfinyl; $C_1$-$C_8$-halogenoalkylsulfinyl; $C_1$-$C_8$-alkylsulfonyl; $C_1$-$C_8$-halogenoalkylsulfonyl; $C_1$-$C_8$-alkylsulfonyloxy; $C_1$-$C_8$-halogenoalkylsulfonyloxy; $C_1$-$C_8$-alkylaminosulfamoyl; di-$C_1$-$C_8$-alkylaminosulfamoyl; ($C_1$-$C_8$-alkoxyimino)-$C_1$-$C_8$-alkyl; ($C_3$-$C_7$-cycloalkoxyimino)-$C_1$-$C_8$-alkyl; hydroxyimino-$C_1$-$C_8$-alkyl; ($C_1$-$C_8$-alkoxyimino)-$C_3$-$C_7$-cycloalkyl; hydroxyimino-$C_3$-$C_7$-cycloalkyl; ($C_1$-$C_8$-alkylimino)-oxy; ($C_1$-$C_8$-alkylimino)-oxy-$C_1$-$C_8$-alkyl; ($C_3$-$C_7$-cycloalkylimino)-oxy-$C_1$-$C_8$-alkyl; ($C_1$-$C_6$-alkylimino)-oxy-$C_3$-$C_7$-cycloalkyl; ($C_1$-$C_8$-alkenyloxyimino)-$C_1$-$C_8$-alkyl; ($C_1$-$C_8$-alkynyloxyimino)-$C_1$-$C_8$-alkyl; (benzyloxyimino)-$C_1$-$C_8$-alkyl; $C_1$-$C_8$-alkoxyalkyl; $C_1$-$C_8$-alkylthioalkyl; $C_1$-$C_8$-alkoxyalkoxyalkyl; $C_1$-$C_8$-halogenoalkoxyalkyl; benzyl; phenyl; 5-membered heteroaryl; 6-membered heteroaryl; benzyloxy; phenyloxy; benzylsulfanyl; benzylamino; phenylsulfanyl; or phenylamino;

$R^4$ represents hydrogen, fluorine, $C_1$-$C_8$-alkyl, $C_1$-$C_8$-haloalkyl or $C_1$-$C_8$-alkyloxy;

$R^5$ represents hydrogen, fluorine, $C_1$-$C_8$-alkyl, $C_1$-$C_8$-haloalkyl or $C_1$-$C_8$-alkyloxy;

or $R^4$ and $R^5$ form together with the carbon atom to which they are attached an optionally halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl ring;

Q represents a 6-membered aromatic cycle of formula (Q-I)

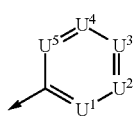

(Q-I)

wherein $U^1$ represents $CX^1$ or N;

wherein $X^1$ represents hydrogen, halogen, nitro, cyano, hydroxy, sulfanyl, carboxaldehyde, substituted or non-substituted carbaldehyde O—($C_1$-$C_8$-alkyl)oxime, pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_3$-$C_7$-halogencycloalkyl having 1 to 5 halogen atoms; substituted or non-substituted $C_3$-$C_7$-cycloalkenyl; substituted or non-substituted $C_1$-$C_8$-halogenoalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted $C_3$-$C_6$-cycloalkoxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, $C_1$-$C_8$-alkylaminocarbonyl; di-$C_1$-$C_8$-alkylaminocarbonyl, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted ($C_1$-$C_8$-alkoxyimino)-$C_1$-$C_8$-alkyl; substituted or non-substituted ($C_3$-$C_7$-cycloalkoxyimino)-$C_1$-$C_8$-alkyl; substituted or non-substituted hydroxyimino-$C_1$-$C_8$-alkyl, substituted or non-substituted phenyloxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

$U^2$ represents $CX^2$ or N;

wherein $X^2$ represents hydrogen, halogen, nitro, cyano, hydroxy, sulfanyl, carboxaldehyde, substituted or non-substituted carbaldehyde O—($C_1$-$C_8$-alkyl)oxime, pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_3$-$C_7$-halogencycloalkyl having 1 to 5 halogen atoms; substituted or non-substituted $C_3$-$C_7$-cycloalkenyl; substituted or non-substituted $C_1$-$C_8$-halogenoalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted $C_3$-$C_6$-cycloalkoxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, $C_1$-$C_8$-alkylaminocarbonyl; di-$C_1$-$C_8$-alkylaminocarbonyl, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted ($C_1$-$C_8$-alkoxyimino)-$C_1$-$C_8$-alkyl; substituted or non-substituted ($C_3$-$C_7$-cycloalkoxyimino)-$C_1$-$C_8$-alkyl; substituted or non-substituted hydroxyimino-$C_1$-$C_8$-alkyl, substituted or non-substituted phenyloxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

$U^3$ represents $CX^3$ or N;

wherein $X^3$ represents hydrogen, halogen, nitro, cyano, hydroxy, sulfanyl, carboxaldehyde, substituted or non-substituted carbaldehyde O—($C_1$-$C_8$-alkyl)oxime, pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_3$-$C_7$-halogencycloalkyl having 1 to 5 halogen atoms; substituted or non-substituted $C_3$-$C_7$-cycloalkenyl; substituted or non-substituted $C_1$-$C_8$-halogenoalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted $C_3$-$C_6$-cycloalkoxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, $C_1$-$C_8$-alkylaminocarbonyl; di-$C_1$-$C_8$-alkylaminocarbonyl, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted ($C_1$-$C_8$-alkoxyimino)-$C_1$-$C_8$-alkyl; substituted or non-substituted ($C_3$-$C_7$-cycloalkoxyimino)-$C_1$-$C_8$-alkyl; substituted or non-substituted hydroxyimino-$C_1$-$C_8$-alkyl, substituted or non-substituted phenyloxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

$U^4$ represents $CX^4$ or N;

wherein $X^4$ represents hydrogen, halogen, nitro, cyano, hydroxy, sulfanyl, carboxaldehyde, substituted or non-substituted carbaldehyde O—($C_1$-$C_8$-alkyl)oxime, pentafluoro-$X^6$-sulfenyl group, substituted or non-substituted $C_1$-$C_8$-alkyl, substituted or non-substituted $C_3$-$C_8$-cycloalkyl, substituted or non-substituted $C_3$-$C_7$-halogencycloalkyl having 1 to 5 halogen atoms; substituted or non-substituted $C_3$-$C_7$-cycloalkenyl; substituted or non-substituted $C_1$-$C_8$-halogenoalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted $C_3$-$C_6$-cycloalkoxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, $C_1$-$C_8$-alkylaminocarbonyl; di-$C_1$-$C_8$-alkylaminocarbonyl, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted ($C_1$-$C_8$-alkoxyimino)-$C_1$-$C_8$-alkyl; substituted or non-substituted ($C_3$-$C_7$-cycloalkoxyimino)-$C_1$-$C_8$-alkyl; substituted or non-substituted hydroxyimino-$C_1$-$C_8$-alkyl, substituted or non-substituted phenyloxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

$U^5$ represents $CX^5$ or N;

wherein $X^5$ represents hydrogen, halogen, nitro, cyano, hydroxy, sulfanyl, carboxaldehyde, substituted or non-substituted carbaldehyde O—($C_1$-$C_8$-alkyl)oxime, pentafluoro-$\lambda^6$-sulfenyl group, substituted or non-substituted $C_1$-$C_8$-alkyl, substituted or non-substituted $C_3$-$C_8$-cycloalkyl, substituted or non-substituted $C_3$-$C_7$-halogencycloalkyl having 1 to 5 halogen atoms; substituted or non-substituted $C_3$-$C_7$-cycloalkenyl; substituted or non-substituted $C_1$-$C_8$-halogenoalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_2$-$C_8$-alkenyloxy, substituted or non-substituted $C_3$-$C_8$-alkynyloxy, substituted or non-substituted $C_3$-$C_6$-cycloalkoxy, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, $C_1$-$C_8$-alkylaminocarbonyl; di-$C_1$-$C_8$-alkylaminocarbonyl, substituted or non-substituted $C_1$-$C_8$-alkoxycarbonyl, substituted or non-substituted $C_1$-$C_8$-alkylcarbonyloxy, substituted or non-substituted $C_1$-$C_8$-alkylsulfinyl, substituted or non-substituted $C_1$-$C_8$-alkylsulfonyl, substituted or non-substituted ($C_1$-$C_8$-alkoxyimino)-$C_1$-$C_8$-alkyl; substituted or non-substituted ($C_3$-$C_7$-cycloalkoxyimino)-$C_1$-$C_8$-alkyl; substituted or non-substituted hydroxyimino-$C_1$-$C_8$-alkyl, substituted or non-substituted phenyloxy, substituted or non-substituted phenylsulfenyl, substituted or non-substituted aryl, substituted or non-substituted tri($C_1$-$C_8$-alkyl)-silyloxy, substituted or non-substituted tri($C_1$-$C_8$-alkyl)-silyl, substituted or non-substituted heterocyclyl, substituted or non-substituted heterocyclyloxy;

and wherein at most two of $U^1$, $U^2$, $U^3$, $U^4$ or $U^5$ can represent N;

or $U^1$ and $U^2$ or $U^2$ and $U^3$ or $U^3$ and $U^4$ form together an additional saturated or unsaturated 4 to 6-membered halogen- or $C_1$-$C_8$-alkyl-substituted or non-substituted ring;

and/or a salt and/or N-oxide thereof.

2. Imidazole derivative of the formula (I) and/or a salt and/or N-oxide thereof according to claim 1, wherein $R^1$ represents in each case optionally branched $C_1$-$C_8$-alkyl, $C_1$-$C_8$-haloalkyl, $C_2$-$C_7$-alkenyl, $C_2$-$C_7$-haloalkenyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl;

$R^2$ represents H, $C_1$-$C_8$-alkyl, halogen- or $C_1$-$C_8$-alkoxy-substituted or non-substituted —C(O)—$C_1$-$C_8$-alkyl;

$R^3$ represents halogen; hydroxyl; cyano; isocyano; nitro; carboxaldehyde, hydroxycarbonyl, $C_1$-$C_8$-alkyl; $C_1$-$C_8$-haloalkyl; $C_1$-$C_8$-cyanoalkyl; $C_1$-$C_8$-alkyloxy; $C_1$-$C_8$-halogenalkyloxy; $C_3$-$C_7$-cycloalkyl; $C_3$-$C_7$-halogencycloalkyl; $C_2$-$C_8$-alkenyl; $C_2$-$C_8$-alkynyl; $C_2$-$C_8$-alkenyloxy; $C_2$-$C_8$-halogenalkenyloxy; $C_3$-$C_8$-alkynyloxy; $C_3$-$C_8$-halogenoalkynyloxy; $C_1$-$C_8$-alkylsulfanyl; $C_1$-$C_8$-halogenoalkylsulfanyl; $C_1$-$C_8$-alkylcarbonyl; $C_1$-$C_8$-halogenoalkylcarbonyl; arylcarbonyl; aryl-$C_1$-$C_6$-alkylcarbonyl; $C_3$-$C_8$-cycloalkylcarbonyl; $C_3$-$C_8$-halogenocycloalkylcarbonyl; aminothiocarbonyl; $C_1$-$C_8$-alkoxycarbonyl; $C_1$-$C_8$-halogenoalkoxycarbonyl; $C_3$-$C_8$-cycloalkoxycarbonyl; $C_1$-$C_8$-alkylcarbonyloxy; $C_1$-$C_8$-halogenoalkylcarbonyloxy; $C_3$-$C_8$-cycloalkylcarbonyloxy; benzyl; phenyl; 5-membered heteroaryl; 6-membered heteroaryl; benzyloxy; or phenyloxy; wherein the benzyl, phenyl, 5-membered heteroaryl, 6-membered heteroaryl, benzyloxy or phenyloxy may be optionally substituted by one or more group(s) selected from halogen; hydroxyl; cyano; isocyano; amino; sulfanyl; pentafluoro-$\lambda^6$-sulfanyl; $C_1$-$C_8$-alkyl;

$C_1$-$C_8$-haloalkyl; $C_1$-$C_8$-alkyloxy; $C_1$-$C_8$-halogenalkyloxy; tri($C_1$-$C_8$-alkyl)silyl; $C_3$-$C_7$-cycloalkyl; $C_2$-$C_8$-alkenyl; $C_2$-$C_8$-alkynyl;

$R^4$ represents hydrogen, fluorine, $C_1$-$C_4$-alkyl;

$R^5$ represents hydrogen, fluorine, $C_1$-$C_4$-alkyl;

or $R^4$ and $R^5$ form together with the carbon atom to which they are attached an optionally halogen-, $C_1$-$C_4$-alkyl-substituted $C_3$-$C_6$-cycloalkyl ring;

Q represents a 6-membered aromatic cycle of formula (Q-I-1) to (Q-I-10)

(Q-I-1)
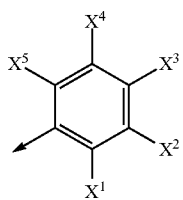

(Q-I-2)
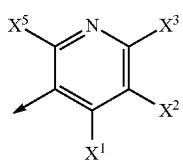

(Q-I-3)
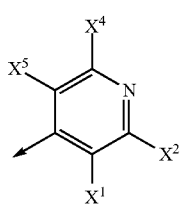

(Q-I-4)
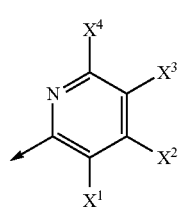

(Q-I-5)
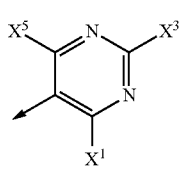

(Q-I-6)
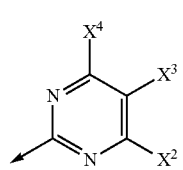

(Q-I-7)
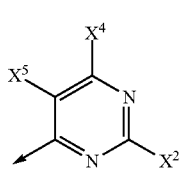

(Q-I-8)
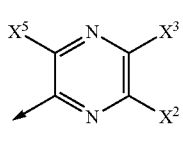

(Q-I-9)
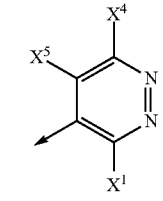

-continued (Q-I-10)
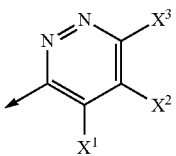

wherein $X^1$, $X^2$, $X^3$, $X^4$ or $X^5$ independent from each other have the same definition as given in claim 1; optionally independent from each other represent hydrogen or halogen.

3. Imidazole derivative of the formula (I) and/or a salt and/or N-oxide thereof according to claim 1, wherein Q represents a, optionally substituted, phenyl, 3-pyridyl or 4-pyridyl of formula (Q-I-1) to (Q-I-3)

(Q-I-1)
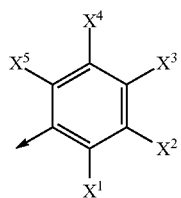

(Q-I-2)
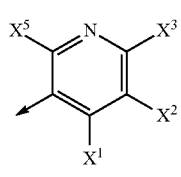

(Q-I-3)
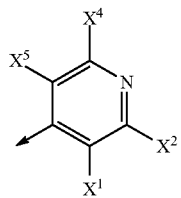

wherein $X^1$, $X^2$, $X^3$, $X^4$ or $X^5$ independent from each other have the same definition as given in claim 1 or 2; optionally independent from each other represent hydrogen or halogen.

4. Imidazole derivative of the formula (I) and/or a salt and/or N-oxide thereof according to claim 1, wherein $R^3$ represents halogen; cyano; carboxaldehyde, hydroxycarbonyl, $C_1$-$C_4$-alkyl; $C_1$-$C_4$-haloalkyl; $C_1$-$C_4$-cyanoalkyl; $C_1$-$C_4$-alkyloxy; $C_1$-$C_4$-halogenalkyloxy; $C_3$-$C_7$-cycloalkyl; $C_3$-$C_7$-halogencycloalkyl; $C_2$-$C_5$-alkenyl; $C_2$-$C_5$-alkynyl; $C_1$-$C_4$-alkylsulfanyl; $C_1$-$C_4$-halogenoalkylsulfanyl; $C_1$-$C_4$-alkylcarbonyl; $C_1$-$C_4$-halogenoalkylcarbonyl; $C_1$-$C_4$-alkoxycarbonyl; $C_1$-$C_4$-halogenoalkoxycarbonyl; benzyl; phenyl; furyl; pyrrolyl; thienyl; pyridyl; benzyloxy; or phenyloxy; wherein the benzyl, phenyl, 5-membered heteroaryl, 6-membered heteroaryl, benzyloxy or phenyloxy may be optionally substituted by one or more group(s) selected from halogen; $C_1$-$C_8$-alkyl; $C_1$-$C_8$-haloalkyl; $C_1$-$C_8$-alkyloxy; $C_1$-$C_8$-halogenalkyloxy;

Q represents a, optionally substituted, phenyl, 3-pyridyl or 4-pyridyl of formula (Q-I-1) to (Q-I-3)

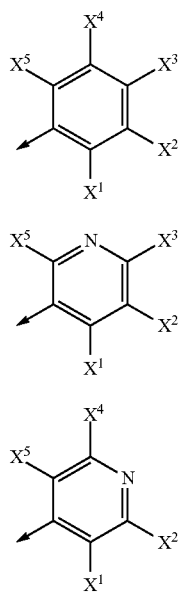

(Q-I-1)

(Q-I-2)

(Q-I-3)

wherein $X^1$, $X^2$, $X^3$, $X^4$ or $X^5$ independent from each other have the same definition as given in claim 1; optionally independent from each other represent hydrogen or halogen.

5. Imidazole derivative of the formula (I) and/or a salt and/or N-oxide thereof according to claim 2, wherein $X^1$, $X^2$, $X^3$, $X^4$ or $X^5$ independent from each other represent hydrogen or halogen.

6. Imidazole derivative of the formula (I) and/or a salt and/or N-oxide thereof according to claim 3, wherein $X^1$, $X^2$, $X^3$, $X^4$ or $X^5$ independent from each other represent hydrogen or halogen.

7. Imidazole derivative of the formula (I) and/or a salt and/or N-oxide thereof according to claim 4, wherein $X^1$, $X^2$, $X^3$, $X^4$ or $X^5$ independent from each other represent hydrogen or halogen.

8. Imidazole derivative of the formula (I) and/or a salt and/or N-oxide thereof according to claim 1, wherein Q is 2-fluorophenyl, $R^1$ is 1-chlorocyclopropyl, $R^2$ is H, $R^3$ is cyano, $R^4$ is H, and $R^5$ is H.

9. Imidazole derivative of the formula (I) and/or a salt and/or N-oxide thereof according to claim 1, wherein Q is 3-chloro-2-fluorophenyl, $R^1$ is 1-chlorocyclopropyl, $R^2$ is H, $R^3$ is cyano, $R^4$ is H, and $R^5$ is H.

10. Composition for controlling harmful microorganisms, optionally for controlling phytopathogenic harmful fungi, comprising a content of at least one compound of the formula (I) and/or a salt and/or N-oxide thereof according to claim 1, in addition to one or more extenders and/or surfactants.

11. Composition according to claim 10 comprising at least one further active ingredient selected from the group consisting of insecticides, attractants, sterilants, bactericides, acaricides, nematicides, fungicides, growth regulators, herbicides, fertilizers, safeners and semiochemicals.

12. A product comprising a compound of the formula (I) and/or a salt and/or N-oxide thereof according to claim 1 for control of harmful microorganisms, optionally phytopathogenic harmful fungi, in crop protection and/or for protection of one or more materials.

13. A product comprising a compound of the formula (I) and/or a salt and/or N-oxide thereof according to claim 1 for treatment of one or more transgenic plants.

14. A product comprising a compound of the formula (I) and/or a salt and/or N-oxide thereof according to claim 1 for treatment of seed and/or seed of transgenic plants.

15. Seed treated with a product according to claim 14.

16. Process for producing a composition for controlling harmful microorganisms, optionally for controlling phytopathogenic harmful fungi, comprising mixing a compound of the formula (I) and/or a salt and/or N-oxide thereof according to claim 1 with one or more extenders and/or surfactants.

17. Method for controlling harmful microorganisms in crop protection and in the protection of one or more materials, comprising applying a compound of the formula (I) and/or a salt and/or N-oxide thereof according to claim 1 to the harmful microorganisms and/or a habitat thereof.

18. Method for controlling phytopathogenic harmful fungi in crop protection and in the protection of one or more materials, comprising applying a compound of the formula (I) and/or a salt and/or N-oxide thereof according to claim 1 to the phytopathogenic harmful fungi and/or a habitat thereof.

* * * * *